(12) United States Patent
Schlothauer

(10) Patent No.: US 12,398,203 B2
(45) Date of Patent: Aug. 26, 2025

(54) METHOD FOR PRODUCING BISPECIFIC ANTIBODIES COMPRISING A Y436A FC-REGION MUTATION FOR IMPROVED PROTEIN A-BINDING

(71) Applicant: Hoffmann-La Roche Inc., Little Falls, NJ (US)

(72) Inventor: Tilman Schlothauer, Penzberg (DE)

(73) Assignee: Hoffmann-La Roche Inc.

( * ) Notice: Subject to any disclaimer, the term of this patent is extended or adjusted under 35 U.S.C. 154(b) by 18 days.

(21) Appl. No.: 18/079,307

(22) Filed: Dec. 12, 2022

(65) Prior Publication Data

US 2023/0183330 A1 Jun. 15, 2023

Related U.S. Application Data

(60) Continuation of application No. 16/244,378, filed on Jan. 10, 2019, now Pat. No. 11,555,067, which is a division of application No. 15/210,464, filed on Jul. 14, 2016, now abandoned, which is a continuation of application No. PCT/EP2015/050389, filed on Jan. 2, 2015.

(30) Foreign Application Priority Data

Jan. 15, 2014 (EP) ...................................... 1415322
Apr. 25, 2014 (EP) .................................... 14165924

(51) Int. Cl.
| | | |
|---|---|---|
| C07K 16/22 | (2006.01) | |
| A61K 9/00 | (2006.01) | |
| A61K 39/00 | (2006.01) | |
| A61K 39/395 | (2006.01) | |
| A61K 39/40 | (2006.01) | |
| A61K 45/06 | (2006.01) | |
| C07K 16/12 | (2006.01) | |

(52) U.S. Cl.
CPC ............ *C07K 16/22* (2013.01); *A61K 9/0019* (2013.01); *A61K 9/0048* (2013.01); *A61K 39/3955* (2013.01); *A61K 39/40* (2013.01); *A61K 45/06* (2013.01); *C07K 16/1271* (2013.01); *A61K 2039/505* (2013.01); *C07K 2317/31* (2013.01); *C07K 2317/33* (2013.01); *C07K 2317/524* (2013.01); *C07K 2317/526* (2013.01); *C07K 2317/53* (2013.01); *C07K 2317/54* (2013.01); *C07K 2317/64* (2013.01); *C07K 2317/71* (2013.01); *C07K 2317/92* (2013.01); *C07K 2317/94* (2013.01)

(58) Field of Classification Search
CPC ............. A61K 9/0019; A61K 39/3955; A61K 39/40; A61K 2039/505; C07K 16/1271; C07K 2317/524; C07K 2317/526; C07K 2317/53; C07K 2317/71

See application file for complete search history.

(56) References Cited

U.S. PATENT DOCUMENTS

| | | | |
|---|---|---|---|
| 7,923,538 B2 | 4/2011 | Shitara et al. | |
| 9,217,880 B2 | 12/2015 | Pugh et al. | |
| 10,195,262 B2 | 2/2019 | Wacker et al. | |
| 10,316,092 B2 | 6/2019 | Yao et al. | |
| 2007/0219133 A1* | 9/2007 | Lazar ....................... | A61P 29/00 |
| | | | 514/19.6 |
| 2009/0162360 A1* | 6/2009 | Klein ...................... | C07K 16/22 |
| | | | 435/69.6 |
| 2010/0272720 A1* | 10/2010 | Lo ............................ | A61P 7/06 |
| | | | 530/391.1 |
| 2016/0231320 A1 | 8/2016 | Young et al. | |

FOREIGN PATENT DOCUMENTS

| | | | |
|---|---|---|---|
| BR | 102016022721 A2 | 5/2018 | |
| CA | 3159061 A1 | 8/2013 | |
| EP | 1601697 B1 | 5/2007 | |
| WO | 9734631 A1 | 9/1997 | |
| WO | 2005077981 A2 | 8/2005 | |
| WO | WO 2011008517 A2 | 1/2011 | |
| WO | 2012069557 A1 | 5/2012 | |
| WO | 2012093125 A1 | 7/2012 | |
| WO | 2013056233 A1 | 4/2013 | |
| WO | 2013063702 A1 | 5/2013 | |
| WO | 2013166594 A1 | 11/2013 | |
| WO | WO-2014006217 A1 * | 1/2014 | ............. A61P 29/00 |
| WO | 2015057668 A1 | 4/2015 | |

OTHER PUBLICATIONS

Hober S,e t al. (2007) Journal of Chromatography B, 848:40-47. (doi:10.1016/j.jchromb.2006.09.030).*
The English translation of the Chinese Office Action, mailed on Aug. 28, 2023, in the related Chinese Patent Appl. No. 202110445639.0.
The US Office Action, mailed on Sep. 22, 2023, in the related U.S. Appl. No. 15/947,424.
The English translation (Google Translate) of the Argentina Office Action, mailed on Dec. 22, 2023, in related Argentina Application No. 20140101718.
US Office Action, mailed on Feb. 16, 2024, in related U.S. Appl. No. 16/590,938.
The Third Party Observations, posted on Dec. 1, 2023, in the related European Patent Appl. No. 15700545.5.
The Chinese Office Action, mailed on Feb. 27, 2023, in the related Chinese Patent Appl. No. 201911344011.0.
The English translation of the Chinese Office Action, mailed on Nov. 25, 2022, in the related Chinese Patent Appl. No. 201911266804.5.

(Continued)

*Primary Examiner* — Robert S Landsman

(57) ABSTRACT

Herein is reported a polypeptide comprising a first polypeptide and a second polypeptide each comprising in N-terminal to C-terminal direction at least a portion of an immunoglobulin hinge region, which comprises one or more cysteine residues, an immunoglobulin CH2-domain and an immunoglobulin CH3-domain, wherein the first, the second, or the first and the second polypeptide comprise the mutation Y436A (numbering according to the EU index).

7 Claims, 27 Drawing Sheets

Specification includes a Sequence Listing.

(56) References Cited

OTHER PUBLICATIONS

The US Office Action, mailed on Dec. 30, 2022, in the related U.S. Appl. No. 16/590,938.
The US Office Action, mailed on Jan. 12, 2023, in the related U.S. Appl. No. 15/947,377.
DeLano et al., "Convergent Solutions to Binding at a Protein-Protein Interface," Science, 287:1279-1283, Feb. 18, 2000.
Jansson et al., "All individual domains of staphylococcal protein A show Fab binding," FEMS Immunology and Medical Microbiology 20 (1998) 69-78.
The English translation of the Chinese Office Action, mailed on Jan. 24, 2024, in the related Chinese Patent Appl. No. 202110445639.0.
US Office Action, mailed on Mar. 13, 2024, in related U.S. Appl. No. 17/373,062.
The International Search Report and Written Opinion, mailed on Apr. 28, 2015, in related International Patent application No. PCT/EP2015/050425.
The English translation of the Chinese Office Action, mailed on Jul. 8, 2023, in the related Chinese Patent Appl. No. 201480024044.6.
The US Office Action, mailed on Jul. 5, 2023, in the related U.S. Appl. No. 16/590,938.
The US Office Action, mailed on Aug. 31, 2023, in the related U.S. Appl. No. 17/373,062.
The English translation of the Japanese Office Action, mailed on Aug. 29, 2023, in the related Japanese Patent Appl. No. 2022-010878.
The US Office Action, mailed on Sep. 23, 2024, in the related U.S. Appl. No. 15/947,424.
The US Office Action, mailed on Jan. 16, 2025, in the related U.S. Appl. No. 17/373,062.
Tustian et al., "Development of purification processes for fully human bispecific antibodies based upon modification of protein A binding avidity," MAbs May-Jun. 2016;8(4):828-38.
The English translation of the Reexamination Notification, mailed on Apr. 17, 2025, in the related Chinese Appl. No. 201480023252.4.

* cited by examiner

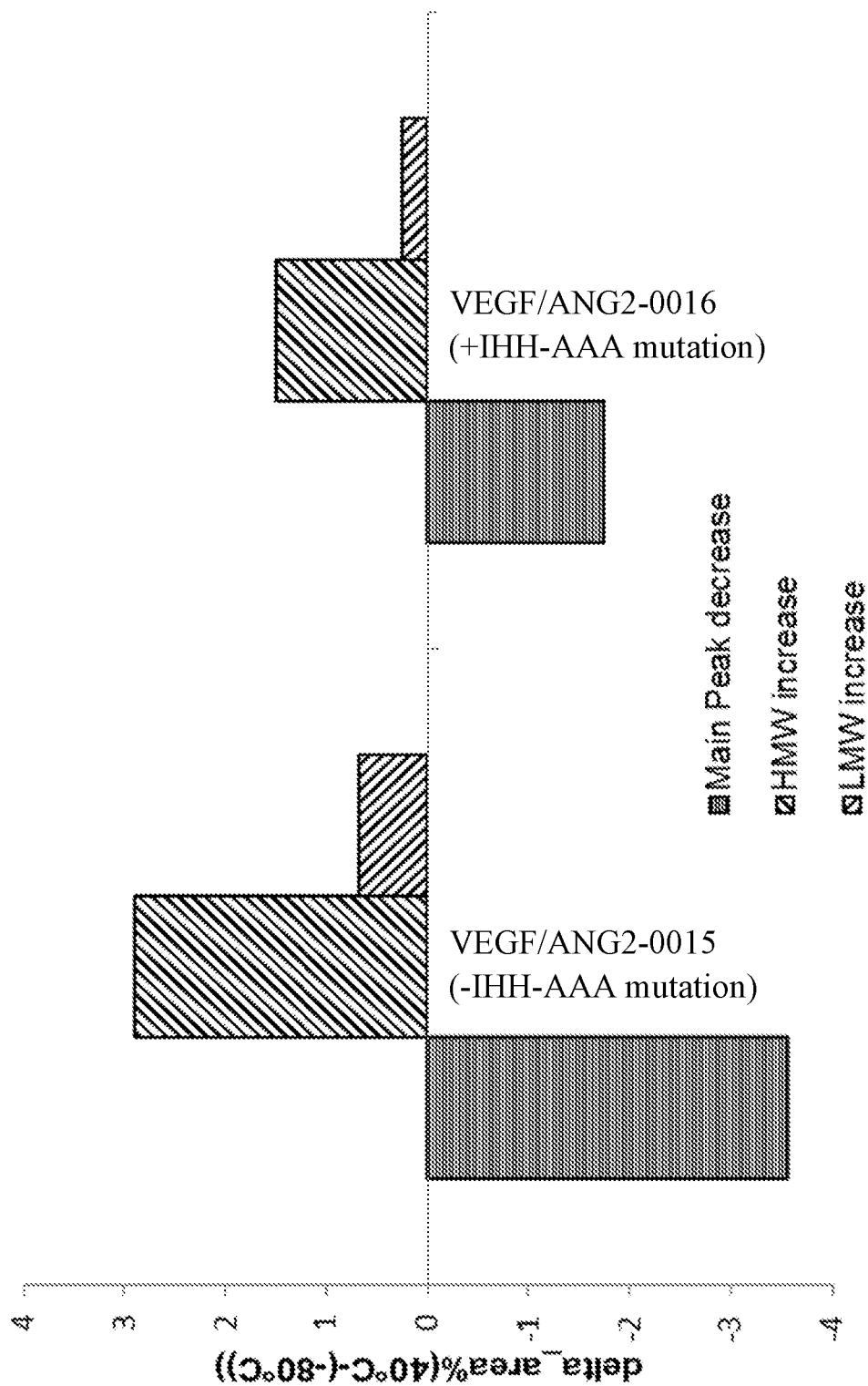

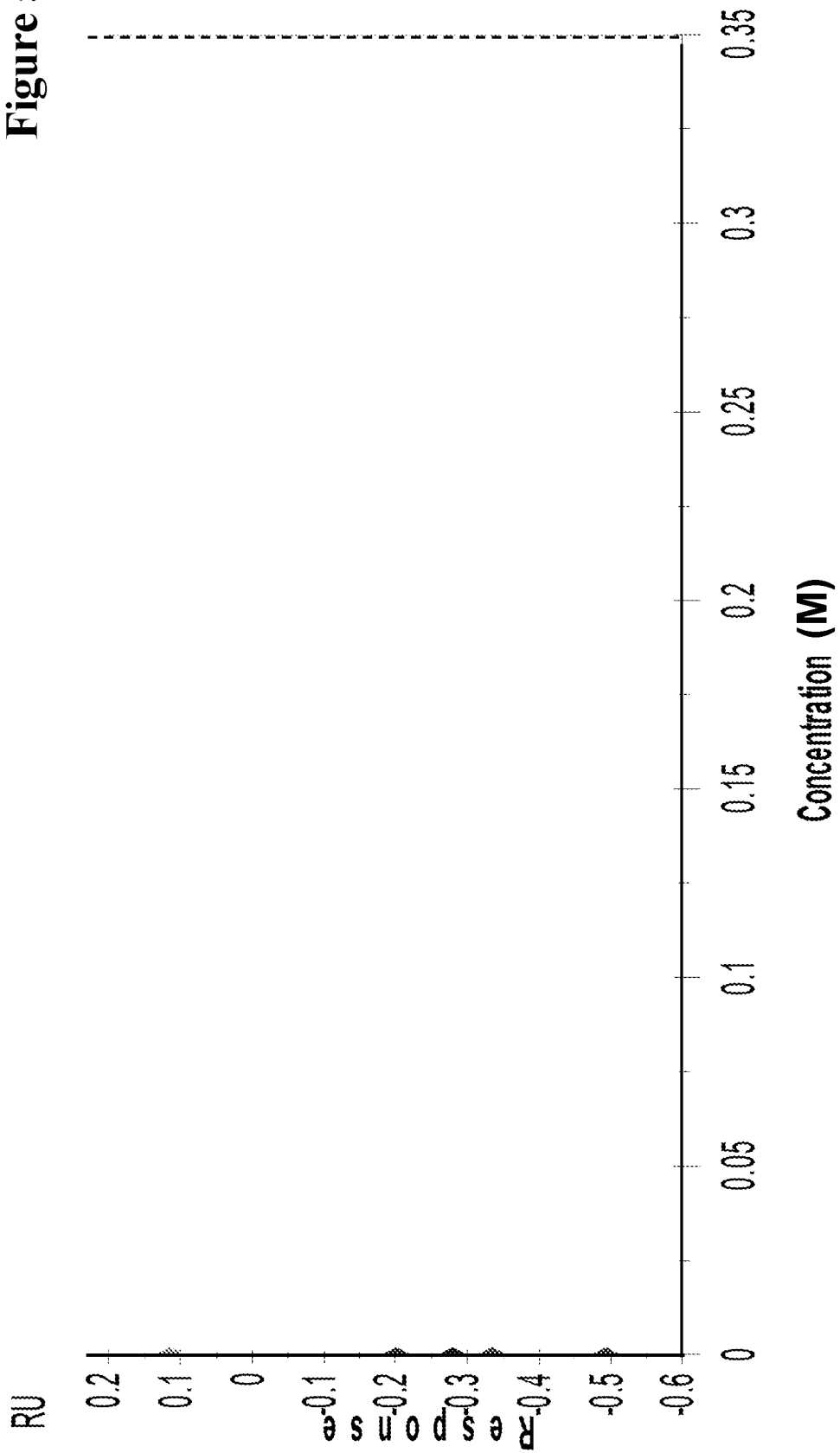

Figure 7A
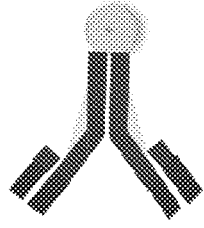
mAb<Id-<Ang2>>M-
2.6.81-Dig(XOSu)
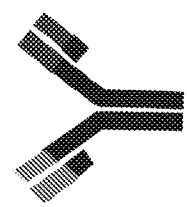
<VEGF/Ang2> rH-IgG
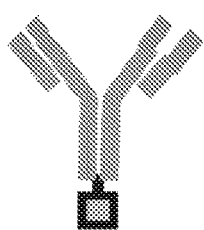
mAb<Id<VEGF>>M-
2.45.51-Bi(DDS)
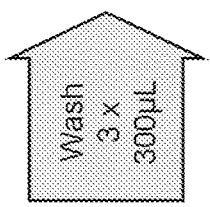
Anti-Dig-POD
+ ABTS → S

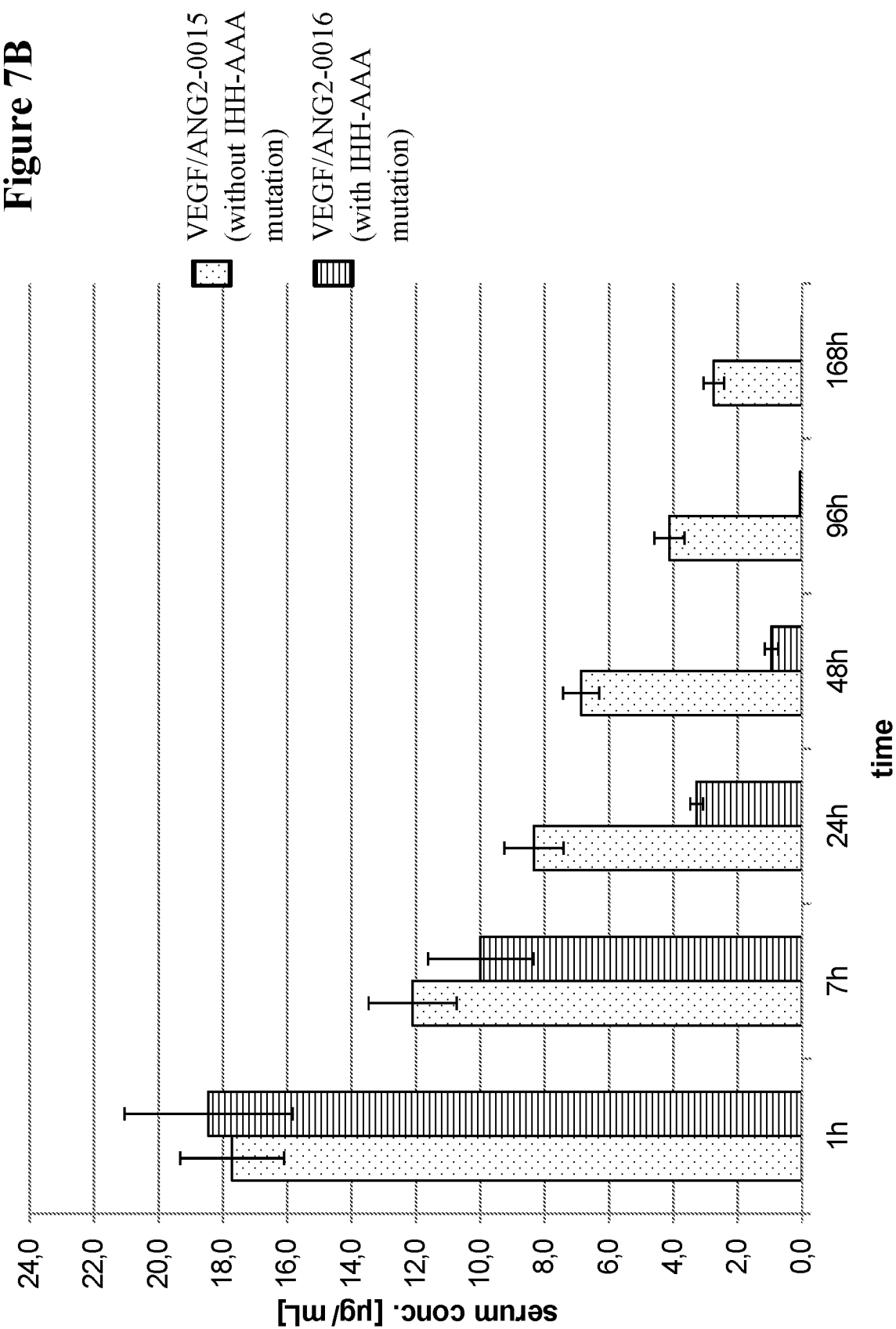

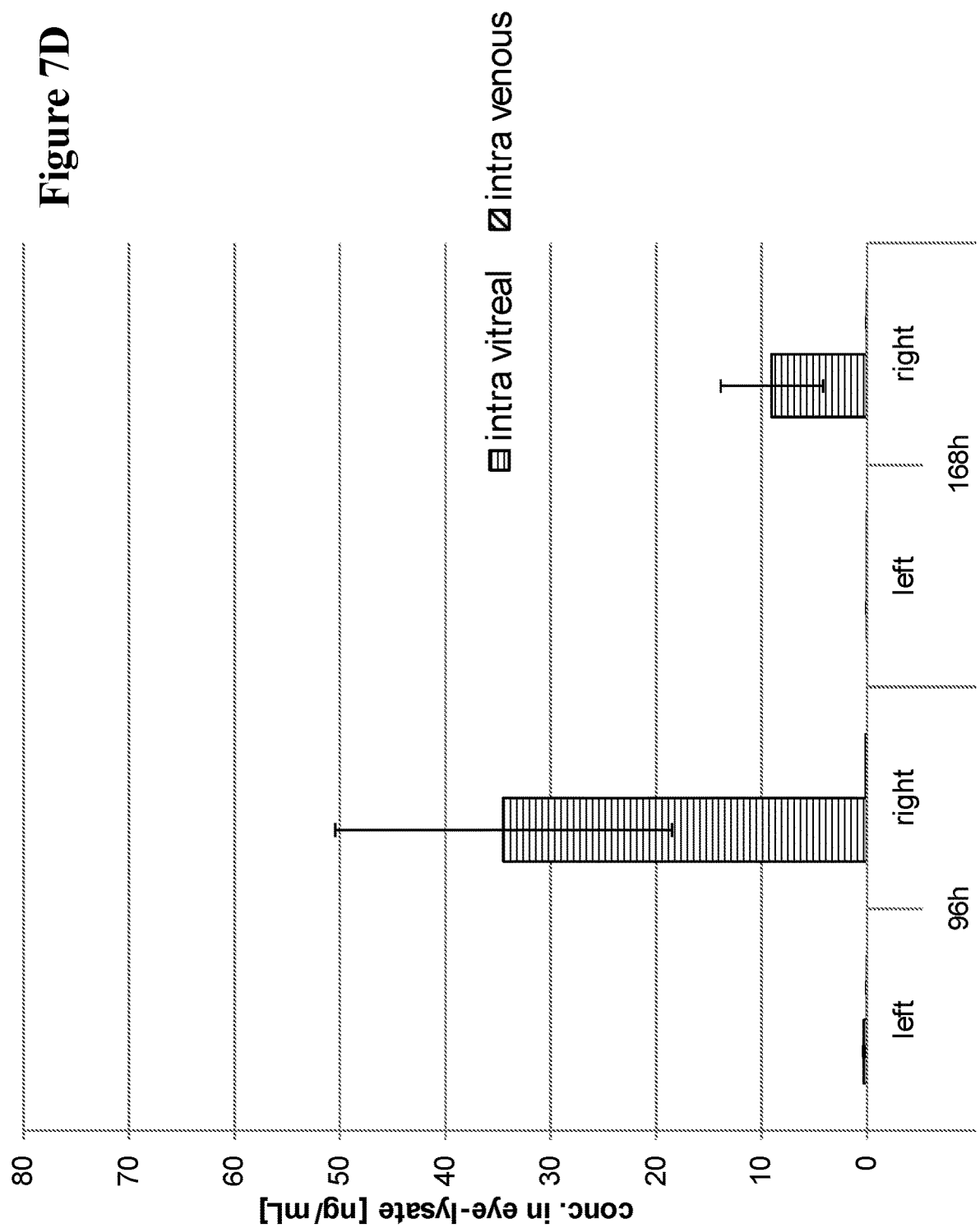

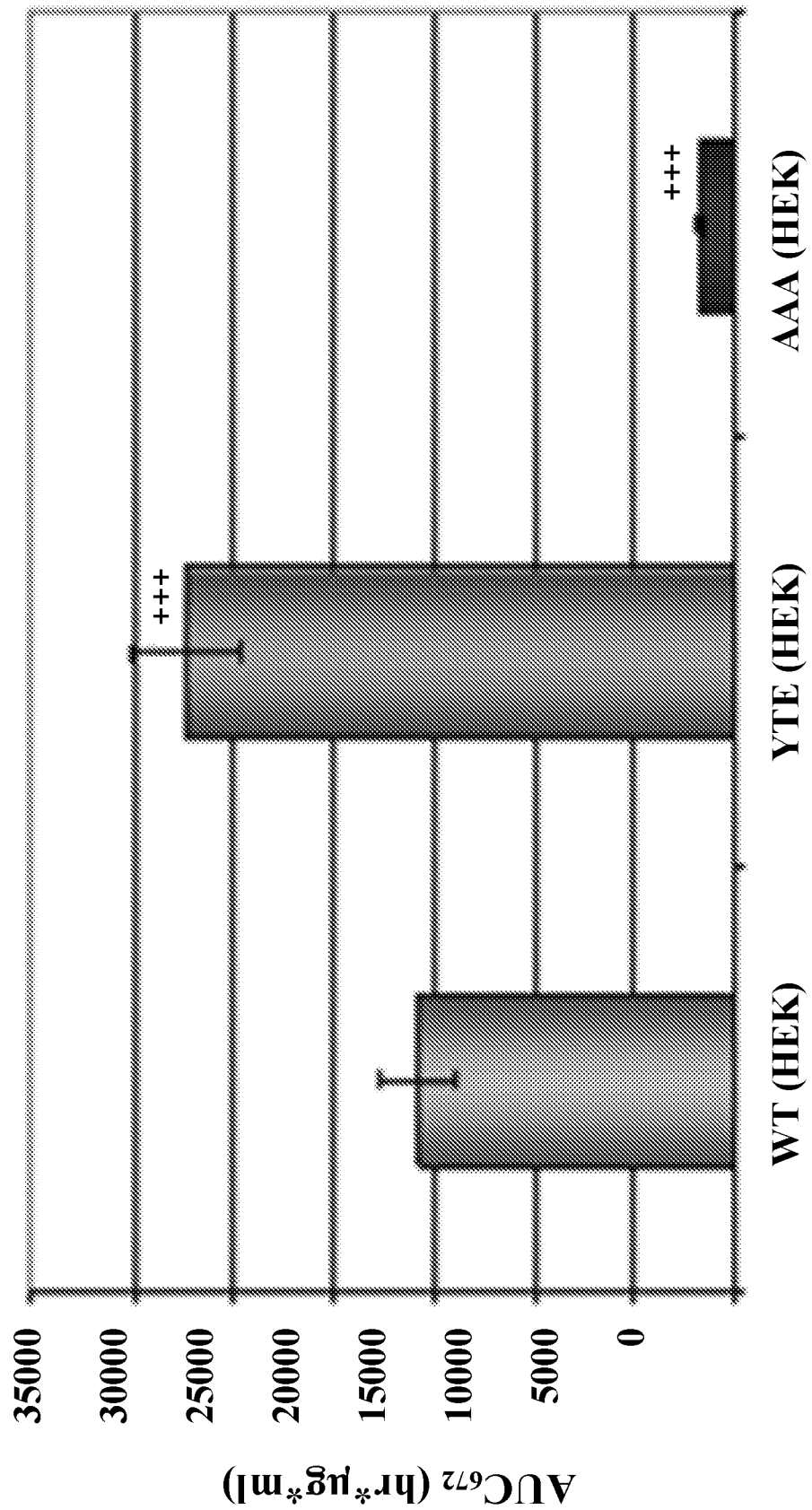

| Knob | | | Hole | | | |
|---|---|---|---|---|---|---|
| Pos 1 | Pos 2 | Pos 3 | Pos 1 | Pos 2 | Pos 3 | |
| I253A | H310A | H435A | I253A | H310A | H435A | No binding |
| --- | --- | --- | I253A | H310A | H435A | Binding |
| I253A | H310A | H435A | --- | H310A | --- | No binding |
| I253A | H310A | H435A | --- | --- | H435A | No binding |

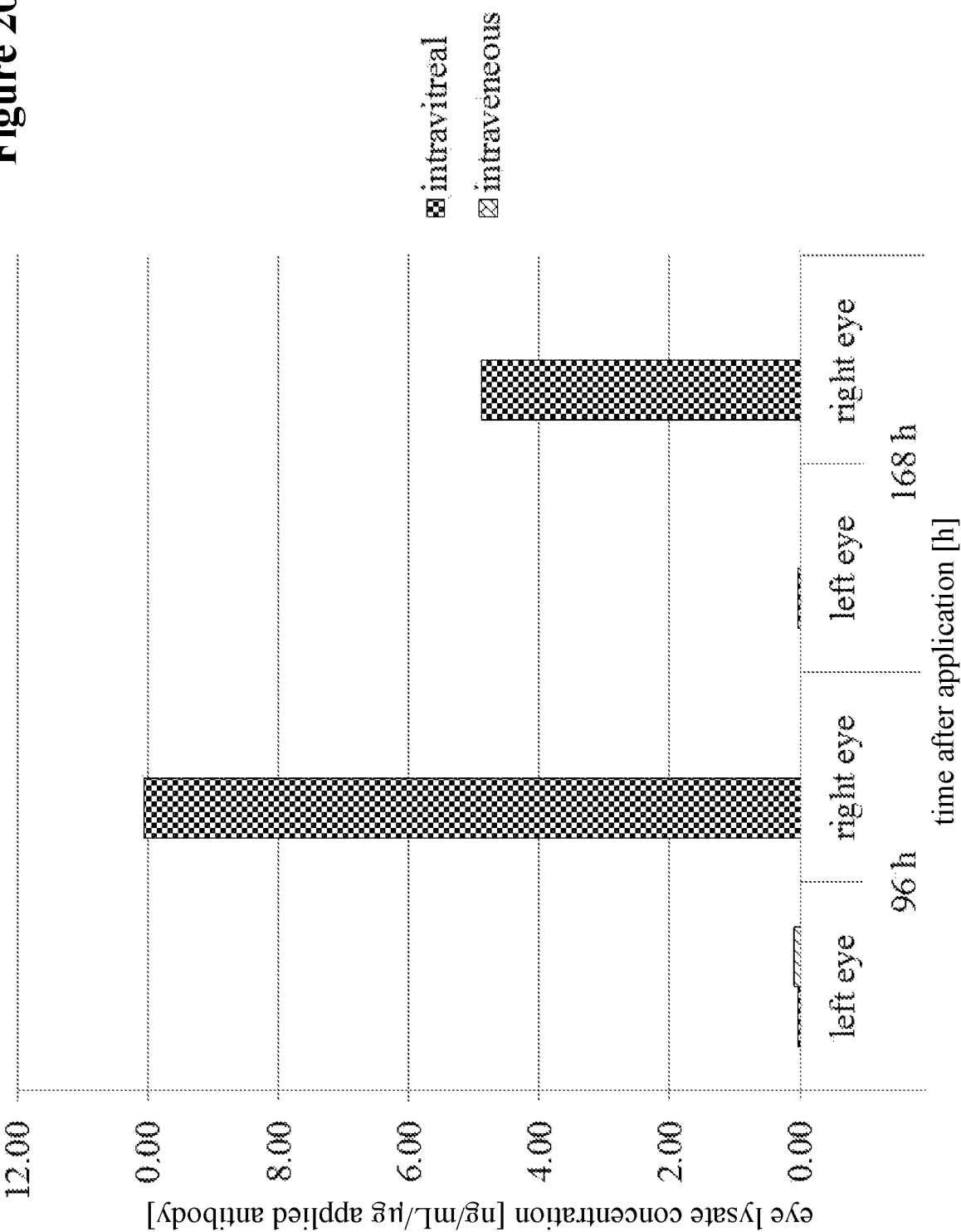

METHOD FOR PRODUCING BISPECIFIC ANTIBODIES COMPRISING A Y436A FC-REGION MUTATION FOR IMPROVED PROTEIN A-BINDING

CROSS REFERENCE TO RELATED APPLICATIONS

This application claims priority to and is a continuation of Ser. No. 16/244,378, filed, Jan. 10, 2019, which in turn is a Divisional of U.S. patent application Ser. No. 15/210,464, filed Jul. 14, 2016, now abandoned, which in turn is a continuation of National Stage Application of PCT/EP2015/050389, filed Jan. 12, 2015, which in turn claims priority from European Application No. 14165924.3, filed on Apr. 25, 2014 and European Application No. 14151322.6, filed on Jan. 15, 2014 Each of these applications is hereby incorporated by reference herein in its entirety.

SEQUENCE LISTING

The instant application contains a Sequence Listing submitted via EFS-Web and hereby incorporated by reference in its entirety. Said XML, copy, created on Feb. 14, 2023, is named 107793-103372_P31954-US2_SL.xml, and is 161,295 bytes in size.

FIELD OF THE INVENTION

Herein are reported IgG Fc-regions that have been modified with respect to their purification properties.

BACKGROUND OF THE INVENTION

The demand for cost efficient production processes has led to the necessity of optimization of the downstream purification, including one or more affinity chromatography steps. Larger volumes to be processed and harder requirements for the cleaning-in-place (CIP) protocols are some of the features that need to be solved (Hober, S., J. Chrom. B. 848 (2007) 40-47).

The purification of monoclonal antibodies by means of selective Fc-region affinity ligands is the most promising methodology for the large-scale production of therapeutic monoclonal antibodies. In fact, this procedure does not require establishing any interaction with the antigen specific part of the antibody, i.e. the Fab domain, which is, thus, left intact and can retain its properties (see Salvalaglio, M., et al., J. Chrom. A 1216 (2009) 8678-8686).

Due to its selectiveness, an affinity-purification step is employed early in the purification chain and thereby the number of successive unit operations can be reduced (see Hober supra; MacLennan, J., Biotechnol. 13 (1995) 1180; Harakas, N. K., Bioprocess Technol. 18 (1994) 259).

The ligands most adopted to bind selectively IgG are Staphylococcal protein A and protein G, which are able to establish highly selective interactions with the Fc-region of most IgGs in a region known as "consensus binding site" (CBS) (DeLano, W. L., et al., Science 287 (2000) 1279), which is located at the hinge region between the CH2 and CH3 domains of the Fc-region.

Staphylococcal protein A (SPA) is a cell wall associated protein domain exposed on the surface of the Gram-positive bacterium Staphylococcus aureus. SPA has high affinity to IgG from various species, for instance human, rabbit and guinea pig IgG but only weak interaction with bovine and mouse IgG (see the following Table) (see Hober supra; Duhamel, R. C., et al., J. Immunol. Methods 31 (1979) 211; Bjork, L. and Kronvall, G., Immunol. J. 133 (1984) 969; Richman, D. D., et al., J. Immunol. 128 (1982) 2300; Amersham Pharmacia Biotech, Handbook, Antibody Purification (2000)).

| species | subclass | protein A binding |
| --- | --- | --- |
| human | IgG1 | ++ |
| | IgG2 | ++ |
| | IgG3 | -- |
| | IgG4 | ++ |
| | IgA | variable |
| | IgD | - |
| | IgM | variable |
| rabbit | no distinction | ++ |
| guinea pig | IgG1 | ++ |
| | IgG2 | ++ |
| bovine | | + |
| mouse | IgG1 | + |
| | IgG2a | ++ |
| | IgG2b | + |
| | IgG3 | + |
| | IgM | variable |
| chicken | IgY | - |

++: strong binding/+: medium binding/-: weak or no interaction

The heavy chain hinge-region between the CH2 and CH3 domains of IgG is able to bind several proteins beyond protein A, such as the neonatal Fc receptor (FcRn) (see DeLano and Salvalaglio supra).

The SPA CBS comprehends a hydrophobic pocket on the surface of the antibody. The residues composing the IgG CBS are Ile 253, Ser 254, Met 252, Met 423, Tyr 326, His 435, Asn 434, His 433, Arg 255 and Glu 380 (numbering of the IgG heavy chain residues according to the Kabat EU index numbering system). The charged amino acids (Arg 255, Glu 380) are placed around a hydrophobic knob formed by Ile 253 and Ser 254. This (can) result in the establishment of polar and hydrophilic interactions (see Salvalaglio supra).

In general, the protein A-IgG interaction can be described using two main binding sites: the first is positioned in the heavy chain CH2 domain and is characterized by hydrophobic interactions between Phe 132, Leu 136, Ile 150 (of protein A) and the IgG hydrophobic knob constituted by Ile 253 and Ser 254, and by one electrostatic interaction between Lys 154 (protein A) and Thr 256 (IgG). The second site is located in the heavy chain CH3 domain and is dominated by electrostatic interactions between Gln 129 and Tyr 133 (protein A) and His 433, Asn 434, and His 435 (IgG) (see Salvalaglio supra).

Lindhofer, H., et al. (J. Immunol. 155 (1995) 219-225) report preferential species-restricted heavy/light chain pairing in rat/mouse quadromas.

Jedenberg, L., et al. (J. Immunol. Meth. 201 (1997) 25-34) reported that SPA-binding analyses of two Fc variants (Fc13 and Fc31, each containing an isotypic dipeptide substitution from the respective other isotype) showed that Fc1 and Fc31 interact with SPA, while Fc3 and Fc13 lack detectable SPA binding. The rendered SPA binding of the Fc-region variant Fc31 is concluded to result from the introduced dipeptide substitution R435H and F436Y.

Today, the focus with respect to therapeutic monoclonal antibodies is on the generation and use of bispecific or even multispecific antibodies specifically binding to two or more targets (antigens).

The basic challenge in generating multispecific heterodimeric IgG antibodies from four antibody chains (two different heavy chains and two different light chains) in one expression cell line is the so-called chain association issue (see Klein, C., et al., mAbs 4 (2012) 653-663). The required use of different chains as the left and the right arm of the multispecific antibody leads to antibody mixtures upon expression in one cell: the two heavy chains are able to (theoretically) associate in four different combinations (two thereof are identical), and each of those can associate in a stochastic manner with the light chains, resulting in $2^4$ (=a total of 16) theoretically possible chain combinations. Of the 16 theoretically possible combinations ten can be found of which only one corresponds to the desired functional bispecific antibody (De Lau, W.B., et al., J. Immunol. 146 (1991) 906-914). The difficulties in isolating this desired bispecific antibody out of complex mixtures and the inherent poor yield of 12.5% at a theoretical maximum make the production of a bispecific antibody in one expression cell line extremely challenging.

To overcome the chain association issue and enforce the correct association of the two different heavy chains, in the late 1990s Carter et al. from Genentech invented an approach termed "knobs-into-holes" (KiH) (see Carter, P., J. Immunol. Meth. 248 (2001) 7-15; Merchant, A. M., et al., Nat. Biotechnol. 16 (1998) 677-681; Zhu, Z., et al., Prot. Sci. 6 (1997) 781-788; Ridgway, J.B., et al., Prot. Eng. 9 (1996) 617-621; Atwell, S., et al., J. Mol. Biol. 270(1997) 26-35; and U.S. Pat. No. 7,183,076). Basically, the concept relies on modifications of the interface between the two CH3 domains of the two heavy chains of an antibody where most interactions occur. A bulky residue is introduced into the CH3 domain of one antibody heavy chain and acts similarly to a key ("knob"). In the other heavy chain, a "hole" is formed that is able to accommodate this bulky residue, mimicking a lock. The resulting heterodimeric Fc-region can be further stabilized by the introduction/formation of artificial disulfide bridges. Notably, all KiH mutations are buried within the CH3 domains and not "visible" to the immune system. In addition, properties of antibodies with KiH mutations such as (thermal) stability, FcγR binding and effector functions (e.g., ADCC, FcRn binding) and pharmacokinetic (PK) behavior are not affected.

Correct heavy chain association with heterodimerization yields above 97% can be achieved by introducing six mutations: S354C, T366W in the "knob" heavy chain and Y349C, T366S, L368A, Y407V in the "hole" heavy chain (see Carter supra; numbering of the residues according to the Kabat EU index numbering system). While hole-hole homodimers may occur, knob-knob homodimers typically are not observed. Hole-hole dimers can either be depleted by selective purification procedures or by procedures as outlined below.

While the issue of random heavy chain association has been addressed, also correct light chain association has to be ensured. Similar to the KiH CH3 domain approach, efforts have been undertaken to investigate asymmetric light chain-heavy chain interactions that might ultimately lead to full bispecific IgGs.

Roche recently developed the CrossMab approach as a possibility to enforce correct light chain pairing in bispecific heterodimeric IgG antibodies when combining it with the KiH technology (see Klein supra; Schaefer. W., et al., Proc. Natl. Acad. Sci. USA 108 (2011) 11187-11192; Cain, C., SciBX 4 (2011) 1-4). This allows the generation of bispecific or even multispecific antibodies in a generic fashion. In this format, one arm of the intended bispecific antibody is left untouched. In the second arm, the whole Fab region, or the VH-VL domains or the CH1-CL domains are exchanged by domain crossover between the heavy and light chain. As a consequence, the newly formed "crossed" light chain does not associate with the (normal, i.e. not-crossed) heavy chain Fab region of the other arm of the bispecific antibody any longer. Thus, the correct "light chain" association can be enforced by this minimal change in domain arrangement (see Schaefer supra).

Zhu et al. introduced several sterically complementary mutations, as well as disulfide bridges, in the two VL/VH interfaces of diabody variants. When the mutations VL Y87A/F98M and VH V37F/L45W were introduced into the anti-p185HER2 VL/VH interface, a heterodimeric diabody was recovered with >90% yield while maintaining overall yield and affinity compared with the parental diabody (see Zhu supra).

Researchers from Chugai have similarly designed bispecific diabodies by introduction of mutations into the VH-VL interfaces (mainly conversion of Q39 in VH and Q38 in VL to charged residues) to foster correct light chain association (WO 2006/106905; Igawa, T., et al., Prot. Eng. Des. Sel. 23 (2010) 667-677).

In WO2011097603 a common light chain mouse is reported.

In WO2010151792 a bispecific antibody format providing ease of isolation is provided, comprising immunoglobulin heavy chain variable domains that are differentially modified, i.e. heterodimeric, in the CH3 domain, wherein the differential modifications are non-immunogenic or substantially non-immunogenic with respect to the CH3 modifications, and at least one of the modifications results in a differential affinity for the bispecific antibody for an affinity reagent such as protein A, and the bispecific antibody is isolable from a disrupted cell, from medium, or from a mixture of antibodies based on its affinity for protein A.

The neonatal Fc-receptor (FcRn) is important for the metabolic fate of antibodies of the IgG class in vivo. The FcRn functions to salvage IgG from the lysosomal degradation pathway, resulting in reduced clearance and increased half-life. It is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of an antibody of the class IgG. The interaction between an antibody of the class IgG and the FcRn is pH dependent and occurs in a 1:2 stoichiometry, i.e. one IgG antibody molecule can interact with two FcRn molecules via its two heavy chain Fc-region polypeptides (see e.g. Huber, A. H., et al., J. Mol. Biol. 230 (1993) 1077-1083).

Thus, the in vitro FcRn binding properties/characteristics of an IgG are indicative of its in vivo pharmacokinetic properties in the blood circulation.

In the interaction between the FcRn and the Fc-region of an antibody of the IgG class different amino acid residues of the heavy chain CH2- and CH3-domain are participating.

Different mutations that influence the FcRn binding and therewith the half-life in the blood circulation are known. Fc-region residues critical to the mouse Fc-region-mouse FcRn interaction have been identified by site-directed mutagenesis (see e.g. Dall'Acqua, W. F., et al. J. Immunol 169 (2002) 5171-5180). Residues I253, H310, H433, N434 and H435 (numbering according to Kabat EU index numbering system) are involved in the interaction (Medesan, C., et al., Eur. J. Immunol. 26 (1996) 2533-2536; Firan, M., et al., Int. Immunol. 13 (2001) 993-1002; Kim, J. K., et al., Eur. J. Immunol. 24 (1994) 542-548). Residues I253, H310, and H435 were found to be critical for the interaction of human Fc-region with murine FcRn (Kim, J. K., et al., Eur. J. Immunol. 29 (1999) 2819-2885).

Methods to increase Fc-region (and likewise IgG) binding to FcRn have been performed by mutating various amino acid residues in the Fc-region: Thr 250, Met 252, Ser 254, Thr 256, Thr 307, Glu 380, Met 428, His 433, and Asn 434 (see Kuo, T. T., et al., J. Clin. Immunol. 30 (2010) 777-789; Ropeenian, D. C., et al., Nat. Rev. Immunol. 7 (2007) 715-725).

The combination of the mutations M252Y, S254T, T256E have been described by Dall'Acqua et al. to improve FcRn binding by protein-protein interaction studies (Dall'Acqua, W. F., et al. J. Biol. Chem. 281 (2006) 23514-23524). Studies of the human Fc-region-human FcRn complex have shown that residues I253, S254, H435 and Y436 are crucial for the interaction (Firan, M., et al., Int. Immunol. 13 (2001) 993-1002; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

In WO 2014/006217 dimeric proteins with triple mutations are reported. Crystal structure at 2.8 Angstrom of an FcRn/heterodimeric Fc complex regarding the mechanism of pH-dependent binding was reported by Martin, W., et al. (Mol. Cell. 7 (2001) 867-877). In U.S. Pat. No. 6,277,375, immunoglobulin like domains with increased half-lives are reported. Shields, R. L., et al., reported high resolution mapping of the binding site on human IgG1 for Fc gamma RI, Fc gamma Rh, Fc gamma RIII, and FcRn and design of IgG1 variants with improved binding to the Fc gamma R (Biochem. Mol. Biol. 276 (2001) 6591-6604). The delineation of the amino acid residues involved in transcytosis and catabolism of mouse IgG1 was reported by Medesan, C., et al. (J. Immunol. 158 (1997) 2211-2217). In US 2010/0272720 antibody fusion proteins with a modified FcRn binding site are reported. The production of heterodimeric proteins is reported in WO 2013/060867. Qiao, S.-W., et al. reported the dependence of antibody-mediated presentation of antigen on FcRn (Proc. Natl. Acad. Sci. USA 105 (2008) 9337-9342.

SUMMARY OF THE INVENTION

Herein are reported variant Fc-regions that specifically bind to Staphylococcus protein A and that do not bind to human FcRn. These variant Fc-regions contain specific amino acid mutations in the CH2- and CH3-domain. It has been found that these mutations, when used either in the hole chain or the knob chain of a heterodimeric Fc-region allow for the purification of the heterodimeric Fc-region, i.e. the separation of a heterodimeric Fc-region from a homodimeric Fc-region.

One aspect as reported herein is the use of the mutation Y436A for increasing the binding of a (dimeric) Fc-region polypeptide to protein A.

One aspect as reported herein is a (dimeric) polypeptide comprising
a first polypeptide comprising in N-terminal to C-terminal direction at least a portion of an immunoglobulin hinge region, which comprises one or more cysteine residues, an immunoglobulin CH2-domain and an immunoglobulin CH3-domain, and a second polypeptide comprising in N-terminal to C-terminal direction at least a portion of an immunoglobulin hinge region, which comprises one or more cysteine residues, an immunoglobulin CH2-domain and an immunoglobulin CH3-domain, wherein the first, the second, or the first and the second polypeptide comprise the mutation Y436A (numbering according to the Kabat EU index numbering system), and wherein the first polypeptide and the second polypeptide are connected by one or more disulfide bridges in the at least a portion of an immunoglobulin hinge region.

In one embodiment the first and the second polypeptide comprise the mutation Y436A.

In one embodiment the (dimeric) polypeptide does not specifically bind to the human FcRn and does specifically bind to Staphylococcal protein A.

In one embodiment the (dimeric) polypeptide is a homodimeric polypeptide.

In one embodiment the (dimeric) polypeptide is a heterodimeric polypeptide.

In one embodiment the first polypeptide further comprises the mutations Y349C, T366S, L368A and Y407V ("hole") and the second polypeptide comprises the mutations S354C and T366W ("knob").

In one embodiment the first polypeptide further comprises the mutations S354C, T366S, L368A and Y407V ("hole") and the second polypeptide comprises the mutations Y349C and T366W ("knob").

In one embodiment
i) the first and the second polypeptide each comprise the mutations H310A, H433A and Y436A, or
ii) the first and the second polypeptide each further comprise the mutations L251D, L314D and L432D, or
iii) the first and the second polypeptide each further comprise the mutations L251S, L314S and L432S, or
iv) the first polypeptide comprises the mutations I253A, H310A and H435A and the second polypeptide comprises the mutations H310A, H433A and Y436A, or
v) the first polypeptide comprises the mutations I253A, H310A and H435A and the second polypeptide comprises the mutations L251D, L314D and L432D, or
vi) the first polypeptide comprises the mutations I253A, H310A and H435A and the second polypeptide comprises the mutations L251S, L314S and L432S.

In one embodiment the immunoglobulin hinge region, the immunoglobulin CH2-domain, and the immunoglobulin CH3-domain of the first and the second polypeptide are of the human IgG1 subclass. In one embodiment the first polypeptide and the second polypeptide each further comprise the mutations L234A and L235A. In one embodiment the first polypeptide and the second polypeptide each further comprise the mutation P329G. In one embodiment the first polypeptide and the second polypeptide each further comprise the mutations L234A, L235A and P329G.

In one embodiment the immunoglobulin hinge region, the immunoglobulin CH2-domain and the immunoglobulin CH3-domain of the first and the second polypeptide are of the human IgG2 subclass. In one embodiment the first polypeptide and the second polypeptide each further comprise the mutations H268Q, V309L, A330S and P331S.

In one embodiment the immunoglobulin hinge region, the immunoglobulin CH2-domain and the immunoglobulin CH3-domain of the first and the second polypeptide are of the human IgG2 subclass. In one embodiment the first polypeptide and the second polypeptide each further comprise the mutations V234A, G237A, P238S, H268A, V309L, A330S and P331S.

In one embodiment the immunoglobulin hinge region, the immunoglobulin CH2-domain and the immunoglobulin CH3-domain of the first and the second polypeptide are of the human IgG4 subclass. In one embodiment the first polypeptide and the second polypeptide each further comprise the mutations S228P and L235EA. In one embodiment the first polypeptide and the second polypeptide each further comprise the mutation P329G. In one embodiment the first polypeptide and the second polypeptide each further comprise the mutations S228P, L235E and P329G.

In one embodiment the immunoglobulin hinge region, the immunoglobulin CH2-domain and the immunoglobulin CH3-domain of the first and the second polypeptide are of the human IgG4 subclass. In one embodiment the first polypeptide and the second polypeptide each further comprise the mutations S228P, L234A and L235A. In one embodiment the first polypeptide and the second polypeptide each further comprise the mutation P329G. In one embodiment the first polypeptide and the second polypeptide each further comprise the mutations S228P, L234A, L235A and P329G.

In one embodiment the (dimeric) polypeptide is an Fc-region fusion polypeptide.

In one embodiment the (dimeric) polypeptide is an (full length) antibody.

In one embodiment the (full length) antibody is a monospecific antibody. In one embodiment the monospecific antibody is a monovalent monospecific antibody. In one embodiment the monospecific antibody is a bivalent monospecific antibody.

In one embodiment the (full length) antibody is a bispecific antibody. In one embodiment the bispecific antibody is a bivalent bispecific antibody. In one embodiment the bispecific antibody is a tetravalent bispecific antibody.

In one embodiment the (full length) antibody is a trispecific antibody. In one embodiment the trispecific antibody is a trivalent trispecific antibody. In one embodiment the trispecific antibody is a tetravalent trispecific antibody.

One aspect as reported herein is method of treatment of a patient suffering from ocular vascular diseases by administering a (dimeric) polypeptide or an antibody as reported herein to a patient in the need of such treatment.

One aspect as reported herein is a (dimeric) polypeptide or an antibody as reported herein for intravitreal application.

One aspect as reported herein is a (dimeric) polypeptide or an antibody as reported herein for use as a medicament.

One aspect as reported herein is a (dimeric) polypeptide or an antibody as reported herein for the treatment of vascular eye diseases.

One aspect as reported herein is a pharmaceutical formulation comprising a (dimeric) polypeptide or an antibody as reported herein and optionally a pharmaceutically acceptable carrier.

For using an antibody that targets/binds to antigens not only present in the eye but also in the remaining body, a short systemic half-live after passage of the blood-ocular-barrier from the eye into the blood is beneficial in order to avoid systemic side effects.

Additionally an antibody that specifically binds to ligands of a receptor is only effective in the treatment of eye-diseases if the antibody-antigen complex is removed from the eye, i.e. the antibody functions as a transport vehicle for receptor ligands out of the eye and thereby inhibits receptor signaling.

It has been found by the current inventors that an antibody comprising an Fc-region that does not bind to the human neonatal Fc-receptor, i.e. a (dimeric) polypeptide as reported herein, is transported across the blood-ocular barrier. This is surprising as the antibody does not bind to human FcRn although binding to FcRn is considered to be required for transport across the blood-ocular-barrier.

One aspect as reported herein is the use of a (dimeric) polypeptide or an antibody as reported herein for the transport of a soluble receptor ligand from the eye over the blood-ocular-barrier into the blood circulation.

One aspect as reported herein is the use of a (dimeric) polypeptide or an antibody as reported herein for the removal of one or more soluble receptor ligands from the eye.

One aspect as reported herein is the use of a (dimeric) polypeptide or an antibody as reported herein for the treatment of eye diseases, especially of ocular vascular diseases.

One aspect as reported herein is the use of a (dimeric) polypeptide or an antibody as reported herein for the transport of one or more soluble receptor ligands from the intravitreal space to the blood circulation.

One aspect as reported herein is a (dimeric) polypeptide or an antibody as reported herein for use in treating an eye disease.

One aspect as reported herein is a (dimeric) polypeptide or an antibody as reported herein for use in the transport of a soluble receptor ligand from the eye over the blood-ocular-barrier into the blood circulation.

One aspect as reported herein is a (dimeric) polypeptide or an antibody as reported herein for use in the removal of one or more soluble receptor ligands from the eye.

One aspect as reported herein is a (dimeric) polypeptide or an antibody as reported herein for use in treating eye diseases, especially ocular vascular diseases.

One aspect as reported herein is a (dimeric) polypeptide or an antibody as reported herein for use in the transport of one or more soluble receptor ligands from the intravitreal space to the blood circulation.

One aspect as reported herein is a method of treating an individual having an ocular vascular disease comprising administering to the individual an effective amount of a (dimeric) polypeptide or an antibody as reported herein.

One aspect as reported herein is a method for transporting a soluble receptor ligand from the eye over the blood-ocular-barrier into the blood circulation in an individual comprising administering to the individual an effective amount of a (dimeric) polypeptide or an antibody as reported herein to transport a soluble receptor ligand from the eye over the blood-ocular-barrier into the blood circulation.

One aspect as reported herein is a method for the removal of one or more soluble receptor ligands from the eye in an individual comprising administering to the individual an effective amount of a (dimeric) polypeptide or an antibody as reported herein to remove one or more soluble receptor ligands from the eye.

One aspect as reported herein is a method for the transport of one or more soluble receptor ligands from the intravitreal space to the blood circulation in an individual comprising administering to the individual an effective amount of a (dimeric) polypeptide or an antibody as reported herein to transport one or more soluble receptor ligands from the intravitreal space to the blood circulation.

One aspect as reported herein is a method for transporting a soluble receptor ligand from the intravitreal space or the eye over the blood-ocular-barrier into the blood circulation in an individual comprising administering to the individual an effective amount of a (dimeric) polypeptide or an antibody as reported herein to transport a soluble receptor ligand from the eye over the blood-ocular-barrier into the blood circulation.

In one embodiment the (dimeric) polypeptide is a bispecific antibody. In one embodiment the bispecific antibody is a bivalent bispecific antibody. In one embodiment the bispecific antibody is a tetravalent bispecific antibody.

In one embodiment the (dimeric) polypeptide is a trispecific antibody. In one embodiment the trispecific antibody is a trivalent trispecific antibody. In one embodiment the trispecific antibody is a tetravalent trispecific antibody.

In one embodiment the first polypeptide further comprises the mutations Y349C, T366S, L368A and Y407V, and the second polypeptide further comprises the mutations S354C and T366W.

In one embodiment the first polypeptide further comprises the mutations S354C, T366S, L368A and Y407V and the second polypeptide further comprises the mutations Y349C and T366W.

In one embodiment
i) the first and the second polypeptide comprise the mutations H310A, H433A and Y436A, or
ii) the first and the second polypeptide further comprise the mutations L251D, L314D and L432D, or
iii) the first and the second polypeptide further comprise the mutations L251S, L314S and L432S, or
iv) the first polypeptide comprises the mutations I253A, H310A and H435A and the second polypeptide comprises the mutations H310A, H433A and Y436A, or
v) the first polypeptide further comprises the mutations I253A, H310A and H435A and the second polypeptide further comprises the mutations L251D, L314D and L432D, or
vi) the first polypeptide further comprises the mutations I253A, H310A and H435A and the second polypeptide further comprises the mutations L251S, L314S and L432S.

In one embodiment the (dimeric) polypeptide is a CrossMab.

In one embodiment the (dimeric) polypeptide is an Fc-region fusion polypeptide.

In one embodiment the antibody or the Fc-region fusion polypeptide is of the subclass IgG1. In one embodiment the antibody or the Fc-region fusion polypeptide further comprise the mutations L234A and L235A. In one embodiment the antibody or the Fc-region fusion polypeptide further comprise the mutation P329G.

In one embodiment the antibody or the Fc-region fusion polypeptide is of the subclass IgG2. In one embodiment the antibody or the Fc-region fusion polypeptide further comprise the mutations V234A, G237A, P238S, H268A, V309L, A330S, and P331S.

In one embodiment the antibody or the Fc-region fusion polypeptide is of the subclass IgG4. In one embodiment the antibody or the Fc-region fusion polypeptide further comprise the mutations S228P and L235E. In one embodiment the antibody or the Fc-region fusion polypeptide further comprise the mutation P329G.

BRIEF DESCRIPTION OF THE DRAWINGS

FIG. 4: Seven day storage at 40° C. at 100 mg/mL (decrease of Main Peak and High Molecular Weight (HMW) increase) (comparison of anti-VEGF/ANG2 antibody as reported herein VEGF/ANG2-0016 (with IHH-AAA mutation) which showed a lower aggregation with reference antibody VEGF/ANG2-0015 (without such IHH-AAA mutation)).

FIGS. 5A and 5B: FcRn steady state affinity of 5A: VEGF/ANG2-0015 (without IHH-AAA mutation) and 5B: VEGF/ANG2-0016 (with IHH-AAA mutation).

FIG. 7A: Schematic pharmacokinetic (PK) ELISA assay principle for determination of concentrations of anti-VEGF/ANG2 antibodies in serum and whole eye lysates.

FIG. 7B: Serum concentration after intravenous (i.v.) application: comparison of VEGF/ANG2-0015 without IHH-AAA mutation and VEGF/ANG2-0016 with IHH-AAA mutation.

FIG. 7D: Eye lysates concentration of VEGF/ANG2-0016 (with IHH-AAA mutation) in right and left eye (after intravitreal application only into the right eye in comparison to intravenous application): significant concentrations could be detected only in the right eye after intravitreal application; after intravenous application no concentration in eye lysates could be detected due to the low serum half-life of VEGF/ANG2-0016 (with IHH-AAA mutation).

FIGS. 8A-8C: Antibodies engineered with respect to their ability to bind FcRn display prolonged (YTE mutation) or shortened (IHH-AAA mutation) in vivo half-lives, enhanced (YTE mutation) or reduced binding (IHH-AAA mutation) compared to the reference wild-type (wt) antibody in SPR analysis as well as enhanced or reduced retention time in FcRn column chromatography; FIG. 8A) PK data after single i.v. bolus application of 10 mg/kg into huFcRn transgenic male C57BL/6J mice+/−276: AUC data for wt IgG as well as YTE and IHH-AAA Fc-region-modified IgGs; FIG. 8B) BIAcore sensorgram; FIG. 8C) FcRn affinity column elution; wild-type anti-IGF-1R antibody (reference), YTE-mutant of anti-IGF-1R antibody, IHH-AAA-mutant of anti-IGF-1R antibody.

FIG. 20: Comparison of eye lysate concentration after intravitreal and intravenous application of antibody IGF-1R 0045.

DETAILED DESCRIPTION OF EMBODIMENTS OF THE INVENTION

I. Definitions

Figure 1:
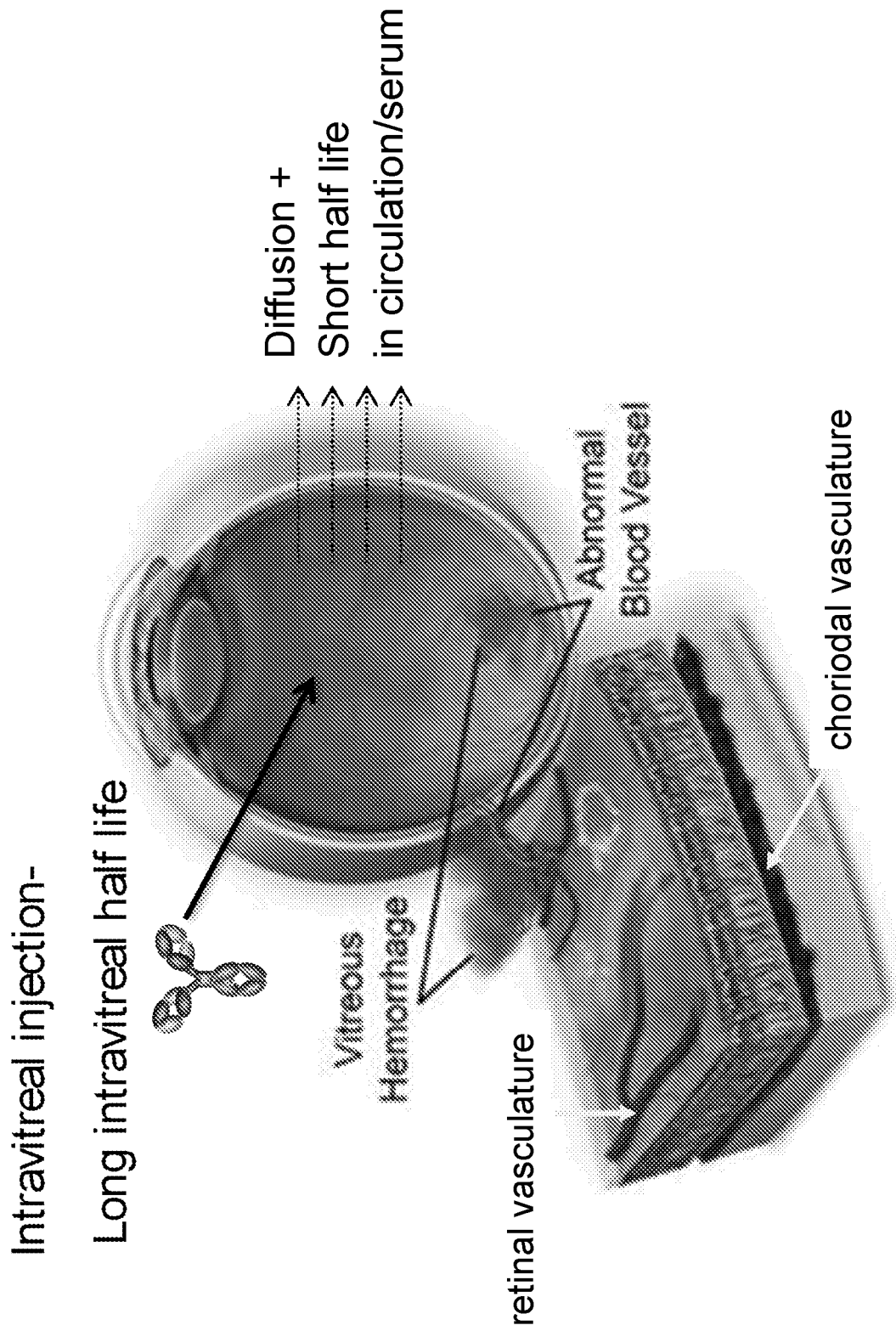
FIG. 1: Scheme of concept and advantages of anti-VEGF/ANG2 antibodies of the IgG1 or IgG4 subclass with IHH-AAA mutation (combination of mutations I253A, H310A and H435A (numbering according to the Kabat EU index numbering system)).

The term "about" denotes a range of +/−20% of the thereafter following numerical value. In one embodiment the term "about" denotes a range of +/−10% of the thereafter following numerical value. In one embodiment the term "about" denotes a range of +/−5% of the thereafter following numerical value.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence alterations. In some embodiments, the number of amino acid alterations are 10 or less, 9 or less, 8 or less, 7 or less, 6 or less, 5 or less, 4 or less, 3 or less, or 2 or less.

In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "alteration" denotes the mutation (substitution), insertion (addition), or deletion of one or more amino acid residues in a parent antibody or fusion polypeptide, e.g. a fusion polypeptide comprising at least an FcRn binding portion of an Fc-region, to obtain a modified antibody or fusion polypeptide. The term "mutation" denotes that the specified amino acid residue is substituted for a different amino acid residue. For example, the mutation L234A denotes that the amino acid residue lysine at position 234 in an antibody Fc-region (polypeptide) is substituted by the amino acid residue alanine (substitution of lysine with alanine) (numbering according to the Kabat EU index numbering system).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype and the Kabat EU index numbering system (see pages 661-723) is used for the constant heavy chain domains (CH1, Hinge, CH2 and CH3).

A "naturally occurring amino acid residue" denotes an amino acid residue from the group consisting of alanine (three letter code: Ala, one letter code: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophane (Trp, W), tyrosine (Tyr, Y), and valine (Val, V).

The term "amino acid mutation" denotes the substitution of at least one existing amino acid residue with another different amino acid residue (=replacing amino acid residue). The replacing amino acid residue may be a "naturally occurring amino acid residues" and selected from the group consisting of alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V). The replacing amino acid residue may be a "non-naturally occurring amino acid residue." See e.g. U.S. Pat. No. 6,586,207, WO 98/48032, WO 03/073238, US 2004/0214988, WO 2005/35727, WO 2005/74524, Chin, J.W., et al., J. Am. Chem. Soc. 124 (2002) 9026-9027; Chin, J. W. and Schultz, P. G., ChemBioChem 11 (2002) 1135-1137; Chin, J. W., et al., Proc Natl Acad Sci USA (2002) 99(17): 11020-11024; and, Wang, L. and Schultz, P. G., Chem. (2002) 1-10 (all entirely incorporated by reference herein).

The term "amino acid insertion" denotes the (additional) incorporation of at least one amino acid residue at a predetermined position in an amino acid sequence. In one embodiment the insertion will be the insertion of one or two amino acid residues. The inserted amino acid residue(s) can be any naturally occurring or non-naturally occurring amino acid residue.

The term "amino acid deletion" denotes the removal of at least one amino acid residue at a predetermined position in an amino acid sequence.

The term "ANG-2" as used herein refers to human angiopoietin-2 (ANG-2) (alternatively abbreviated with ANGPT2 or ANG2) (SEQ ID NO: 31) which is described e.g. in Maisonpierre, P.C., et al, Science 277 (1997) 55-60 and Cheung, A. H., et al., Genomics 48 (1998) 389-91. The angiopoietins-1 (SEQ ID NO: 32) and -2 were discovered as ligands for the Ties, a family of tyrosine kinases that is selectively expressed within the vascular endothelium (Yancopoulos, G. D., et al., Nature 407 (2000) 242-248). There are now four definitive members of the angiopoietin family. Angiopoietin-3 and -4 (ANG-3 and ANG-4) may represent widely diverged counterparts of the same gene locus in mouse and man (Kim, I., et al., FEBS Let, 443 (1999) 353-356; Kim, I., et al., J. Biol. Chem. 274 (1999) 26523-26528). ANG-1 and ANG-2 were originally identified in tissue culture experiments as agonist and antagonist, respectively (see for ANG-1: Davis, S., et al., Cell 87 (1996) 1161-1169; and for ANG-2: Maisonpierre, P. C., et al., Science 277 (1997) 55-60). All of the known angiopoietins bind primarily to Tie2 (SEQ ID NO: 33), and both ANG-1 and -2 bind to Tie2 with an affinity of 3 nM (Kd) (Maisonpierre, P. C., et al., Science 277 (1997) 55-60).

The term "antibody" is used herein in the broadest sense and encompasses various antibody structures, including but not limited to, monoclonal antibodies, multispecific antibodies (e.g. bispecific antibodies, trispecific antibodies), and antibody fragments so long as they exhibit the desired antigen-, and/or protein A and/or FcRn-binding activity.

The term "asymmetric Fc-region" denotes a pair of Fc-region polypeptides that have different amino acid residues at corresponding positions according to the Kabat EU index numbering system.

The term "asymmetric Fc-region with respect to FcRn binding" denotes an Fc-region that consists of two polypeptide chains that have different amino acid residues at corresponding positions, whereby the positions are determined according to the Kabat EU index numbering system, whereby the different positions affect the binding of the Fc-region to the human neonatal Fc-receptor (FcRn). For the purpose herein, the differences between the two polypeptide chains of the Fc-region in an "asymmetric Fc-region with respect to FcRn binding" do not include differences that have been introduced to facilitate the formation of heterodimeric Fc-regions, e.g. for the production of bispecific antibodies. These differences can also be asymmetric, i.e. the two chains have differences at non-corresponding amino acid residues according to the Kabat EU index numbering system. These differences facilitate heterodimerization and reduce homodimerization. Examples of such differences are the so-called "knobs into holes" substitutions (see, e.g., U.S. Pat. No. 7,695,936 and US 2003/0078385). The following knobs and holes substitutions in the individual polypeptide chains of an Fc-region of an IgG antibody of subclass IgG1 have been found to increase heterodimer formation: 1) Y407T in one chain and T366Y in the other chain; 2) Y407A in one chain and T366W in the other chain; 3) F405A in one chain and T394W in the other chain; 4) F405W in one chain and T394S in the other chain; 5) Y407T in one chain and T366Y in the other chain; 6) T366Y and F405A in one chain and T394W and Y407T in the other chain; 7) T366W and F405W in one chain and T394S and Y407A in the other chain; 8) F405W and Y407A in one chain and T366W and T394S in the other chain; and 9) T366W in one chain and T366S, L368A, and Y407V in the other chain, whereby the last listed is especially suited. In addition, changes creating new disulfide bridges between the two Fc-region polypeptide chains facilitate heterodimer formation (see, e.g., US 2003/0078385). The following substitutions resulting in appropriately spaced apart cysteine residues for the formation of new intra-chain disulfide bonds in the individual polypeptide chains of an Fc-region of an IgG antibody of subclass IgG1 have been found to increase heterodimer formation: Y349C in one chain and S354C in the other; Y349C in one chain and E356C in the other; Y349C in one chain and E357C in the other; L351C in one chain and S354C in the other; T394C in one chain and E397C in the other; or D399C in one chain and K392C in the other. Further examples of heterodimerization facilitating amino acid changes are the so-called "charge pair substitutions" (see, e.g., WO 2009/089004). The following charge pair substitutions in the individual polypeptide chains of an Fc-region of an IgG antibody of subclass IgG1 have been found to increase heterodimer formation: 1) K409D or K409E in one chain and D399K or D399R in the other chain; 2) K392D or K392E in one chain and D399K or D399R in the other chain; 3) K439D or K439E in one chain and E356K or E356R in the other chain; 4) K370D or K370E in one chain and E357K or E357R in the other chain; 5) K409D and K360D in one chain plus D399K and E356K in the other chain; 6) K409D and K370D in one chain plus D399K and E357K in the other chain; 7) K409D and K392D in one chain plus D399K, E356K, and E357K in the other chain; 8) K409D and K392D in one chain and D399K in the other chain; 9) K409D and K392D in one chain and D399K and E356K in the other chain; 10) K409D and K392D in one chain and D399K and D357K in the other chain; 11) K409D and K370D in one chain and D399K and D357K in the other chain; 12) D399K in one chain and K409D and K360D in the other chain; and 13) K409D and K439D in one chain and D399K and E356K on the other.

The term "binding (to an antigen)" denotes the binding of an antibody to its antigen in an in vitro assay, in one embodiment in a binding assay in which the antibody is bound to a surface and binding of the antigen to the antibody is measured by Surface Plasmon Resonance (SPR). Binding means a binding affinity ($K_D$) of $10^{-8}$M or less, in some embodiments of $10^{-13}$ to $10^{-8}$M, in some embodiments of $10^{-13}$ to $10^{-9}$M.

Binding can be investigated by a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D(k_d/k_a)$.

The term "chimeric" antibody refers to an antibody in which a portion of the heavy and/or light chain is derived from a particular source or species, while the remainder of the heavy and/or light chain is derived from a different source or species.

The term "CH2-domain" denotes the part of an antibody heavy chain polypeptide that extends approximately from EU position 231 to EU position 340 (EU numbering system according to Kabat). In one embodiment a CH2 domain has the amino acid sequence of SEQ ID NO: 09: APELLGG PSVFLFPPKP KDTLMISRTP EVTCVWDVS HEDPE-

VKFNW YVDGVEVHNA KTKPREEQ E STYRWSVLT VLHQDWLNGK EYKCKVSNKA LPAPIEKTIS KAK.

The term "CH3-domain" denotes the part of an antibody heavy chain polypeptide that extends approximately from EU position 341 to EU position 446. In one embodiment the CH3 domain has the amino acid sequence of SEQ ID NO: 10: GQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "comparable length" denotes that two polypeptides comprise the identical number of amino acid residues or can be different in length by one or more and up to 10 amino acid residues at most. In one embodiment the (Fc-region) polypeptides comprise the identical number of amino acid residues or differ by a number of from 1 to 10 amino acid residues. In one embodiment the (Fc-region) polypeptides comprise the identical number of amino acid residues or differ by a number of from 1 to 5 amino acid residues. In one embodiment the (Fc-region) polypeptides comprise the identical number of amino acid residues or differ by a number of from 1 to 3 amino acid residues.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B-cell activation.

An "effective amount" of an agent, e.g., a pharmaceutical formulation, refers to an amount effective, at dosages and for periods of time necessary, to achieve the desired therapeutic or prophylactic result.

The term "Fc-fusion polypeptide" denotes a fusion of a binding domain (e.g. an antigen binding domain such as a single chain antibody, or a polypeptide such as a ligand of a receptor) with an antibody Fc-region that exhibits the desired target-, protein A- and FcRn-binding activity.

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from Cys226, or from Pro230, to the carboxyl-terminus of the heavy chain. In one embodiment the Fc-region has the amino acid sequence of SEQ ID NO: 60. However, the C-terminal lysine (Lys447) of the Fc-region may or may not be present.

The term "FcRn" denotes the human neonatal Fc-receptor. FcRn functions to salvage IgG from the lysosomal degradation pathway, resulting in reduced clearance and increased half-life. The FcRn is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of IgG. The interaction between IgG and FcRn is strictly pH dependent and occurs in a 1:2 stoichiometry, with one IgG binding to two FcRn molecules via its two heavy chains (Huber, A. H., et al., J. Mol. Biol. 230 (1993) 1077-1083). FcRn binding occurs in the endosome at acidic pH (pH<6.5) and IgG is released at the neutral cell surface (pH of about 7.4). The pH-sensitive nature of the interaction facilitates the FcRn-mediated protection of IgGs pinocytosed into cells from intracellular degradation by binding to the receptor within the acidic environment of endosomes. FcRn then facilitates the recycling of IgG to the cell surface and subsequent release into the blood stream upon exposure of the FcRn-IgG complex to the neutral pH environment outside the cell.

The term "FcRn binding portion of an Fc-region" denotes the part of an antibody heavy chain polypeptide that extends approximately from EU position 243 to EU position 261 and approximately from EU position 275 to EU position 293 and approximately from EU position 302 to EU position 319 and approximately from EU position 336 to EU position 348 and approximately from EU position 367 to EU position 393 and EU position 408 and approximately from EU position 424 to EU position 440. In one embodiment one or more of the following amino acid residues according to the EU numbering of Kabat are altered F243, P244, P245 P, K246, P247, K248, D249, T250, L251, M252, 1253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, 1336, S337, K338, A339, K340, G341, Q342, P343, R344, E345, P346, Q347, V348, C367, V369, F372, Y373, P374, S375, D376, 1377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440 (EU numbering).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" denotes an antibody having a structure substantially similar to a native antibody structure comprising four polypeptides or having heavy chains that contain an Fc-region as defined herein. A full length antibody may comprise further domains, such as e.g. a scFv or a scFab conjugated to one or more of the chains of the full length antibody. These conjugates are also encompassed by the term full length antibody.

The term "dimeric polypeptide" denotes a complex comprising at least two polypeptides that are associated covalently. The complex may comprise further polypeptides that are also associated covalently or non-covalently with the other polypeptides. In one embodiment the dimeric polypeptide comprises two or four polypeptides.

The terms "heterodimer" or "heterodimeric" denote a molecule that comprises two polypeptides (e.g. of comparable length), wherein the two polypeptides have an amino acid sequence that have at least one different amino acid residue in a corresponding position, whereby corresponding position is determined according to the Kabat EU index numbering system.

The terms "homodimer" and "homodimeric" denote a molecule that comprises two polypeptides of comparable length, wherein the two polypeptides have an amino acid sequence that is identical in corresponding positions, whereby corresponding positions are determined according to the Kabat EU index numbering system.

A dimeric polypeptide as reported herein can be homodimeric or heterodimeric which is determined with respect to mutations or properties in focus. For example, with respect to FcRn and/or protein A binding (i.e. the focused on properties) a dimeric polypeptide is homodimeric (i.e. both polypeptides of the dimeric polypeptide comprise these mutations) with respect to the mutations H310A, H433A and Y436A (these mutations are in focus with respect to FcRn and/or protein A binding property of the dimeric polypeptide) but at the same time heterodimeric with respect to the mutations Y349C, T366S, L368A and Y407V (these mutations are not in focus as these mutations are directed to the heterodimerization of the dimeric polypeptide and not to the FcRn/protein A binding properties) as well as the mutations S354C and T366W, respectively (the first set is comprised only in the first polypeptide whereas the second set is comprised only in the second polypeptide). Further for example, a dimeric polypeptide as reported herein can be heterodimeric with respect to the mutations I253A, H310A, H433A, H435A and Y436A (i.e. these mutations are directed all to the FcRn and/or protein A binding properties of the dimeric polypeptide), i.e. one polypeptide comprises the mutations I253A, H310A and H435A, whereas the other polypeptide comprises the mutations H310A, H433A and Y436A.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda MD (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

The term "derived from" denotes that an amino acid sequence is derived from a parent amino acid sequence by introducing alterations at at least one position. Thus, a derived amino acid sequence differs from the corresponding parent amino acid sequence at at least one corresponding position (numbering according to Kabat EU index for antibody Fc-regions). In one embodiment an amino acid sequence derived from a parent amino acid sequence differs by one to fifteen amino acid residues at corresponding positions. In one embodiment an amino acid sequence derived from a parent amino acid sequence differs by one to ten amino acid residues at corresponding positions. In one embodiment an amino acid sequence derived from a parent amino acid sequence differs by one to six amino acid residues at corresponding positions. Likewise, a derived amino acid sequence has a high amino acid sequence identity to its parent amino acid sequence. In one embodiment an amino acid sequence derived from a parent amino acid sequence has 80% or more amino acid sequence identity. In one embodiment an amino acid sequence derived from a parent amino acid sequence has 90% or more amino acid sequence identity. In one embodiment an amino acid sequence derived from a parent amino acid sequence has 95% or more amino acid sequence identity.

The term "human Fc-region polypeptide" denotes an amino acid sequence which is identical to a "native" or "wild-type" human Fc-region polypeptide. The term "variant (human) Fc-region polypeptide" denotes an amino acid sequence which derived from a "native" or "wild-type" human Fc-region polypeptide by virtue of at least one "amino acid alteration." A "human Fc-region" consists of two human Fc-region polypeptides. A "variant (human) Fc-region" consists of two Fc-region polypeptides, whereby both can be variant (human) Fc-region polypeptides, or one is a human Fc-region polypeptide and the other is a variant (human) Fc-region polypeptide.

In one embodiment the human Fc-region polypeptide has the amino acid sequence of a human IgG1 Fc-region polypeptide of SEQ ID NO: 60, or of a human IgG2 Fc-region polypeptide of SEQ ID NO: 61, or of a human IgG4 Fc-region polypeptide of SEQ ID NO: 63 with the mutations as reported herein. In one embodiment the variant (human) Fc-region polypeptide is derived from an Fc-region polypeptide of SEQ ID NO: 60, or 61, or 63 and has at least one amino acid mutation compared to the Fc-region polypeptide of SEQ ID NO: 60, or 61, or 63. In one embodiment the variant (human) Fc-region polypeptide comprises/has from about one to about ten amino acid mutations, and in one embodiment from about one to about five amino acid mutations. In one embodiment the variant (human) Fc-region polypeptide has at least about 80% homology with a human Fc-region polypeptide of SEQ ID NO: 60, or 61, or 63. In one embodiment the variant (human) Fc-region polypeptide has least about 90% homology with a human Fc-region polypeptide of SEQ ID NO: 60, or 61, or 63. In one embodiment the variant (human) Fc-region polypeptide has at least about 95% homology with a human Fc-region polypeptide of SEQ ID NO: 60, or 61, or 63.

The variant (human) Fc-region polypeptide derived from a human Fc-region polypeptide of SEQ ID NO: 60, or 61, or 63 is defined by the amino acid alterations that are contained. Thus, for example, the term P329G denotes a variant (human) Fc-region polypeptide derived human Fc-region polypeptide with the mutation of proline to glycine at amino acid position 329 relative to the human Fc-region polypeptide of SEQ ID NO: 60, or 61, or 63.

For all positions discussed in the present invention, numbering is according to the Kabat EU index numbering system.

A human IgG1 Fc-region polypeptide has the following amino acid sequence:

(SEQ ID NO: 60)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

A human IgG1 Fc-region derived Fc-region polypeptide with the mutations L234A, L235A has the following amino acid sequence:

(SEQ ID NO: 64)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with Y349C, T366S, L368A and Y407V mutations has the following amino acid sequence:

(SEQ ID NO: 65)
DKTHTCPPCPAPELLGGPSVFLEPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with S354C, T366W mutations has the following amino acid sequence:

(SEQ ID NO: 66)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with L234A, L235A mutations and Y349C, T366S, L368A, Y407V mutations has the following amino acid sequence:

(SEQ ID NO: 67)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with a L234A, L235A and S354C, T366W mutations has the following amino acid sequence:

(SEQ ID NO: 68)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with a P329G mutation has the following amino acid sequence:

(SEQ ID NO: 69)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with L234A, L235A mutations and P329G mutation has the following amino acid sequence:

(SEQ ID NO: 70)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with a P239G mutation and Y349C, T366S, L368A, Y407V mutations has the following amino acid sequence:

(SEQ ID NO: 71)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with a P329G mutation and S354C, T366W mutation has the following amino acid sequence:

(SEQ ID NO: 72)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with L234A, L235A, P329G and Y349C, T366S, L368A, Y407V mutations has the following amino acid sequence:

(SEQ ID NO: 73)
DKTHTCPPCPAPEAAGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALGAPIEKTISKAKGQPREPQVCTLPPSRDELTKNQVSLSCAVK
GFYPSDIAVEWESNGQPENNYKTTPPVLDSDGSFFLVSKLTVDKSRWQQG
NVFSCSVMHEALHNHYTQKSLSLSPGK.

A human IgG1 Fc-region derived Fc-region polypeptide with L234A, L235A, P329G mutations and S354C, T366W mutations has the following amino acid sequence:

(SEQ ID NO: 74)
DKTHTCPPCPAPEAAGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALGAPIEKTISKAKGQPREPQVYTLPPCRDELTKNQVSLWCLVK
GFYPSDIAVEWESNGQPENNYKTTPPVLDSDGSFFLYSKLTVDKSRWQQG
NVFSCSVMHEALHNHYTQKSLSLSPGK.

A human IgG4 Fc-region polypeptide has the following amino acid sequence:

(SEQ ID NO: 63)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with S228P and L235E mutations has the following amino acid sequence:

(SEQ ID NO: 75)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with S228P, L235E mutations and P329G mutation has the following amino acid sequence:

(SEQ ID NO: 76)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with S354C, T366W mutations has the following amino acid sequence:

(SEQ ID NO: 77)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPCQEEMTKNQVSLWCL
VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with Y349C, T366S, L368A, Y407V mutations has the following amino acid sequence:

(SEQ ID NO: 78)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.

A human IgG4 Fc-region derived Fc-region polypeptide with a S228P, L235E and S354C, T366W mutations has the following amino acid sequence:

(SEQ ID NO: 79)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPCQEEMTKNQVSLWCL
VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with a S228P, L235E and Y349C, T366S, L368A, Y407V mutations has the following amino acid sequence:

(SEQ ID NO: 80)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.

A human IgG4 Fc-region derived Fc-region polypeptide with a P329G mutation has the following amino acid sequence:

(SEQ ID NO: 81)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with a P239G and Y349C, T366S, L368A, Y407V mutations has the following amino acid sequence:

(SEQ ID NO: 82)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.

A human IgG4 Fc-region derived Fc-region polypeptide with a P329G and S354C, T366W mutations has the following amino acid sequence:

(SEQ ID NO: 83)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVYTLPPCQEEMTKNQVSLWCL
VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with a S228P, L235E, P329G and Y349C, T366S, L368A, Y407V mutations has the following amino acid sequence:

(SEQ ID NO: 84)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.

A human IgG4 Fc-region derived Fc-region polypeptide with a S228P, L235E, P329G and S354C, T366W mutations has the following amino acid sequence:

(SEQ ID NO: 85)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVYTLPPCQEEMTKNQVSLWCL
VKGFYPSDIAVEWESNGQPENNYKTTPPVLDSDGSFFLYSRLTVDKSRWQ
EGNVFSCSVMHEALHNHYTQKSLSLSLGK.

An alignment of the different human Fc-regions is shown below (Kabat EU index numbering system):

```
                                                        2
                                                        1
                                                        6(IgG1,2,4)
        IGG1   .......... .......... .......... .......... .....EPKSC
        IGG2   .......... .......... .......... .......... .....ERKCC
        IGG3   KTPLGDTTHT CPRCPEPKSC DTPPPCPRCP EPKSCDTPPP CPRCPEPKSC
        IGG4   .......... .......... .......... .......... .....ESKYG
               -- HINGE ------------------------------------------

2                    2
                         3                    5
                         0                    0
        IGG1   DKTHTCPPCP APELLGGPSV FLFPPKPKDT LMISRTPEVT CVVVDVSHED
        IGG2   ...VECPPCP APP.VAGPSV FLFPPKPKDT LMISRTPEVT CVVVDVSHED
        IGG3   DTPPPCPRCP APELLGGPSV FLFPPKPKDT LMISRTPEVT CVVVDVSHED
        IGG4   ...PPCPSCP APEFLGGPSV FLFPPKPKDT LMISRTPEVT CVVVDVSQED
               -- HINGE -|-- CH2 -----------------------------------

3
                                             0
                                             0
        IGG1   PEVKFNWYVD GVEVHNAKTK PREEQYNSTY RVVSVLTVLH QDWLNGKEYK
        IGG2   PEVQFNWYVD GVEVHNAKTK PREEQFNSTF RVVSVLTVVH QDWLNGKEYK
        IGG3   PEVQFKWYVD GVEVHNAKTK PREEQYNSTF RVVSVLTVLH QDWLNGKEYK
        IGG4   PEVQFNWYVD GVEVHNAKTK PREEQFNSTY RVVSVLTVLH QDWLNGKEYK
               -- CH2 ------------------------------------------

3
                                             5
                                             0
        IGG1   CKVSNKALPA PIEKTISKAK GQPREPQVYT LPPSRDELTK NQVSLTCLVK
        IGG2   CKVSNKGLPA PIEKTISKTK GQPREPQVYT LPPSREEMTK NQVSLTCLVK
        IGG3   CKVSNKALPA PIEKTISKTK GQPREPQVYT LPPSREEMTK NQVSLTCLVK
        IGG4   CKVSNKGLPS SIEKTISKAK GQPREPQVYT LPPSQEEMTK NQVSLTCLVK
               -- CH2 ------- CH2 --|-- CH3 ------------------------

4
                                             0
                                             0
        IGG1   GFYPSDIAVE WESNGQPENN YKTTPPVLDS DGSFFLYSKL TVDKSRWQQG
        IGG2   GFYPSDISVE WESNGQPENN YKTTPPMLDS DGSFFLYSKL TVDKSRWQQG
        IGG3   GFYPSDIAVE WESSGQPENN YNTTPPMLDS DGSFFLYSKL TVDKSRWQQG
        IGG4   GFYPSDIAVE WESNGQPENN YKTTPPVLDS DGSFFLYSRL TVDKSRWQEG
               -- CH3 ------------------------------------------
```

```
                    4
                    4
                    7
IGG1    NVFSCSVMHE ALHNHYTQKS LSLSPGK  (SEQ ID NO: 113)
IGG2    NVFSCSVMHE ALHNHYTQKS LSLSPGK  (SEQ ID NO: 114)
IGG3    NIFSCSVMHE ALHNRFTQKS LSLSPGK  (SEQ ID NO: 115)
IGG4    NVFSCSVMHE ALHNHYTQKS LSLSLGK  (SEQ ID NO: 63)
        -- CH3 ---------------------|
```

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3). HVRs as denoted herein include (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A.M., J. Mol. Biol. 196 (1987) 901-917);

(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, MD (1991), NIH Publication 91-3242.);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to the Kabat EU index numbering system (Kabat et al., supra).

The term "IGF-1R" as used herein, refers to any native IGF-1R from any vertebrate source, including mammals such as primates (e.g. humans) and rodents (e.g., mice and rats), unless otherwise indicated. The term encompasses "full-length," unprocessed IGF-1R as well as any form of IGF-1R that results from processing in the cell. The term also encompasses naturally occurring variants of IGF-1R, e.g., splice variants or allelic variants. The amino acid sequence of human IGF-1R is shown in SEQ ID NO: 11.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., size exclusion chromatography, ion exchange or reverse phase HPLC) methods. For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-IGF-1R antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CHL CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

The term "peptidic linker" as used herein denotes a peptide with amino acid sequences, which is in one embodiment of synthetic origin. The peptidic linker is in one embodiment a peptide with an amino acid sequence with a length of at least 30 amino acids, in one embodiment with a length of 32 to 50 amino acids. In one embodiment the peptidic linker is a peptide with an amino acid sequence with a length of 32 to 40 amino acids. In one embodiment the peptidic linker is (GxS)n with G=glycine, S=serine, (x=3, n=8, 9 or 10) (SEQ ID NO: 116) or (x=4 and n=6, 7 or 8) (SEQ ID NO: 117), in one embodiment with x=4, n=6 or 7 (SEQ ID NO: 119), in one embodiment with x=4, n=7 (SEQ ID NO: 120). In one embodiment the peptidic linker is (G4S)6G2 (SEQ ID NO: 118).

The term "recombinant antibody," as used herein, denotes all antibodies (chimeric, humanized and human) that are prepared, expressed, created or isolated by recombinant means. This includes antibodies isolated from a host cell such as a NSO or CHO cell, or from an animal (e.g. a mouse) that is transgenic for human immunoglobulin genes, or antibodies expressed using a recombinant expression vector transfected into a host cell. Such recombinant antibodies have variable and constant regions in a rearranged form. The recombinant antibodies can be subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or Fc-region fusion polypeptides as reported herein are used to delay development of a disease or to slow the progression of a disease.

The term "valent" as used within the current application denotes the presence of a specified number of binding sites in a (antibody) molecule. As such, the terms "bivalent," "tetravalent," and "hexavalent" denote the presence of two binding site, four binding sites, and six binding sites, respectively, in a (antibody) molecule. The bispecific antibodies as reported herein are in one preferred embodiment "bivalent."

The term "variable region" or "variable domain" refer to the domain of an antibody heavy or light chain that is involved in binding of the antibody to its antigen. The variable domains of the heavy chain and light chain (VH and VL, respectively) of an antibody generally have similar structures, with each domain comprising four framework regions (FRs) and three hypervariable regions (HVRs) (see, e.g., Kindt, T. J. et al. Kuby Immunology, 6th ed., W. H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S. et al., J. Immunol. 150 (1993) 880-887; Clackson, T. et al., Nature 352 (1991) 624-628).

The term "ocular vascular disease" includes, but is not limited to intraocular neovascular syndromes such as diabetic retinopathy, diabetic macular edema, retinopathy of prematurity, neovascular glaucoma, retinal vein occlusions, central retinal vein occlusions, macular degeneration, age-related macular degeneration, retinitis pigmentosa, retinal angiomatous proliferation, macular telangectasia, ischemic retinopathy, iris neovascularization, intraocular neovascularization, corneal neovascularization, retinal neovascularization, choroidal neovascularization, and retinal degeneration (see e.g. Garner, A., Vascular diseases, In: Pathobiology of ocular disease, A dynamic approach, Garner, A., and Klintworth, G. K., (eds.), 2nd edition, Marcel Dekker, New York (1994), pp. 1625-1710).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "VEGF" as used herein refers to human vascular endothelial growth factor (VEGF/VEGF-A) the 165-amino acid human vascular endothelial cell growth factor (amino acid 27-191 of precursor sequence of human VEGF165: SEQ ID NO: 30; amino acids 1-26 represent the signal peptide), and related 121, 189, and 206 vascular endothelial cell growth factor isoforms, as described by Leung, D. W., et al., Science 246 (1989) 1306-1309; Houck et al., Mol. Endocrin. 5 (1991) 1806-1814; Keck, P. J., et al., Science 246 (1989) 1309-1312 and Connolly, D. T., et al., J. Biol. Chem. 264 (1989) 20017-20024; together with the naturally occurring allelic and processed forms of those growth factors. VEGF is involved in the regulation of normal and abnormal angiogenesis and neovascularization associated with tumors and intraocular disorders (Ferrara, N., et al., Endocrin. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H. F., et al., Am. J. Pathol. 146 (1995) 1029-1039). VEGF is a homodimeric glycoprotein that has been isolated from several sources and includes several isoforms. VEGF shows highly specific mitogenic activity for endothelial cells.

The term "with (the) mutation IHH-AAA" as used herein refers to the combination of the mutations I253A (Ile253Ala), H310A (His310Ala), and H435A (His435Ala) and the term "with (the) mutation HHY-AAA" as used herein refers to the combination of the mutations H310A (His310Ala), H433A (His433Ala), and Y436A (Tyr436Ala) and the term "with (the) mutation YTE" as used herein refers to the combination of mutations M252Y (Met252Tyr), S254T (Ser254Thr), and T256E (Thr256Glu) in the constant heavy chain region of IgG1 or IgG4 subclass, wherein the numbering is according to the Kabat EU index numbering system.

The term "with (the) mutations P329G LALA" as used herein refers to the combination of the mutations L234A (Leu235Ala), L235A (Leu234Ala) and P329G (Pro329Gly) in the constant heavy chain region of IgG1 subclass, wherein the numbering is according to the Kabat EU index numbering system. The term "with (the) mutation SPLE" as used herein refers to the combination of the mutations S228P (Ser228Pro) and L235E (Leu235Glu) in the constant heavy chain region of IgG4 subclass, wherein the numbering is according to the Kabat EU index numbering system. The term "with (the) mutation SPLE and P329G" as used herein refers to the combination of the mutations S228P (Ser228Pro), L235E (Leu235Glu) and P329G (Pro329Gly) in the constant heavy chain region of IgG4 subclass, wherein the numbering is according to the Kabat EU index numbering system.

II. COMPOSITIONS AND METHODS

In one aspect, the invention is based, in part, on the finding that the introduction of the mutation Y436A in one or both Fc-region polypeptides of an Fc-region can increase the binding of an Fc-region to Staphylococcal protein A.

In one aspect, the invention is based, in part, on the finding that specific mutations or combination of mutations which influence the binding of an immunoglobulin Fc-region to the neonatal Fc-receptor (FcRn), i.e. which reduce or even eliminate the binding of the Fc-region to FcRn, do not simultaneously eliminate the binding of the Fc-region to Staphylococcal protein A. This has a profound effect on the purification process that can be employed as, e.g. no specific and species limited affinity chromatography materials, such as e.g. KappaSelect which only binds to antibodies comprising a kappa light chain, are required. Thus, with the combination of mutations as reported herein it is possible at the same time to reduce or even eliminate the binding to FcRn while maintaining the binding to Staphylococcal protein A.

In one aspect, the invention is based, in part, on the finding that by using different mutations in the Fc-regions of each heavy chain of a heterodimeric molecule (such as e.g. a bispecific antibody) a heterodimeric molecule can be provided that on the one hand has a reduced or even eliminated binding to FcRn but on the other hand maintains the ability to bind to Staphylococcal protein A. This binding to Staphylococcal protein A can be used to separate the heterodimeric molecule from homodimeric by-products. For example by combining the mutations I253A, H310A and H435A in one heavy chain Fc-region with the mutations H310A, H433A and Y436A in the other heavy chain Fc-region using the knobs-into-hole approach a heterodimeric Fc-region can be obtained that on the one hand does not bind to FcRn (both sets of mutations are silent with respect to the human FcRn) but maintains binding to Staphylococcal protein A (the heavy chain Fc-region with the mutations I253A, H310A and H435A does not bind to FcRn and does not bind to Staphylococcal protein A, whereas the heavy chain Fc-region with the mutations H310A, H433A and Y436A does not bind to FcRn but does still bind to Staphylococcal protein A). Thus, standard protein A affinity chromatography can be used to remove the homodimeric hole-hole by-product as this no longer binds to Staphylococcal protein A). Thus, by combining the knobs-into-holes approach with the mutations I253A, H310A and H435A in the hole chain and the mutations H310A, H433A and Y436A in the knobs chain, the purification/separation of the heterodimeric knobs-into-holes product from the homodimeric hole-hole by-product can be facilitated.

In one aspect, the invention is based, in part, on the finding that antibodies for intravitreal application are beneficial that do not have FcRn-binding as these antibodies can cross the blood-retinal-barrier, do not have substantially prolonged or shortened half-lives in the eye, and are cleared fast from the blood circulation resulting in no or very limited systemic side effects outside the eye. Antibodies of the invention are useful, e.g., for the diagnosis or treatment of ocular vascular diseases.

The invention is based, at least in part, on the finding that by using different mutations in each of the Fc-region polypeptides of an Fc-region in a heterodimeric molecule (such as e.g. a bispecific antibody) a heterodimeric molecule can be provided that has tailor-made FcRn-binding and therewith antibodies can be provided that have a tailor-made systemic half-life.

The combination of mutations I253A, H310A, H435A, or L251D, L314D, L432D, or L251S, L314S, L432S result in a loss of the binding to protein A, whereas the combination of mutations I253A, H310A, H435A, or H310A, H433A, Y436A, or L251D, L314D, L432D result in a loss of the binding to the human neonatal Fc receptor.

The following table presents an exemplary overview of the amino acid residues in an Fc-region that are involved in interactions or have been changed to modify interactions.

| residue | interaction with protein A | FcRn | KiH knob | KiH hole | protein A binding | effect of mutations on FcRn binding |
|---|---|---|---|---|---|---|
| Pro238 | | | | | | P238A increase |
| Thr250 | | | | | | T250Q/M428L increase |
| Leu251 | main-chain contact | | | | | |
| Met252 | hydrophobic packing | | | | | M252W increase; M252Y increase; M252Y/T256Q increase; M252F/T256D increase; M252Y/S254T/T256E increase |
| Ile253 | main-chain contact; hydrogen bonding; significant binding reduction if mutated to Ala | interaction | | | | I253A reduction |
| Ser254 | polar interaction; hydrogen bonding | | | | | S254A reduction; M252Y/S254T/T256E increase |
| Arg255 | salt-bridge | | | | | R255A reduction |
| Thr256 | | | | | | T256A increase; T256Q increase; T256P increase; M252Y/T256Q reduction; M252F/T256D reduction; M252Y/S254T/T256E increase |
| Pro257 | | | | | | P257I/Q311I increase; P257I/N434H increase |
| Glu272 | | | | | | E272A increase |
| Asp280 | | | | | | D280K increase |
| His285 | | | | | | reduction |
| Lys288 | | | | | | K288A reduction; K288A/N434A increase |
| Val305 | | | | | | V305A increase |
| Thr307 | | | | | | T307A increase; T307A/E380A/N434A increase; T307Q/N434A increase; T307Q/N434S increase; T307Q/E380A/N434A increase |
| Val308 | | | | | | V308P/N434A increase |
| Leu309 | | | | | | L309A reduction |
| His310 | | interaction | | | | H310A reduction; H310Q/H433N reduction |
| Gln311 | polar or charged interaction | | | | | Q311A increase; P257I/Q311I increase |
| Asp312 | | | | | | D312A increase |
| Leu314 | hydrophobic interaction | | | | | |

-continued

| residue | interaction with protein A | FcRn | KiH knob | KiH hole | protein A binding | effect of mutations on FcRn binding |
|---|---|---|---|---|---|---|
| Lys317 | | | | | | K317A increase |
| Ala339 | | | | | | A339T increase |
| Tyr349 | | | | Y349C | | |
| Ser354 | | | S354C | | | |
| Thr366 | | | T366W | T366S | | |
| Leu368 | | | | L368A | | |
| Asp376 | | | | | | D376A increase; D376V/N434H increase |
| Ala378 | | | | | | A378Q increase |
| Glu380 | salt-bridge | | | | | E380A increase E380A/N434A increase; T307A/E380A/N434A increase; T307Q/E380A/N434A increase |
| Glu382 | | | | | | E382A increase |
| Gly385 | | | | | | G385H increase; G385A/Q386P/N389S increase |
| Gln386 | | | | | | G385A/Q386P/N389S increase |
| Asn389 | | | | | | G385A/Q386P/N389S increase |
| Tyr407 | | | | Y407V | | |
| Ser415 | | | | | | S415A reduction |
| Ser424 | | | | | | S424A increase |
| Met428 | | | | | | M428L increase; T250Q/M428L increase |
| Leu432 | polar or charged interaction | | | | | |
| His433 | polar or charged interaction; salt-bridge | interaction | | | | H433A reduction; H310Q/H433N reduction; H433K/N434F/Y436H increase; H433R/N434Y/Y436H increase; H433K/N434F increase |
| Asn434 | hydrogen bonding; significant binding reduction if replaced by Ala | interaction | | | | N434W/Y/F/A/H increase; K288A/N434A increase; E380A/N434A increase; T307A/E380A/N434A increase; N434F/Y436H increase; H433K/N434F/Y436H increase; H433R/N434Y/Y436H increase; H433K/N434F increase; P257I/N434H increase; D376V/N434H increase; T307Q/N434A increase; T307Q/N434S increase; V308P/N434A increase; T307Q/E380A/N434A increase |
| His435 | hydrophobic packing; significant binding reduction if mutated to Ala | interaction | | | H435R/Y436F eliminates binding to protein A | H435A reduction; H435R reduction |
| Tyr436 | hydrophobic packing; significant binding reduction if replaced by Ala | interaction | | | H435R/Y436F eliminates binding to protein A | Y436A reduction; N434F/Y436H increase; H433K/N434F/Y436H increase; H433R/N434Y/Y436H increase |

The modifications as reported herein, which can be used in combination with the mutation Y436A, alter the binding specificity for one or more Fc receptors such as the human FcRn. At the same time, some of the mutations which alter the binding to human FcRn also alter the binding to Staphylococcal protein A. This reduction in binding to Staphylococcal protein A can be reduced or even overcome by using the additional mutation Y436A.

In one embodiment the combination of mutations as reported herein does alter or does substantially alter the serum half-life of the dimeric polypeptide as compared with a corresponding dimeric polypeptide that lacks this combination of mutations. In one embodiment the combination of mutations further does not alter or does not substantially alter the binding of the dimeric polypeptide to Staphylococcal protein A as compared with a corresponding dimeric polypeptide that lacks this combination of mutations.

A. The neonatal Fc-receptor (FcRn)

The neonatal Fc-receptor (FcRn) is important for the metabolic fate of antibodies of the IgG class in vivo. The FcRn functions to salvage wild-type IgG from the lysosomal degradation pathway, resulting in reduced clearance and increased half-life. It is a heterodimeric protein consisting of two polypeptides: a 50 kDa class I major histocompatibility complex-like protein (a-FcRn) and a 15 kDa β2-microglobulin (β2m). FcRn binds with high affinity to the CH2-CH3 portion of the Fc-region of an antibody of the class IgG. The interaction between an antibody of the class IgG and the FcRn is pH dependent and occurs in a 1:2 stoichiometry, i.e. one IgG antibody molecule can interact with two FcRn molecules via its two heavy chain Fc-region polypeptides (see e.g. Huber, A. H., et al., J. Mol. Biol. 230 (1993) 1077-1083).

Thus, the in vitro FcRn binding properties/characteristics of an IgG are indicative of its in vivo pharmacokinetic properties in the blood circulation.

In the interaction between the FcRn and the Fc-region of an antibody of the IgG class, different amino acid residues of the heavy chain CH2- and CH3-domain participate. The amino acid residues interacting with the FcRn are located approximately between EU position 243 and EU position 261, approximately between EU position 275 and EU position 293, approximately between EU position 302 and EU position 319, approximately between EU position 336 and EU position 348, approximately between EU position 367 and EU position 393, at EU position 408, and approximately between EU position 424 and EU position 440. More specifically, the following amino acid residues according to the EU numbering of Kabat are involved in the interaction between the Fc-region and the FcRn: F243, P244, P245 P, K246, P247, K248, D249, T250, L251, M252, 1253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, 1336, S337, K338, A339, K340, G341, Q342, P343, R344, E345, P346, Q347, V348, C367, V369, F372, Y373, P374, S375, D376, 1377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440.

Site-directed mutagenesis studies have proven that the critical binding sites in the Fc-region of IgGs for FcRn are Histidine 310, Histidine 435, and Isoleucine 253 and to a lesser extent Histidine 433 and Tyrosine 436 (see e.g. Kim, J.K., et al., Eur. J. Immunol. 29 (1999) 2819-2825; Raghavan, M., et al., Biochem. 34 (1995) 14649-14657; Medesan, C., et al., J Immunol. 158 (1997) 2211-2217).

Methods to increase IgG binding to FcRn have been performed by mutating IgG at various amino acid residues: Threonine 250, Methionine 252, Serine 254, Threonine 256, Threonine 307, Glutamic acid 380, Methionine 428, Histidine 433, and Asparagine 434 (see Kuo, T. T., et al., J. Clin. Immunol. 30 (2010) 777-789).

In some cases, antibodies with reduced half-life in the blood circulation are desired. For example, drugs for intravitreal application should have a long half-live in the eye and a short half-life in the blood circulation of the patient. Such antibodies also have the advantage of increased exposure to a disease site, e.g. in the eye.

Different mutations that influence the FcRn binding and therewith the half-life in the blood circulation are known. Fc-region residues critical to the mouse Fc-region-mouse FcRn interaction have been identified by site-directed mutagenesis (see e.g. Dall'Acqua, W. F., et al. J. Immunol 169 (2002) 5171-5180). Residues 1253, H310, H433, N434, and H435 (EU numbering according to Kabat) are involved in the interaction (Medesan, C., et al., Eur. J. Immunol. 26 (1996) 2533-2536; Firan, M., et al., Int. Immunol. 13 (2001) 993-1002; Kim, J.K., et al., Eur. J. Immunol. 24 (1994) 542-548). Residues 1253, H310, and H435 were found to be critical for the interaction of human Fc with murine FcRn (Kim, J.K., et al., Eur. J. Immunol. 29 (1999) 2819-2855). Residues M252Y, S254T, T256E have been described by Dall'Acqua et al. to improve FcRn binding by protein-protein interaction studies (Dall'Acqua, W.F., et al. J. Biol. Chem. 281 (2006) 23514-23524). Studies of the human Fc-human FcRn complex have shown that residues 1253, S254, H435, and Y436 are crucial for the interaction (Firan, M., et al., Int. Immunol. 13 (2001) 993-1002; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined. Exemplary mutations and their effect on FcRn binding are listed in the following Table.

| mutation | effect on FcRn binding | half-live in the circulation | reference |
|---|---|---|---|
| H285<br>H310Q/H433N<br>(murine IgG1) | reduced<br>(murine) | reduced<br>(in mouse) | Kim, J. K., Scand. J. Immunol. 40 (1994) 457-465 |
| I253A<br>H310A<br>H435A<br>H436A<br>(murine IgG1) | reduced<br>(murine) | reduced<br>(in mouse) | Ghetie, V. and Ward, E. S., Immunol. Today 18 (1997) 592-598 |

-continued

| mutation | effect on FcRn binding | half-live in the circulation | reference |
|---|---|---|---|
| T252L/T254S/T256F T252A/T254S/T256A (murine IgG1) | increased (murine) | increased (in mouse) | Ghetie, V. and Ward, E. S., Immunol. Today 18 (1997) 592-598 |
| I253A H310A H435A H436A H433A/N434Q (murine IgG1) | reduced (murine) | reduced (in mouse) | Medesan, C., et al., J. Immunol. 158 (1997) 2211-2217 |
| I253A H310A H435A H435R (human IgG1) | reduced H310A: <0.1 rel. binding to muFcRn (murine) | reduced (in mouse) | Kim, J. K., Eur. J. Immunol. 29 (1999) 2819-2825 |
| H433A (human IgG1) | 1.1 rel. binding to muFcRn, 0.4 rel. binding hu FcRn (murine) | | Kim, J. K., Eur. J. Immunol. 29 (1999) 2819-2825 |
| I253A S254A H435A Y436A (human IgG1) | reduced <0.1 relative binding to huFcRn | reduced | Shields, R. L., et al., J. Biol. Chem. 276 (2001) 6591-6604 |
| R255A K288A L309A S415A H433A (human IgG1) | reduced (human) | reduced | Shields, R. L., et al., J. Biol. Chem. 276 (2001) 6591-6604 |
| P238A T256A E272A V305A T307A Q311A D312A K317A D376A A378Q E380A E382A S424A N434A K288A/N434A E380A/N434A T307A/E380A/N434A (human IgG1) | increased (human) | increased | Shields, R. L., et al., J. Biol. Chem. 276 (2001) 6591-6604 |
| H435A (humanized IgG1) | reduced <0.1 rel. binding to huFcRn | reduced | Firan, M., et al., Int. Immunol. 13 (2001) 993-1002 |
| I253A (no binding) M252W M252Y M252Y/T256Q M252F/T256D N434F/Y436H M252Y/S254T/T256E G385A/Q386P/N389S H433K/N434F/Y436H H433R/N434Y/Y436H G385R/Q386T/P387R/N389P M252Y/S254T/T256E/H433K/ N434F/Y436H M252Y/S254T/T256E/G385R/ Q386T/P387R/N389P (human IgG1) | increased (murine and human) | reduced (in mouse) | Dall'Acqua, J. Immunol. 169 (2002) 5171-5180 |
| M428L T250Q/M428L (human IgG2) | increased (human) | increased (in monkey) | Hinton, P. R., et al., J. Biol. Chem. 279 (2004) 6213-6216 |

-continued

| mutation | effect on FcRn binding | half-live in the circulation | reference |
| --- | --- | --- | --- |
| M252Y/S254T/T256E + H433K/N434F (human IgG) | increased (human) | increased (in mouse) | Vaccaro, C., et al., Nat. Biotechnol. 23 (2005) 1283-1288 |
| T307A/E380A/N434A (chimeric IgG1) | increased | increased in transgenic mouse | Pop, L. M., et al., Int. Immunopharmacol. 5 (2005) 1279-1290 |
| T250Q<br>E380A<br>M428L<br>N434A<br>K288A/N434A<br>E380A/N434A<br>T307A/E380A/N434A<br>(human IgG1) | increased (human) | increased in transgenic mouse | Petkova, S. B., et al., Int. Immunol 18 (2006) 1759-1769 |
| I253A (human IgG1) | reduced (human) | reduced in transgenic mouse | Petkova, S. B., et al., Int. Immunol 18 (2006) 1759-1769 |
| S239D/A330L/I332E M252Y/S254T/T256E (humanized) | increased (human and Cynomolgus) | increased in Cynomolgus | Dall'Acqua, W. F., et al., J. Biol. Chem. 281 (2006) 23514-23524 |
| T250Q<br>M428L<br>T250Q/M428L<br>(human IgG1) | increased (human) | increased in Rhesus apes | Hinton, P. R., et al., J. Immunol. 176 (2006) 346-356 |
| T250Q/M428L P257I/Q311I (humanized IgG1) | increased (mouse and Cynomolgus) | no change in Cynomolgus increased in mouse | Datta-Mannan, A., et al., J. Biol. Chem. 282 (2007) 1709-1717 |
| P257I/Q311I P257I/N434H D376V/N434H (humanized IgG1) | increased at pH 6 (human, Cynomolgus, mouse) | reduced in mice P257I/N434H reduced in Cynomolgus | Datta-Mannan, A., et al., Drug Metab. Dispos. 35 (2007) 86-94 |
| abrogate FcRn binding:<br>I253<br>H310<br>H433<br>H435<br>reduce FcRn binding:<br>Y436<br>increased FcRn binding:<br>T250<br>N252<br>S254<br>T256<br>T307<br>M428<br>N434 | increased and reduced | reducing the binding ability of IgG for FcRn reduces its serum persistence; a higher-affinity FcRn-IgG interaction prolongs the half-lives of IgG and Fc-coupled drugs in the serum | Ropeenian, D. C. and Akilesh, S., Nat. Rev. Immunol. 7 (2007) 715-725 |
| N434A<br>T307Q/N434A<br>T307Q/N434S<br>V308P/N434A<br>T307Q/E380A/N434A<br>(human IgG1) | increased (Cynomolgus monkey) | increased in Cynomolgus monkey | Yeung, Y. A., et al., Cancer Res. 70 (2010) 3269-3277 |
| 256P<br>280K<br>339T<br>385H<br>428L<br>434W/Y/F/A/H<br>(human IgG) | increased at neutral pH | | WO 2011/122011 |

It has been found that one mutation, one-sided in one Fc-region polypeptide, is sufficient to weaken the binding significantly. The more mutations that are introduced into the Fc-region, the weaker the binding to the FcRn becomes. But one-sided asymmetric mutations are not sufficient to completely inhibit FcRn binding. Mutations on both sides are necessary to completely inhibit FcRn binding.

The results of a symmetric engineering of an IgG1 Fc-region to influence FcRn binding is shown in the following table (alignment of mutations and retention time on an FcRn-affinity chromatography column).

| effector function influencing mutations | FcRn-binding influencing mutation 1 | FcRn-binding influencing mutation 2 | FcRn-binding influencing mutation 3 | FcRn-affinity column retention time [min] |
|---|---|---|---|---|
| L234A/L235A/P329G | — | — | — | 45.3 |
| L234A/L235A/P329G | I253A | H310A | H435A | 2.3 |
| L234A/L235A/P329G | I253A | — | — | 2.7 |
| L234A/L235A/P329G | — | H310A | — | 2.4 |
| L234A/L235A/P329G | — | — | H435A | 2.7 |
| L234A/L235A/P329G | I253A | H310A | — | 2.3 |
| L234A/L235A/P329G | I253A | — | H435A | 2.3 |
| L234A/L235A/P329G | — | H310A | H435A | 2.4 |
| L234A/L235A/P329G | — | H310A | Y436A | 2.3 |
| L234A/L235A/P329G | H310A | H433A | Y436A | 2.4 |
| L234A/L235A/P329G | — | — | Y436A | 41.3 |

Retention times below 3 minutes correspond to no binding as the substance is in the flow-through (void peak).

The single mutation H310A is the most silent symmetrical mutation to delete any FcRn-binding.

The symmetric single mutation I253A and H435A result in a relative shift of retention time of 0.3 to 0.4 min. This can be generally regarded as a non-detectable binding.

The single mutation Y436A results in detectable interaction strength to the FcRn affinity column. Without being bound by theory this mutation could have an effect on FcRn mediated half-life in vivo, which can be differentiated from a zero interaction such as the combination of the I253A, H310A and H435A mutations (IHH-AAA mutation).

The results obtained with a symmetrically modified anti-HER2 antibody are presented in the following table (see WO 2006/031370 for reference).

| mutation | retention time [min] |
|---|---|
| I253H | no binding |
| M252D | no binding |
| S254D | no binding |
| R255D | 41.4 |
| M252H | 43.6 |
| K288E | 45.2 |
| L309H | 45.5 |
| E258H | 45.6 |
| T256H | 46.0 |
| K290H | 46.2 |
| D98E | 46.2 |
| wild-type | 46.3 |
| K317H | 46.3 |
| Q311H | 46.3 |
| E430H | 46.4 |
| T307H | 47.0 |
| N434H | 52.0 |

Figure 9:
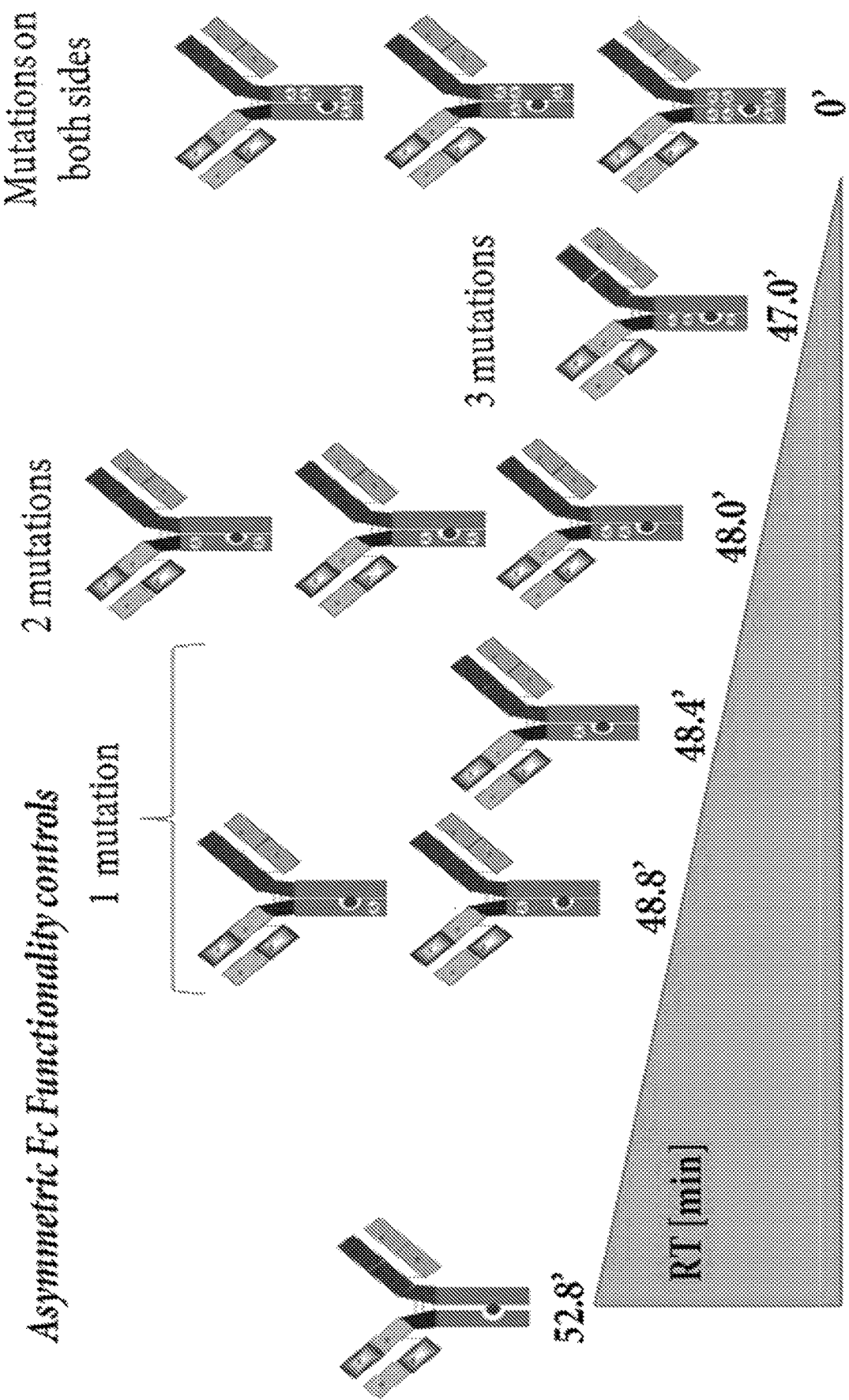
FIG. 9: Change of retention time in an FcRn affinity chromatography depending on the number of mutations introduced into the Fc-region.
Figure 10:
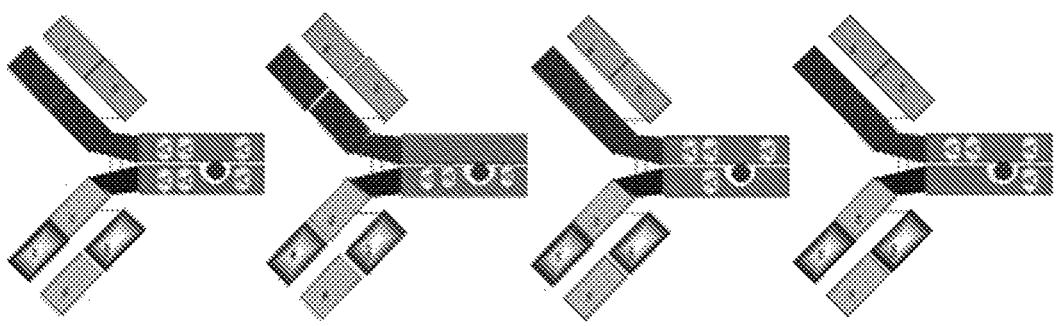
FIG. 10: Change of FcRn-binding depending on asymmetric distribution of mutations introduced into the Fc-region.
Figure 11:
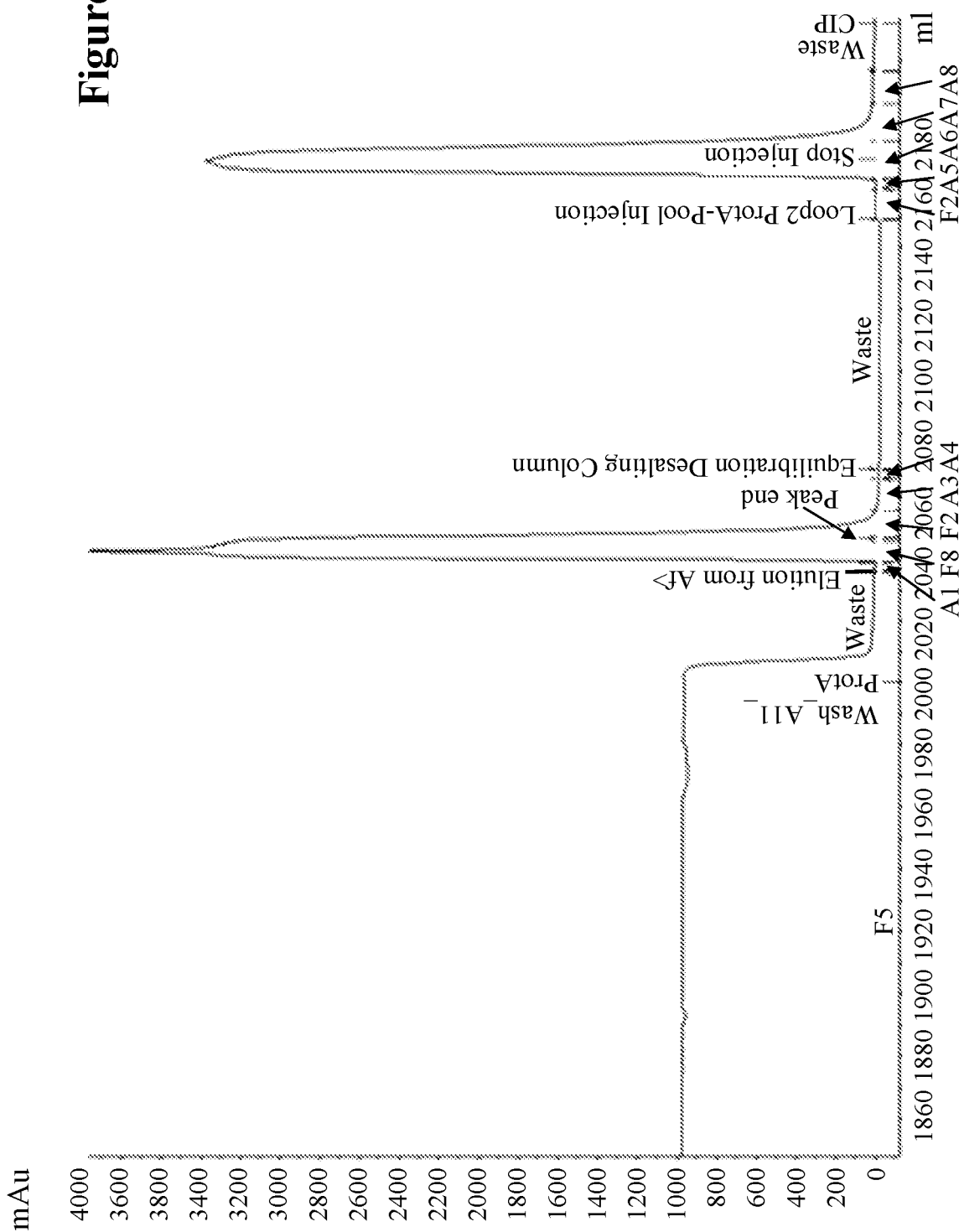
FIG. 11: Elution chromatogram of a bispecific anti-VEGF/ANG2 antibody (VEGF/ANG2-0121) with the combination of the mutations H310A, H433A and Y436A in both heavy chains from two consecutive protein A affinity chromatography columns.
Figure 12:
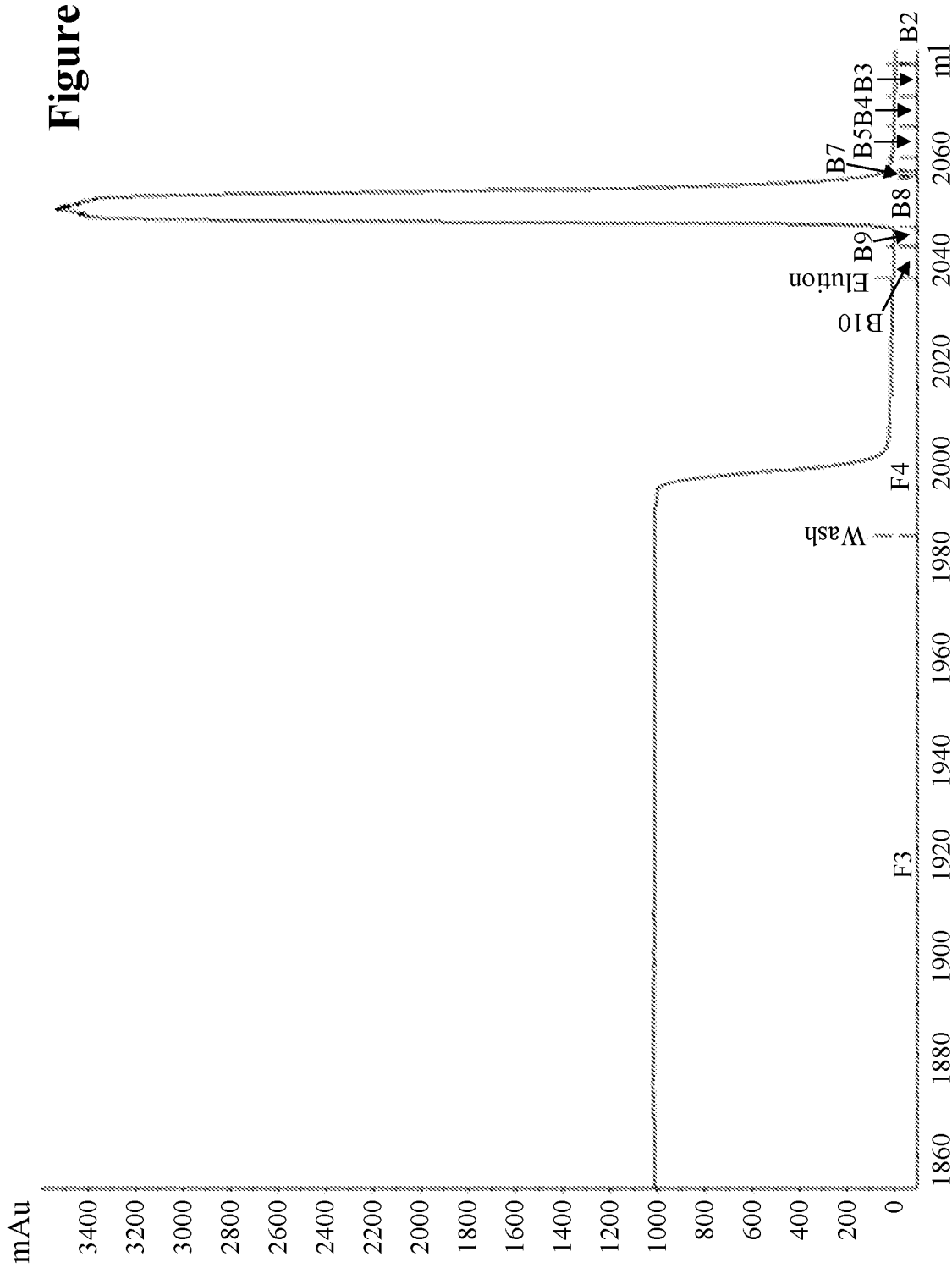
FIG. 12: Elution chromatogram of an anti-IGF-1R antibody (IGF-1R-0045) with the mutations H310A, H433A and Y436A in both heavy chains from a protein A affinity chromatography column.
Figure 13:
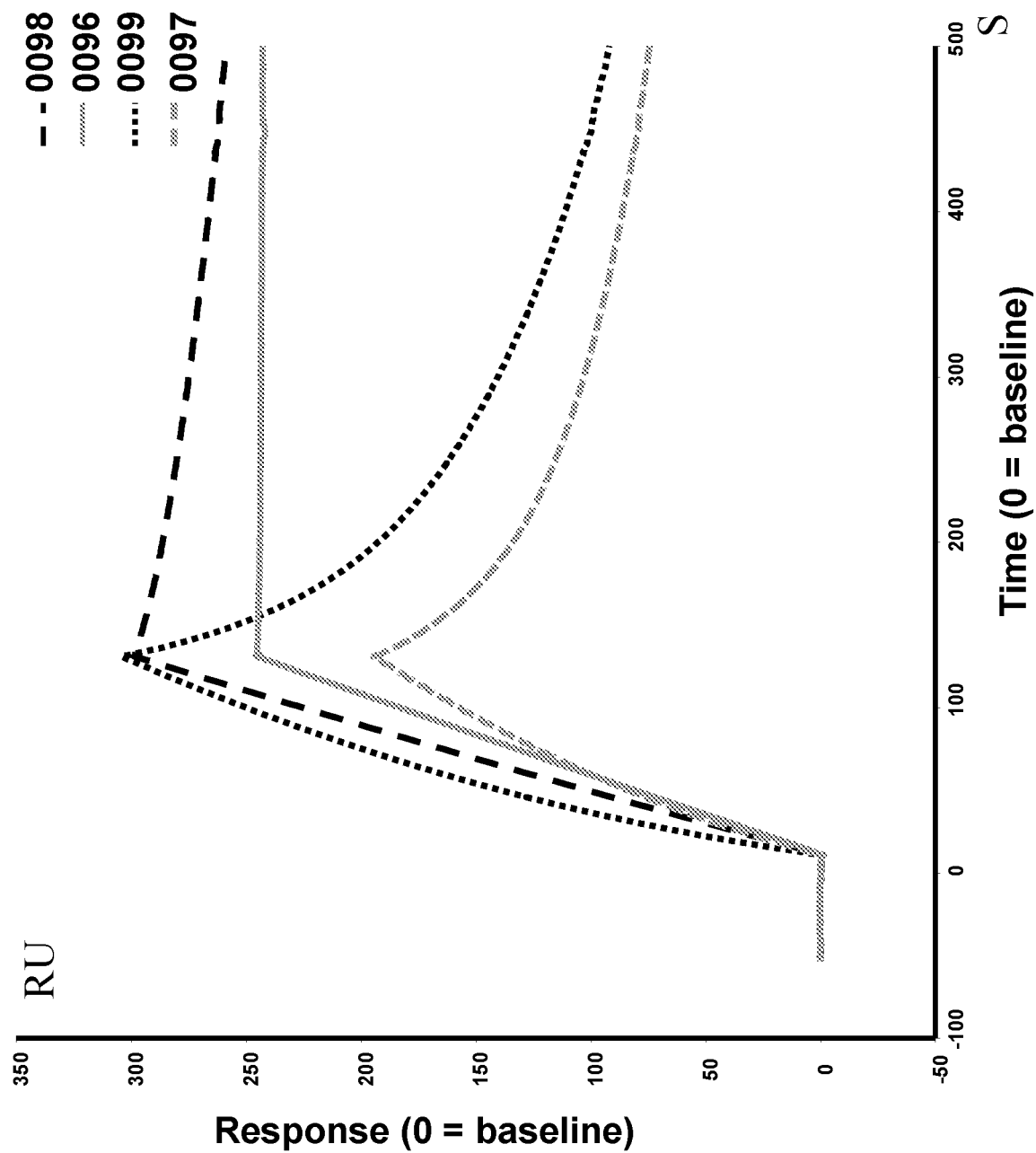
FIG. 13: Binding of IgG Fc-region modified anti-VEGF/ANG2 antibodies to immobilized protein A on a CM5 chip.
Figure 14:
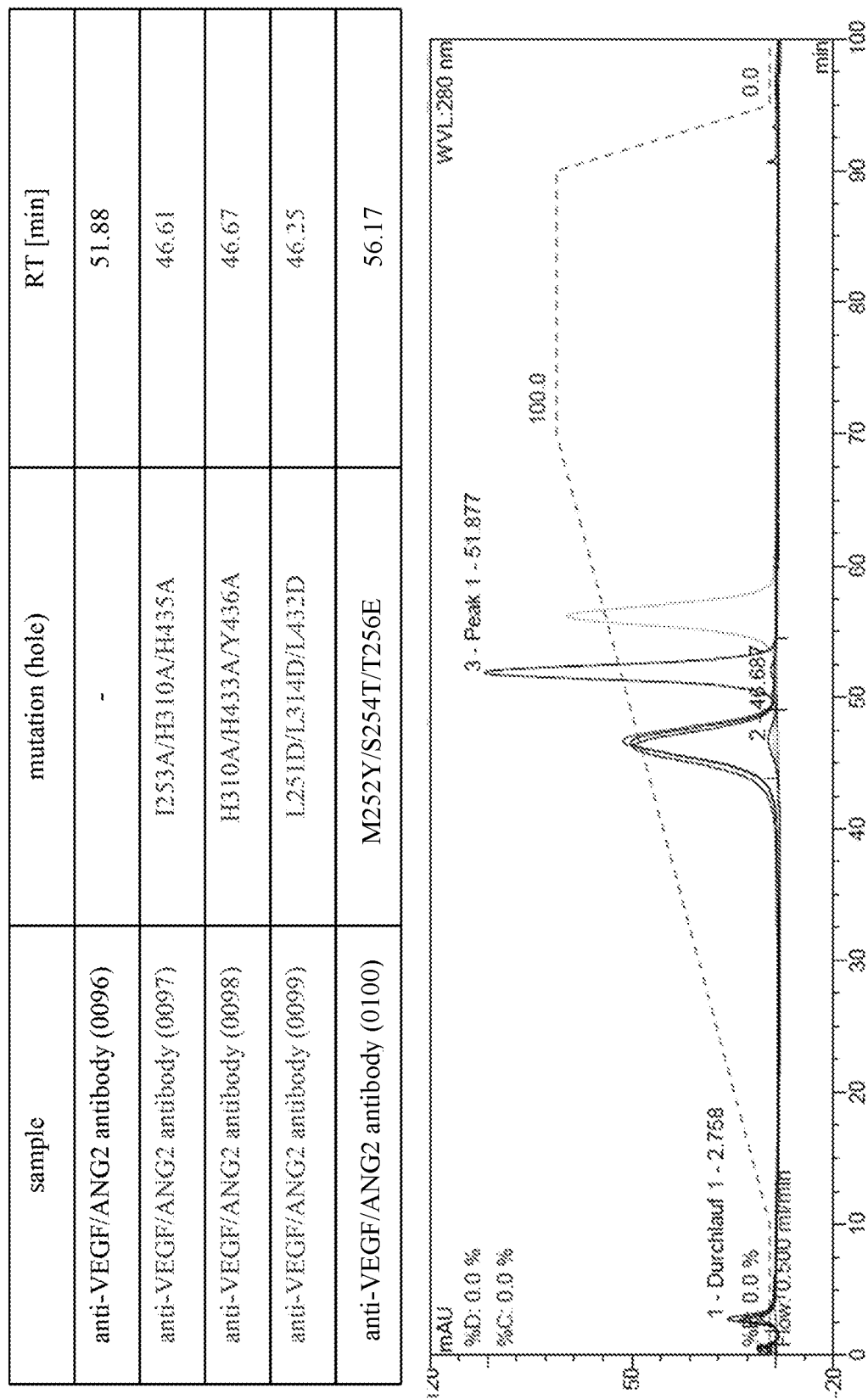
FIG. 14: Elution chromatogram of different anti-VEGF/ANG2 antibodies on an FcRn affinity column.

The effect of the introduction of asymmetric FcRn-binding affecting mutations in the Fc-region has been exemplified with a bispecific antibody assembled using the knobs-into-holes technology (see e.g. U.S. Pat. No/7,695,936, US 2003/0078385; "hole chain" mutations: S354C/T366W, "knob chain" mutations: Y349C/T366S/L368A/Y407V). The effect of the asymmetrically introduced mutations on FcRn-binding can easily be determined using an FcRn affinity chromatography method (see FIG. 9 and the following Table). Antibodies that have a later elution from the FcRn affinity column, i.e. that have a longer retention time on the FcRn affinity column, have a longer half-life in vivo, and vice versa.

| FcRn affecting mutation | retention time on FcRn affinity column |
|---|---|
| one chain with M252Y/S254T/T256E | 56.2 min. |
| none | 51.8 min. |
| one chain with I253A or H435A | 48.8 min. |
| one chain with H310A | 48.4 min. |
| one chain with I253A/H435A or I253A/H310A or H310A/H435A | 48.0 min. |
| one chain with H310A/H433A/Y436A | 46.7 min. |
| one chain with I253A/H310A/H435A | 46.6 min. |
| one chain with L251D/L314D/L432D | 46.3 min. |
| first chain with I253A/H310A/H435A and second chain with H310A or H435A or I253A/H310A/H435A | no binding |

The effect of the introduction of asymmetric FcRn-binding affecting mutations in the Fc-region has further been exemplified with a monospecific anti-IGF-1R antibody assembled using the knobs-into-holes technology in order to allow the introduction of asymmetric mutations (see e.g. U.S. Pat. No. 7,695,936, US 2003/0078385; "hole chain" mutations: S354C/T366W, "knob chain" mutations: Y349C/T366S/L368A/Y407V). The effect of the asymmetrically introduced mutations on FcRn-binding can easily be determined using an FcRn affinity chromatography method (see the following Table). Antibodies that have a later elution from the FcRn affinity column, i.e. that have a longer retention time on the FcRn affinity column, have a longer half-life in vivo, and vice versa.

| FcRn affecting mutation | retention time on FcRn affinity column |
|---|---|
| one chain with M252Y/S254T/T256E | 57.6 min. |
| none | 53.0 min. |
| one chain with H310A/H433A/Y436A | 42.4 min. |
| one chain with I253A/H310A/H435A | 42.0 min. |
| one chain with L251D/L314D/L432D | 40.9 min. |
| first chain with I253A/H310A/H435A and second chain with H310A or H435A or I253A/H310A/H435A | no binding |

The asymmetric IHH-AAA and LLL-DDD mutations (LLL-DDD mutation=combination of the mutations L251D, L314D and L432D) show weaker binding than the corresponding parent or wild-type antibody.

The symmetric HHY-AAA mutation (=combination of the mutations H310A, H433A and Y436A) results in an Fc-region that does no longer bind to the human FcRn whereas the binding to protein A is maintained (see FIGS. 11, 12, 13 and 14).

The effect of the introduction of asymmetric FcRn-binding affecting mutations in the Fc-region has further been exemplified with a monospecific anti-IGF-1R antibody (IGF-1R), a bispecific anti-VEGF/ANG2 antibody (VEGF/ANG2), and a full length antibody with fusions to the C-terminus of both heavy chains (fusion) assembled using the knobs-into-holes technology in order to allow the introduction of asymmetric mutations (see e.g. U.S. Pat. No. 7,695,936, US 2003/0078385; "hole chain" mutations: S354C/T366W, "knob chain" mutations: Y349C/T366S/L368A/Y407V). The effect of the introduced mutations on FcRn-binding and protein A binding can easily be determined using an FcRn affinity chromatography method, a protein A affinity chromatography method and SPR-based methods (see the following Table).

| antibody | further mutation in knob chain | further mutation in hole chain | FcR binding affecting mutations | FcRn binding (SPR) | FcRn binding (column) | protein A binding (SPR) | protein A binding (column) |
|---|---|---|---|---|---|---|---|
| VEGF/ANG2 0096 | none | none | L234A L235A P329G | yes | yes | stable binding | yes |
| VEGF/ANG2 0097 | none | I253A H310A H435A | L234A L235A P329G | yes | yes | fast off-rate | yes |
| VEGF/ANG2 0098 | none | H310A H433A Y436A | L234A L235A P329G | yes | yes | stable binding | yes |
| VEGF/ANG2 0099 | none | L251D L314D L432D | L234A L235A P329G | reduced | reduced | fast off-rate | yes |
| VEGF/ANG2 0100 | none | M252Y S254T T256E | L234A L235A P329G | increased | increased | n.d. | yes |
| VEGF/ANG2 0016 | I253A H310A H435A | I253A H310A H435A | L234A L235A P329G | n.d. | no | n.d. | no |
| VEGF/ANG2 0121 | H310A H433A Y436A | H310A H433A Y436A | L234A L235A P329G | n.d. | n.d. | n.d. | yes |
| IGF-1R 0033 | | | | none | none | n.d. | yes |
| IGF-1R 0034 | none | I253A H310A H435A | L234A L235A P329G | n.d. | yes | n.d. | yes |
| IGF-1R 0035 | none | H310A H433A Y436A | none | reduced | reduced | n.d. | yes |
| IGF-1R 0037 | none | L251D L314D L432D | L234A L235A P329G | n.d. | yes | n.d. | yes |
| IGF-1R 0036 | none | M252Y S254T T256E | L234A L235A P329G | n.d. | yes | n.d. | yes |
| IGF-1R 0045 | H310A H433A Y436A | H310A H433A Y436A | none | n.d. | n.d. | n.d. | yes |
| fusion 0008 | none | none | L234A L235A P329G | n.d. | yes | n.d. | n.d. |
| fusion 0019 | I253A | I253A | L234A L235A P329G | n.d. | no | n.d. | n.d. |
| fusion 0020 | H310A | H310A | L234A L235A P329G | n.d. | no | n.d. | n.d. |
| fusion 0021 | H435A | H435A | L234A L235A P329G | n.d. | no | n.d. | n.d. |
| fusion 0038 | Y436A | Y436A | L234A L235A P329G | n.d. | reduced | n.d. | n.d. |
| fusion 0022 | I253A H310A | I253A H310A | L234A L235A P329G | n.d. | no | n.d. | n.d. |
| fusion 0023 | I253A H435A | I253A H435A | L234A L235A P329G | n.d. | no | n.d. | n.d. |
| fusion 0036 | H310A H435A | H310A H435A | L234A L235A P329G | n.d. | no | n.d. | n.d. |
| fusion 0037 | H310A Y436A | H310A Y436A | L234A L235A P329G | n.d. | no | n.d. | n.d. |
| fusion 0018 | I253A H310A H435A | I253A H310A H435A | L234A L235A P329G | n.d. | no | n.d. | n.d. |
| fusion 0019 | H310A H433A Y436A | H310A H433A Y436A | L234A L235A P329G | n.d. | no | n.d. | n.d. |

One aspect as reported herein is an antibody or Fc-region fusion polypeptide comprising the variant human IgG class Fc-region as reported herein.

The Fc-region (dimeric polypeptide) as reported herein, when contained in an Fc-region fusion polypeptide or a full length antibody confers the above described characteristics to the molecule. The fusion partner can be any molecule having a biological activity who's in vivo half-live shall be reduced or increased, i.e. who's in vivo half-live shall be clearly defined and tailor-made for its intended application.

Fc-region fusion polypeptides may comprise e.g. a variant (human) IgG class Fc-region as reported herein and a receptor protein that binds to a target including a ligand, such as, for example, TNFR-Fc-region fusion polypeptide (TNFR=human tumor necrosis factor receptor), or IL-1R-Fc-region fusion polypeptide (IL-1R=human interleukin-1 receptor), or VEGFR-Fc-region fusion polypeptides (VEGFR=human vascular endothelial growth factor receptor), or ANG2R-Fc-region fusion polypeptides (ANG2R=human angiopoietin 2 receptor).

Fc-region fusion polypeptides may comprise e.g. a variant (human) IgG class Fc-region as reported herein and an antibody fragment that binds to a target including, such as, for example, an antibody Fab fragment, scFvs (see e.g. Nat. Biotechnol. 23 (2005) 1126-1136), or domain antibodies (dAbs) (see e.g. WO 2004/058821, WO 2003/002609).

Fc-region fusion polypeptides may comprise e.g. a variant (human) human IgG class Fc-region as reported herein and a receptor ligand (either naturally occurring or artificial).

Antibodies, e.g. full length antibodies or CrossMabs, can comprise a variant (human) human IgG class Fc-region as reported herein.

B. Ocular Vascular Diseases

Ocular vascular diseases are any pathological condition characterized by altered or unregulated proliferation and invasion of new blood vessels into the structures of ocular tissues such as the retina or cornea.

In one embodiment the ocular vascular disease is selected from the group consisting of wet age-related macular degeneration (wet AMD), dry age-related macular degeneration (dry AMD), diabetic macular edema (DME), cystoid macular edema (CME), non-proliferative diabetic retinopathy (NPDR), proliferative diabetic retinopathy (PDR), cystoid macular edema, vasculitis (e.g. central retinal vein occlusion), papilloedema, retinitis, conjunctivitis, uveitis, choroiditis, multifocal choroiditis, ocular histoplasmosis, blepharitis, dry eye (Sjogren's disease), and other ophthalmic diseases wherein the eye disease or disorder is associated with ocular neovascularization, vascular leakage, and/or retinal edema.

The antibody comprising the dimeric polypeptide as reported herein is useful in the prevention and treatment of wet AMD, dry AMD, CME, DME, NPDR, PDR, blepharitis, dry eye and uveitis, in one preferred embodiment wet AMD, dry AMD, blepharitis, and dry eye, also in one preferred embodiment CME, DME, NPDR and PDR, also in one preferred embodiment blepharitis, and dry eye, in particular wet AMD and dry AMD, and also particularly wet AMD.

In some embodiments, the ocular vascular disease is selected from the group consisting of wet age-related macular degeneration (wet AMD), macular edema, retinal vein occlusions, retinopathy of prematurity, and diabetic retinopathy.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, Sjogren's disease, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegener's sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retinitis pigmentosa, retina edema (including macular edema), Eale's disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma, and post-laser complications.

Other diseases include, but are not limited to, diseases associated with rubeosis (neovascularization of the angle) and diseases caused by the abnormal proliferation of fibrovascular or fibrous tissue including all forms of proliferative vitreoretinopathy.

Retinopathy of prematurity (ROP) is a disease of the eye that affects prematurely born babies. It is thought to be caused by disorganized growth of retinal blood vessels which may result in scarring and retinal detachment. ROP can be mild and may resolve spontaneously, but may lead to blindness in serious cases. As such, all preterm babies are at risk for ROP, and very low birth weight is an additional risk factor. Both oxygen toxicity and relative hypoxia can contribute to the development of ROP.

Macular degeneration is a medical condition predominantly found in elderly adults in which the center of the inner lining of the eye, known as the macula area of the retina, suffers thinning, atrophy, and in some cases, bleeding. This can result in loss of central vision, which entails inability to see fine details, to read, or to recognize faces. According to the American Academy of Ophthalmology, it is the leading cause of central vision loss (blindness) in the United States today for those over the age of fifty years. Although some macular dystrophies that affect younger individuals are sometimes referred to as macular degeneration, the term generally refers to age-related macular degeneration (AMD or ARMD).

Age-related macular degeneration begins with characteristic yellow deposits in the macula (central area of the retina which provides detailed central vision, called fovea) called drusen between the retinal pigment epithelium and the underlying choroid. Most people with these early changes (referred to as age-related maculopathy) have good vision. People with drusen can go on to develop advanced AMD. The risk is considerably higher when the drusen are large and numerous and associated with disturbance in the pigmented cell layer under the macula. Large and soft drusen are related to elevated cholesterol deposits and may respond to cholesterol lowering agents or the Rheo Procedure.

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. While no treatment is available for this condition, vitamin supplements with high doses of antioxidants, lutein and zeaxanthin, have been demonstrated by the National Eye Institute and others to slow the progression of dry macular degeneration and in some patients, improve visual acuity.

Retinitis pigmentosa (RP) is a group of genetic eye conditions. In the progression of symptoms for RP, night blindness generally precedes tunnel vision by years or even decades. Many people with RP do not become legally blind until their 40s or 50s and retain some sight all their life. Others go completely blind from RP, in some cases as early as childhood. Progression of RP is different in each case. RP is a type of hereditary retinal dystrophy, a group of inherited disorders in which abnormalities of the photoreceptors (rods and cones) or the retinal pigment epithelium (RPE) of the retina lead to progressive visual loss. Affected individuals first experience defective dark adaptation or nyctalopia (night blindness), followed by reduction of the peripheral visual field (known as tunnel vision) and, sometimes, loss of central vision late in the course of the disease.

Macular edema occurs when fluid and protein deposits collect on or under the macula of the eye, a yellow central area of the retina, causing it to thicken and swell. The swelling may distort a person's central vision, as the macula is near the center of the retina at the back of the eyeball. This area holds tightly packed cones that provide sharp, clear central vision to enable a person to see form, color, and detail that is directly in the line of sight. Cystoid macular edema is a type of macular edema that includes cyst formation.

C. Antibody Purification with a Staphylococcus Protein A Affinity Chromatography Column In one aspect, a dimeric polypeptide comprising a first polypeptide and a second polypeptide each comprising in N-terminal to C-terminal direction at least a portion of an immunoglobulin hinge region, which comprises one or more cysteine residues, an immunoglobulin CH2-domain, and an immunoglobulin CH3-domain, wherein the first, the second, or the first and the second polypeptide comprise the mutation Y436A (numbering according to the Kabat EU index numbering system) is provided.

This dimeric polypeptide has, due to the mutation, the properties of improved binding to Staphylococcal protein A.

Thus, these antibodies can be purified, i.e. separated from unwanted by-products by using conventional protein A affinity materials, such as MABSELECTSURE™. It is not required to use highly sophisticated but species limited affinity materials, such as e.g. KappaSelect, which is only useable with antibodies comprising a light chain of the kappa subclass. Additionally it is not required to adopt the purification method if a modification/exchange of the light chain subclass is made (see FIGS. 11 and 12, respectively).

One aspect as reported herein is a method for producing a dimeric polypeptide as reported herein comprising the following steps:

a) cultivating a mammalian cell comprising one or more nucleic acids encoding a dimeric polypeptide as reported herein, b) recovering the dimeric polypeptide from the cultivation medium, and c) purifying the dimeric polypeptide with a protein A affinity chromatography and thereby producing the dimeric polypeptide.

One aspect as reported herein is the use of the mutation Y436A for increasing the binding of a dimeric Fc-region polypeptide to protein A.

Figure 15:
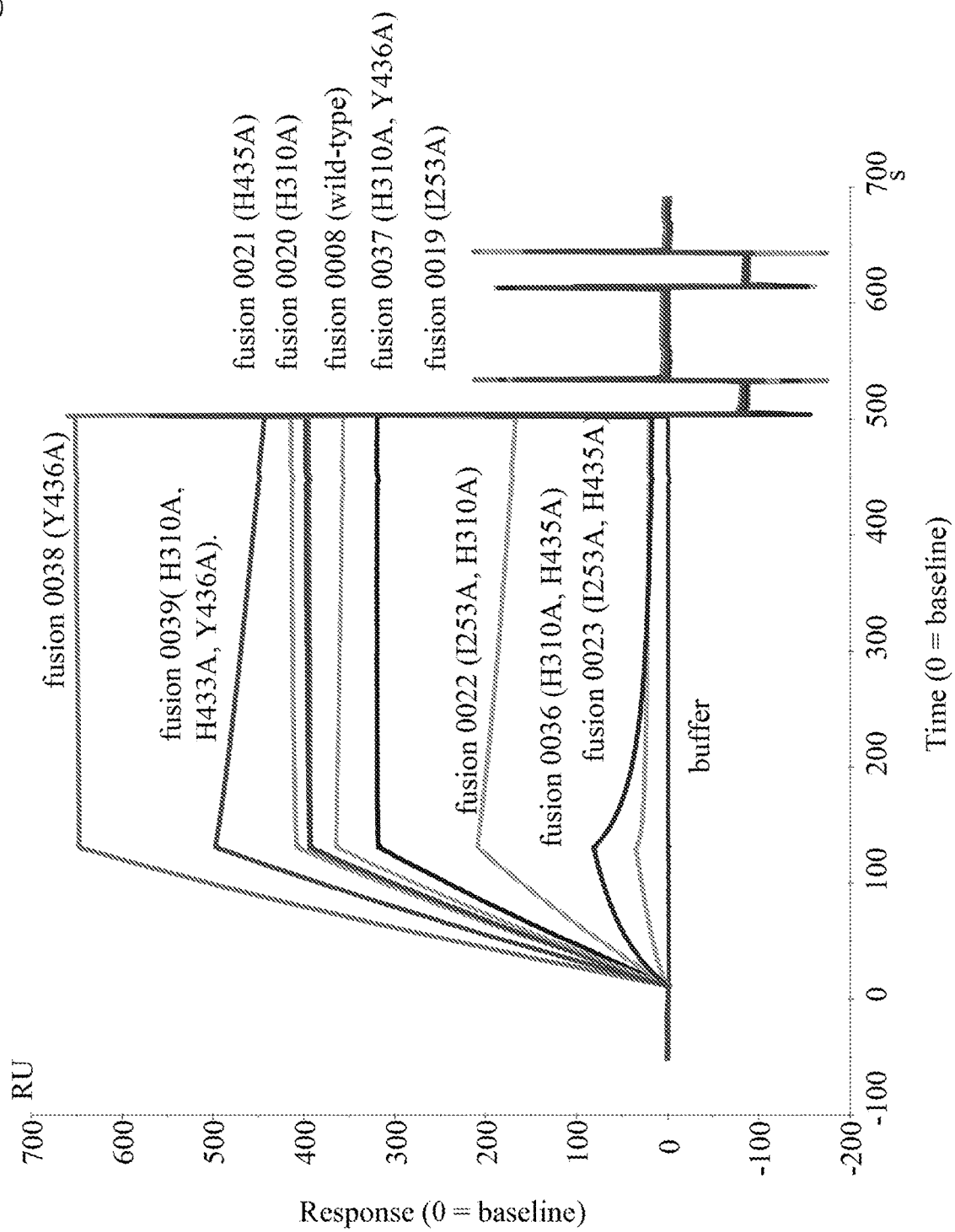
FIG. 15: Binding of different fusion polypeptides to Staphylococcal protein A (SPR).
Figure 16:
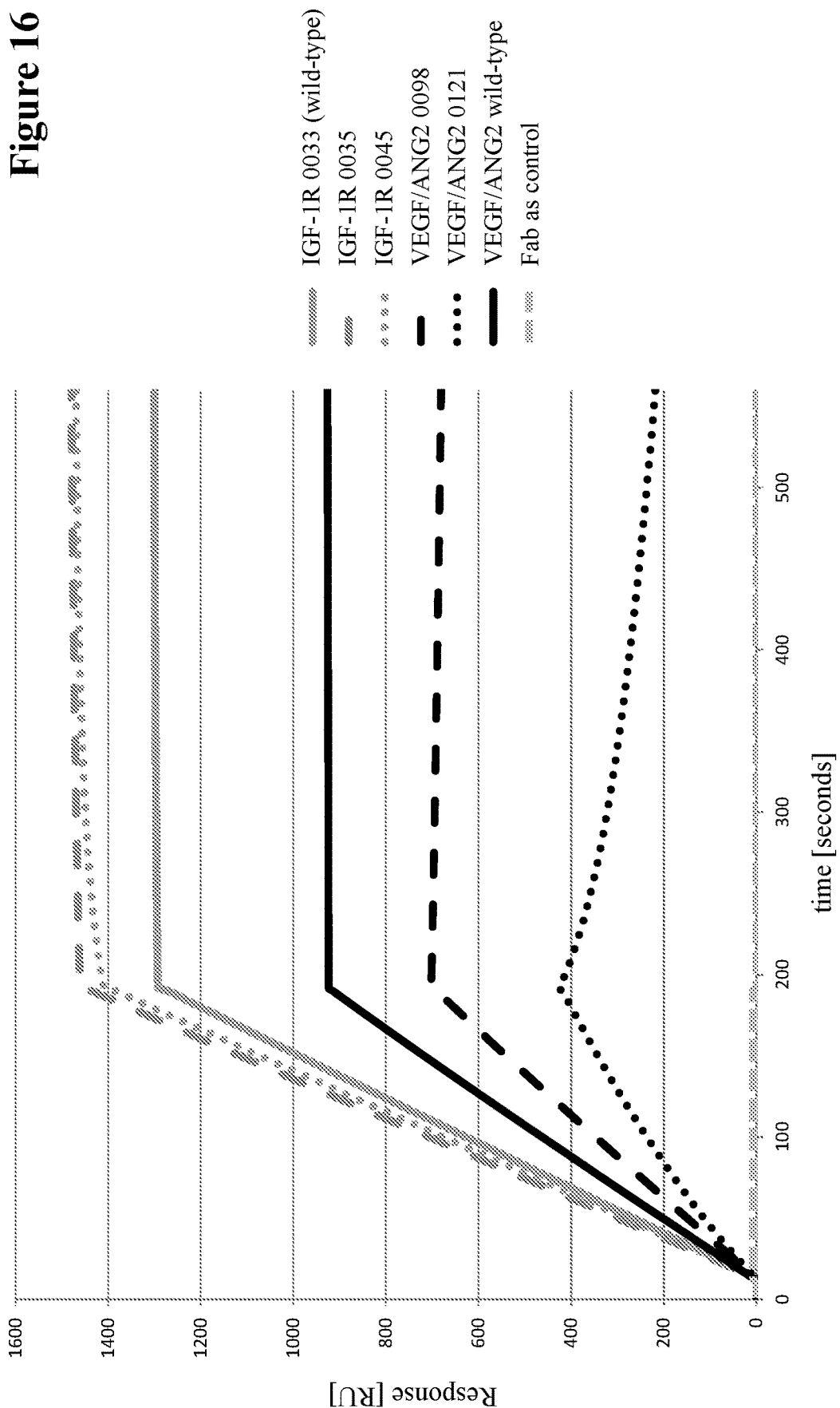
FIG. 16: Binding of different anti-VEGF/ANG2 antibody and anti-IGF-1R antibody mutants to immobilized protein A (SPR).

It has been found that by introducing the mutation Y436A, the binding to Staphylococcal protein A (SPA) can be increased. This is advantageous e.g. if additional mutations are introduced that reduce the binding to SPA, such as e.g. I253A and H310A or H310A and H435A (see FIG. 15).

The dimeric polypeptide as reported herein is produced by recombinant means. Thus, one aspect of the current invention is a nucleic acid encoding the dimeric polypeptide as reported herein and a further aspect is a cell comprising the nucleic acid encoding the dimeric polypeptide as reported herein. Methods for recombinant production are widely known in the state of the art and comprise protein expression in prokaryotic and eukaryotic cells with subsequent isolation of the dimeric polypeptide and usually purification to a pharmaceutically acceptable purity. For the expression of the dimeric polypeptides as aforementioned in a host cell, nucleic acids encoding the respective first and second polypeptides are inserted into expression vectors by standard methods. Expression is performed in appropriate prokaryotic or eukaryotic host cells like CHO cells, NSO cells, SP2/0 cells, HEK293 cells, COS cells, PER.C6 cells, yeast, or E. coli cells, and the dimeric polypeptide is recovered from the cells (cultivation supernatant or cells after lysis).

General methods for recombinant production of antibodies are well-known in the state of the art and described, for example, in the review articles of Makrides, S.C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

Accordingly, one aspect as reported herein is a method for the production of a dimeric polypeptide as reported herein, comprising the steps of a) transforming a host cell with one or more vectors comprising nucleic acid molecules encoding a dimeric polypeptide as reported herein, b) culturing the host cell under conditions that allow synthesis of the dimeric polypeptide, and c) recovering the dimeric polypeptide from the culture and thereby producing the dimeric polypeptide.

In one embodiment the recovering step under c) includes the use of an immunoglobulin Fc-region specific capture reagent. In one embodiment this Fc-region specific capture reagent is used in a bind-and-elute-mode). Examples of such Fc-region specific capture reagents are e.g. Staphylococcus protein A-based affinity chromatography columns, which are based on a highly rigid agarose base matrix that allows high flow rates and low back pressure at large scale. They feature a ligand that binds to the dimeric polypeptide, i.e. its Fc-region. The ligands are attached to the matrix via a long hydrophilic spacer arm to make it easily available for binding to the target molecule.

The dimeric polypeptides as reported herein are suitably separated from the culture medium by conventional immunoglobulin purification procedures such as, for example, protein A-Sepharose, hydroxylapatite chromatography, gel electrophoresis, dialysis, or affinity chromatography. B-cells or hybridoma cells can serve as a source of DNA and RNA encoding the dimeric polypeptide. DNA and RNA encoding the monoclonal antibodies are readily isolated and sequenced using conventional procedures. Once isolated, the DNA may be inserted into expression vectors, which are then transfected into host cells such as HEK 293 cells, CHO cells, or myeloma cells that do not otherwise produce dimeric polypeptides, to obtain the synthesis of recombinant monoclonal dimeric polypeptides in the host cells.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art (see Ausubel, F., et al., ed. Current Protocols in Molecular Biology, Greene Publishing and Wiley Interscience, New York (1987)). Different methods are well established and in widespread use for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

One aspect of the invention is a pharmaceutical formulation comprising a dimeric polypeptide or an antibody as reported herein. Another aspect of the invention is the use of a dimeric polypeptide or an antibody as reported herein for the manufacture of a pharmaceutical formulation. A further aspect of the invention is a method for the manufacture of a pharmaceutical formulation comprising a dimeric polypeptide or an antibody as reported herein. In another aspect, the present invention provides a formulation, e.g. a pharmaceutical formulation, containing a dimeric polypeptide or an antibody as reported herein, formulated together with a pharmaceutical carrier.

A formulation as reported herein can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

Many possible modes of delivery can be used, including, but not limited to intraocular application or topical application. In one embodiment the application is intraocular and includes, but is not limited to, subconjunctval injection, intracanieral injection, injection into the anterior chamber via the termporai limbus, intrastromal injection, intracorneal injection, subretinal injection, aqueous humor injection, subtenon injection or sustained delivery device, intravitreal injection (e.g., front, mid or back vitreal injection). In one embodiment the application is topical and includes, but is not limited to, eye drops to the cornea.

In one embodiment the dimeric polypeptide as reported herein or the pharmaceutical formulation as reported herein is administered via intravitreal application, e.g. via intravitreal injection. This can be performed in accordance with standard procedures known in the art (see, e.g., Ritter et al., J. Clin. Invest. 116 (2006) 3266-3276; Russelakis-Carneiro et al., Neuropathol. Appl. Neurobiol. 25 (1999) 196-206; and Wray et al., Arch. Neurol. 33 (1976) 183-185).

In some embodiments, therapeutic kits of the invention can contain one or more doses of a dimeric polypeptide as reported herein present in a pharmaceutical formulation as described herein, a suitable device for intravitreal injection of the pharmaceutical formulation, and an instruction detailing suitable subjects and protocols for carrying out the injection. In these embodiments, the formulations are typically administered to the subject in need of treatment via intravitreal injection. This can be performed in accordance with standard procedures known in the art. See, e.g., Ritter et al., J. Clin. Invest. 116 (2006) 3266-3276; Russelakis-Carneiro et al., Neuropathol. Appl. Neurobiol. 25 (1999) 196-206; and Wray et al., Arch. Neurol. 33 (1976) 183-185.

The formulation may also contain adjuvants such as preservatives, wetting agents, emulsifying agents and dispersing agents. Prevention of the presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the formulations. In addition, prolonged absorption of the injectable pharmaceutical form may be brought about by the inclusion of agents which delay absorption such as aluminum monostearate and gelatin.

Regardless of the route of administration selected, the compounds as reported herein, which may be used in a suitable hydrated form, and/or the pharmaceutical formulations as reported herein, are formulated into pharmaceutically acceptable dosage forms by conventional methods known to those of skill in the art.

Actual dosage levels of the active ingredients in the pharmaceutical formulation as reported herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health, and prior medical history of the patient being treated, and like factors well known in the medical arts.

The formulation must be sterile and fluid to the extent that the formulation is deliverable by syringe. In addition to water, the carrier in one preferred embodiment is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The formulation can comprise an ophthalmic depot formulation comprising an active agent for subconjunctival administration. The ophthalmic depot formulation comprises microparticles of essentially pure active agent, e.g., a dimeric polypeptide as reported herein. The microparticles comprising a dimeric polypeptide as reported herein can be embedded in a biocompatible pharmaceutically acceptable polymer or a lipid encapsulating agent. The depot formulations may be adapted to release all, or substantially all, the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g. by gelifying or precipitating.

Another aspect of the invention is a dimeric polypeptide or an antibody as reported herein for use in the treatment of ocular vascular diseases.

One embodiment of the invention is a dimeric polypeptide or an antibody as reported herein for use in the treatment of ocular vascular diseases.

Another aspect of the invention is the pharmaceutical formulation for use in the treatment of ocular vascular diseases.

Another aspect of the invention is the use of a dimeric polypeptide or an antibody as reported herein for the manufacture of a medicament for the treatment of ocular vascular disease.

Another aspect of the invention is method of treating a patient suffering from ocular vascular diseases by administering a dimeric polypeptide or an antibody as reported herein to a patient in the need of such treatment.

It is herewith expressly stated that the term "comprising" as used herein comprises the term "consisting of." Thus, all aspects and embodiments that contain the term "comprising" are likewise disclosed with the term "consisting of"

D. Modifications

In a further aspect, a dimeric polypeptide according to any of the above embodiments may incorporate any of the features, singly or in combination, as described in Sections 1-6 below:

1. Antibody Affinity

In one embodiment, Kd is measured using a BIACORE® surface plasmon resonance assay. For example, an assay using a BIACORE®-2000 or a BIACORE®-3000 (GE Healthcare Inc., Piscataway, N.J.) is performed at 25° C. with immobilized binding partner CM5 chips at ~10 response units (RU). In one embodiment, carboxymethylated dextran biosensor chips (CM5, GE Healthcare Inc.) are activated with N-ethyl-N'-(3-dimethylaminopropyl)-carbodiimide hydrochloride (EDC) and N-hydroxysuccinimide (NHS) according to the supplier's instructions. The binding partner is diluted with 10 mM sodium acetate, pH 4.8, to 5 μg/mL (~0.2 μM) before injection at a flow rate of 5 μl/minute to achieve approximately 10 response units (RU) of coupled binding partner. Following the injection of the binding partner, 1 M ethanolamine is injected to block non-reacted groups. For kinetics measurements, two-fold serial dilutions of the dimeric polypeptide containing fusion polypeptide or antibody (0.78 nM to 500 nM) are injected in PBS with 0.05% polysorbate 20 (TWEEN-20™) surfactant (PBST) at 25° C. at a flow rate of approximately 25 μL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen, Y. et al., J. Mol. Biol. 293 (1999) 865-881). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Chimeric and Humanized Antibodies

In certain embodiments, a dimeric polypeptide as reported herein is a chimeric antibody. Certain chimeric antibodies are described, e.g., in U.S. Pat. No. 4,816,567; and Morrison, S. L., et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al., Proc. Natl. Acad. Sci. USA 86 (1989) 10029-10033; U.S. Pat. Nos. 5,821,337; 7,527,791; 6,982,321; and 7,087,409; Kashmiri, S. V., et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); Osbourn, J. et al., Methods 36 (2005) 61-68; and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308; framework regions derived from the consensus sequence of human antibodies of a particular subgroup of light or heavy chain variable regions (see, e.g., Carter, P., et al., Proc. Natl. Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

3. Human Antibodies

In certain embodiments, a dimeric polypeptide as reported herein is a human antibody. Human antibodies can be produced using various techniques known in the art. Human antibodies are described generally in van Dijk, M. A. and van de Winkel, J. G., Curr. Opin. Pharmacol. 5 (2001) 368-374, and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol.133 (1984) 3001-3005; Brodeur, B. R., et al., Monoclonal Antibody Production Techniques and Applications, Marcel Dekker, Inc., New York (1987), pp. 51-63; and Boerner, P., et al., J. Immunol. 147 (1991) 86-95). Human antibodies generated via human B-cell hybridoma technology are also described in Li, J., et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines); Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937;and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Antibodies

In certain embodiments a dimeric polypeptide as reported herein is a library-derived antibody. Library-derived antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G., et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D., et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

5. Multispecific Antibodies

In certain embodiments, a dimeric polypeptide as reported herein is a multispecific antibody, e.g. a bispecific antibody. Multispecific antibodies are monoclonal antibodies that have binding specificities for at least two different sites. In certain embodiments, one of the binding specificities is for a first antigen and the other is for a different, second antigen. In certain embodiments, bispecific antibodies may bind to two different epitopes of the same antigen. Bispecific antibodies may also be used to localize cytotoxic agents to cells which express at least one of the antigens. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (scFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

6. Antibody Variants

In certain embodiments, a dimeric polypeptide as reported herein is an antibody. In further embodiments amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table below under the heading of "preferred substitutions." More substantial changes are provided in the following Table under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H.R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two, or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen can be used. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region. See, e.g., Wright, A. and Morrison, S.L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y., et al., Biotechnol. Bioeng. 94 (2006) 680-688; and WO 2003/085107).

Antibody variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more further amino acid modifications may be introduced into a dimeric polypeptide as reported herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution/mutation) at one or more amino acid positions.

In certain embodiments, the invention contemplates a dimeric polypeptide that possesses some but not all effector functions, which make it a desirable candidate for applications in which the half-life of the dimeric polypeptide in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the dimeric polypeptide antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest are described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assay methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the dimeric polypeptide is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006) 1759-1769).

Dimeric polypeptides with reduced effector function include those with substitution of one or more of Fc-region residues 238, 265, 269, 270, 297, 327, and 329 (U.S. Pat. No. 6,737,056). Such Fc-region variants include Fc-regions with substitutions at two or more of amino acid positions 265, 269, 270, 297, and 327, including the so-called "DANA" Fc-region mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R.L. et al., J. Biol. Chem. 276 (2001) 6591-6604)

In certain embodiments, a dimeric polypeptide variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593; and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc-region variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered dimeric polypeptides, e.g., in analogy to "thioMAbs," in which one or more residues of an antibody are substituted with cysteine residues. In particular embodiments, the substituted residues occur at accessible sites of the dimeric polypeptide. By substituting those residues with cysteine, reactive thiol groups are thereby positioned at accessible sites of the dimeric polypeptide and may be used to conjugate the dimeric polypeptide to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered dimeric polypeptides may be generated as described, e.g., in U.S. Pat. No. 7,521,541.

e) Derivatives

In certain embodiments, a dimeric polypeptide as reported herein may be further modified to contain additional non-proteinaceous moieties that are known in the art and readily available. The moieties suitable for derivatization of the dimeric polypeptide include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or non-branched. The number of polymers attached to the dimeric polypeptide may vary, and if more than one polymer is attached, they can be the same or different molecules. In general, the number and/or type of polymers used for derivatization can be determined based on considerations including, but not limited to, the particular properties or functions of the dimeric polypeptide to be improved, whether the dimeric polypeptide derivative will be used in a therapy under defined conditions, etc.

In another embodiment, conjugates of a dimeric polypeptide as reported herein and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the dimeric polypeptide-non-proteinaceous moiety are killed.

f) Heterodimerization

There exist several approaches for CH3-modifications to enforce the heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the first CH3 domain and the second CH3 domains are both engineered in a complementary manner so that each CH3 domain (or the heavy chain comprising it) can no longer homodimerize with itself but is forced to heterodimerize with the complementary-engineered other CH3 domain (so that the first and second CH3 domain heterodimerize and no homodimers between the two first or the two second CH3 domains are formed). These different approaches for improved heavy chain heterodimerization are contemplated as different alternatives in combination with the heavy—light chain modifications (VH and VL exchange/replacement in one binding arm and the introduction of substitutions of charged amino acids with opposite charges in the CH1/CL interface) in the multispecific antibodies according to the invention which reduce light chain mispairing an Bence-Jones type side products.

In one preferred embodiment of the invention (in case the multispecific antibody comprises CH3 domains in the heavy chains) the CH3 domains of said multispecific antibody according to the invention can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681; WO 98/050431. In this method the interaction surfaces of the two CH3 domains are altered to increase the heterodimerization of both heavy chains containing these two CH3 domains. Each of the two CH3 domains (of the two heavy chains) can be the "knob", while the other is the "hole." The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

Thus in one embodiment of the invention said multispecific antibody (comprises a CH3 domain in each heavy chain and) is further characterized in that the first CH3 domain of the first heavy chain of the antibody under a) and the second CH3 domain of the second heavy chain of the antibody under b) each meet at an interface which comprises an original interface between the antibody CH3 domains.

wherein said interface is altered to promote the formation of the multispecific antibody, wherein the alteration is characterized in that:

i) the CH3 domain of one heavy chain is altered, so that within the original interface of the CH3 domain of one heavy chain that meets the original interface of the CH3 domain of the other heavy chain within the multispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and ii) the CH3 domain of the other heavy chain is altered, so that within the original interface of the second CH3 domain that meets the original interface of the first CH3 domain within the multispecific antibody an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one preferred embodiment, said multispecific antibody comprises a amino acid T366W mutation in the first CH3 domain of the "knobs chain" and amino acid T366S, L368A, Y407V mutations in the second CH3 domain of the "hole chain." An additional interchain disulfide bridge between the CH3 domains can also be used (Merchant, A. M., et al., Nature Biotech. 16 (1998) 677-681) e.g. by introducing an amino acid Y349C mutation into the CH3 domain of the "hole chain" and an amino acid E356C mutation or an amino acid S354C mutation into the CH3 domain of the "knobs chain."

In one preferred embodiment, said multispecific antibody (which comprises a CH3 domain in each heavy chain) comprises amino acid S354C, T366W mutations in one of the two CH3 domains and amino acid Y349C, T366S, L368A, Y407V mutations in the other of the two CH3 domains (the additional amino acid S354C mutation in one CH3 domain and the additional amino acid Y349C mutation in the other CH3 domain forming an interchain disulfide bridge) (numbering according to Kabat).

Other techniques for CH3-modifications to force the heterodimerization are contemplated as alternatives of the invention and described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1 870 459A1, can be used alternatively. This approach is based on the introduction of substitutions/mutations of charged amino acids with the opposite charge at specific amino acid positions of the CH3/CH3 domain interface between both heavy chains. One preferred embodiment for said multispecific antibody are amino acid R409D; K370E mutations in the first CH3 domain of the multispecific antibody, and amino acid D399K, E357K mutations in the second CH3 domain of the multispecific antibody (numbering according to Kabat).

In another embodiment said multispecific antibody comprises an amino acid T366W mutation in the CH3 domain of the "knobs chain" and amino acid T366S, L368A, Y407V mutations in the CH3 domain of the "hole chain" and additionally, amino acid R409D; K370E mutations in the CH3 domain of the "knobs chain" and amino acid D399K; E357K mutations in the CH3 domain of the "hole chain."

In another embodiment said multispecific antibody comprises amino acid S354C, T366W mutations in one of the two CH3 domains, and amino acid Y349C, T366S, L368A, Y407V mutations in the other of the two CH3 domains, or said multispecific antibody comprises amino acid Y349C, T366W mutations in one of the two CH3 domains, and amino acid S354C, T366S, L368A, Y407V mutations in the other of the two CH3 domains, and additionally amino acid R409D; K370E mutations in the CH3 domain of the "knobs chain" and amino acid D399K; E357K mutations in the CH3 domain of the "hole chain."

In one embodiment the heterodimerization approach described in WO2013/157953 can be used. In one embodiment a first CH3 domain comprises amino acid T366K mutation and a second CH3 domain polypeptide comprises amino acid L351D mutation. In a further embodiment the first CH3 domain further comprises an amino acid L351K mutation. In a further embodiment the second CH3 domain further comprises an amino acid mutation selected from Y349E, Y349D, and L368E (preferably L368E).

In one embodiment the heterodimerization approach described in WO2012/058768 can be used. In one embodiment a first CH3 domain comprises amino acid L351Y, Y407A mutations and a second CH3 domain comprises amino acid T366A, K409F mutations. In a further embodiment the second CH3 domain comprises a further amino acid mutation at position T411, D399, S400, F405, N390, or K392 e.g. selected from a) T411 N, T411R, T411Q, T411 K, T411D, T411E or T411W, b) D399R, D399W, D399Y or D399K, c S400E, S400D, S400R, or S400K F4051, F405M, F405T, F4055, F405V or F405W N390R, N390K or N390D K392V, K392M, K392R, K392L, K392F or K392E. In a further embodiment a first CH3 domain comprises amino acid L351Y, Y407A mutations and a second CH3 domain comprises amino acid T366V, K409F mutations. In a further embodiment a first CH3 domain comprises amino acid Y407A mutations and a second CH3 domain comprises amino acid T366A, K409F mutations. In a further embodiment the second CH3 domain comprises a further amino acid K392E, T411E, D399R and S400R mutations.

In one embodiment the heterodimerization approach described in WO2011/143545 can be used, e.g. with the amino acid modification at a position selected from the group consisting of 368 and 409.

In one embodiment the heterodimerization approach described in WO2011/090762 which also uses the knobs-into-holes technology described above can be used. In one embodiment a first CH3 domain comprises amino acid T366W mutations and a second CH3 domain comprises amino acid Y407A mutations. In one embodiment a first CH3 domain comprises amino acid T366Y mutations and a second CH3 domain comprises amino acid Y407T mutations.

In one embodiment the multispecific antibody is of IgG2 isotype and the heterodimerization approach described in WO2010/129304 can be used alternatively.

In one embodiment the heterodimerization approach described in WO2009/089004 can be used alternatively. In one embodiment a first CH3 domain comprises amino acid substitution of K392 or N392 with a negative-charged amino acid (e.g. glutamic acid (E), or aspartic acid (D), preferably K392D or N392D) and a second CH3 domain comprises amino acid substitution of D399, E356, D356, or E357 with a positive-charged amino acid (e.g. Lysine (K) or arginine (R), preferably D399K, E356K, D356K, or E357K and more preferably D399K and E356K. In a further embodiment the first CH3 domain further comprises an amino acid substitution of K409 or R409 with a negative-charged amino acid (e.g. glutamic acid (E), or aspartic acid (D), preferably K409D or R409D. In a further embodiment the first CH3 domain further or alternatively comprises amino acid substitution of K439 and/or K370 with a negative-charged amino acid (e.g. glutamic acid (E), or aspartic acid (D)).

In one embodiment the heterodimerization approach described in WO 2007/147901 can be used. In one embodiment a first CH3 domain comprises amino acid K253E, D282K, and K322D mutations and a second CH3 domain comprises amino acid D239K, E240K, and K292D mutations.

In one embodiment the heterodimerization approach described in WO2007/110205 can be used alternatively.

E. Recombinant Methods and Compositions

Antibodies may be produced using recombinant methods and compositions, e.g., as described in U.S. Pat. No. 4,816,567. In one embodiment, isolated nucleic acid(s) encoding a dimeric polypeptide as reported herein is (are) provided. Such nucleic acid may encode an amino acid sequence comprising the first polypeptide and/or an amino acid sequence comprising the second polypeptide of the dimeric polypeptide. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the first polypeptide of the dimeric polypeptide and an amino acid sequence comprising the second polypeptide of the dimeric polypeptide, or (2) a first vector comprising a nucleic acid that encodes an amino acid sequence comprising the first polypeptide of the dimeric polypeptide and a second vector comprising a nucleic acid that encodes an amino acid sequence comprising the second polypeptide of the dimeric polypeptide. In one embodiment, the host cell is eukaryotic, e.g. a Chinese Hamster Ovary (CHO) cell or lymphoid cell (e.g., Y0, NS0, Sp20 cell). In one embodiment, a method of making a dimeric polypeptide as reported herein is provided, wherein the method comprises culturing a host cell comprising a nucleic acid encoding the dimeric polypeptide, as provided above, under conditions suitable for expression of the dimeric polypeptide, and optionally recovering the antibody from the host cell (or host cell culture medium).

For recombinant production of a dimeric polypeptide as reported herein, nucleic acid encoding a dimeric polypeptide, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the variant Fc-region polypeptide(s) and the heavy and light chains of the antibody).

Suitable host cells for cloning or expression of dimeric polypeptide-encoding vectors include prokaryotic or eukaryotic cells described herein. For example, dimeric polypeptides may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B.K.C. (ed.), Humana Press, Totowa, N.J. (2003), pp. 245-254, describing expression of antibody fragments in E. colt). After expression, the dimeric polypeptide may be isolated from the bacterial cell paste in a soluble fraction and can be further purified.

In addition to prokaryotes, eukaryotic microbes such as filamentous fungi or yeast are suitable cloning or expression hosts for dimeric polypeptide-encoding vectors, including fungi and yeast strains whose glycosylation pathways have been "humanized" resulting in the production of a dimeric polypeptide with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of a glycosylated dimeric polypeptide are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (HEK293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TM cells, as described, e.g., in Mather, J.P., et al., Annals N.Y. Acad. Sci. 383 (1982) 44-68; MRC 5 cells; and FS4 cells. Other useful mammalian host cell lines include Chinese hamster ovary (CHO) cells, including DHFR$^-$ CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B.K.C. (ed.), Humana Press, Totowa, N.J. (2004), pp. 255-268.

F. Combination Treatment

In certain embodiments the dimeric polypeptide as reported herein or pharmaceutical formulation as reported herein is administered alone (without an additional therapeutic agent) for the treatment of one or more ocular vascular diseases described herein.

In other embodiments the dimeric polypeptide antibody or pharmaceutical formulation as reported herein is administered in combination with one or more additional therapeutic agents or methods for the treatment of one or more vascular eye diseases described herein.

In other embodiments, the dimeric polypeptide or pharmaceutical formulation as reported herein is formulated in combination with one or more additional therapeutic agents and administered for the treatment of one or more vascular eye diseases described herein.

In certain embodiments, the combination treatments provided herein include that the dimeric polypeptide or pharmaceutical formulation as reported herein is administered sequentially with one or more additional therapeutic agents for the treatment of one or more ocular vascular diseases described herein.

The additional therapeutic agents include, but are not limited to, Tryptophanyl-tRNA synthetase (TrpRS), EyeOOl (anti-VEGF PEGylated aptamer), squalamine, RETAANE™ (anecortave acetate for depot suspension; Alcon, Inc.), Combretastatin A4 Prodrug (CA4P), MACU-GEN™, MIFEPREX™ (mifepristone-ru486), subtenon triamcinolone acetonide, intravitreal crystalline triamcinolone acetonide, Prinomastat (AG3340-synthetic matrix metalloproteinase inhibitor, Pfizer), fluocinolone acetonide (including fluocinolone intraocular implant, Bausch & Lomb/Control Delivery Systems), VEGFR inhibitors (Sugen), VEGF-Trap (Regeneron/Aventis), VEGF receptor tyrosine kinase inhibitors such as 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787) and SU1 1248 (sunitinib), linomide, and inhibitors of integrin vβ3 function and angiostatin.

Other pharmaceutical therapies that can be used in combination with the dimeric polypeptide or pharmaceutical formulation as reported herein, including, but not limited to, VISUDYNE™ with use of a non-thermal laser, PKC 412, Endovion (NeuroSearch A/S), neurotrophic factors, including by way of example Glial Derived Neurotrophic Factor and Ciliary Neurotrophic Factor, diatazem, dorzolamide, Phototrop, 9-cis-retinal eye medication (including Echo Therapy) including phospholine iodide or echothiophate or carbonic anhydrase inhibitors, AE-941 (AEterna Laboratories, Inc.), Sirna-027 (Sima Therapeutics, Inc.), pegaptanib (NeXstar Pharmaceuticals/Gilead Sciences), neurotrophins (including, by way of example only, NT-4/5, Genentech), Candy (Acuity Pharmaceuticals), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc.), ATX-S10 (Hamamatsu Photonics), TGF-beta 2 (Genzyme/Celtrix), tyrosine kinase inhibitors (Allergan, SUGEN, Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), cyclosporin A, Timited retinal translocation, photodynamic therapy, (including, by way of example only, receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; motexafin lutetium, Pharmacyclics, Inc.), antisense oligonucleotides (including, by way of example, products tested by Novagali Pharma SA and ISIS-13650, Isis Pharmaceuticals), laser photocoagulation, drusen lasering, macular hole surgery, macular translocation surgery, implantable miniature telescopes, Phi-Motion Angiography (also known as Micro-Laser Therapy and Feeder Vessel Treatment), Proton Beam Therapy, microstimulation therapy, Retinal Detachment and Vitreous Surgery, Scleral Buckle, Submacular Surgery, Transpupillary Thermotherapy, Photosystem I therapy, use of RNA interference (RNAi), extracorporeal rheopheresis (also known as membrane differential filtration and Rheotherapy), microchip implantation, stem cell therapy, gene replacement therapy, ribozyme gene therapy (including gene therapy for hypoxia response element, Oxford Biomedica; Lentipak, Genetix; PDEF gene therapy, GenVec), photoreceptor/retinal cells transplantation (including transplantable retinal epithelial cells, Diacrin, Inc.; retinal cell transplant, Cell Genesys, Inc.), and acupuncture.

Any anti-angiogenic agent can be used in combination with the dimeric polypeptide or pharmaceutical formulation as reported herein, including, but not limited to, those listed by Carmeliet and Jain (Nature 407 (2000) 249-257). In certain embodiments, the anti-angiogenic agent is another VEGF antagonist or a VEGF receptor antagonist such as VEGF variants, soluble VEGF receptor fragments, aptamers capable of blocking VEGF or VEGFR, neutralizing anti-VEGFR antibodies, low molecular weight inhibitors of VEGFR tyrosine kinases and any combinations thereof and these include anti-VEGF aptamers (e.g. Pegaptanib), soluble recombinant decoy receptors (e.g. VEGF Trap). In certain embodiments, the anti-angiogenic agent is include corticosteroids, angiostatic steroids, anecortave acetate, angiostatin, endostatin, small interfering RNA's decreasing expression of VEGFR or VEGF ligand, post-VEGFR blockade with tyrosine kinase inhibitors, MMP inhibitors, IGFBP3, SDF-1 blockers, PEDF, gamma-secretase, Delta-like ligand 4, integrin antagonists, HIF-1 alpha blockade, protein kinase CK2 blockade, and inhibition of stem cell (i.e. endothelial progenitor cell) homing to the site of neovascularization using vascular endothelial cadherin (CD-144) and stromal derived factor (SDF)-I antibodies. Small molecule RTK inhibitors targeting VEGF receptors including PTK787 can also be used. Agents that have activity against neovascularization that are not necessarily anti-VEGF compounds can also be used and include anti-inflammatory drugs, m-Tor inhibitors, rapamycin, everolismus, temsirolismus, cyclospohne, anti-TNF agents, anti-complement agents, and non-steroidal anti-inflammatory agents. Agents that are neuroprotective and can potentially reduce the progression of dry macular degeneration can also be used, such as the class of drugs called the "neurosteroids." These include drugs such as dehydroepiandrosterone (DHEA) (Brand names: Prastera (R) and Fidelin(R)), dehydroepiandrosterone sulfate, and pregnenolone sulfate. Any AMD (age-related macular degeneration) therapeutic agent can be used in combination with the dimeric polypeptide or pharmaceutical formulation as reported herein, including but not limited to verteporfin in combination with PDT, pegaptanib sodium, zinc, or an antioxidant(s), alone or in any combination.

G. Pharmaceutical Formulations

Pharmaceutical formulations of a dimeric polypeptide as reported herein are prepared by mixing such dimeric polypeptide having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

H. Therapeutic Methods and Compositions

Any of the dimeric polypeptides as reported herein may be used in therapeutic methods.

In one aspect, a dimeric polypeptide as reported herein for use as a medicament is provided. In further aspects, a dimeric polypeptide for use in treating ocular vascular diseases is provided. In certain embodiments, a dimeric polypeptide for use in a method of treatment is provided. In certain embodiments, the invention provides a dimeric polypeptide for use in a method of treating an individual having an ocular vascular disease comprising administering to the individual an effective amount of the dimeric polypeptide as reported herein. In one such embodiment, the method further comprises administering to the individual an effective amount of at least one additional therapeutic agent, e.g., as described above in section D. In further embodiments, the invention provides a dimeric polypeptide for use in inhibiting angiogenesis in the eye. In certain embodiments, the invention provides a dimeric polypeptide for use in a method of inhibiting angiogenesis in an individual comprising administering to the individual an effective amount of the dimeric polypeptide to inhibit angiogenesis. An "individual" according to any of the above embodiments is in one preferred embodiment a human.

In a further aspect, the invention provides for the use of a dimeric polypeptide in the manufacture or preparation of a medicament. In one embodiment, the medicament is for treatment of an ocular vascular disease. In a further embodiment, the medicament is for use in a method of treating an ocular vascular disease comprising administering to an individual having an ocular vascular disease an effective amount of the medicament. In one such embodiment, the method further comprises administering to the individual an effective amount of at least one additional therapeutic agent, e.g., as described above. In a further embodiment, the medicament is for inhibiting angiogenesis. In a further embodiment, the medicament is for use in a method of inhibiting angiogenesis in an individual comprising administering to the individual an amount effective of the medicament to inhibit angiogenesis. An "individual" according to any of the above embodiments may be a human.

In a further aspect, the invention provides a method for treating a vascular eye disease. In one embodiment, the method comprises administering to an individual having such a vascular eye disease an effective amount of a dimeric polypeptide as reported herein. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis in the eye in an individual. In one embodiment, the method comprises administering to the individual an effective amount of a dimeric polypeptide as reported herein to inhibit angiogenesis. In one embodiment, an "individual" is a human.

In a further aspect, the invention provides pharmaceutical formulations comprising any of the dimeric polypeptides as reported herein, e.g., for use in any of the above therapeutic methods. In one embodiment, a pharmaceutical formulation comprises any of the dimeric polypeptides as reported herein and a pharmaceutically acceptable carrier. In another embodiment, a pharmaceutical formulation comprises any of the dimeric polypeptides as reported herein and at least one additional therapeutic agent, e.g., as described below.

A dimeric polypeptide as reported herein can be used either alone or in combination with other agents in a therapy. For instance, a dimeric polypeptide as reported herein may be co-administered with at least one additional therapeutic agent A dimeric polypeptide as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Dimeric polypeptides as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The dimeric polypeptide need not be, but is optionally formulated with one or more agents currently used to prevent or treat the disorder in question. The effective amount of such other agents depends on the amount of dimeric polypeptide present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a dimeric polypeptide as reported herein (when used alone or in combination with one or more other additional therapeutic agents) will depend on the type of disease to be treated, the type of dimeric polypeptide, the severity and course of the disease, whether the dimeric polypeptide is administered for preventive or therapeutic purposes, previous therapy, the patient's clinical history and response to the dimeric polypeptide, and the discretion of the attending physician. The dimeric polypeptide is suitably administered to the patient at one time or over a series of treatments. Depending on the type and severity of the disease, about 1 µg/kg to 15 mg/kg (e.g. 0.5 mg/kg-10 mg/kg) of dimeric polypeptide can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the dimeric polypeptide would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the dimeric polypeptide). An initial higher loading dose, followed by one or more lower doses may be administered. The progress of this therapy is easily monitored by conventional techniques and assays.

III. ARTICLES OF MANUFACTURE

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself, or combined with another composition effective for treating, preventing and/or diagnosing the condition and may have a sterile access port (for example the container may be an intravenous solution bag or a vial having a stopper pierceable by a hypodermic injection needle). At least one active agent in the composition is a dimeric polypeptide as reported herein. The label or package insert indicates that the composition is used for treating the condition of choice. Moreover, the article of manufacture may comprise (a) a first container with a composition contained therein, wherein the composition comprises a dimeric polypeptide as reported herein; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate as reported herein in place of or in addition to a dimeric polypeptide as reported herein.

IV. SPECIFIC EMBODIMENTS

1. A dimeric polypeptide comprising
    a first polypeptide and a second polypeptide each comprising in N-terminal to C-terminal direction at least a portion of an immunoglobulin hinge region, which comprises one or more cysteine residues, an immunoglobulin CH2-domain and an immunoglobulin CH3-domain,
    wherein
        i) the first and the second polypeptide comprise the mutations H310A, H433A and Y436A, or
        ii) the first and the second polypeptide comprise the mutations L251D, L314D and L432D, or
        iii) the first and the second polypeptide comprise the mutations L251S, L314S and L432S, or
        iv) the first polypeptide comprises the mutations I253A, H310A and H435A and the second polypeptide comprises the mutations H310A, H433A and Y436A, or
        v) the first polypeptide comprises the mutations I253A, H310A and H435A and the second polypeptide comprises the mutations L251D, L314D and L432D, or
        vi) the first polypeptide comprises the mutations I253A, H310A and H435A and the second polypeptide comprises the mutations L251S, L314S and L432S.
2. The dimeric polypeptide according to item 1, characterized in that the dimeric polypeptide does not specifically bind to the human FcRn and does specifically bind to Staphylococcal protein A.
3. The dimeric polypeptide according to any one of items 1 to 2, characterized in that the dimeric polypeptide is a homodimeric polypeptide.
4. The dimeric polypeptide according to any one of items 1 to 2, characterized in that the dimeric polypeptide is a heterodimeric polypeptide.
5. The dimeric polypeptide according to any one of items 1 to 4, characterized in that i) the first polypeptide further comprises the mutations Y349C, T366S, L368A and Y407V and the second polypeptide comprises the mutations S354C and T366W, or ii) the first polypeptide further comprises the mutations S354C, T366S, L368A and Y407V and the second polypeptide comprises the mutations Y349C and T366W.
6. The dimeric polypeptide according to any one of items 1 to 5, characterized in that the immunoglobulin hinge region, the immunoglobulin CH2-domain and the immunoglobulin CH3-domain are of the human IgG1 subclass.
7. The dimeric polypeptide according to any one of items 1 to 6, characterized in that the first polypeptide and the second polypeptide further comprise the mutations L234A and L235A.
8. The dimeric polypeptide according to any one of items 1 to 5, characterized in that the immunoglobulin hinge region, the immunoglobulin CH2-domain and the immunoglobulin CH3-domain are of the human IgG2 subclass optionally with the mutations V234A, G237A, P238S, H268A, V309L, A330S and P331S.
9. The dimeric polypeptide according to any one of items 1 to 5, characterized in that the immunoglobulin hinge region, the immunoglobulin CH2-domain and the immunoglobulin CH3-domain are of the human IgG4 subclass.
10. The dimeric polypeptide according to any one of items 1 to 5 and 9, characterized in that the first polypeptide and the second polypeptide further comprise the mutations S228P and L235E.
11. The dimeric polypeptide according to any one of items 1 to 10, characterized in that the first polypeptide and the second polypeptide further comprise the mutation P329G.
12. The dimeric polypeptide according to any one of items 1 to 11, characterized in that the dimeric polypeptide is an Fc-region fusion polypeptide.
13. The dimeric polypeptide according to any one of items 1 to 11, characterized in that the dimeric polypeptide is an (full length) antibody.
14. The dimeric polypeptide according to any one of items 1 to 11 and 13, characterized in that the (full length) antibody is a monospecific antibody.
15. The dimeric polypeptide according to any one of items 1 to 11 and 13 to 14, characterized in that the monospecific antibody is a monovalent monospecific antibody.
16. The dimeric polypeptide according to any one of items 1 to 11 and 13 to 15, characterized in that the monospecific antibody is a bivalent monospecific antibody.
17. The dimeric polypeptide according to any one of items 1 to 11 and 13, characterized in that the (full length) antibody is a bispecific antibody.
18. The dimeric polypeptide according to any one of items 1 to 11 and 13 and 17, characterized in that the bispecific antibody is a bivalent bispecific antibody.
19. The dimeric polypeptide according to any one of items 1 to 11 and 13 and 17 to 18, characterized in that the bispecific antibody is a tetravalent bispecific antibody.
20. The dimeric polypeptide according to any one of items 1 to 11 and 13, characterized in that the (full length) antibody is a trispecific antibody.
21. The dimeric polypeptide according to any one of items 1 to 11 and 13 and 20, characterized in that the trispecific antibody is a trivalent trispecific antibody.
22. The dimeric polypeptide according to any one of items 1 to 11 and 13 and 20 to 21, characterized in that the trispecific antibody is a tetravalent trispecific antibody.
23. A dimeric polypeptide comprising
  a first polypeptide and a second polypeptide each comprising in N-terminal to C-terminal direction at least a portion of an immunoglobulin hinge region, which comprises one or more cysteine residues, an immunoglobulin CH2-domain and an immunoglobulin CH3-domain,
  wherein the first, the second or the first and the second polypeptide comprise the mutation Y436A (numbering according to the EU index).
24. The dimeric polypeptide according to item 23, characterized in that the first and the second polypeptide comprise the mutation Y436A.
25. The dimeric polypeptide according to any one of items 23 to 24, characterized in that the dimeric polypeptide does not specifically bind to the human FcRn and does specifically bind to Staphylococcal protein A.
26. The dimeric polypeptide according to any one of items 23 to 25, characterized in that the dimeric polypeptide is a homodimeric polypeptide.
27. The dimeric polypeptide according to any one of items 23 to 25, characterized in that the dimeric polypeptide is a heterodimeric polypeptide.
28. The dimeric polypeptide according to any one of items 23 to 27, characterized in that
  a) the first polypeptide further comprises the mutations Y349C, T366S, L368A and Y407V and the second polypeptide comprises the mutations S354C and T366W, or
    the first polypeptide further comprises the mutations S354C, T366S, L368A and Y407V and the second polypeptide comprises the mutations Y349C and T366W, and/or
  b) i) the first and the second polypeptide comprise the mutations H310A, H433A and Y436A, or
    ii) the first and the second polypeptide comprise the mutations L251D, L314D and L432D, or
    iii) the first and the second polypeptide comprise the mutations L251S, L314S and L432S, or
    iv) the first polypeptide comprises the mutations I253A, H310A and H435A and the second polypeptide comprises the mutations H310A, H433A and Y436A, or
    v) the first polypeptide comprises the mutations I253A, H310A and H435A and the second polypeptide comprises the mutations L251D, L314D and L432D, or
    vi) the first polypeptide comprises the mutations I253A, H310A and H435A and the second polypeptide comprises the mutations L251S, L314S and L432S.
29. The dimeric polypeptide according to any one of items 23 to 28, characterized in that the immunoglobulin hinge region, the immunoglobulin CH2-domain and the immunoglobulin CH3-domain are of the human IgG1 subclass.
30. The dimeric polypeptide according to any one of items 23 to 29, characterized in that the first polypeptide and the second polypeptide further comprise the mutations L234A and L235A.
31. The dimeric polypeptide according to any one of items 23 to 28, characterized in that the immunoglobulin hinge region, the immunoglobulin CH2-domain and the immunoglobulin CH3-domain are of the human IgG2 subclass optionally with the mutations V234A, G237A, P238S, H268A, V309L, A330S and P331S.

32. The dimeric polypeptide according to any one of items 23 to 28, characterized in that the immunoglobulin hinge region, the immunoglobulin CH2-domain and the immunoglobulin CH3-domain are of the human IgG4 subclass.
33. The dimeric polypeptide according to any one of items 23 to 28 and 32, characterized in that the first polypeptide and the second polypeptide further comprise the mutations S228P and L235E.
34. The dimeric polypeptide according to any one of items 23 to 33, characterized in that the first polypeptide and the second polypeptide further comprise the mutation P329G.
35. The dimeric polypeptide according to any one of items 23 to 34, characterized in that the dimeric polypeptide is an Fc-region fusion polypeptide.
36. The dimeric polypeptide according to any one of items 23 to 34, characterized in that the dimeric polypeptide is an (full length) antibody.
37. The dimeric polypeptide according to any one of items 23 to 34 and 36, characterized in that the (full length) antibody is a monospecific antibody.
38. The dimeric polypeptide according to any one of items 23 to 34 and 36 to 37, characterized in that the monospecific antibody is a monovalent monospecific antibody.
39. The dimeric polypeptide according to any one of items 23 to 34 and 36 to 38, characterized in that the monospecific antibody is a bivalent monospecific antibody.
40. The dimeric polypeptide according to any one of items 23 to 34 and 36, characterized in that the (full length) antibody is a bispecific antibody.
41. The dimeric polypeptide according to any one of items 23 to 34 and 36 and 40, characterized in that the bispecific antibody is a bivalent bispecific antibody.
42. The dimeric polypeptide according to any one of items 23 to 34 and 36 and 40 to 41, characterized in that the bispecific antibody is a tetravalent bispecific antibody.
43. The dimeric polypeptide according to any one of items 23 to 34 and 36, characterized in that the (full length) antibody is a trispecific antibody.
44. The dimeric polypeptide according to any one of items 23 to 34 and 36 and 43, characterized in that the trispecific antibody is a trivalent trispecific antibody.
45. The dimeric polypeptide according to any one of items 23 to 34 and 36 and 43 to 44, characterized in that the trispecific antibody is a tetravalent trispecific antibody.
46. A dimeric polypeptide comprising
    a first polypeptide comprising in N-terminal to C-terminal direction a first heavy chain variable domain, an immunoglobulin CH1-domain of the subclass IgG1, an immunoglobulin hinge region of the subclass IgG1, an immunoglobulin CH2-domain of the subclass IgG1 and an immunoglobulin CH3-domain of the subclass IgG1,
    a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1 and an immunoglobulin CH3-domain of the subclass IgG1,
    a third polypeptide comprising in N-terminal to C-terminal direction a first light chain variable domain and a light chain constant domain,
    a fourth polypeptide comprising in N-terminal to C-terminal direction a second light chain variable domain and a light chain constant domain,
    wherein the first heavy chain variable domain and the first light chain variable domain form a first binding site that specifically binds to a first antigen,
    wherein the second heavy chain variable domain and the second light chain variable domain form a second binding site that specifically binds to a second antigen,
    wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W,
    wherein the first and the second polypeptide further comprise the mutations L234A, L235A and P329G, and
    wherein
        i) the first and the second polypeptide comprise the mutations H310A, H433A and Y436A, or
        ii) the first and the second polypeptide comprise the mutations L251D, L314D and L432D, or
        iii) the first and the second polypeptide comprise the mutations L251S, L314S and L432S, or
        iv) the first polypeptide comprises the mutations I253A, H310A and H435A and the second polypeptide comprises the mutations H310A, H433A and Y436A, or
        v) the first polypeptide comprises the mutations I253A, H310A and H435A and the second polypeptide comprises the mutations L251D, L314D and L432D, or
        vi) the first polypeptide comprises the mutations I253A, H310A and H435A and the second polypeptide comprises the mutations L251S, L314S and L432S.
47. A dimeric polypeptide comprising
    a first polypeptide comprising in N-terminal to C-terminal direction a first heavy chain variable domain, an immunoglobulin light chain constant domain, an immunoglobulin hinge region of the subclass IgG1, an immunoglobulin CH2-domain of the subclass IgG1 and an immunoglobulin CH3-domain of the subclass IgG1,
    a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1 and an immunoglobulin CH3-domain of the subclass IgG1,
    a third polypeptide comprising in N-terminal to C-terminal direction a first light chain variable domain and an immunoglobulin CH1-domain of the subclass IgG1,
    a fourth polypeptide comprising in N-terminal to C-terminal direction a second light chain variable domain and a light chain constant domain,
    wherein the first heavy chain variable domain and the first light chain variable domain form a first binding site that specifically binds to a first antigen, wherein the second heavy chain variable domain and the second light chain variable domain form a second binding site that specifically binds to a second antigen, wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W, wherein the first and the second polypeptide further comprise the mutations L234A, L235A and P329G, and wherein
  i) the first and the second polypeptide comprise the mutations H310A, H433A and Y436A, or
  ii) the first and the second polypeptide comprise the mutations L251D, L314D and L432D, or
  iii) the first and the second polypeptide comprise the mutations L251S, L314S and L432S, or
  iv) the first polypeptide comprises the mutations I253A, H310A and H435A and the second polypeptide comprises the mutations H310A, H433A and Y436A, or
  v) the first polypeptide comprises the mutations I253A, H310A and H435A and the second polypeptide comprises the mutations L251D, L314D and L432D, or
  vi) the first polypeptide comprises the mutations I253A, H310A and H435A and the second polypeptide comprises the mutations L251S, L314S and L432S.

48. A dimeric polypeptide comprising
  a first polypeptide comprising in N-terminal to C-terminal direction a first heavy chain variable domain, an immunoglobulin CH1-domain of the subclass IgG4, an immunoglobulin hinge region of the subclass IgG4, an immunoglobulin CH2-domain of the subclass IgG4 and an immunoglobulin CH3-domain of the subclass IgG4,
  a second polypeptide comprising in N-terminal to C-terminal direction a second heavy chain variable domain, an immunoglobulin CH1-domain of the subclass IgG4, an immunoglobulin hinge region of the subclass IgG4, an immunoglobulin CH2-domain of the subclass IgG4 and an immunoglobulin CH3-domain of the subclass IgG4,
  a third polypeptide comprising in N-terminal to C-terminal direction a first light chain variable domain and a light chain constant domain,
  a fourth polypeptide comprising in N-terminal to C-terminal direction a second light chain variable domain and a light chain constant domain,
  wherein the first heavy chain variable domain and the first light chain variable domain form a first binding site that specifically binds to a first antigen,
  wherein the second heavy chain variable domain and the second light chain variable domain form a second binding site that specifically binds to a second antigen,
  wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W,
  wherein the first and the second polypeptide further comprise the mutations S228P, L235E and P329G, and
  wherein
    i) the first and the second polypeptide comprise the mutations H310A, H433A and Y436A, or
    ii) the first and the second polypeptide comprise the mutations L251D, L314D and L432D, or
    iii) the first and the second polypeptide comprise the mutations L251S, L314S and L432S, or
    iv) the first polypeptide comprises the mutations I253A, H310A and H435A and the second polypeptide comprises the mutations H310A, H433A and Y436A, or
    v) the first polypeptide comprises the mutations I253A, H310A and H435A and the second polypeptide comprises the mutations L251D, L314D and L432D, or
    vi) the first polypeptide comprises the mutations I253A, H310A and H435A and the second polypeptide comprises the mutations L251S, L314S and L432S.

49. A dimeric polypeptide comprising
  a first polypeptide comprising in N-terminal to C-terminal direction a first heavy chain variable domain, an immunoglobulin light chain constant domain, an immunoglobulin hinge region of the subclass IgG4, an immunoglobulin CH2-domain of the subclass IgG4 and an immunoglobulin CH3-domain of the subclass IgG4,
  a second polypeptide comprising in N-terminal to C-terminal direction a second heavy chain variable domain, an immunoglobulin CH1-domain of the subclass IgG4, an immunoglobulin hinge region of the subclass IgG4, an immunoglobulin CH2-domain of the subclass IgG4 and an immunoglobulin CH3-domain of the subclass IgG4,
  a third polypeptide comprising in N-terminal to C-terminal direction a first light chain variable domain and an immunoglobulin CH1-domain of the subclass IgG4,
  a fourth polypeptide comprising in N-terminal to C-terminal direction a second light chain variable domain and a light chain constant domain,
  wherein the first heavy chain variable domain and the first light chain variable domain form a first binding site that specifically binds to a first antigen,
  wherein the second heavy chain variable domain and the second light chain variable domain form a second binding site that specifically binds to a second antigen,
  wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W,
  wherein the first and the second polypeptide further comprise the mutations S228P, L235E and P329G, and
  wherein
    i) the first and the second polypeptide comprise the mutations H310A, H433A and Y436A, or ii) the first and the second polypeptide comprise the mutations L251D, L314D and L432D, or iii) the first and the second polypeptide comprise the mutations L251S, L314S and L432S, or iv) the first polypeptide comprises the mutations I253A, H310A and H435A and the second polypeptide comprises the mutations H310A, H433A and Y436A, or v) the first polypeptide comprises the mutations I253A, H310A and H435A and the second polypeptide comprises the mutations L251D, L314D and L432D, or vi) the first polypeptide comprises the mutations I253A, H310A and H435A and the second polypeptide comprises the mutations L251S, L314S and L432S.

50. A dimeric polypeptide comprising
a first polypeptide comprising in N-terminal to C-terminal direction a first heavy chain variable domain, an immunoglobulin CH1-domain of the subclass IgG1, an immunoglobulin hinge region of the subclass IgG1, an immunoglobulin CH2-domain of the subclass IgG1, an immunoglobulin CH3-domain of the subclass IgG1, a peptidic linker and a first scFv,
a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1, an immunoglobulin CH3-domain of the subclass IgG1, a peptidic linker and a second scFv,
a third polypeptide comprising in N-terminal to C-terminal direction a first light chain variable domain and a light chain constant domain,
a fourth polypeptide comprising in N-terminal to C-terminal direction a second light chain variable domain and a light chain constant domain,
wherein the first heavy chain variable domain and the first light chain variable domain form a first binding site that specifically binds to a first antigen, the second heavy chain variable domain and the second light chain variable domain form a second binding site that specifically binds to a first antigen, the first and the second scFv specifically bind to a second antigen,
wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W,
wherein the first and the second polypeptide further comprise the mutations L234A, L235A and P329G, and
wherein
i) the first and the second polypeptide comprise the mutations H310A, H433A and Y436A, or
ii) the first and the second polypeptide comprise the mutations L251D, L314D and L432D, or
iii) the first and the second polypeptide comprise the mutations L251S, L314S and L432S, or
iv) the first polypeptide comprises the mutations I253A, H310A and H435A and the second polypeptide comprises the mutations H310A, H433A and Y436A, or v) the first polypeptide comprises the mutations I253A, H310A and H435A and the second polypeptide comprises the mutations L251D, L314D and L432D, or vi) the first polypeptide comprises the mutations I253A, H310A and H435A and the second polypeptide comprises the mutations L251S, L314S and L432S.

51. A dimeric polypeptide comprising
a first polypeptide comprising in N-terminal to C-terminal direction a first heavy chain variable domain, an immunoglobulin light chain constant domain, an immunoglobulin hinge region of the subclass IgG1, an immunoglobulin CH2-domain of the subclass IgG1, an immunoglobulin CH3-domain of the subclass IgG1, a peptidic linker and a first scFv,
a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1, an immunoglobulin CH3-domain of the subclass IgG1, a peptidic linker and a second scFv,
a third polypeptide comprising in N-terminal to C-terminal direction a first light chain variable domain and an immunoglobulin CH1-domain of the subclass IgG1,
a fourth polypeptide comprising in N-terminal to C-terminal direction a second light chain variable domain and a light chain constant domain,
wherein the first heavy chain variable domain and the first light chain variable domain form a first binding site that specifically binds to a first antigen, the second heavy chain variable domain and the second light chain variable domain form a second binding site that specifically binds to a first antigen, and the first and the second scFv specifically bind to a second antigen,
wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W,
wherein the first and the second polypeptide further comprise the mutations L234A, L235A and P329G, and
wherein
i) the first and the second polypeptide comprise the mutations H310A, H433A and Y436A, or
ii) the first and the second polypeptide comprise the mutations L251D, L314D and L432D, or
iii) the first and the second polypeptide comprise the mutations L251S, L314S and L432S, or
iv) the first polypeptide comprises the mutations I253A, H310A and H435A and the second polypeptide comprises the mutations H310A, H433A and Y436A, or
v) the first polypeptide comprises the mutations I253A, H310A and H435A and the second polypeptide comprises the mutations L251D, L314D and L432D, or vi) the first polypeptide comprises the mutations I253A, H310A and H435A and the second polypeptide comprises the mutations L251S, L314S and L432S.

52. A method for producing a dimeric polypeptide according to any one of items 1 to 51 comprising the following steps:
   a) cultivating a mammalian cell comprising one or more nucleic acids encoding the dimeric polypeptide according to any one of items 1 to 51,
   b) recovering the dimeric polypeptide from the cultivation medium, and
   c) purifying the dimeric polypeptide with a protein A affinity chromatography.

53. Use of the mutation Y436A for increasing the binding of a dimeric polypeptide to protein A.

54. Use of the mutations H310A, H433A and Y436A for separating heterodimeric polypeptides from homodimeric polypeptides.

55. Use of the mutations L251D, L314D, L432D, or the mutations L251S, L314S, L432S for separating heterodimeric polypeptides from homodimeric polypeptides.

56. Use of the mutations I253A, H310A and H435A in a first polypeptide in combination with the mutations H310A, H433A and Y436A in a second polypeptide for separating heterodimeric polypeptides comprising the first and the second polypeptide from homodimeric polypeptides.

57. Use of the mutations I253A, H310A and H435A in a first polypeptide in combination with the mutations L251D, L314D, L432D or the mutations L251S, L314S, L432S in a second polypeptide for separating heterodimeric polypeptides comprising the first and the second polypeptide from homodimeric polypeptides.

58. The use according to any one of items 53 to 57, characterized in that i) the first polypeptide further comprises the mutations Y349C, T366S, L368A and Y407V and the second polypeptide further comprises the mutations S354C and T366W, or ii) the first polypeptide comprises the mutations S354C, T366S, L368A and Y407V and the second polypeptide comprises the mutations Y349C and T366W.

59. A method of treatment of a patient suffering from ocular vascular diseases by administering a dimeric polypeptide according to any one of items 1 to 51 to a patient in the need of such treatment.

60. A dimeric polypeptide according to any one of items 1 to 51 for intravitreal application.

61. A dimeric polypeptide according to any one of items 1 to 51 for the treatment of vascular eye diseases.

62. A pharmaceutical formulation comprising a dimeric polypeptide according to any one of items 1 to 51 and optionally a pharmaceutically acceptable carrier.

63. Use of a dimeric polypeptide according to any one of items 1 to 51 for the transport of a soluble receptor ligand from the eye over the blood-ocular-barrier into the blood circulation.

64. Use of a dimeric polypeptide according to any one of items 1 to 51 for the removal of one or more soluble receptor ligands from the eye.

65. Use of a dimeric polypeptide according to any one of items 1 to 51 for the treatment of eye diseases, especially of ocular vascular diseases.

66. Use of a dimeric polypeptide according to any one of items 1 to 51 for the transport of one or more soluble receptor ligands from the intravitreal space to the blood circulation.

67. A dimeric polypeptide according to any one of items 1 to 51 for use in treating an eye disease.

68. A dimeric polypeptide according to any one of items 1 to 51 for use in the transport of a soluble receptor ligand from the eye over the blood-ocular-barrier into the blood circulation.

69. A dimeric polypeptide according to any one of items 1 to 51 for use in the removal of one or more soluble receptor ligands from the eye.

70. A dimeric polypeptide according to any one of items 1 to 51 for use in treating eye diseases, especially ocular vascular diseases.

71. A dimeric polypeptide according to any one of items 1 to 51 for use in the transport of one or more soluble receptor ligands from the intravitreal space to the blood circulation.

72. A method of treating an individual having an ocular vascular disease comprising administering to the individual an effective amount of a dimeric polypeptide according to any one of items 1 to 51.

73. A method for transporting a soluble receptor ligand from the eye over the blood-ocular-barrier into the blood circulation in an individual comprising administering to the individual an effective amount of a dimeric polypeptide according to any one of items 1 to 51 to transport a soluble receptor ligand from the eye over the blood-ocular-barrier into the blood circulation.

74. A method the removal of one or more soluble receptor ligands from the eye in an individual comprising administering to the individual an effective amount of a dimeric polypeptide according to any one of items 1 to 51 to remove one or more soluble receptor ligands from the eye.

75. A method for the transport of one or more soluble receptor ligands from the intravitreal space to the blood circulation in an individual comprising administering to the individual an effective amount of a dimeric polypeptide according to any one of items 1 to 51 to transport of one or more soluble receptor ligands from the intravitreal space to the blood circulation.

76. A method for transporting a soluble receptor ligand from the intravitreal space or the eye over the blood-ocular-barrier into the blood circulation in an individual comprising administering to the individual an effective amount of a dimeric polypeptide according to any one of items 1 to 51 to transport a soluble receptor ligand from the eye over the blood-ocular-barrier into the blood circulation.

V. EXAMPLES

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Methods

Electrospray Ionization Mass Spectrometry (ESI-MS)

Protein aliquots (50 µg) were deglycosylated by adding 0.5 µL N-Glycanase plus (Roche) and sodium phosphate buffer (0.1 M, pH 7.1) to obtain a final sample volume of 115 µL. The mixture was incubated at 37° C. for 18 h. Afterwards for reduction and denaturing 60 µL 0.5 M TCEP (Pierce) in 4 M guanidine * HCl (Pierce) and 50 µL 8 M guanidine * HCl were added. The mixture was incubated at 37° C. for 30 min. Samples were desalted by size exclusion chromatography (Sepharose G-25, isocratic, 40% acetonitrile with 2% formic acid). ESI mass spectra (+ve) were recorded on a Q-TOF instrument (maXis, Bruker) equipped with a nano ESI source (TriVersa NanoMate, Advion). MS parameter settings were as follows: Transfer: Funnel RF, 400 Vpp; ISCID Energy, 0 eV; Multipole RF, 400 Vpp; Quadrupole: Ion Energy, 4.0 eV; Low Mass, 600 m/z; Source: Dry Gas, 8 L/min; Dry Gas Temperature, 160° C.; Collision Cell: Collision Energy, 10 eV; Collision RF: 2000 Vpp; Ion Cooler: Ion Cooler RF, 300 Vpp; Transfer Time: 120 µs; Pre Puls Storage, 10 µs; scan range m/z 600 to 2000. For data evaluation in-house developed software (MassAnalyzer) was used.

FcRn Surface Plasmon Resonance (SPR) Analysis

The binding properties of wild-type antibody and the mutants to FcRn were analyzed by surface plasmon resonance (SPR) technology using a BIAcore T100 instrument (BIAcore AB, Uppsala, Sweden). This system is well established for the study of molecular interactions. It allows a continuous real-time monitoring of ligand/analyte bindings and thus the determination of kinetic parameters in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to an immobilized ligand on the surface the mass increases, in case of dissociation the mass decreases. In the current assay, the FcRn receptor was immobilized onto a BIAcore CM5-biosensor chip (GE Healthcare Bioscience, Uppsala, Sweden) via amine coupling to a level of 400 Response units (RU). The assay was carried out at room temperature with PBS, 0.05% Tween20 pH 6.0 (GE Healthcare Bioscience) as running and dilution buffer. 200 nM of samples were injected at a flow rate of 50 µL/min at room temperature. Association time was 180 sec., dissociation phase took 360 sec. Regeneration of the chip surface was reached by a short injection of HBS-P, pH 8.0. Evaluation of SPR-data was performed by comparison of the biological response signal height at 180 sec. after injection and at 300 sec. after injection. The corresponding parameters are the RU max level (180 sec. after injection) and late stability (300 sec. after end of injection).

Protein A Surface Plasmon Resonance (SPR) Analysis

The assay is based on surface plasmon resonance spectroscopy. Protein A is immobilized onto the surface of a SPR biosensor. By injecting the sample into the flow cells of the SPR spectrometer it forms a complex with the immobilized protein A resulting in an increasing mass on the sensor chip surface, and therefore to a higher response (as 1 RU is defined as 1 pg/mm²). Afterwards the sensor chip is regenerated by dissolving the sample-protein A-complex. The gained responses are then evaluated for the signal high in response units (RU) and the dissociation behavior Around 3500 response units (RU) of protein A (20 µg/mL) were coupled onto a CMS chip (GE Healthcare) at pH 4.0 by using the amine coupling kit of GE Healthcare.

The sample and system buffer was HBS-P+ (0.01 M HEPES, 0.15 M NaCl, 0.005% Surfactant P20 Sterile-filtered, pH 7.4). Flow cell temperature was set to 25° C. and sample compartment temperature to 12° C. The system was primed with running buffer. Then, 5 nM solutions of the sample constructs were injected for 120 seconds with a flow rate of 30 µL/min, followed by a 300 seconds dissociation phase. Then the sensor chip surface was regenerated by two 30 seconds long injections of Glycine-HCl pH 1.5 at a flow rate of 30 µL/min. Each sample was measured as a triplicate.

Bispecific Antibodies and Their Respective Sequences

| Description | Sequences |
|---|---|
| anti-VEGF/ANG2 CrossMab IgG1 with IHH-AAA mutations | SEQ ID NO: 34, SEQ ID NO: 35, SEQ ID NO: 36, SEQ ID NO: 37 |
| anti-VEGF/ANG2 CrossMab IgG1 wild type (without IHH-AAA mutations) | SEQ ID NO: 52, SEQ ID NO: 53, SEQ ID NO: 54, SEQ ID NO: 55 |
| anti-VEGF/ANG2 CrossMab IgG1 with IHH-AAA mutations and P329G LALA mutations | SEQ ID NO: 38, SEQ ID NO: 39, SEQ ID NO: 40, SEQ ID NO: 41 |
| anti-VEGF/ANG2 CrossMab IgG1 with P329G LALA mutations only (without IHH-AAA mutations) | SEQ ID NO: 56, SEQ ID NO: 57, SEQ ID NO: 58, SEQ ID NO: 59 |
| anti-VEGF/ANG2 CrossMab IgG4 with IHH-AAA mutations and with SPLE mutations | SEQ ID NO: 42, SEQ ID NO: 43, SEQ ID NO: 44, SEQ ID NO: 45 |
| anti-VEGF/ANG2 OAscFab IgG1 with IHH-AAA mutations | SEQ ID NO: 46, SEQ ID NO: 47, SEQ ID NO: 48 |
| <VEGF-ANG-2> OAscFab IgG4 with IHH-AAA mutations and with SPLE mutations | SEQ ID NO: 49, SEQ ID NO: 50, SEQ ID NO: 51 |
| anti-VEGF/ANG2 CrossMab IgG1 with HHY-AAA mutations | SEQ ID NO: 102, SEQ ID NO: 103, SEQ ID NO: 36, SEQ ID NO: 37 |
| anti-VEGF/ANG2 CrossMab IgG1 with HHY-AAA mutations and P329G LALA mutations | SEQ ID NO: 104, SEQ ID NO: 105, SEQ ID NO: 36, SEQ ID NO: 37 |
| anti-VEGF/ANG2 CrossMab IgG4 with HHY-AAA mutations and with SPLE mutations | SEQ ID NO: 106, SEQ ID NO: 107, SEQ ID NO: 58, SEQ ID NO: 59 |
| <VEGF-ANG-2> OAscFab IgG1 with HHY-AAA mutations | SEQ ID NO: 108, SEQ ID NO: 109, SEQ ID NO: 48 |
| <VEGF-ANG-2> OAscFab IgG4 with HHY-AAA mutations and with SPLE mutations | SEQ ID NO: 110, SEQ ID NO: 111, SEQ ID NO: 51 |

The term "with (the) mutation IHH-AAA" as used herein refers the combination of the mutations I253A (Ile253Ala), H310A (His310Ala), and H435A (His435Ala) in a constant heavy chain region of IgG1 or IgG4 subclass (numbering according to the Kabat EU index numbering system), the term "with (the) mutation HEY-AAA" as used herein refers the combination of the mutations H310A (His310Ala), H433A (His433Ala) and Y436A (Tyr436Ala) in a constant heavy chain region of IgG1 or IgG4 subclass (numbering according to the Kabat EU index numbering system), the term "with (the) mutation P329G LALA" as used herein refers to the combination of the mutations L234A (Leu234Ala), L235A (Leu235Ala) and P329G (Pro329Gly)

in a constant heavy chain region of IgG1 subclass (numbering according to the Kabat EU index numbering system), and the term "with (the) mutation SPLE" as used herein refers to the combination of the mutations S228P (Ser228Pro) and L235E (Leu235Glu) in a constant heavy chain region of IgG4 subclass (numbering according to the Kabat EU index numbering system).

| Description | Sequences |
|---|---|
| <IGF-1R> IgG1 wt | SEQ ID NO: 88 |
| | SEQ ID NO: 89 |
| <IGF-1R> IgG1 with I253A, H310A, H435A | SEQ ID NO: 88 |
| | SEQ ID NO: 90 |
| <IGF-1R> IgG1 with M252Y, S254T, T256E | SEQ ID NO: 88 |
| | SEQ ID NO: 91 |
| <IgF-1R> IgG1 wt, KiH | SEQ ID NO: 88 |
| | SEQ ID NO: 92 |
| | SEQ ID NO: 93 |
| <IgF-1R> IgG1 knob wt, hole I253A, H310A, H435A | SEQ ID NO: 88 |
| | SEQ ID NO: 94 |
| | SEQ ID NO: 95 |
| <IGF-1R> IgG1 knob wt, hole H310A, H433A, Y436A | SEQ ID NO: 88 |
| | SEQ ID NO: 96 |
| | SEQ ID NO: 97 |
| <IGF-1R> IgG1 knob wt, hole M252Y, S254T, T256E | SEQ ID NO: 88 |
| | SEQ ID NO: 98 |
| | SEQ ID NO: 99 |
| <IGF-1R> IgG1 knob wt, hole L251D, L314D, L432D | SEQ ID NO: 88 |
| | SEQ ID NO: 100 |
| | SEQ ID NO: 101 |
| <IGF-1R> IgG1 with H310A, H433A, Y436A | SEQ ID NO: 88 |
| | SEQ ID NO: 112 |

General

General information regarding the nucleotide sequences of human immunoglobulin light and heavy chains is given in: Kabat, E. A., et al., Sequences of Proteins of Immunological Interest, 5th ed., Public Health Service, National Institutes of Health, Bethesda, MD (1991). Amino acid residues of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md. (1991)).

Recombinant DNA Techniques

Standard methods were used to manipulate DNA as described in Sambrook, J. et al., Molecular Cloning: A laboratory manual; Cold Spring Harbor Laboratory Press, Cold Spring Harbor, New York (1989). The molecular biological reagents were used according to the manufacturer's instructions.

Gene Synthesis

Desired gene segments were ordered according to given specifications at Geneart (Regensburg, Germany).

DNA Sequence Determination

DNA sequences were determined by double strand sequencing performed at MediGenomix GmbH (Martinsried, Germany) or SequiServe GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described antibodies expression vectors for transient expression (e.g. in HEK293-F cells) based either on a cDNA organization with or without a CMV-Intron A promoter or on a genomic organization with a CMV promoter were used.

Beside the antibody expression cassette the vectors contained:

an origin of replication which allows replication of this vector in *E. coli,* a β-lactamase gene which confers ampicillin resistance in *E. coli,* and the dihydrofolate reductase gene from Mus musculus as a selectable marker in eukaryotic cells.

The transcription unit of the antibody gene was composed of the following elements:

unique restriction site(s) at the 5' end, the immediate early enhancer and promoter from the human cytomegalovirus, in the case of the cDNA organization followed by the Intron A sequence, a 5'-untranslated region of a human immunoglobulin gene, a nucleic acid encoding an immunoglobulin heavy chain signal sequence, a nucleic acid encoding the human antibody chain (wild-type or with domain exchange) either as cDNA or in genomic organization with the immunoglobulin exon-intron organization, a 3' non-translated region with a polyadenylation signal sequence, and unique restriction site(s) at the 3' end.

The nucleic acids encoding the antibody chains were generated by PCR and/or gene synthesis and assembled by known recombinant methods and techniques by connection of the according nucleic acid segments e.g. using unique restriction sites in the respective vectors. The subcloned nucleic acid sequences were verified by DNA sequencing. For transient transfections, larger quantities of the vectors were prepared by vector preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The bispecific antibodies were expressed by transient co-transfection of the respective expression vectors in HEK29-F cells growing in suspension as described below.

Example 1

Expression and Purification

Transient Transfections in HEK293-F System

The monospecific and bispecific antibodies were generated by transient transfection with the respective vectors (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serum-free FREESTYLE™ 293 expression medium (Invitrogen) were transfected with a mix of the respective expression vectors and 293FECTIN™ or fectin (Invitrogen). For 2 L shake flask (Corning) HEK293-F cells were seeded at a density of $1*10^6$ cells/mL in 600 mL and incubated at 120 rpm, 8% $CO_2$. The day after the cells were transfected at a cell density of approx. $1.5*10^6$ cells/mL with approx. 42 mL mix of A) 20 mL Opti-MEM (Invitrogen) with 600 µg total vector DNA (1 µg/mL) encoding the heavy or modified heavy chain, respectively and the corresponding light chain in an equimolar ratio and B) 20 ml Opti-MEM with 1.2 mL 293 fectin or fectin (2 µL/mL). According to the glucose consumption, glucose solution was added during the course of the fermentation. The supernatant containing the secreted antibody was harvested after 5-10 days and antibodies were either directly purified from the supernatant or the supernatant was frozen and stored.

Purification

Bispecific antibodies were purified from cell culture supernatants by affinity chromatography using MABSE-LECTSURE-SEPHAROSE™ (for non-IHH-AAA mutants) (GE Healthcare, Sweden) or KappaSelect-Agarose (for IHH-AAA mutants) (GE Healthcare, Sweden), hydrophobic interaction chromatography using butyl-Sepharose (GE Healthcare, Sweden) and Superdex 200 size exclusion (GE Healthcare, Sweden) chromatography.

Briefly, sterile filtered cell culture supernatants were captured on a MABSELECTSURE™ resin equilibrated (non-IHH-AAA mutations and wild-type antibodies) with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The IHH-AAA mutants were captured on a KappaSelect resin equilibrated with 25 mM Tris, 50 mM NaCl, pH 7.2, washed with equilibration buffer and eluted with 25 mM sodium citrate pH 2.9. The eluted antibody fractions were pooled and neutralized with 2 M Tris, pH 9.0. The antibody pools were prepared for hydrophobic interaction chromatography by adding 1.6 M ammonium sulfate solution to a final concentration of 0.8 M ammonium sulfate and the pH adjusted to pH 5.0 using acetic acid. After equilibration of the butyl-Sepharose resin with 35 mM sodium acetate, 0.8 M ammonium sulfate, pH 5.0, the antibodies were applied to the resin, washed with equilibration buffer and eluted with a linear gradient to 35 mM sodium acetate pH 5.0. The (monospecific or bispecific) antibody containing fractions were pooled and further purified by size exclusion chromatography using a Superdex 200 26/60 GL (GE Healthcare, Sweden) column equilibrated with 20 mM histidine, 140 mM NaCl, pH 6.0. The (monospecific or bispecific) antibody containing fractions were pooled, concentrated to the required concentration using Vivaspin ultrafiltration devices (Sartorius Stedim Biotech S. A., France) and stored at −80° C.

TABLE

Yields of bispecific <VEGF-ANG-2> antibodies

| | VEGF/ANG2-0015 (without IHH-AAA mutation) | VEGF/ANG2-0016 (with IHH-AAA mutation) | VEGF/ANG2-0121 (with HHY-AAA mutation) |
|---|---|---|---|
| titer supernatant | 64 µg/mL, (2 L = 128 mg) | n.a. (2 L scale) | 60.8 µg/mL (2 L = 121.60 mg) |
| protein A (MabSelectSure) | 118 mg (~70% monomer) | n.a. | 100.5 mg (pool1 + pool2) |
| Kappa Select | n.a. | 117 mg (~83% monomer) | n.a. |
| Butyl Sepharose | 60 mg | 57 mg | 49 mg |
| SEC | 35 mg (>95% monomer) | 38 mg (>95% monomer) | 32.4 mg (>95% monomer) |

Purity and antibody integrity were analyzed after each purification step by CE-SDS using microfluidic Labchip technology (Caliper Life Science, USA). Five µL of protein solution was prepared for CE-SDS analysis using the HT Protein Express Reagent Kit according manufacturer's instructions and analyzed on Labchip GXII system using a HT Protein Express Chip. Data were analyzed using Labchip GX Software.

TABLE

Removal of typical side products by different sequential purification steps determined by CE-SDS.

| | VEGF/ANG2-0015 | | | | | | VEGF/ANG2-0016 | | | | | |
|---|---|---|---|---|---|---|---|---|---|---|---|---|
| purification | % peak area* * analysis: CE-SDS (Caliper Labchip GXII) | | | | | | | | | | | |
| step | mAb | ¾Ab | (HC)2 | ½Ab | (LC)2 | LC | mAb | ¾Ab | (HC)2 | ½Ab | (LC)2 | LC |
| MAb Select Sure | 55.7 | 19 | 10.6 | 9.8 | 3.5 | 0.9 | — | | | | | |
| Kappa Select | | | — | | | | 63 | 13.4 | 3.5 | 6.1 | 5.8 | 7.4 |
| ButylSepharose | 81.4 | 1.9 | 2.3 | 8.2 | 3.6 | 1.8 | 76.2 | 1.3 | 0.7 | 8.3 | 7.7 | 5.8 |
| Superdex 200 SEC | 92.4 | 1.8 | 2.6 | 1.4 | 0.5 | 0.5 | 99 | 1.1 | n.d. | n.d. | n.d. | n.d. |

The aggregate content of antibody samples was analyzed by high-performance SEC using a Superdex 200 analytical size-exclusion column (GE Healthcare, Sweden) in 2xPBS (20 mM $Na_2HPO_4$, 2 mM $KH_2PO_4$, 274 mM NaCl and 5.4 mM KCl, pH 7.4) running buffer at 25° C. 25 µg protein were injected on the column at a flow rate of 0.75 mL/min and eluted isocratic over 50 minutes.

Analogously, the anti-VEGF/ANG2 antibodies VEGF/ANG2-0012 and VEGF/ANG2-0201 were prepared and purified with the following yields:

| | VEGF/ANG2-0012 (with IHH-AAA mutation) | VEGF/ANG2-0201 (without IHH-AAA mutation) |
|---|---|---|
| titer //amount scale | — 2.1 L | 36 µg/mL/72 mg 2 L |
| protein A (MabSelectSure) | — | 66 mg (~95% monomer) |
| KappaSelect | 43 mg (~65% monomer) | — |
| Butyl Sepharose | — | 45 mg |

|  | VEGF/ANG2-0012 (with IHH-AAA mutation) | VEGF/ANG2-0201 (without IHH-AAA mutation) |
|---|---|---|
| SEC | 14 mg | 21 mg (>98% monomer) |
| yield hydroxylapatite | 8.5 mg (>98% monomer) |  |
| total yield (recovery) | 8.5 mg (20%) | 21 mg (30%) |

Also the anti-VEGF/ANG2 bispecific antibodies anti-VEGF/ANG2 CrossMAb IgG4 with IHH-AAA mutation and with SPLE mutation (SEQ ID NO: 42, SEQ ID NO: 43, SEQ ID NO: 44, SEQ ID NO: 45), anti-VEGF/ANG2 OAscFab IgG1 with IHH-AAA mutation (SEQ ID NO: 46, SEQ ID NO: 47, SEQ ID NO: 48), anti-VEGF/ANG2 OAscFab IgG4 with IHH-AAA mutation and with SPLE mutation (SEQ ID NO: 49, SEQ ID NO: 50, SEQ ID NO: 51), anti-VEGF/ANG2 CrossMab IgG1 with HHY-AAA mutation and P329G LALA mutation (SEQ ID NO: 90, SEQ ID NO: 91, SEQ ID NO: 40, SEQ ID NO: 41), anti-VEGF/ANG2 CrossMab IgG4 with HHY-AAA mutation and SPLE mutation (SEQ ID NO: 92, SEQ ID NO: 93, SEQ ID NO: 44, SEQ ID NO: 45), anti-VEGF/ANG2 OAscFab IgG1 with HHY-AAA mutation (SEQ ID NO: 94, SEQ ID NO: 95, SEQ ID NO: 48), and anti-VEGF/ANG2 OAscFab IgG4 with HHY-AAA mutation and SPLE mutation (SEQ ID NO: 96, SEQ ID NO: 97, SEQ ID NO: 51) and also the anti-IGF-1R monospecific antibodies anti-IGF-1R wild-type (SEQ ID NO: 88, SEQ ID NO: 89), anti-IGF-1R IgG1 with IHH-AAA mutation (SEQ ID NO: 88, SEQ ID NO: 90), anti-IGF-1R IgG1 with YTE mutation (SEQ ID NO: 88, SEQ ID NO: 91), anti-IGF-1R IgG1 wild-type with KiH mutation (SEQ ID NO: 88, SEQ ID NO: 92, SEQ ID NO: 93), anti-IGF-1R IgG1 with KiH mutation and the IHH-AAA mutation in the hole chain (SEQ ID NO: 88, SEQ ID NO: 94, SEQ ID NO: 95), anti-IGF-1R IgG1 with KiH mutation and the HHY-AAA mutation in the hole chain (SEQ ID NO: 88, SEQ ID NO: 96, SEQ ID NO: 97), anti-IGF-1R IgG1 with KiH mutation and the YTE mutation (SEQ ID NO: 88, SEQ ID NO: 98, SEQ ID NO: 99), anti-IGF-1R IgG1 with KiH mutation and the DDD mutation (SEQ ID NO: 88, SEQ ID NO: 100, SEQ ID NO: 101), and anti-IGF-1R IgG1 with HHY-AAA mutation (SEQ ID NO: 88, SEQ ID NO: 112) can be prepared and purified analogously.

Example 2

Analytics & Developability
Small-Scale DLS-Based Viscosity Measurement.

Viscosity measurement was essentially performed as described in (He, F. et al., Analytical Biochemistry 399 (2009) 141-143). Briefly, samples are concentrated to various protein concentrations in 200 mM arginine succinate, pH 5.5, before polystyrene latex beads (300 nm diameter) and Polysorbate 20 (0.02% v/v) are added. Samples are transferred into an optical 384-well plate by centrifugation through a 0.4 µm filter plate and covered with paraffin oil. The apparent diameter of the latex beads is determined by dynamic light scattering at 25° C. The viscosity of the solution can be calculated as $\eta=\eta 0(rh/rh,0)$ ($\eta$: viscosity; $\eta 0$: viscosity of water; rh: apparent hydrodynamic radius of the latex beads; rh,0: hydrodynamic radius of the latex beads in water).

To allow comparison of various samples at the same concentration, viscosity-concentration data were fitted with the Mooney equation (Equation 1) (Mooney, M., Colloid. Sci., 6 (1951) 162-170; Monkos, K., Biochem. Biophys. Acta 304 (1997) 1339) and data interpolated accordingly.

$$\eta = \eta_0 \exp\left(\frac{S\Phi}{1-K\Phi}\right) \qquad \text{Equation 1}$$

(S: hydrodynamic interaction parameter of the protein; K: self-crowding factor; $\Phi$: volume fraction of the dissolved protein)

Figure 2:
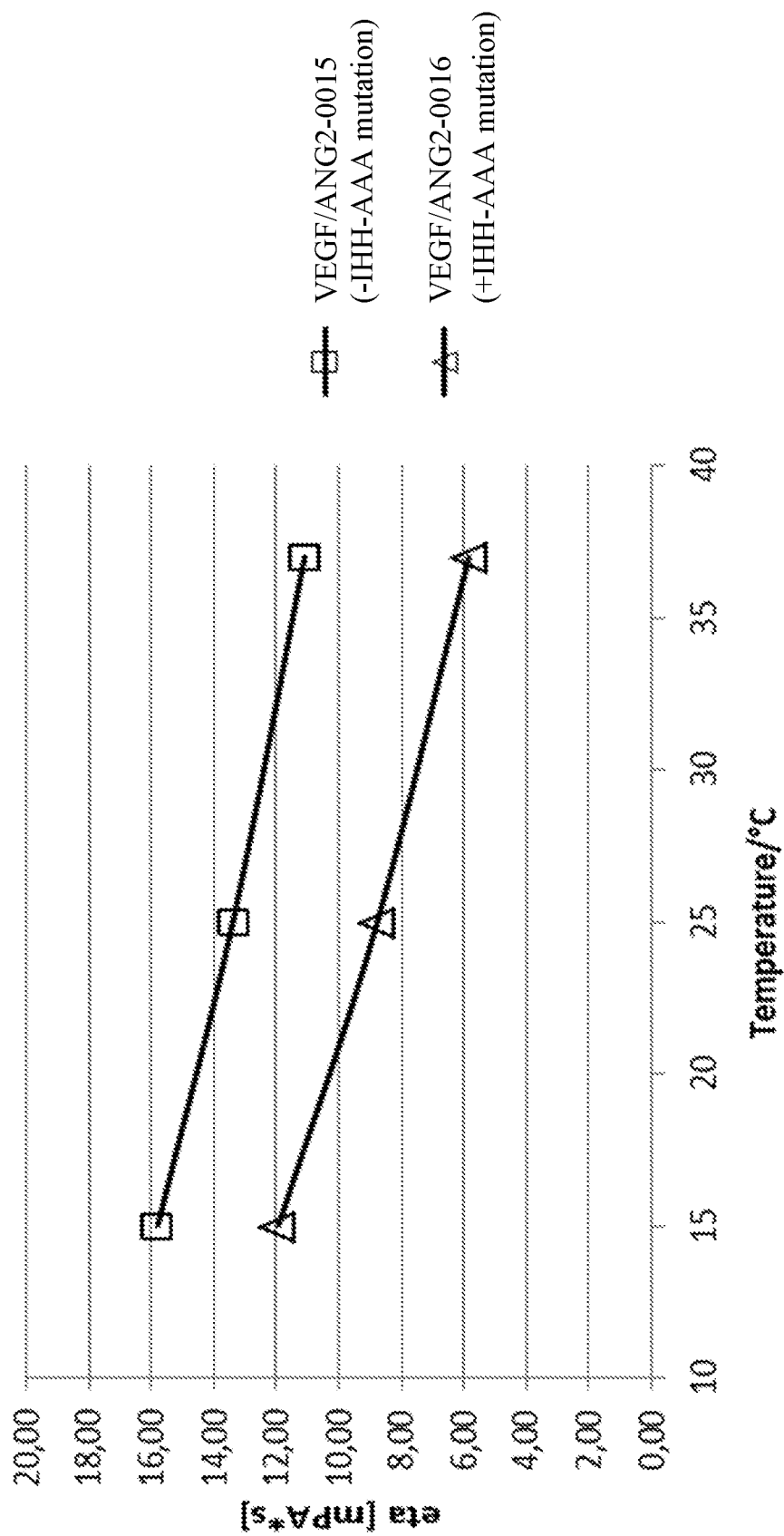
FIG. 2: Small-scale DLS-based viscosity measurement: Extrapolated viscosity at 150 mg/mL in 200 mM arginine/succinate buffer, pH 5.5 (comparison of anti-VEGF/ANG2 antibody VEGF/ANG2-0016 (with IHH-AAA mutation) with reference antibody VEGF/ANG2-0015 (without such IHH-AAA mutation)).

Results are shown in FIG. 2: VEGF/ANG2-0016 with IHH-AAA mutation in the Fc-region shows a lower viscosity at all measured temperatures compared to VEGF/ANG2-0015 without the IHH-AAA mutation in the Fc-region.

DLS Aggregation Onset Temperature

Figure 3:
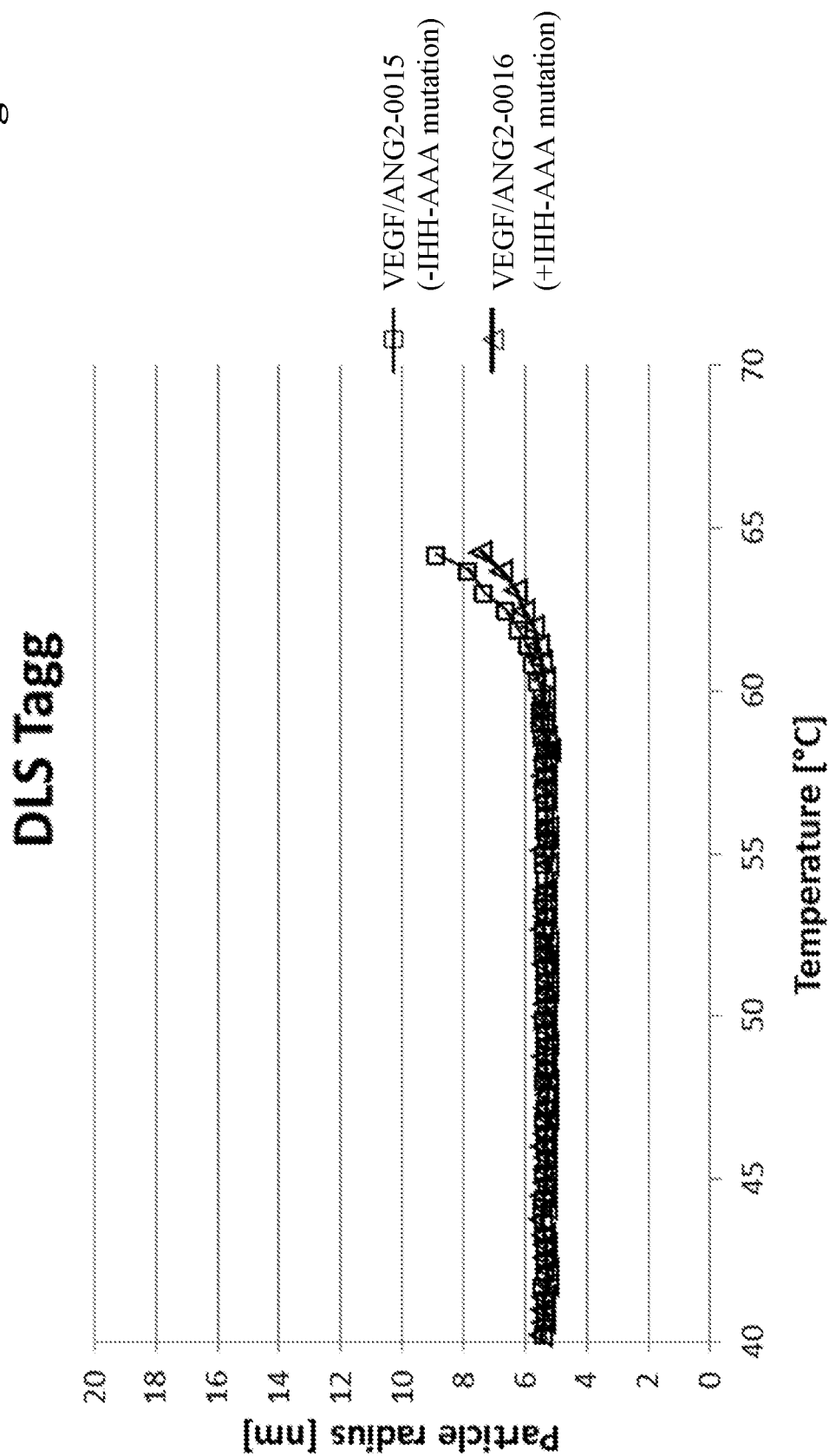
FIG. 3: DLS Aggregation depending on temperature (including DLS aggregation onset temperature) in 20 mM histidine buffer, 140 mM NaCl, pH 6.0 (comparison of anti-VEGF/ANG2 antibody as reported herein VEGF/ANG2-0016 (with IHH-AAA mutation) with reference antibody VEGF/ANG2-0015 (without such IHH-AAA mutation)).

Samples are prepared at a concentration of 1 mg/mL in 20 mM histidine/histidine hydrochloride, 140 mM NaCl, pH 6.0, transferred into an optical 384-well plate by centrifugation through a 0.4 µm filter plate and covered with paraffin oil. The hydrodynamic radius is measured repeatedly by dynamic light scattering while the samples are heated with a rate of 0.05° C./min from 25° C. to 80° C. The aggregation onset temperature is defined as the temperature at which the hydrodynamic radius starts to increase. Results are shown in FIG. 3. In FIG. 3 the aggregation of VEGF/ANG2-0015 without the IHH-AAA mutation versus VEGF/ANG2-0016 with IHH-AAA mutation in the Fc-region is shown. VEGF/ANG2-0016 showed an aggregation onset temperature of 61° C. whereas VEGF/ANG2-0015 without the IHH-AAA mutation showed an onset temperature of 60° C.

DLS Time-Course

Samples are prepared at a concentration of 1 mg/mL in 20 mM histidine/histidine hydrochloride, 140 mM NaCl, pH 6.0, transferred into an optical 384-well plate by centrifugation through a 0.4 µm filter plate and covered with paraffin oil. The hydrodynamic radius is measured repeatedly by dynamic light scattering while the samples are kept at a constant temperature of 50° C. for up to 145 hours. In this experiment, aggregation tendencies of the native, unfolded protein at elevated temperature would lead to an increase of the average particle diameter over time. This DLS-based method is very sensitive for aggregates because these contribute over-proportionally to the scattered light intensity. Even after 145 hours at 50° C. (a temperature close to the aggregation-onset temperature, see above), an average particle diameter increase of only less than 0.5 nm was found for both VEGF/ANG2-0015 and VEGF/ANG2-0016.

Seven Day Storage at 40° C. at 100 mg/mL

Samples are concentrated to a final concentration of 100 mg/mL in 200 mM arginine succinate, pH 5.5, sterile filtered and quiescently stored at 40° C. for 7 days. Before and after storage, the content of high and low molecular weight species (EIMWs and LMWs, respectively) is determined by size-exclusion chromatography. The difference in UMW and LMW content between the stored sample and a sample measured immediately after preparation is reported as "UMW increase" and "LMW increase," respectively. Results are shown in the Table below and FIG. 4, which show that VEGF/ANG2-0015 (without IHH-AAA mutation) shows a higher reduction of the main peak and a higher UMW increase compared to VEGF/ANG2-0016 (with IHH-AAA mutation). Surprisingly VEGF/ANG2-0016 (with IHH-AAA mutation) showed a lower aggregation tendency compared to VEGF/ANG2-0015 (without IHH-AAA mutation).

TABLE

Delta Main-, HMW and LMW peaks after 7 d at 40° C.

| | delta_area % (40° C.-(−80° C.)) | | |
|---|---|---|---|
| | main Peak | HMW | LMW |
| VEGF/ANG2-0015 (without IHH-AAA mutation) | −3.56 | 2.89 | 0.67 |
| VEGF/ANG2-0016 (with IHH-AAA mutation) | −1.74 | 1.49 | 0.25 |

The functional analysis of anti-VEGF/ANG2 bispecific antibodies was assessed by Surface Plasmon Resonance (SPR) using a BIAcore® T100 or T200 instrument (GE Healthcare) at 25° C. The BIAcore® system is well established for the study of molecule interactions. SPR-technology is based on the measurement of the refractive index close to the surface of a gold coated biosensor chip. Changes in the refractive index indicate mass changes on the surface caused by the interaction of immobilized ligand with analyte injected in solution. The mass increases if molecules bind immobilized ligands on the surface, and vice versa, the mass decreases in case of dissociation of the analyte from the immobilized ligand (reflecting complex dissociation). SPR allows a continuous real-time monitoring of ligand/analyte binding and thus determination of the association rate constant (ka), dissociation rate constant (kd), and the equilibrium constant (KD).

Example 3

Binding to VEGF, ANG2, FcgammaR and FcRn
VEGF Isoforms Kinetic Affinity Including Assessment of Species-Cross-Reactivity Around 12,000 resonance units (RU) of the capturing system (10 µg/mL goat anti human F(ab)'$_2$; Order Code: 28958325; GE Healthcare Bio-Sciences AB, Sweden) were coupled on a CM5 chip (GE Healthcare BR-1005-30) at pH 5.0 by using an amine coupling kit supplied by GE Healthcare. The sample and system buffer was PBS-T (10 mM phosphate buffered saline including 0.05% Tween20) pH 7.4. The flow cell was set to 25° C.—and the sample block set to 12° C.—and primed with running buffer twice. The bispecific antibody was captured by injecting a 50 nM solution for 30 seconds at a flow of 5 µL/min. Association was measured by injection of human hVEGF121, mouse mVEGF120 or rat rVEGF164 in various concentrations in solution for 300 seconds at a flow of 30 µL/min starting with 300 nM in 1:3 dilutions. The dissociation phase was monitored for up to 1200 seconds and triggered by switching from the sample solution to running buffer. The surface was regenerated by 60 seconds washing with a Glycine pH 2.1 solution at a flow rate of 30 µL/min. Bulk refractive index differences were corrected by subtracting the response obtained from a goat anti human F(ab')$_2$ surface. Blank injections are also subtracted (=double referencing). For calculation of apparent KD and other kinetic parameters, the Langmuir 1:1 model was used. Results are shown below.

ANG2 Solution Affinity Including Assessment of Species-Cross-Reactivity

Solution affinity measures the affinity of an interaction by determining the concentration of free interaction partners in an equilibrium mixture. The solution affinity assay involves the mixing of an anti-VEGF/ANG2 antibody, kept at a constant concentration, with a ligand (=ANG2) at varying concentrations. Maximum possible resonance units (e.g. 17,000 resonance units (RU)) of an antibody was immobilized on the CM5 chip (GE Healthcare BR-1005-30) surface at pH 5.0 using an amine coupling kit supplied by GE Healthcare. The sample and system buffer was HBS-P pH 7.4. Flow cell was set to 25° C. and sample block to 12° C. and primed with running buffer twice. To generate a calibration curve, increasing concentrations of ANG2 were injected into a BIAcore flow-cell containing the immobilized anti-VEGF/ANG2 antibody. The amount of bound ANG2 was determined as resonance units (RU) and plotted against the concentration. Solutions of each ligand (11 concentrations from 0 to 200 nM for the anti-VEGF/ANG2 antibody) were incubated with 10 nM ANG2 and allowed to reach equilibrium at room temperature. Free ANG2 concentrations were determined from the calibration curve generated before and after measuring the response of solutions with known amounts of ANG2. A 4-parameter fit was set with XLfit4 (IDBS Software) using Model 201 using free ANG2 concentration as y-axis and used concentration of antibody for inhibition as x-axis. The affinity was calculated by determining the inflection point of this curve. The surface was regenerated by one time 30 seconds washing with a 0.85% $H_3PO_4$ solution at a flow rate of 30 µL/min. Bulk refractive index differences were corrected by subtracting the response obtained from a blank-coupled surface. Results are shown in below.

FcRn Steady State Affinity

Figure 5A:
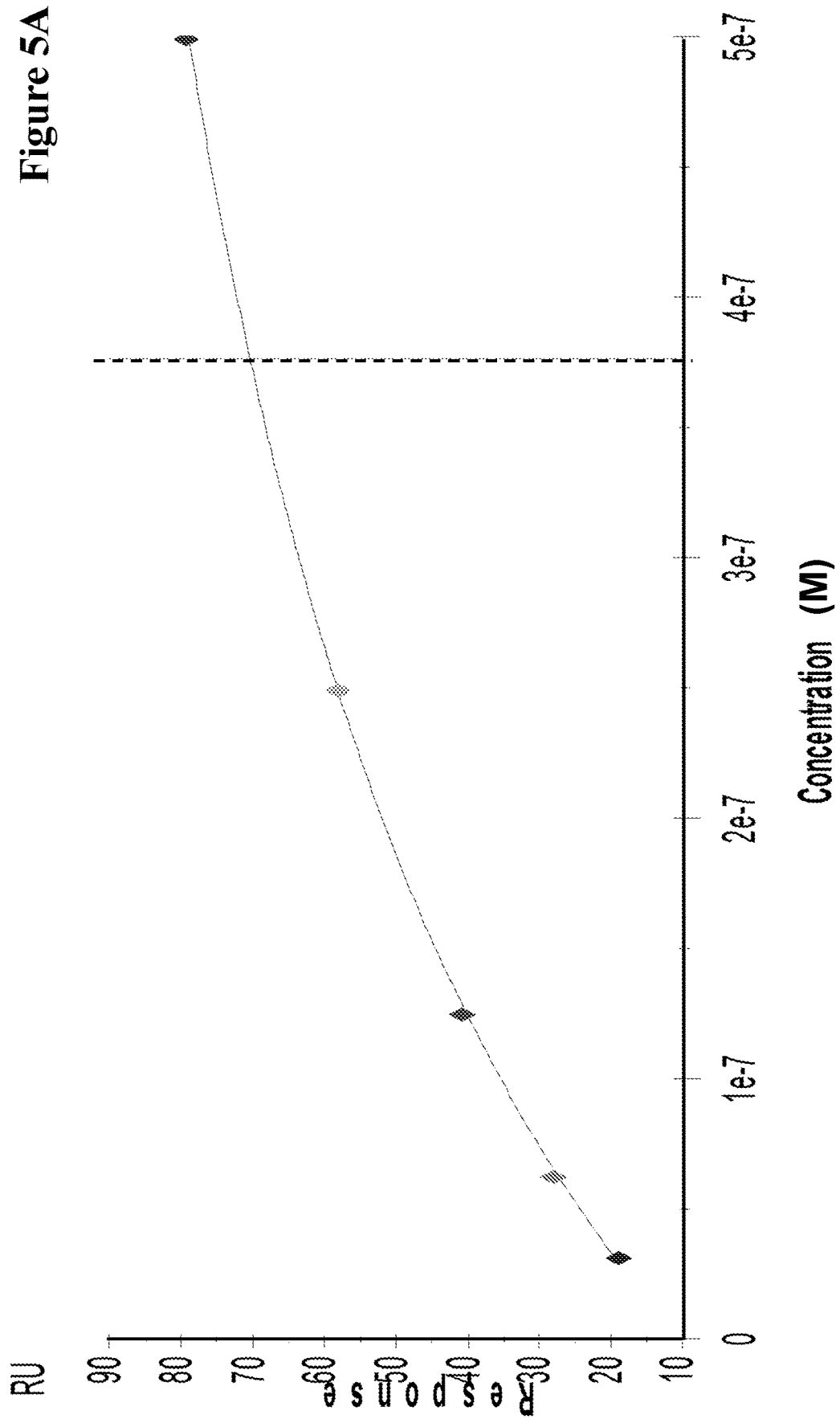

For FcRn measurement, a steady state affinity was used to compare bispecific antibodies against each other. Human FcRn was diluted into coupling buffer (10 µg/mL, Na-Acetate, pH 5.0) and immobilized on a C1-Chip (GE Healthcare BR-1005-35) by targeted immobilization procedure using a BIAcore wizard to a final response of 200 RU. Flow cell was set to 25° C. and sample block to 12° C. and primed with running buffer twice. The sample and system buffer was PBS-T (10 mM phosphate buffered saline including 0.05% Tween20) pH 6.0. To assess different IgG concentrations for each antibody, a concentration of 62.5 nM, 125 nM, 250 nM, and 500 nM was prepared. Flow rate was set to 30 µL/min and the different samples were injected consecutively onto the chip surface choosing 180 seconds association time. The surface was regenerated by injected PBS-T pH 8 for 60 seconds at a flow rate of 30 µL/min. Bulk refractive index differences were corrected by subtracting the response obtained from a blank surface. Buffer injections are also subtracted (=double referencing). For calculation of steady state affinity the method from the BIA-Evaluation software was used. Briefly, the RU values were plotted against the analyzed concentrations, yielding a dose-response curve. Based on a 2-parametric fit, the upper asymptote is calculated, allowing the determination of the half-maximal RU value and hence the affinity. Results are shown in FIG. 5 and the Table below. Analogously the affinity to Cynomolgus, mouse and rabbit FcRn can be determined.

FcgammaRIIIa Measurement

Figure 6:
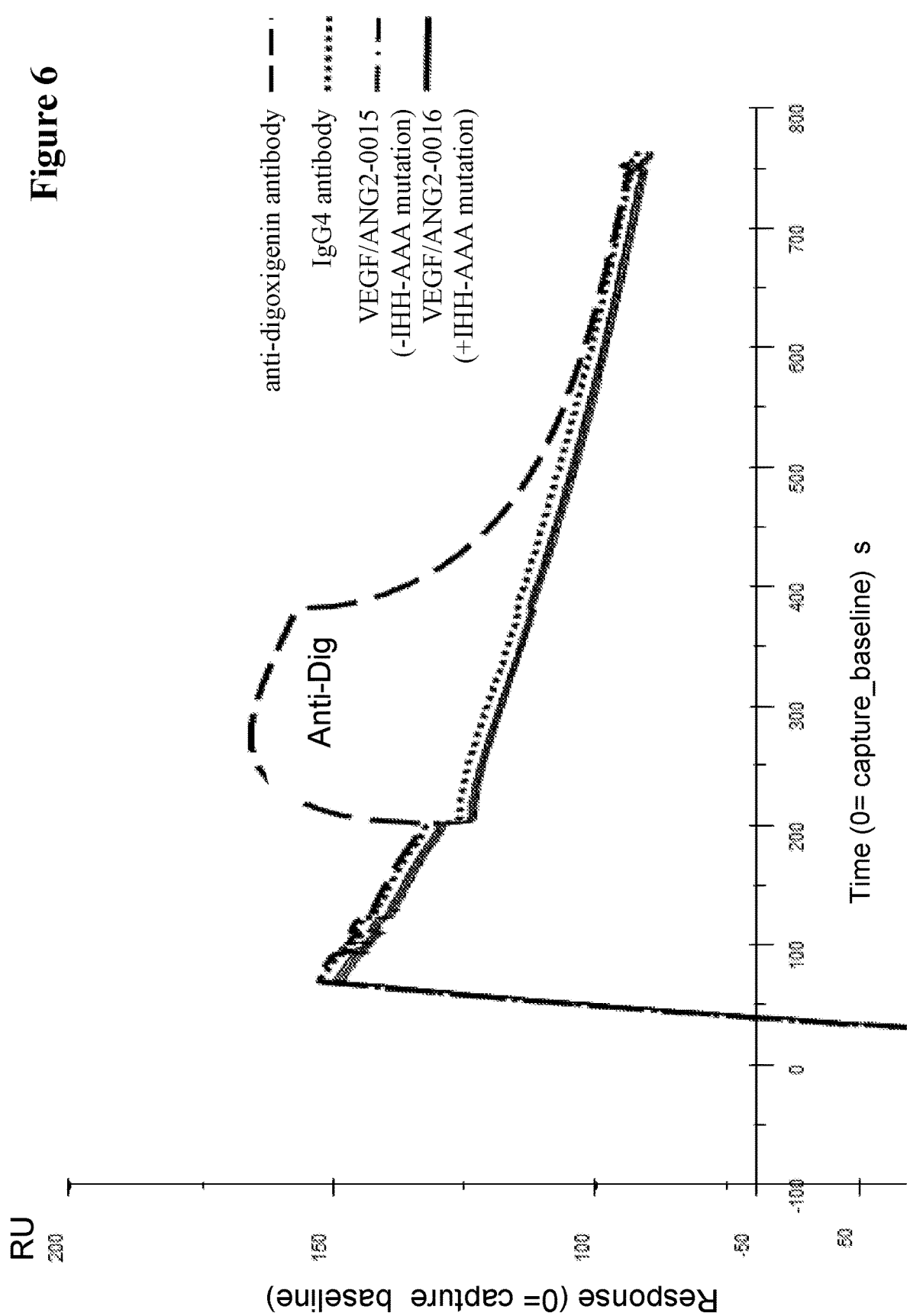
FIG. 6: FcgammaRIIIa interaction measurement of VEGF/ANG2-0015 without IHH-AAA mutation and VEGF/ANG2-0016 with IHH-AAA mutation (both are IgG1 subclass with P329G LALA mutations; as controls an anti-digoxygenin antibody (anti-Dig antibody) of IgG1 subclass and an IgG4 based antibody were used).

For FcgammaRIIIa measurement a direct binding assay was used. Around 3,000 resonance units (RU) of the capturing system (1 µg/mL Penta-His; Qiagen) were coupled on a CM5 chip (GE Healthcare BR-1005-30) at pH 5.0 by using an amine coupling kit supplied by GE Healthcare. The sample and system buffer was HBS-P+ pH 7.4. The flow cell was set to 25° C.—and sample block to 12° C.—and primed with running buffer twice. The FcgammaRIIIa-His-receptor was captured by injecting a 100 nM solution for 60 seconds at a flow of 5 µL/min. Binding was measured by injection of 100 nM of bispecific antibody or monospecific control antibodies (anti-digoxygenin antibody for IgG1 subclass and an IgG4 subclass antibody) for 180 seconds at a flow of 30 µL/min. The surface was regenerated by 120 seconds washing with Glycine pH 2.5 solution at a flow rate of 30 µL/min. Because FcgammaRIIIa binding differs from the Langmuir 1:1 model, only binding/no binding was determined with this assay. In a similar manner FcgammaRIa and FcgammaRIIa binding can be determined. Results are shown in FIG. 6, where it follows that by introduction of the mutations P329G LALA, no more binding to FcgammaRIIIa could be detected.

Assessment of Independent VEGF- and ANG2-Binding to the Anti-VEGF/ANG2 Antibodies Around 3,500 resonance units (RU) of the capturing system (10 µg/mL goat anti-human IgG; GE Healthcare Bio-Sciences AB, Sweden) were coupled on a CM4 chip (GE Healthcare BR-1005-34) at pH 5.0 by using an amine coupling kit supplied by GE Healthcare. The sample and system buffer was PBS-T (10 mM phosphate buffered saline including 0.05% Tween20) pH 7.4. The temperature of the flow cell was set to 25° C. and of the sample block to 12° C. Before capturing, the flow cell was primed with running buffer twice.

The bispecific antibody was captured by injecting a 10 nM solution for 60 seconds at a flow of 5 µL/min. Independent binding of each ligand to the bispecific antibody was analyzed by determining the active binding capacity for each ligand, either added sequentially or simultaneously (flow of 30 µL/min):

1. Injection of human VEGF with a concentration of 200 nM for 180 seconds (identifies the single binding of the antigen).
2. Injection of human ANG2 with a concentration of 100 nM for 180 seconds (identifies single binding of the antigen).
3. Injection of human VEGF with a concentration of 200 nM for 180 seconds followed by an additional injection of human ANG2 with a concentration of 100 nM for 180 seconds (identifies binding of ANG2 in the presence of VEGF).
4. Injection of human ANG2 with a concentration of 100 nM for 180 seconds followed by an additional injection of human VEGF with a concentration of 200 nM (identifies binding of VEGF in the presence of ANG2).
5. Co-injection of human VEGF with a concentration of 200 nM and of human ANG2 with a concentration of 100 nM for 180 seconds (identifies the binding of VEGF and of ANG2 at the same time).

The surface was regenerated by 60 seconds washing with a 3 M $MgCl_2$ solution at a flow rate of 30 µL/min. Bulk refractive index differences were corrected by subtracting the response obtained from a goat anti-human IgG surface.

The bispecific antibody is able to bind both antigens mutual independently if the resulting final signal of the approaches 3, 4 & 5 equals or is similar to the sum of the individual final signals of the approaches 1 and 2. Results are shown in the Table below, where both antibodies VEGF/ANG2-0016, VEGF/ANG2-0012 are shown to be able to bind mutual independently to VEGF and ANG2.

Assessment of Simultaneous VEGF- and ANG2-Binding to the Anti-VEGF/ANG2 Antibodies First, around 1,600 resonance units (RU) of VEGF (20 µg/mL) were coupled on a CM4 chip (GE Healthcare BR-1005-34) at pH 5.0 by using an amine coupling kit supplied by GE Healthcare. The sample and system buffer was PBS-T (10 mM phosphate buffered saline including 0.05% Tween20) pH 7.4. Flow cell was set to 25° C. and sample block to 12° C. and primed with running buffer twice. Second, 50 nM solution of the bispecific antibody was injected for 180 seconds at a flow of 30 µL/min. Third, hANG2 was injected for 180 seconds at a flow of 30 µL/min. The binding response of hANG2 depends from the amount of the bispecific antibody bound to VEGF and shows simultaneous binding. The surface was regenerated by 60 seconds washing with a 0.85% $H_3PO_4$ solution at a flow rate of 30 µL/min. Simultaneous binding is shown by an additional specific binding signal of hANG2 to the previous VEGF bound anti-VEGF/ANG2 antibodies. For both bispecific antibodies VEGF/ANG2-0015 and VEGF/ANG2-0016 simultaneous VEGF- and ANG2-binding to the anti-VEGF/ANG2 antibodies could be detected (data not shown).

TABLE

Results: Kinetic affinities to VEGF isoforms from different species

| | VEGF/ANG2-0015 - apparent affinity | VEGF/ANG2-0016 - apparent affinity | VEGF/ANG2-0012 - apparent affinity | VEGF/ANG2-0201 - apparent affinity |
|---|---|---|---|---|
| human VEGF 121 | ≤1 pM (out of BIAcore specification) | ≤1 pM (out of BIAcore specification) | ≤1 pM (out of BIAcore specification) | ≤1 pM (out of BIAcore specification) |
| mouse VEGF 120 | no binding | no binding | no binding | no binding |
| rat VEGF 164 | 13 nM | 14 nM | 24 nM | 35 nM |

TABLE

Results: Solution affinities to ANG2

| | VEGF/ANG2-0015 KD [nM] | VEGF/ANG2-0016 KD [nM] | VEGF/ANG2-0012 KD [nM] | VEGF/ANG2-0201 KD [nM] |
|---|---|---|---|---|
| human ANG2 | 8 | 20 | 20 | n.d. |
| cyno ANG2 | 5 | 13 | 10 | n.d. |
| mouse ANG2 | 8 | 13 | 8 | n.d. |
| rabbit ANG2 | 4 | 11 | 8 | n.d. |

TABLE

Results: Affinity to FcRn of anti-VEGF/ANG2 antibodies

| | VEGF/ANG2-0015 [affinity] | VEGF/ANG2-0016 [affinity] | VEGF/ANG2-0012 [affinity] | VEGF/ANG2-0201 [affinity] |
|---|---|---|---|---|
| human FcRn | 0.8 µM | no binding | no binding | 0.8 µM |
| cynomolgus FcRn | 0.9 µM | no binding | no binding | 1.0 µM |
| mouse FcRn | 0.2 µM | no binding | no binding | 0.2 µM |

TABLE

Results Binding to FcgammaRI - IIIa

| | VEGF/ANG2-0015 | VEGF/ANG2-0016 | VEGF/ANG2-0012 | VEGF/ANG2-0201 |
|---|---|---|---|---|
| FcγRIa | no binding | no binding | binding | binding |
| FcγRIIa | no binding | no binding | no binding | binding |
| FcγRIIIa | no binding | no binding | no binding | binding |

TABLE

Results: Independent binding of VEGF- and ANG2 to anti-VEGF/ANG2 antibodies

| | ANG2 [RUmax] | VEGF [RUmax] | first VEGF then ANG2 [RUmax] | first ANG2 then VEGF [RUmax] | Co-injection ANG2 + VEGF [RUmax] |
|---|---|---|---|---|---|
| VEGF/ANG2-0016 | 174 | 50 | 211 | 211 | 211 |
| VEGF/ANG2-0012 | 143 | 43 | 178 | 177 | 178 |

Example 4

Mass Spectrometry

This section describes the characterization of anti-VEGF/ANG2 antibodies with emphasis on the correct assembly. The expected primary structures were confirmed by electrospray ionization mass spectrometry (ESI-MS) of the deglycosylated, and intact or IdeS-digested (IgG-degrading enzyme of S. pyogenes) anti-VEGF/ANG2 antibodies. The IdeS-digestion was performed with 100 µg purified antibody incubated with 2 ug IdeS protease (Fabricator) in 100 mmol/L $NaH_2PO_4/Na_2HPO_4$, pH 7.1 at 37° C. for 5 h. Subsequently, the antibodies were deglycosylated with N-Glycosidase F, Neuraminidase and O-glycosidase (Roche) in 100 mmol/L $NaH_2PO_4/Na_2HPO_4$, pH 7.1 at 37° C. for up to 16 hours at a protein concentration of 1 mg/mL and subsequently desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

The masses obtained for the IdeS-digested, deglycosylated (Table below), or intact, deglycosylated (Table below) molecules correspond to the predicted masses deduced from the amino acid sequences for the anti-VEGF/ANG2 antibodies consisting of two different light chains $LC_{ANG2}$ and $LC_{Lucentis}$, and two different heavy chains $HC_{ANG2}$ and $HC_{Lucentis}$.

TABLE

Masses of the deglycosylated and IdeS-digested bispecific anti-VEGF/ANG2 antibodies VEGF/ANG2-0201 (without IHH-AAA mutation) and VEGF/ANG2-0012 (with IHH-AAA mutation)

| | $F(ab')_2$ of the anti-VEGF/ANG2 antibody | | deglycosylated Fc-region of the anti-VEGF/ANG2 antibody | |
|---|---|---|---|---|
| sample | predicted average mass [Da] | observed average mass [Da] | predicted average mass [Da] | observed average mass [Da] |
| VEGF/ANG2-0201 | 99360.8 | 99360.7 | 47439.2 | 47430.1 |
| VEGF/ANG2-0012 | 99360.8 | 99361.1 | 47087.7 | 47082.0 |

TABLE

Masses of the deglycosylated anti-VEGF/ANG2 antibodies VEGF/ANG2-0016 (with IHH-AAA mutation) and VEGF/ANG2-0015 (without IHH-AAA mutation)

| | deglycosylated anti-VEGF/ANG2 antibody | |
|---|---|---|
| | predicted average mass [Da] | observed average mass [Da] |
| VEGF/ANG2-0016 | 146156.9 | 146161.2 |
| VEGF/ANG2-0015 | 146505.3 | 146509.4 |

Example 5

FcRn Chromatography

Coupling to Streptavidin Sepharose:

One gram streptavidin sepharose (GE Healthcare) was added to the biotinylated and dialyzed receptor and incubated for two hours with shaking. The receptor derivatized sepharose was filled in a 1 mL XK column (GE Healthcare).

Chromatography Using the FcRn Affinity Column:

Conditions:

column dimensions: 50 mm×5 mm bed height: 5 cm loading: 50 µg sample equilibration buffer: 20 mM IVIES, with 150 mM NaCl, adjusted to pH 5.5 elution buffer: 20 mM Tris/HCl, with 150 mM NaCl, adjusted to pH 8.8 elution: 7.5 CV equilibration buffer, in 30 CV to 100% elution buffer, 10 CV elution buffer Human FcRn Affinity Column Chromatography In the following Table of retention times of anti-VEGF/ANG2 antibodies on affinity columns comprising human FcRn are given. Data were obtained using the conditions above.

TABLE

Results: retention times of anti-VEGF/ANG2 antibodies

| antibody | retention time [min] |
|---|---|
| VEGF/ANG2-0015 (without IHH-AAA mutation) | 78.5 |
| VEGF/ANG2-0201 (without IHH-AAA mutation) | 78.9 |
| VEGF/ANG2-0012 (with IHH-AAA mutation) | 2.7 (void-peak) |
| VEGF/ANG2-0016 (with IHH-AAA mutation) | 2.7 (void-peak) |

Example 6

Pharmacokinetic (PK) Properties of Antibodies with IHH-AAA Mutation

PK Data with FcRn Mice Transgenic for Human FcRn

In life phase:

The study included female C57BL/6J mice (background); mouse FcRn deficient, but hemizygous transgenic for human FcRn (huFcRn, line 276 -/tg)

Part 1:

All mice were injected once intravitreally into the right eye with 2 µL/animal of the appropriate solution (i.e. 21 µg compound/animal (VEGF/ANG2-0015 (without IHH-AAA mutation)) or 23.6 µg compound/animal (VEGF/ANG2-0016 (with IHH-AAA mutation)).

Mice were allocated to 2 groups with 6 animals each. Blood samples are taken from group 1 at 2, 24 and 96 hours and from group 2 at 7, 48 and 168 hours after dosing.

Injection into the vitreous of the right mouse eye was performed using the NanoFil Microsyringe system for nanoliter injection from World Precision Instruments, Inc., Berlin, Germany. Mice were anesthetized with 2.5% Isoflurane and for visualization of the mouse eye a Leica MZFL 3 microscope with a 40 fold magnification and a ring-light with a Leica KL 2500 LCD lightning was used. Subsequently, 2 µL of the compound were injected using a 35-gauge needle.

Blood was collected via the retrobulbar venous plexus of the contralateral eye from each animal for the determination of the compound levels in serum.

Serum samples of at least 50 µL were obtained from blood after 1 hour at RT by centrifugation (9,300×g) at 4° C. for 3 min. Serum samples were frozen directly after centrifugation and stored frozen at −80° C. until analysis. Treated eyes of the animals of group 1 were isolated 96 hours after treatment and of the animals of group 2 168 hours after treatment. Samples were stored frozen at −80° C. until analysis.

Part 2:

All mice were injected once intravenously via the tail vein with 200 µL/animal of the appropriate solution (i.e. 21 µg compound/animal (VEGF/ANG2-0015 (without IHH-AAA mutation)) or 23.6 µg compound/animal (VEGF/ANG2-0016 (with IHH-AAA mutation)).

Mice were allocated to 2 groups with 5 animals each. Blood samples are taken from group 1 at 1, 24 and 96 hours and from group 2 at 7, 48 and 168 hours after dosing. Blood was collected via the retrobulbar venous plexus from each animal for the determination of the compound levels in serum.

Serum samples of at least 50 µL were obtained from blood after 1 hour at RT by centrifugation (9,300×g) at 4° C. for 3 min. Serum samples were frozen directly after centrifugation and stored frozen at −80° C. until analysis.

Preparation of Whole Eye Lysates (Mice)

The eye lysates were gained by physico-chemical disintegration of the whole eye from laboratory animals. For mechanical disruption, each eye was transferred into a 1.5 mL micro vial with conical bottom. After freeze and thawing, the eyes were washed with 1 mL cell washing buffer once (Bio-Rad, Bio-Plex Cell Lysis Kit, Cat. No. 171-304011). In the following step, 500 µL of freshly prepared cell lysis buffer were added and the eyes were grinded using a 1.5 mL tissue grinding pestle (Kimble Chase, 1.5 mL pestle, Art. No. 749521-1500). The mixture was then frozen and thawed five times and grinded again. To separate lysate from remaining tissue the samples were centrifuged for 4 min at 4,500 g. After centrifuging, supernatant was collected and stored at −20° C. until further analysis in the quantification ELISA.

Analysis

The concentrations of the anti-VEGF/ANG2 antibodies in mice serum and eye lysates were determined with an enzyme linked immunosorbent assay (ELISA)

For quantification of anti-VEGF/ANG2 antibodies in mouse serum samples and eye lysates, a standard solid-phase serial sandwich immunoassay with biotinylated and digoxigenylated monoclonal antibodies used as capture and detection antibodies was performed. To verify the integrity of the bispecificity of the analyte, the biotinylated capture antibody recognizes the VEGF-binding site whereas the digoxigenylated detection antibody will bind to the ANG2 binding site of the analyte. The bound immune complex of capture antibody, analyte and detection antibody on the solid phase of the streptavidin coated micro titer plate (SA-MTP) is then detected with a horseradish-peroxidase coupled to an anti-digoxigenin antibody. After washing unbound material from the SA-MTP and addition of ABTS-substrate, the gained signal is proportional to the amount of analyte bound on the solid phase of the SA-MTP. Quantification is then done by converting the measured signals of the samples into concentrations referring to calibrators analyzed in parallel.

In a first step the SA-MTP was coated with 100 µL/well of biotinylated capture antibody solution (mAb<Id<VEGF>>M-2.45.51-IgG-Bi(DDS), anti-idiotypic antibody) with a concentration of 1 µg/mL for one hour at 500 rpm on a MTP-shaker. Meanwhile calibrators, QC-samples and samples were prepared. Calibrators and QC-samples are diluted to 2% serum matrix; samples were diluted until the signals were within the linear range of the calibrators.

After coating the SA-MTP with capture antibody, the plate was washed three times with washing buffer and 300 µL/well. Subsequently, 100 µL/well of the calibrators, QC-samples and samples were pipetted on the SA-MTP and incubated again for one hour at 500 rpm. The analyte was now bound with its VEGF binding site via the capture antibody to the solid phase of the SA-MTP. After incubation and removal of unbound analyte by washing the plate 100 µL/well of the first detection antibody (mAb<Id-<ANG2>>M-2.6.81-IgG-Dig(XOSu), anti-idiotypic antibody) with a concentration of 250 ng/mL was added to the SA-MTP. Again, the plate was incubated for one hour at 500 rpm on a shaker. After washing, 100 µL/well of the second detection antibody (pAb<Digoxigenin>S-Fab-POD (poly)) at a concentration of 50 mU/mL was added to the wells of the SA-MTP and the plate was incubated again for one hour at 500 rpm. After a final washing step to remove excess detection antibody, 100 µL/well substrate (ABTS) is added. The antibody-enzyme conjugate catalyzes the color reaction of the ABTS® substrate. The signal was then measured by ELISA reader at 405 nm wavelength (reference wavelength: 490 nm ([405/490] nm)).

Pharmacokinetic Evaluation

The pharmacokinetic parameters were calculated by non-compartmental analysis, using the pharmacokinetic evaluation program WINNONLIN™ (Pharsight), version 5.2.1.

Results:

A) Serum Concentrations

Figure 7C:
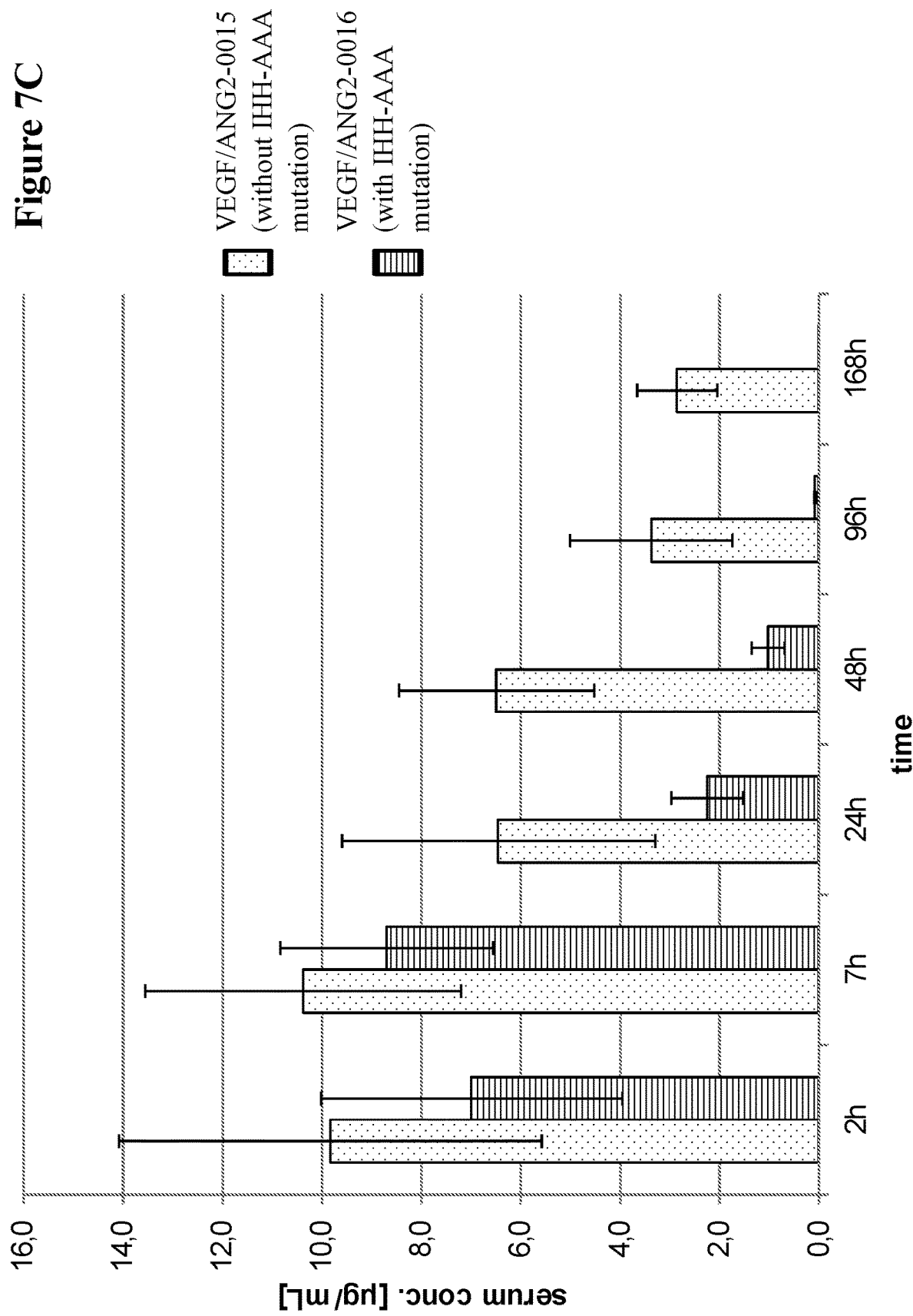
FIG. 7C: Serum concentration after intravitreal application: comparison of VEGF/ANG2-0015 without IHH-AAA mutation and VEGF/ANG2-0016 with IHH-AAA mutation.

Results for serum concentrations are shown in the following Tables and FIGS. 7B to 7C.

TABLE

VEGF/ANG2-0015 (without IHH-AAA mutation): Comparison of serum concentrations after intravitreal and intravenous application

| ID | serum concentration after intravitreal application average conc. [µg/mL] | serum concentration after intravenous application average conc. [µg/mL] |
|---|---|---|
| 1 h |  | 17.7 |
| 2 h | 9.8 |  |
| 7 h | 10.4 | 12.1 |
| 24 h | 6.4 | 8.3 |
| 48 h | 6.5 | 6.9 |
| 96 h | 3.4 | 4.1 |
| 168 h | 2.9 | 2.7 |

TABLE

VEGF/ANG2-0016 (with IHH-AAA mutation): Comparison of serum concentrations after intravitreal and intravenous application

| ID | serum concentration after intravitreal application average conc. [μg/mL] | serum concentration after intravenous application average conc. [μg/mL] |
|---|---|---|
| 1 h |  | 18.4 |
| 2 h | 7.0 |  |
| 7 h | 8.7 | 10.0 |
| 24 h | 2.2 | 3.3 |
| 48 h | 1.0 | 1.0 |
| 96 h | 0.1 | 0.1 |
| 168 h | 0.0 | 0.0 |

TABLE

VEGF/ANG2-0015 (without IHH-AAA mutation) and VEGF/ANG2-0016 (with IHH-AAA mutation): Comparison of serum concentrations after intravitreal application)

| ID | VEGF/ANG2-0015 (without IHH-AAA mutation) average conc. [μg/mL] | VEGF/ANG2-0016 (with IHH-AAA mutation) average conc. [μg/mL] |
|---|---|---|
| 2 h | 9.8 | 7.0 |
| 7 h | 10.4 | 8.7 |
| 24 h | 6.4 | 2.2 |
| 48 h | 6.5 | 1.0 |
| 96 h | 3.4 | 0.1 |
| 168 h | 2.9 | 0.0 |

TABLE

VEGF/ANG2-0015 (without IHH-AAA mutation) and VEGF/ANG2-0016 (with IHH-AAA mutation): Comparison of serum concentrations after intravenous application

| ID | VEGF/ANG2-0015 (without IHH-AAA mutation) average conc. [μg/mL] | VEGF/ANG2-0016 (with IHH-AAA mutation) average conc. [μg/mL] |
|---|---|---|
| 1 h | 17.7 | 18.4 |
| 7 h | 12.1 | 10.0 |
| 24 h | 8.3 | 3.3 |
| 48 h | 6.9 | 1.0 |
| 96 h | 4.1 | 0.1 |
| 168 h | 2.7 | 0.0 |

Results:

B) Concentrations in Eye-Lysates of Left and Right Eyes

Figure 7E:
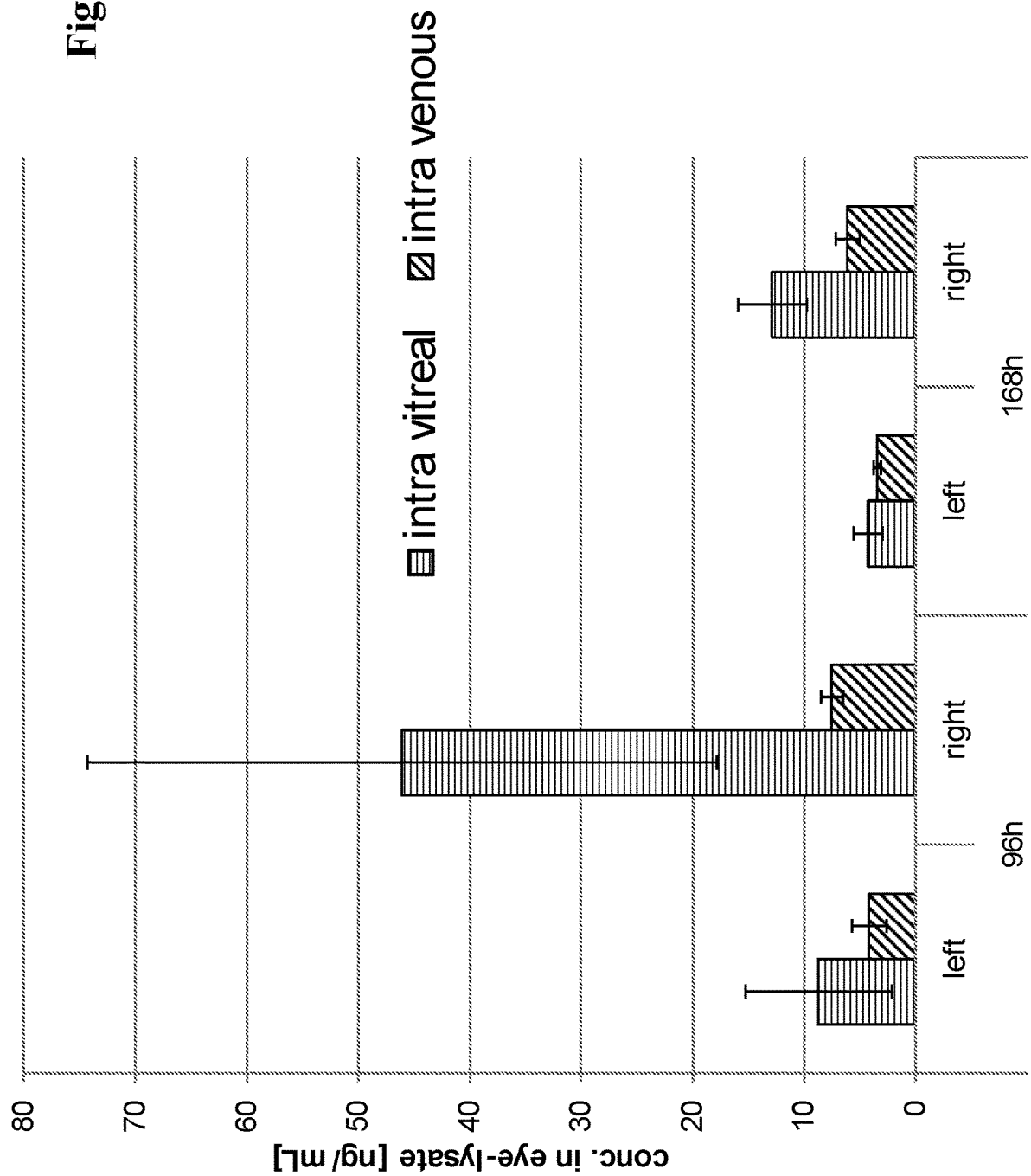
FIG. 7E: Eye lysates concentration of VEGF/ANG2-0015 (without IHH-AAA mutation) in right and left eye (after intravitreal application only into the right eye in comparison to intravenous application): in the right eye (and to some extent in the left eye) after intravitreal application concentrations of VEGF/ANG2-0015 could be detected; this indicates the diffusion from the right eye into serum and from there into the left eye, which can be explained by the long half-life of VEGF/ANG2-0015 (without IHH-AAA mutation); after intravenous application also significant concentrations in eye lysates of both eyes could be detected due to diffusion into the eyes of the serum-stable VEGF/ANG2-0015 (without IHH-AAA mutation).
Figure 8B:
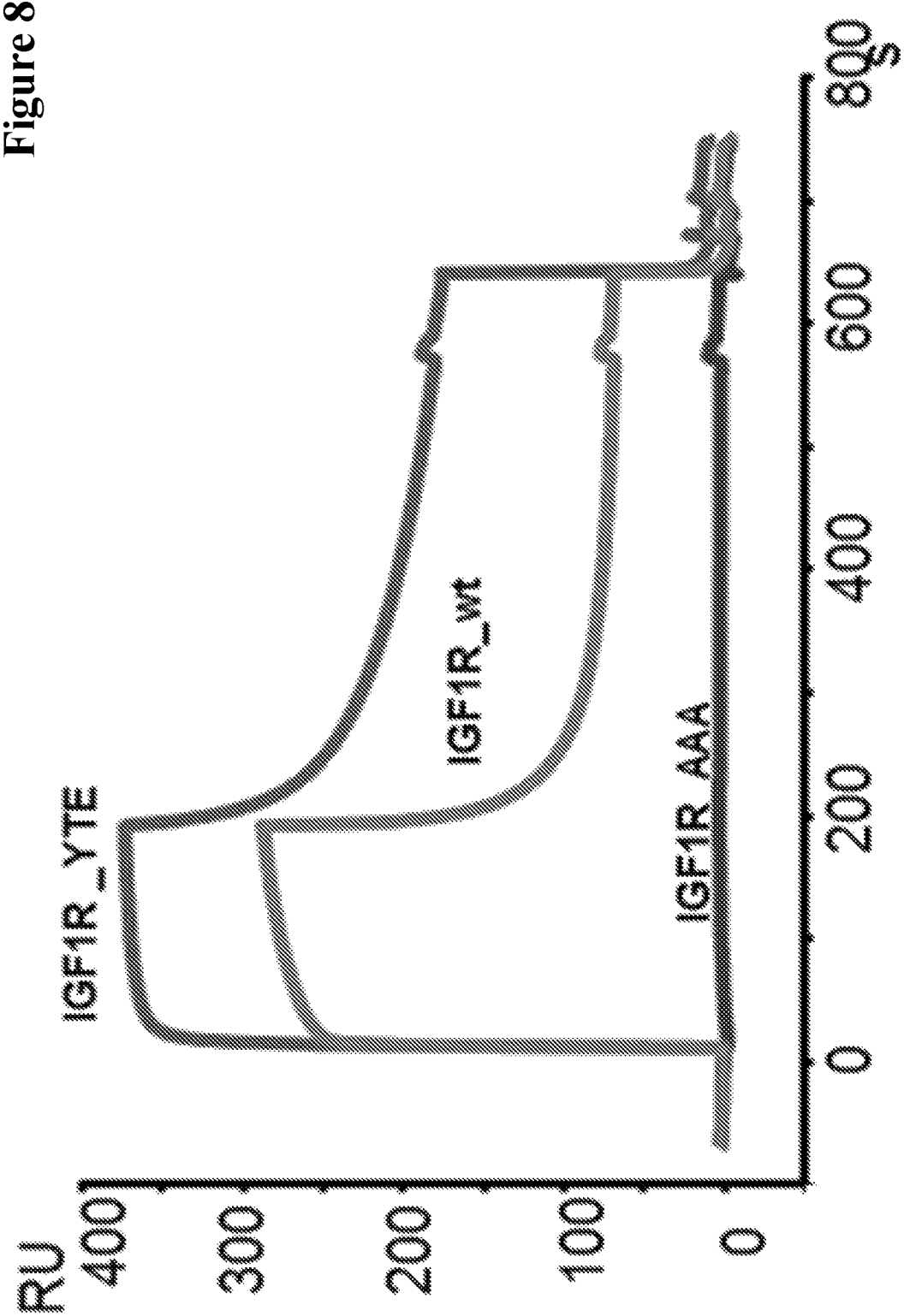
Figure 8C:
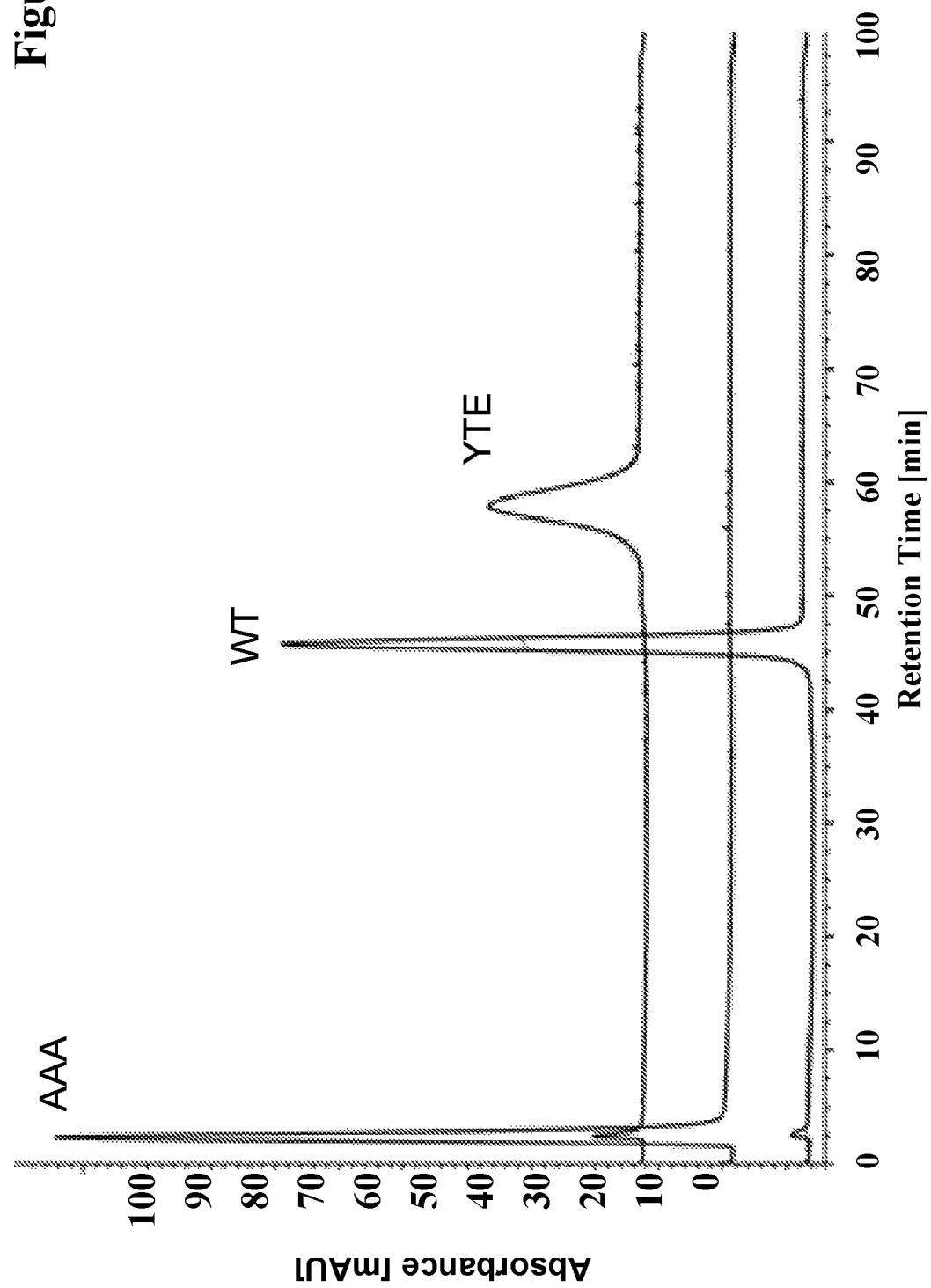

Results for concentrations in eye lysates are shown in the following Tables and FIGS. 7D to 7E.

TABLE

Concentrations of VEGF/ANG2-0015 (without IHH-AAA mutation) in eye lysates after intra vitreal application into right eye
mean conc. values from n = 6 mice

| ID | | mean conc. [ng/mL] |
|---|---|---|
| 96 h | left eye | 8.7 |
|  | right eye | 46.1 |
| 168 h | left eye | 4.3 |
|  | right eye t | 12.9 |

TABLE

Concentrations of VEGF/ANG2-0015 (without IHH-AAA mutation) in eye lysates after intravenous application
mean conc. values from n = 5 mice

| ID | | mean conc. [ng/mL] |
|---|---|---|
| 96 h | left eye | 4.2 |
|  | right eye | 7.5 |
| 168 h | left eye | 3.4 |
|  | right eye | 6.1 |

TABLE

Concentrations of VEGF/ANG2-0016 (with IHH-AAA mutation) in eye lysates after intra vitreal application into right eye
mean conc. values from n = 5 mice

| ID | | mean conc. [ng/mL] |
|---|---|---|
| 96 h | left eye | 0.3 |
|  | right eye | 34.5 |
| 168 h | left eye | 0.1 |
|  | right eye | 9.0 |

TABLE

Concentrations of VEGF/ANG2-0016 (with IHH-AAA mutation) in eye lysates after intravenous application
mean conc. values from n = 5 mice

| ID | | mean conc. [ng/mL] |
|---|---|---|
| 96 h | left eye | 0.0 |
|  | right eye | 0.1 |
| 168 h | left eye | 0.0 |
|  | right eye | 0.1 |

Summary of Results:

After intravitreal application the bispecific anti-VEGF/ANG2 antibody as reported herein VEGF/ANG2-0016 (with IHH-AAA mutation) shows similar concentrations (after 96 and 168 hours) in the eye lysates as compared to the bispecific anti-VEGF/ANG2 antibody without IHH-AAA mutation VEGF/ANG2-0015.

Also after intravitreal application the bispecific anti-VEGF/ANG2 antibody as reported herein VEGF/ANG2-0016 (with IHH-AAA mutation) shows in addition a faster clearance and shorter half-life in the serum as compared to the bispecific anti-VEGF/ANG2 antibody without IHH-AAA mutation VEGF/ANG2-0015.

Example 7

Mouse Cornea Micropocket Angiogenesis Assay

To test the anti-angiogenic effect, bispecific anti-VEGF/ANG2antibody with the respective VEGF binding VH and VL of SEQ ID NO: 20 and 21 and the ANG2 binding VH and VL of SEQ ID NO: 28 and 29 on VEGF-induced angiogenesis in vivo, a mouse corneal angiogenesis assay was performed. In this assay a VEGF soaked Nylaflo disc is implanted into a pocket of the avascular cornea at a fixed distance to the limbal vessels. Vessels immediately grow into the cornea towards the developing VEGF gradient. 8 to 10 weeks old female Balb/c mice were purchased from Charles River, Sulzfeld, Germany. The protocol is modified according to the method described by Rogers, M.S., et al., Nat. Protoc. 2 (2007) 2545-2550. Briefly, micropockets with a width of about 500 μm are prepared under a microscope at approximately 1 mm from the limbus to the top of the cornea using a surgical blade and sharp tweezers in the anesthetized mouse. The disc (Nylaflo®, Pall Corporation, Michigan) with a diameter of 0.6 mm is implanted and the surface of the implantation area was smoothened. Discs are incubated in corresponding growth factor or in vehicle for at least 30 min. After 3, 5 and 7 days (or alternatively only after 3, 5 or 7 days) eyes are photographed and vascular response is measured. The assay is quantified by calculating the percentage of the area of new vessels per total area of the cornea.

The discs are loaded with 300 ng VEGF or with PBS as a control and implanted for 7 days. The outgrowth of vessels from the limbus to the disc is monitored over time on day 3, 5 and/or 7. One day prior to disc implantation, the antibodies are administered intravenously at a dose of 10 mg/kg (due to the intravenous application the serum-stable VEGF/ANG2-0015 (without IHH-AAA mutation) which only differs from VEGF/ANG2-0016 by the IHH-AAA mutation and has the same VEGF and ANG2 binding VHs and VLs to mediate efficacy, is used as surrogate) for testing the anti-angiogenic effect on VEGF-induced angiogenesis in vivo. Animals in the control group receive vehicle. The application volume is 10 mL/kg.

Example 8

Pharmacokinetic (PK) Properties of Antibodies with HHY-AAA Mutation
PK Data with FcRn Mice Transgenic for Human FcRn
In life phase:
The study included female C57BL/6J mice (background); mouse FcRn deficient, but hemizygous transgenic for human FcRn (huFcRn, line 276 -/tg)
Part 1:
All mice were injected once intravitreally into the right eye with the appropriate solution of IGF-1R 0033, IGF-1R 0035, IGF-1R 0045 (i.e. 22.2 µg compound/animal of IGF-1R 0033, 24.4 µg compound/animal IGF-1R 0035, 32.0 µg compound/animal IGF-1R and 32.0 µg compound/animal of IGF-1R 0045).

Thirteen mice were allocated to 2 groups with 6 and 7, respectively, animals each. Blood samples are taken from group 1 at 2, 24 and 96 hours and from group 2 at 7, 48 and 168 hours after dosing.

Injection into the vitreous of the right mouse eye was performed by using the NanoFil Microsyringe system for nanoliter injection from World Precision Instruments, Inc., Berlin, Germany. Mice were anesthetized with 2.5% Isoflurane and for visualization of the mouse eye a Leica MZFL 3 microscope with a 40 fold magnification and a ring-light with a Leica KL 2500 LCD lightning was used. Subsequently, 2 µL of the compound were injected using a 35-gauge needle.

Blood was collected via the retrobulbar venous plexus of the contralateral eye from each animal for the determination of the compound levels in serum.

Serum samples of at least 50 µL were obtained from blood after 1 hour at RT by centrifugation (9,300×g) at 4° C. for 3 min. Serum samples were frozen directly after centrifugation and stored frozen at −80° C. until analysis. Treated eyes of the animals of group 1 were isolated 96 hours after treatment and of the animals of group 2 168 hours after treatment. Samples were stored frozen at −80° C. until analysis.

Part 2:
All mice were injected once intravenously via the tail vein with the appropriate solution of IGF-1R 0033, IGF-1R 0035, IGF-1R 0045 (i.e. 22.2 µg compound/animal of IGF-1R 0033, 24.4 µg compound/animal IGF-1R 0035, 32.0 µg compound/animal IGF-1R and 32.0 µg compound/animal of IGF-1R 0045).

Twelve mice were allocated to 2 groups with 6 animals each. Blood samples are taken from group 1 at 1, 24 and 96 hours and from group 2 at 7, 48 and 168 hours after dosing. Blood was collected via the retrobulbar venous plexus from each animal for the determination of the compound levels in serum.

Serum samples of at least 50 µL were obtained from blood after 1 hour at RT by centrifugation (9,300×g) at 4° C. for 3 min. Serum samples were frozen directly after centrifugation and stored frozen at −80° C. until analysis.
Preparation of Cell Lysis Buffer
Carefully mix 100 µL factor 1, 50 µL factor 2 and 24.73 mL Cell Lysis buffer (all from Bio-Rad, Bio-Plex Cell Lysis Kit, Cat. No. 171-304011) and add 125 µL PMSF solution (174.4 mg phenylmethylsulfonylfluoride diluted in 2.0 mL DMSO).
Preparation of Whole Eye Lysates (Mice)

The eye lysates were gained by physico-chemical disintegration of the whole eye from laboratory animals. For mechanical disruption each eye was transferred into a 1.5 mL micro vial with conical bottom. After thawing, the eyes were washed with 1 mL cell washing buffer once (Bio-Rad, Bio-Plex Cell Lysis Kit, Cat. No. 171-304011). In the following step 500 µL of freshly prepared cell lysis buffer were added and the eyes were grinded using a 1.5 mL tissue grinding pestle (VWR Int., Art. No. 431-0098). The mixture was then frozen and thawed five times and grinded again. To separate lysate from remaining tissue the samples were centrifuged for 4 min. at 4500×g. After centrifuging the supernatant was collected and stored at −20° C. until further analysis in the quantification ELISA
Analysis (Serum)

For quantification of antibodies in mouse serum sample, a standard solid-phase serial sandwich immunoassay with biotinylated and digoxigenated monoclonal antibodies used as capture and detection antibodies is performed. Serum accounts for about 50% of the full blood sample volume.

More detailed, concentrations of the antibodies in mouse serum samples were determined by a human-IgG (Fab) specific enzyme linked immunosorbent assay. Streptavidin coated microtiter plates were incubated with the biotinylated anti-human Fab(kappa) monoclonal antibody M-1.7.10-IgG as capture antibody diluted in assay buffer for one hour at room temperature with agitation. After washing three times with phosphate-buffered saline-polysorbate 20 (Tween20), serum samples at various dilutions were added followed by second incubation for one hour at room temperature. After three repeated washings bound antibody was detected by subsequent incubation with the anti-human Fab(CH1) monoclonal antibody M-1.19.31-IgG conjugated to digoxigenin, followed by an anti-digoxigenin antibody conjugated to horseradish peroxidase (HRP). ABTS (2,2'-azino-bis(3-ethylbenzothiazoline-6-sulphonic acid); Roche Diagnostics GmbH, Mannheim, Germany) was used as HRP substrate to form a colored reaction product. Absorbance of the resulting reaction product was read at 405 nm (ABTS; reference wavelength: 490 nm).

All samples, positive and negative control samples were analyzed in replicates and calibrated against an antibody standard provided.

Analysis (Eye Lysate)

The concentrations of the analytes in mouse eye lysate samples were determined using a qualified electro-chemiluminescence immunoassay (ECLIA) method based on the ELECSYS® instrument platform (Roche Diagnostics GmbH, Mannheim, Germany) under non-GLP conditions.

The undiluted supernatant (eye lysates) was incubated with capture and detection molecules for 9 min. at 37° C. Biotinylated anti-human-Fab(kappa) monoclonal antibody M-1.7.10-IgG was used as capture molecule and a ruthenium(II)tris(bispyridyl)3' labeled anti-human-Fab(CH1) monoclonal antibody M-1.19.31-IgG was used for detection. Streptavidin-coated magnetic microparticles were added and incubated for additional 9 min. at 37° C. to allow binding of preformed immune complexes due to biotin-streptavidin interactions. The microparticles were magnetically captured on an electrode and a chemiluminescent signal generated using the co-reactant tripropyl amine (TPA). The gained signal was measured by a photomultiplier detector.

TABLE

Standard chart IGF-1R 0033

| | concentration [ng/mL] | signal mean counts | standard deviation signal counts | serum-conc. [ng/mL] | recovery [%] |
|---|---|---|---|---|---|
| standard sample 9 | 0 | 1038 | 46 | — | — |
| standard sample 8 | 0.686 | 2682 | 105 | 0.675 | 98 |
| standard sample 7 | 2.06 | 6275 | 791 | 2.06 | 100 |
| standard sample 6 | 6.17 | 15907 | 316 | 6.23 | 101 |
| standard sample 5 | 18.5 | 45455 | 1238 | 18.8 | 102 |
| standard sample 4 | 55.6 | 133940 | 949 | 55.7 | 100 |
| standard sample 3 | 167 | 388069 | 2929 | 165 | 99 |
| standard sample 2 | 500 | 1129804 | 16777 | 503 | 101 |
| standard sample 1 | 1500 | 2956965 | 60287 | 1499 | 100 |

TABLE

Standard chart IGF-1R 0035

| | concentration [ng/mL] | signal mean counts | standard deviation signal counts | serum-conc. [ng/mL] | recovery [%] |
|---|---|---|---|---|---|
| standard sample 9 | 0 | 1024 | 63 | — | — |
| standard sample 8 | 0.686 | 2817 | 38 | 0.681 | 99 |
| standard sample 7 | 2.06 | 6451 | 39 | 2.08 | 101 |
| standard sample 6 | 6.17 | 17100 | 319 | 6.13 | 99 |
| standard sample 5 | 18.5 | 49693 | 713 | 18.6 | 100 |
| standard sample 4 | 55.6 | 146746 | 2575 | 56.1 | 101 |
| standard sample 3 | 167 | 423597 | 5068 | 165 | 99 |
| standard sample 2 | 500 | 1224244 | 11655 | 502 | 100 |
| standard sample 1 | 1500 | 3144901 | 44536 | 1499 | 100 |

TABLE

Standard chart IGF-1R 0045

| | concentration [ng/mL] | signal mean counts | standard deviation signal counts | serum-conc. [ng/mL] | recovery [%] |
|---|---|---|---|---|---|
| standard sample 9 | 0 | 1339 | 545 | — | — |
| standard sample 8 | 0.686 | 3108 | 61 | 0.622 | 91 |
| standard sample 7 | 2.06 | 7032 | 189 | 1.93 | 94 |
| standard sample 6 | 6.17 | 19175 | 750 | 6.10 | 99 |
| standard sample 5 | 18.5 | 55526 | 823 | 18.7 | 101 |
| standard sample 4 | 55.6 | 158591 | 5412 | 55.7 | 100 |
| standard sample 3 | 167 | 456316 | 28759 | 167 | 100 |
| standard sample 2 | 500 | 1274801 | 47532 | 499 | 100 |
| standard sample 1 | 1500 | 3280452 | 239523 | 1501 | 100 |

Results:

A) Serum Concentrations

Figure 17:
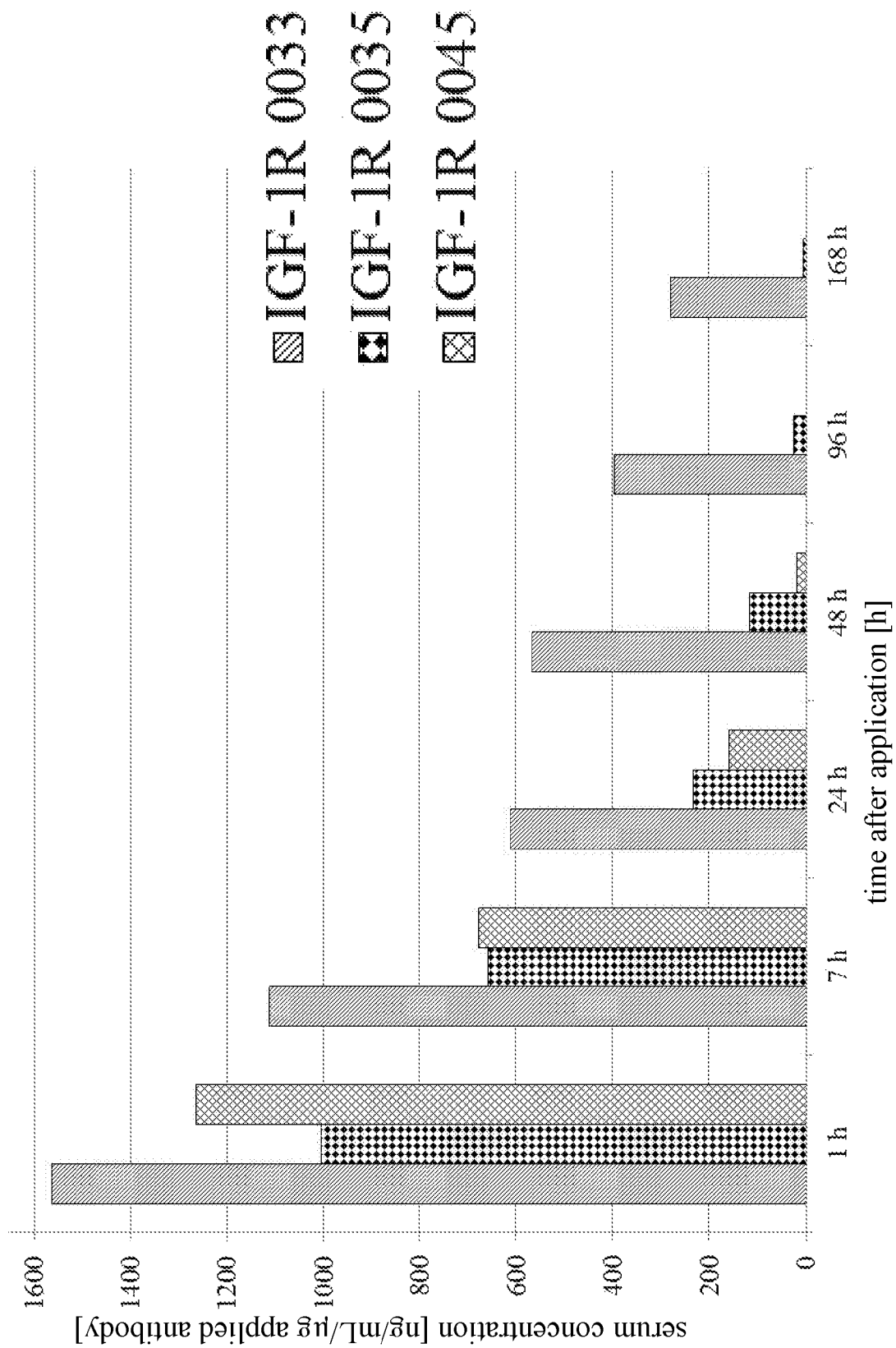
FIG. 17: Comparison of serum concentrations after intravenous application of antibodies IGF-1R 0033, 0035 and 0045.

Results for serum concentrations are shown in the following Tables and FIG. 17.

TABLE

IGF-1R 0033 (without HHY-AAA mutation): Comparison of serum concentrations after intravitreal and intravenous application

| ID | serum concentration after intravitreal application average conc. [μg/mL] | serum concentration after intravenous application average conc. [μg/mL] |
|---|---|---|
| 1 h | n.d. | 34.7 |
| 2 h | 5.9 | n.d. |
| 7 h | 11.1 | 24.7 |
| 24 h | 4.4 | 13.6 |
| 48 h | 7.8 | 12.6 |
| 96 h | 2.1 | 8.9 |
| 168 h | 2.9 | 6.2 |

(n.d. = not determined)

TABLE

IGF-1R 0035 (with HHY-AAA mutation in one Fc-region polypeptide): Comparison of serum concentrations after intravitreal and intravenous application

| ID | serum concentration after intravitreal application average conc. [μg/mL] | serum concentration after intravenous application average conc. [μg/mL] |
|---|---|---|
| 1 h | n.d. | 24.5 |
| 2 h | 7.3 | n.d. |
| 7 h | 7.9 | 16.1 |
| 24 h | 2.3 | 5.7 |
| 48 h | 1.7 | 2.9 |
| 96 h | 0.3 | 0.6 |
| 168 h | 0.1 | 0.2 |

TABLE

IGF-1R 0045 (with HHY-AAA mutation in both Fc-region polypeptides): Comparison of serum concentrations after intravitreal and intravenous application (BLQ = below limit of quantitation)

| ID | serum concentration after intravitreal application average conc. [μg/mL] | serum concentration after intravenous application average conc. [μg/mL] |
|---|---|---|
| 1 h | n.d. | 40.5 |
| 2 h | 13.2 | n.d. |
| 7 h | 9.6 | 21.7 |
| 24 h | 2.2 | 5.1 |
| 48 h | 0.9 | 0.7 |
| 96 h | 0.05 | 0.03 |
| 168 h | 0.01 | BLQ |

TABLE

Comparison of serum concentrations after intravenous application of antibodies IGF-1R 0033, 0035 and 0045 normalized to 1 μg applied antibody

| ID | IGF-1R 0033 | IGF-1R 0035 | IGF-1R 0045 |
|---|---|---|---|
| | average conc. [ng/mL/μg applied antibody] | | |
| 1 h | 1564 | 1006 | 1266 |
| 7 h | 1114 | 659 | 679 |
| 24 h | 613 | 234 | 160 |
| 48 h | 569 | 118 | 21 |
| 96 h | 399 | 26 | 1 |
| 168 h | 280 | 7 | 0 |

Results:

B) Concentrations in Eye-Lysates of Left and Right Eyes

Figure 18:
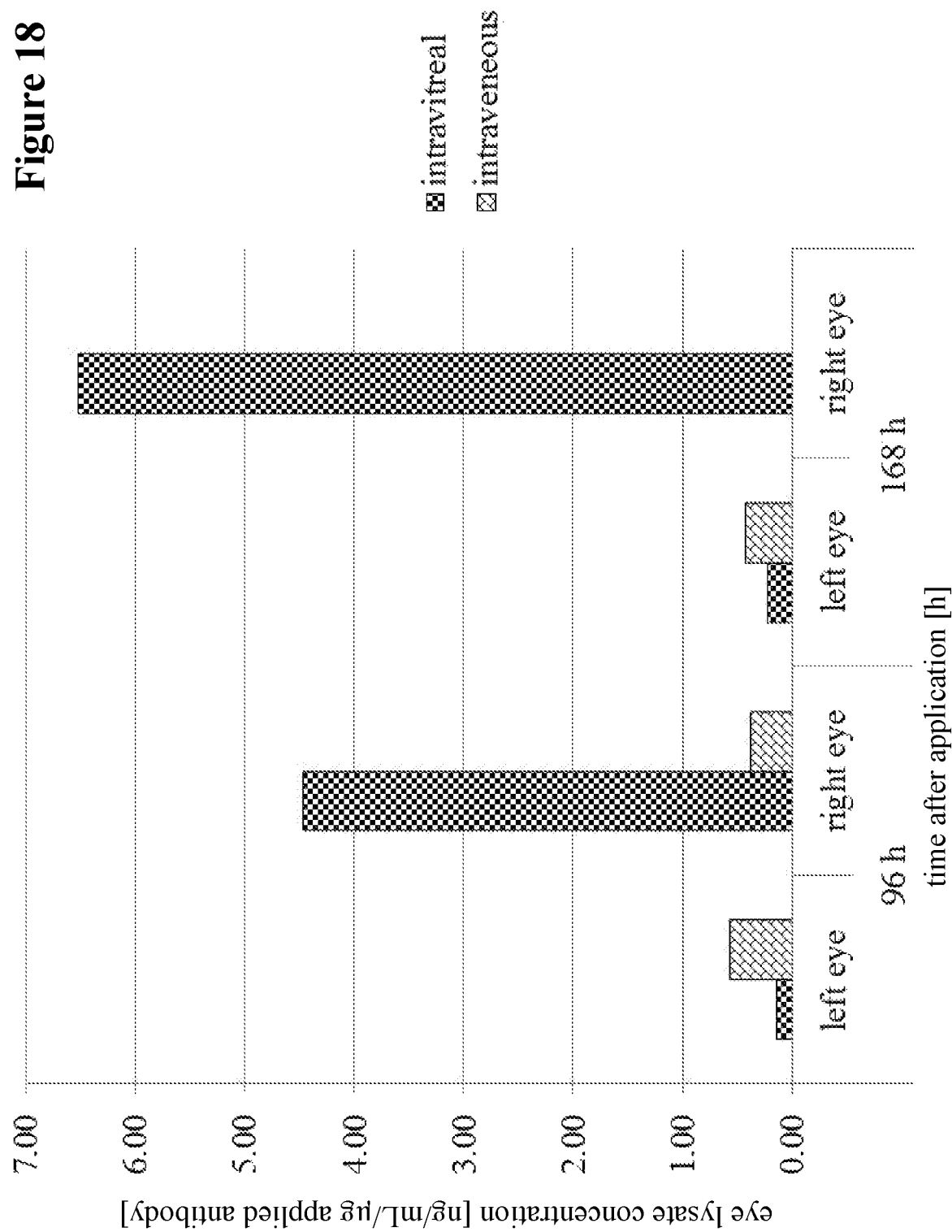
FIG. 18: Comparison of eye lysate concentration after intravitreal and intravenous application of antibody IGF-1R 0033.
Figure 19:
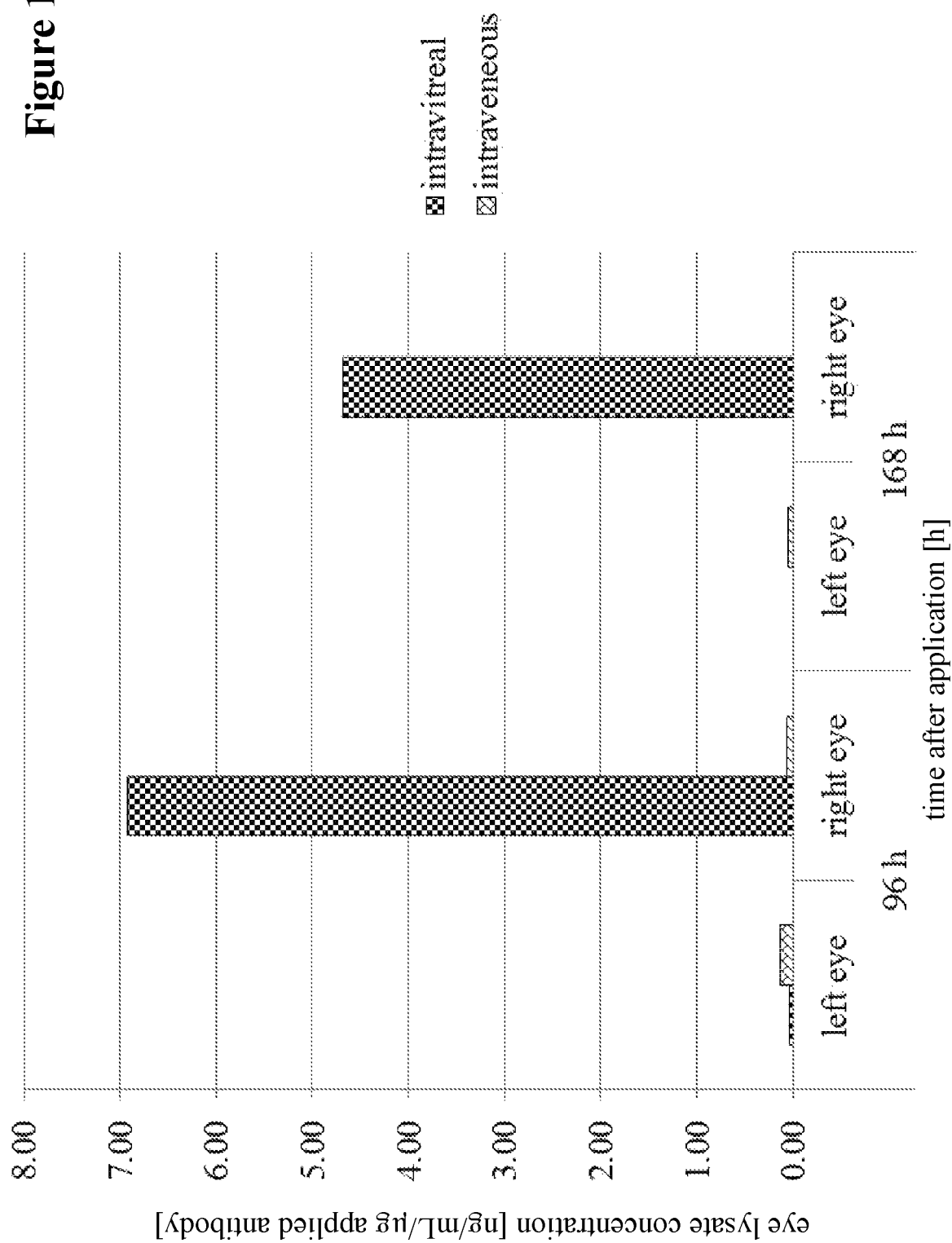
FIG. 19: Comparison of eye lysate concentration after intravitreal and intravenous application of antibody IGF-1R 0035.

Results for concentrations in eye lysates are shown in the following Tables and FIGS. 18 to 20.

TABLE

Concentrations of IGF-1R 0033 (without HHY-AAA mutation) in eye lysates after intravitreal application into the right eye
mean conc. values from n = 7 (96 h) and n = 6 (196 h) mice

| ID | | mean conc. [ng/mL] |
|---|---|---|
| 96 h | left eye | 3.3 |
| | right eye | 99.5 |
| 168 h | left eye | 5.2 |
| | right eye | 144.9 |

TABLE

Concentrations of IGF-1R 0033 (without HHY-AAA mutation) in eye lysates after intravenous application (BLQ = below limit of quantitation)
mean conc. values from n = 5 (96 h) and n = 6 (196 h) mice

| ID | | mean conc. [ng/mL] |
|---|---|---|
| 96 h | left eye | 12.7 |
| | right eye | 8.5 |
| 168 h | left eye | 9.7 |
| | right eye | BLQ |

TABLE

Concentrations of IGF-1R 0035 (with the HHY-AAA mutation in one Fc-region polypeptide) in eye lysates after intravitreal application into the right eye
mean conc. values from n = 6 mice

| ID | | mean conc. [ng/mL] |
|---|---|---|
| 96 h | left eye | 1.1 |
| | right eye | 169.2 |
| 168 h | left eye | 0.3 |
| | right eye | 114.7 |

TABLE

Concentrations of IGF-1R 0035 (with the HHY-AAA mutation in one Fc- region polypeptide) in eye lysates after intravenous application (BLQ = below limit of quantitation)
mean conc. values from n = 6 mice

| ID | | mean conc. [ng/mL] |
|---|---|---|
| 96 h | left eye | 3.7 |
| | right eye | 1.7 |

TABLE-continued

Concentrations of IGF-1R 0035 (with the HHY-AAA mutation in one Fc- region polypeptide) in eye lysates after intravenous application (BLQ = below limit of quantitation) mean conc. values from n = 6 mice

| ID | | mean conc. [ng/mL] |
|---|---|---|
| 168 h | left eye | 1.4 |
| | right eye | 0.3 |

TABLE

Concentrations of IGF-1R 0045 (with the HHY-AAA mutation in both Fc-region polypeptides) in eye lysates after intravitreal application into the right eye mean conc. values from n = 6 mice

| ID | | mean conc. [ng/mL] |
|---|---|---|
| 96 h | left eye | 1.4 |
| | right eye | 322.6 |
| 168 h | left eye | 1.4 |
| | right eye | 156.8 |

TABLE

Concentrations of IGF-1R 0045 (with the HHY-AAA mutation in both Fc-region polypeptides) in eye lysates after intravenous application (BLQ = below limit of quantitation) mean conc. values from n = 6 (96 h) and n = 5 (196 h) mice

| ID | | mean conc. [ng/mL] |
|---|---|---|
| 96 h | left eye | 3.6 |
| | right eye | 1.3 |
| 168 h | left eye | 0.8 |
| | right eye | 0.4 |

TABLE

Concentrations of IGF-1R 0033, 0035 and 0045 in eye lysates after intravitreal application into the right eye normalized to 1 µg applied antibody

| ID | | IGF-1R 0033 | IGF-1R 0035 | IGF-1R 0045 |
|---|---|---|---|---|
| | | mean conc. [ng/mL] | | |
| 96 h | left eye | 0.15 | 0.05 | 0.04 |
| | right eye | 4.48 | 6.93 | 10.08 |
| 168 h | left eye | 0.24 | 0.01 | 0.04 |
| | right eye | 6.53 | 4.70 | 4.90 |

Summary of Results:

After intravitreal application, the anti-IGF-1R antibodies 0035 and 0045 as reported herein (with one sided or both sided HEY-AAA mutation) shows similar concentrations (after 96 and 168 hours) in the eye lysates as compared to the anti-IGF-1R antibody without HEY-AAA mutation (IGF-1R 0033).

Also after intravitreal application the anti-IGF-1R antibodies 0035 and 0045 as reported herein (with one sided or both sided HEY-AAA mutation) shows in addition a faster clearance and shorter half-life in the serum as compared to the anti-IGF-1R antibody without HEY-AAA mutation (IGF-1R 0033).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method for producing a bispecific antibody comprising a first polypeptide and a second polypeptide each comprising, in N-terminal to C-terminal direction, at least a portion of an immunoglobulin hinge region, which comprises one or more cysteine residues, an immunoglobulin CH2-domain and an immunoglobulin CH3-domain,
   wherein the first and/or the second polypeptide comprise the mutation Y436A (numbering according to Kabat), and wherein the antibody is a full-length antibody with a human IgG1 Fc-region (numbering according to Kabat), comprising the steps of:
   a) cultivating a mammalian cell comprising one or more nucleic acids encoding the bispecific antibody,
   b) recovering the bispecific antibody from the cultivation medium, and
   c) purifying the bispecific antibody with a protein A affinity chromatography and thereby producing the bispecific antibody.

2. The method according to claim 1, wherein the antibody is a monoclonal antibody.

3. The method according to claim 1, wherein the antibody is a human, humanized or chimeric antibody.

4. The method according to claim 1, wherein the antibody is a bivalent antibody.

5. The method according to claim 1, wherein the antibody does not specifically bind to the human FcRn and does specifically bind to Staphylococcal protein A.

6. The method according to claim 1, wherein
   i) the first polypeptide is selected from the group comprising
      human IgG1 Fc-region polypeptide,
      human IgG1 Fc-region polypeptide with the mutations L234A, L235A,
      human IgG1 Fc-region polypeptide with the mutations Y349C, T366S, L368A, Y407V,
      human IgG1 Fc-region polypeptide with the mutations S354C, T366S, L368A, Y407V,
      human IgG1 Fc-region polypeptide with the mutations L234A, L235A, Y349C, T366S, L368A, Y407V,
      human IgG1 Fc-region polypeptide with the mutations L234A, L235A, S354C, T366S, L368A, Y407V,
      human IgG1 Fc-region polypeptide with the mutations P329G,
      human IgG1 Fc-region polypeptide with the mutations L234A, L235A, P329G,
      human IgG1 Fc-region polypeptide with the mutations P329G, Y349C, T366S, L368A, Y407V,
      human IgG1 Fc-region polypeptide with the mutations P329G, S354C, T366S, L368A, Y407V, human IgG1 Fc-region polypeptide with the mutations L234A, L235A, P329G, Y349C, T366S, L368A, Y407V, human IgG1 Fc-region polypeptide with the mutations L234A, L235A, P329G, S354C, T366S, L368A, Y407V, human IgG1 with the mutations K392D, and ii) the second polypeptide is selected from the group comprising human IgG1 Fc-region polypeptide, human IgG1 Fc-region polypeptide with the mutations L234A, L235A, human IgG1 Fc-region polypeptide with the mutations S354C, T366W, human IgG1 Fc-region polypeptide with the mutations Y349C, T366W, human IgG1 Fc-region polypeptide with the mutations L234A, L235A, S354C, T366W, human IgG1 Fc-region polypeptide with the mutations L234A, L235A, Y349C, T366W, human IgG1 Fc-region polypeptide with the mutations P329G, human IgG1 Fc-region polypeptide with the mutations L234A, L235A, P329G, human IgG1 Fc-region polypeptide with the mutations P329G, S354C, T366W, human IgG1 Fc-region polypeptide with the mutations P329G, Y349C, T366W, human IgG1 Fc-region polypeptide with the mutations L234A, L235A, P329G, S354C, T366W, human IgG1 Fc-region polypeptide with the mutations L234A, L235A, P329G, Y349C, T366W, human IgG1 with the mutations D399K, D356K, and/or E357K.

7. The method according to claim 1, wherein i) the first Fc-region polypeptide is a human IgG1 Fc-region polypeptide and the second Fc-region polypeptide is a human IgG1 Fc-region polypeptide, or ii) the first Fc-region polypeptide is a human IgG1 Fc-region polypeptide with the mutations L234A, L235A and the second Fc-region polypeptide is a human IgG1 Fc-region polypeptide with the mutations L234A, L235A, or iii) the first Fc-region polypeptide is a human IgG1 Fc-region polypeptide with the mutations L234A, L235A, P329G and the second Fc-region polypeptide is a human IgG1 Fc-region polypeptide with the mutations L234A, L235A, P329G, or iv) the first Fc-region polypeptide is a human IgG1 Fc-region polypeptide with the mutations L234A, L235A, S354C, T366W and the second Fc-region polypeptide is a human IgG1 Fc-region polypeptide with the mutations L234A, L235A, Y349C, T366S, L368A, Y407V, or v) the first Fc-region polypeptide is a human IgG1 Fc-region polypeptide with the mutations L234A, L235A, P329G, S354C, T366W and the second Fc-region polypeptide is a human IgG1 Fc-region polypeptide with the mutations L234A, L235A, P329G, Y349C, T366S, L368A, Y407V.

* * * * *

SEQUENCE LISTING

```
Sequence total quantity: 120
SEQ ID NO: 1             moltype = AA  length = 448
FEATURE                  Location/Qualifiers
source                   1..448
                         mol_type = protein
                         organism = Homo sapiens
SEQUENCE: 1
QVELVESGGG VVQPGRSQRL SCAASGFTFS SYGMHWVRQA PGKGLEWVAI IWFDGSSTYY   60
ADSVRGRFTI SRDNSKNTLY LQMNSLRAED TAVYFCAREL GRRYFDLWGR GTLVSVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALG APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 2             moltype = AA  length = 448
FEATURE                  Location/Qualifiers
source                   1..448
                         mol_type = protein
                         organism = Homo sapiens
SEQUENCE: 2
QVQLVESGGG VVQPGRSLRL SCAASGFTFS SYGMHWVRQA PGKGLEWMAI IWFDGSSKYY   60
GDSVKGRFTI SRDNSKNTLY LQMNSLRADD TAVYYCAREL GRRYFDLWGR GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALG APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448
```

```
SEQ ID NO: 3              moltype = AA   length = 215
FEATURE                   Location/Qualifiers
source                    1..215
                          mol_type = protein
                          organism = Homo sapiens
SEQUENCE: 3
EIVLTQSPAT LSLSPGERAT LSCRASQSVS SYLAWYQQKP GQAPRLLIYD ASKRATGIPA   60
RFSGSGSGTD FTLTISSLEP EDFAVYYCQQ RSKWPPWTFG QGTKVESKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 4              moltype = AA   length = 215
FEATURE                   Location/Qualifiers
source                    1..215
                          mol_type = protein
                          organism = Homo sapiens
SEQUENCE: 4
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSKWPPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 5              moltype = AA   length = 118
FEATURE                   Location/Qualifiers
source                    1..118
                          mol_type = protein
                          organism = Homo sapiens
SEQUENCE: 5
QVELVESGGG VVQPGRSQRL SCAASGFTFS SYGMHWVRQA PGKGLEWVAI IWFDGSSTYY   60
ADSVRGRFTI SRDNSKNTLY LQMNSLRAED TAVYFCAREL GRRYFDLWGR GTLVSVSS   118

SEQ ID NO: 6              moltype = AA   length = 118
FEATURE                   Location/Qualifiers
source                    1..118
                          mol_type = protein
                          organism = Homo sapiens
SEQUENCE: 6
QVQLVESGGG VVQPGRSLRL SCAASGFTFS SYGMHWVRQA PGKGLEWMAI IWFDGSSKYY   60
GDSVKGRFTI SRDNSKNTLY LQMNSLRADD TAVYYCAREL GRRYFDLWGR GTLVTVSS   118

SEQ ID NO: 7              moltype = AA   length = 108
FEATURE                   Location/Qualifiers
source                    1..108
                          mol_type = protein
                          organism = Homo sapiens
SEQUENCE: 7
EIVLTQSPAT LSLSPGERAT LSCRASQSVS SYLAWYQQKP GQAPRLLIYD ASKRATGIPA   60
RFSGSGSGTD FTLTISSLEP EDFAVYYCQQ RSKWPPWTFG QGTKVESK              108

SEQ ID NO: 8              moltype = AA   length = 108
FEATURE                   Location/Qualifiers
source                    1..108
                          mol_type = protein
                          organism = Homo sapiens
SEQUENCE: 8
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSKWPPWTFG QGTKVEIK              108

SEQ ID NO: 9              moltype = AA   length = 107
FEATURE                   Location/Qualifiers
source                    1..107
                          mol_type = protein
                          organism = Homo sapiens
SEQUENCE: 9
APELLGGPSV FLFPPKPKDT LMISRTPEVT CVWDVSHEDP EVKFNWYVDG VEVHNAKTKP   60
REEQESTYRW SVLTVLHQDW LNGKEYKCKV SNKALPAPIE KTISKAK                107

SEQ ID NO: 10             moltype = AA   length = 106
FEATURE                   Location/Qualifiers
source                    1..106
                          mol_type = protein
                          organism = Homo sapiens
SEQUENCE: 10
GQPREPQVYT LPPSRDELTK NQVSLTCLVK GFYPSDIAVE WESNGQPENN YKTTPPVLDS   60
DGSFFLYSKL TVDKSRWQQG NVFSCSVMHE ALHNHYTQKS LSLSPG                 106
```

```
SEQ ID NO: 11              moltype = AA   length = 1337
FEATURE                    Location/Qualifiers
source                     1..1337
                           mol_type = protein
                           organism = Homo sapiens
SEQUENCE: 11
EICGPGIDIR NDYQQLKRLE NCTVIEGYLH ILLISKAEDY RSYRFPKLTV ITEYLLLFRV   60
AGLESLGDLF PNLTVIRGWK LFYNYALVIF EMTNLKDIGL YNLRNITRGA IRIEKNADLC  120
YLSTVDWSLI LDAVSNNYIV GNKPPKECGD LCPGTMEEKP MCEKTTINNE YNYRCWTTNR  180
CQKMCPSTCG KRACTENNEC CHPECLGSCS APDNDTACVA CRHYYYAGVC VPACPPNTYR  240
FEGWRCVDRD FCANILSAES SDSEGFVIHD GECMQECPSG FIRNGSQSMY CIPCEGPCPK  300
VCEEEKKTKT IDSVTSAQML QGCTIFKGNL LINIRRGNNI ASELENFMGL IEVVTGYVKI  360
RHSHALVSLS FLKNLRLILG EEQLEGNYSF YVLDNQNLQQ LWDWDHRNLT IKAGKMYFAF  420
NPKLCVSEIY RMEEVTGTKG RQSKGDINTR NNGERASCES DVLHFTSTTT SKNRIIITWH  480
RYRPPDYRDL ISFTVYYKEA PFKNVTEYDG QDACGSNSWN MVDVDLPPNK DVEPGILLHG  540
LKPWTQYAVY VKAVTLTMVE NDHIRGAKSE ILYIRTNASV PSIPLDVLSA SNSSSQLIVK  600
WNPPSLPNGN LSYYIVRWQR QPQDGYLYRH NYCSKDKIPI RKYADGTIDI EEVTENPKTE  660
VCGGEKGPCC ACPKTEAEKQ AEKEEAEYRK VFENFLHNSI FVPRPERKRR DVMQVANTTM  720
SSRSRNTTAA DTYNITDPEE LETEYPFFES RVDNKERTVI SNLRPFTLYR IDIHSCNHEA  780
EKLGCSASNF VFARTMPAEG ADDIPGPVTW EPRPENSIFL KWPEPENPNG LILMYEIKYG  840
SQVEDQRECV SRQEYRKYGG AKLNRLNPGN YTARIQATSL SGNGSWTDPV FFYVQAKTGY  900
ENFIHLIIAL PVAVLLIVGG LVIMLYVFHR KRNNSRLGNG VLYASVNPEY FSAADVYVPD  960
EWEVAREKIT MSRELGQGSF GMVYEGVAKG VVKDEPETRV AIKTVNEAAS MRERIEFLNE 1020
ASVMKEFNCH HVVRLLGVVS QGQPTLVIME LMTRGDLKSY LRSLRPEMEN NPVLAPPSLS 1080
KMIQMAGEIA DGMAYLNANK FVHRDLAARN CMVAEDFTVK IGDFGMTRDI YETDYYRKGG 1140
KGLLPVRWMS PESLKDGVFT TYSDVWSFGV VLWEIATLAE QPYQGLSNEQ VLRFVMEGGL 1200
LDKPDNCPDM LFELMRMCWQ YNPKMRPSFL EIISSIKEEM EPGFREVSFY YSEENKLPEP 1260
EELDLEPENM ESVPLDPSAS SSSLPLPDRH SGHKAENGPG PGVLVLRASF DERQPYAHMN 1320
GGRKNERALP LPQSSTC                                                1337

SEQ ID NO: 12              moltype = AA   length = 330
FEATURE                    Location/Qualifiers
source                     1..330
                           mol_type = protein
                           organism = Homo sapiens
SEQUENCE: 12
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 13              moltype = AA   length = 327
FEATURE                    Location/Qualifiers
source                     1..327
                           mol_type = protein
                           organism = Homo sapiens
SEQUENCE: 13
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 14              moltype = AA   length = 14
FEATURE                    Location/Qualifiers
source                     1..14
                           mol_type = protein
                           organism = synthetic construct
                           note = heavy chain CDR3H, ranibizumab
SEQUENCE: 14
YPYYYGTSHW YFDV                                                     14

SEQ ID NO: 15              moltype = AA   length = 17
FEATURE                    Location/Qualifiers
source                     1..17
                           mol_type = protein
                           organism = synthetic construct
                           note = heavy chain CDR2H, ranibizumab
SEQUENCE: 15
WINTYTGEPT YAADFKR                                                  17

SEQ ID NO: 16              moltype = AA   length = 5
FEATURE                    Location/Qualifiers
```

```
source                     1..5
                           mol_type = protein
                           organism = synthetic construct
                           note = heavy chain CDR1H, ranibizumab
SEQUENCE: 16
HYGMN                                                                    5

SEQ ID NO: 17              moltype = AA  length = 9
FEATURE                    Location/Qualifiers
source                     1..9
                           mol_type = protein
                           organism = synthetic construct
                           note = light chain CDR3L, ranibizumab
SEQUENCE: 17
QQYSTVPWT                                                                9

SEQ ID NO: 18              moltype = AA  length = 7
FEATURE                    Location/Qualifiers
source                     1..7
                           mol_type = protein
                           organism = synthetic construct
                           note = light chain CDR2L, ranibizumab
SEQUENCE: 18
FTSSLHS                                                                  7

SEQ ID NO: 19              moltype = AA  length = 11
FEATURE                    Location/Qualifiers
source                     1..11
                           mol_type = protein
                           organism = synthetic construct
                           note = light chain CDR1L, ranibizumab
SEQUENCE: 19
SASQDISNYL N                                                            11

SEQ ID NO: 20              moltype = AA  length = 123
FEATURE                    Location/Qualifiers
source                     1..123
                           mol_type = protein
                           organism = synthetic construct
                           note = heavy chain variable domain VH, ranibizumab
SEQUENCE: 20
EVQLVESGGG LVQPGGSLRL SCAASGYDFT HYGMNWVRQA PGKGLEWVGW INTYTGEPTY        60
AADFKRRFTF SLDTSKSTAY LQMNSLRAED TAVYYCAKYP YYYGTSHWYF DVWGQGTLVT       120
VSS                                                                    123

SEQ ID NO: 21              moltype = AA  length = 107
FEATURE                    Location/Qualifiers
source                     1..107
                           mol_type = protein
                           organism = synthetic construct
                           note = light chain variable domain VL, ranibizumab
SEQUENCE: 21
DIQLTQSPSS LSASVGDRVT ITCSASQDIS NYLNWYQQKP GKAPKVLIYF TSSLHSGVPS        60
RFSGSGSGTD FTLTISSLQP EDFATYYCQQ YSTVPWTFGQ GTKVEIK                    107

SEQ ID NO: 22              moltype = AA  length = 20
FEATURE                    Location/Qualifiers
source                     1..20
                           mol_type = protein
                           organism = synthetic construct
                           note = heavy chain CDR3H, Ang2i_LC10 variant
SEQUENCE: 22
SPNPYYYDSS GYYYPGAFDI                                                   20

SEQ ID NO: 23              moltype = AA  length = 17
FEATURE                    Location/Qualifiers
source                     1..17
                           mol_type = protein
                           organism = synthetic construct
                           note = heavy chain CDR2H, Ang2i_LC10 variant
SEQUENCE: 23
WINPNSGGTN YAQKFQG                                                      17

SEQ ID NO: 24              moltype = AA  length = 5
FEATURE                    Location/Qualifiers
source                     1..5
                           mol_type = protein
                           organism = synthetic construct
                           note = heavy chain CDR1H, Ang2i_LC10 variant
```

```
SEQUENCE: 24
GYYMH                                                                     5

SEQ ID NO: 25           moltype = AA   length = 11
FEATURE                 Location/Qualifiers
source                  1..11
                        mol_type = protein
                        organism = synthetic construct
                        note = light chain CDR3L, Ang2i_LC10 variant
SEQUENCE: 25
QVWDSSSDHW V                                                             11

SEQ ID NO: 26           moltype = AA   length = 7
FEATURE                 Location/Qualifiers
source                  1..7
                        mol_type = protein
                        organism = synthetic construct
                        note = light chain CDR2L, Ang2i_LC10 variant
SEQUENCE: 26
DDSDRPS                                                                   7

SEQ ID NO: 27           moltype = AA   length = 11
FEATURE                 Location/Qualifiers
source                  1..11
                        mol_type = protein
                        organism = synthetic construct
                        note = light chain CDR1L, Ang2i_LC10 variant
SEQUENCE: 27
GGNNIGSKSV H                                                             11

SEQ ID NO: 28           moltype = AA   length = 129
FEATURE                 Location/Qualifiers
source                  1..129
                        mol_type = protein
                        organism = synthetic construct
                        note = heavy chain variable domain VH, Ang2i_LC10
                         variant
SEQUENCE: 28
QVQLVQSGAE VKKPGASVKV SCKASGYTFT GYYMHWVRQA PGQGLEWMGW INPNSGGTNY         60
AQKFQGRVTM TRDTSISTAY MELSRLRSDD TAVYYCARSP NPYYYDSSGY YYPGAFDIWG        120
QGTMVTVSS                                                               129

SEQ ID NO: 29           moltype = AA   length = 110
FEATURE                 Location/Qualifiers
source                  1..110
                        mol_type = protein
                        organism = synthetic construct
                        note = light chain variable domain VL, Ang2i_LC10
                         variant
SEQUENCE: 29
SYVLTQPPSV SVAPGQTARI TCGGNNIGSK SVHWYQQKPG QAPVLVVYDD SDRPSGIPER         60
FSGSNSGNTA TLTISRVEAG DEADYYCQVW DSSSDHWVFG GGTKLTVLGQ                  110

SEQ ID NO: 30           moltype = AA   length = 191
FEATURE                 Location/Qualifiers
source                  1..191
                        mol_type = protein
                        organism = Homo sapiens
SEQUENCE: 30
MNFLLSWVHW SLALLLYLHH AKWSQAAPMA EGGGQNHHEV VKFMDVYQRS YCHPIETLVD         60
IFQEYPDEIE YIFKPSCVPL MRCGGCCNDE GLECVPTEES NITMQIMRIK PHQGQHIGEM        120
SFLQHNKCEC RPKKDRARQE NPCGPCSERR KHLFVQDPQT CKCSCKNTDS RCKARQLELN        180
ERTCRCDKPR R                                                            191

SEQ ID NO: 31           moltype = AA   length = 496
FEATURE                 Location/Qualifiers
source                  1..496
                        mol_type = protein
                        organism = Homo sapiens
SEQUENCE: 31
MWQIVFFTLS CDLVLAAAYN NFRKSMDSIG KKQYQVQHGS CSYTFLLPEM DNCRSSSSPY         60
VSNAVQRDAP LEYDDSVQRL QVLENIMENN TQWLMKLENY IQDNMKKEMV EIQQNAVQNQ        120
TAVMIEIGTN LLNQTAEQTR KLTDVEAQVL NQTTRLELQL LEHSLSTNKL EKQILDQTSE        180
INKLQDKNSF LEKKVLAMED KHIIQLQSIK EEKDQLQVLV SKQNSIIEEL EKKIVTATVN        240
NSVLQKQQHD LMETVNNLLT MMSTSNSAKD PTVAKEEQIS FRDCAEVFKS GHTTNGIYTL        300
TFPNSTEEIK AYCDMEAGGG GWTIIQRRED GSVDFQRTWK EYKVGFGNPS GEYWLGNEFV        360
SQLTNQQRYV LKIHLKDWEG NEAYSLYEHF YLSSEELNYR IHLKGLTGTA GKISSISQPG        420
NDFSTKDGDN DKCICKCSQM LTGGWWFDAC GPSNLNGMYY PQRQNTNKFN GIKWYYWKGS        480
GYSLKATTMM IRPADF                                                       496
```

```
SEQ ID NO: 32            moltype = AA   length = 498
FEATURE                  Location/Qualifiers
source                   1..498
                         mol_type = protein
                         organism = Homo sapiens
SEQUENCE: 32
MTVFLSFAFL AAILTHIGCS NQRRSPENSG RRYNRIQHGQ CAYTFILPEH DGNCRESTTD   60
QYNTNALQRD APHVEPDFSS QKLQHLEHVM ENYTQWLQKL ENYIVENMKS EMAQIQQNAV  120
QNHTATMLEI GTSLLSQTAE QTRKLTDVET QVLNQTSRLE IQLLENSLST YKLEKQLLQQ  180
TNEILKIHEK NSLLEHKILE MEGKHKEELD TLKEEKENLQ GLVTRQTYII QELEKQLNRA  240
TTNNSVLQKQ QLELMDTVHN LVNLCTKEGV LLKGGKREEE KPFRDCADVY QAGFNKSGIY  300
TIYINNMPEP KKVFCNMDVN GGGWTVIQHR EDGSLDFQRG WKEYKMGFGN PSGEYWLGNE  360
FIFAITSQRQ YMLRIELMDW EGNRAYSQYD RFHIGNEKQN YRLYLKGHTG TAGKQSSLIL  420
HGADFSTKDA DNDNCMCKCA LMLTGGWWFD ACGPSNLNGM FYTAGQNHGK LNGIKWHYFK  480
GPSYSLRSTT MMIRPLDF                                                498

SEQ ID NO: 33            moltype = AA   length = 1124
FEATURE                  Location/Qualifiers
source                   1..1124
                         mol_type = protein
                         organism = Homo sapiens
SEQUENCE: 33
MDSLASLVLC GVSLLLSGTV EGAMDLILIN SLPLVSDAET SLTCIASGWR PHEPITIGRD   60
FEALMNQHQD PLEVTQDVTR EWAKKVVWKR EKASKINGAY FCEGRVRGEA IRIRTMKMRQ  120
QASFLPATLT MTVDKGDNVN ISFKKVLIKE EDAVIYKNGS FIHSVPRHEV PDILEVHLPH  180
AQPQDAGVYS ARYIGGNLFT SAFTRLIVRR CEAQKWGPEC NHLCTACMNN GVCHEDTGEC  240
ICPPGFMGRT CEKACELHTF GRTCKERCSG QEGCKSYVFC LPDPYGCSCA TGWKGLQCNE  300
ACHPGFYGPD CKLRCSCNNG EMCDRFQGCL CSPGWQGLQC EREGIPRMTP KIVDLPDHIE  360
VNSGKFNPIC KASGWPLPTN EEMTLVKPDG TVLHPKDFNH TDHFSVAIFT IHRILPPDSG  420
VWVCSVNTVA GMVEKPFNIS VKVLPKPLNA PNVIDTGHNF AVINISSEPY FGDGPIKSKK  480
LLYKPVNHYE AWQHIQVTNE IVTLNYLEPR TEYELCVQLV RRGEGGEGHP GPVRRFTTAS  540
IGLPPPRGLN LLPKSQTTLN LTWQPIFPSS EDDFYVEVER RSVQKSDQQN IKVPGNLTSV  600
LLNNLHPREQ YVVRARVNTK AQGEWSEDLT AWTLSDILPF QPENIKISNI THSSAVISWT  660
ILDGYSISSI TIRYKVQGKN EDQHVDVKIK NATITQYQLK GLEPETAYQV DIFAENNIGS  720
SNPAFSHELV TLPESQAPAD LGGGKMLLIA ILGSAGMTCL TVLLAFLIIL QLKRANVQRR  780
MAQAFQNVRE EPAVQFNSGT LALNRKVKNN PDPTIYPVLD WNDIKFQDVI GEGNFGQVLK  840
ARIKKDGLRM DAAIKRMKEY ASKDDHRDFA GELEVLCKLG HHPNIINLLG ACEHRGYLYL  900
AIEYAPHGNL LDFLRKSRVL ETDPAFAIAN STASTLSSQQ LLHFAADVAR GMDYLSQKQF  960
IHRDLAARNI LVGENYVAKI ADFGLSRGQE VYVKKTMGRL PVRWMAIESL NYSVYTTNSD 1020
VWSYGVLLWE IVSLGGTPYC GMTCAELYEK LPQGYRLEKP LNCDDEVYDL MRQCWREKPY 1080
ERPSFAQILV SLNRMLEERK TYVNTTLYEK FTYAGIDCSA EEAA                  1124

SEQ ID NO: 34            moltype = AA   length = 453
FEATURE                  Location/Qualifiers
source                   1..453
                         mol_type = protein
                         organism = synthetic construct
                         note = Heavy chain 1 of CrossMAb IgG1 with AAA
                         mutations (VEGFang2-0012)
SEQUENCE: 34
EVQLVESGGG LVQPGGSLRL SCAASGYDFT HYGMNWVRQA PGKGLEWVGW INTYTGEPTY   60
AADFKRRFTF SLDTSKSTAY LQMNSLRAED TAVYYCAKYP YYYGTSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMAS RTPEVTCVVV DVSHEDPEVK FNWYVDGVEV HNAKTKPREE  300
QYNSTYRVVS VLTVLAQDWL NGKEYKCKVS NKALPAPIEK TISKAKGQPR EPQVYTLPPC  360
RDELTKNQVS LWCLVKGFYP SDIAVEWESN GQPENNYKTT PPVLDSDGSF FLYSKLTVDK  420
SRWQQGNVFS CSVMHEALHN AYTQKSLSLS PGK                               453

SEQ ID NO: 35            moltype = AA   length = 463
FEATURE                  Location/Qualifiers
source                   1..463
                         mol_type = protein
                         organism = synthetic construct
                         note = Heavy chain 2 of CrossMAb IgG1 with AAA
                         mutations (VEGFang2-0012)
SEQUENCE: 35
QVQLVQSGAE VKKPGASVKV SCKASGYTFT GYYMHWVRQA PGQGLEWMGW INPNSGGTNY   60
AQKFQGRVTM TRDTSISTAY MELSRLRSDD TAVYYCARSP NPYYYDSSGY YYPGAFDIWG  120
QGTMVTVSSA SVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECDKTH  240
TCPPCPAPEL LGGPSVFLFP PKPKDTLMAS RTPEVTCVVV DVSHEDPEVK FNWYVDGVEV  300
HNAKTKPREE QYNSTYRVVS VLTVLAQDWL NGKEYKCKVS NKALPAPIEK TISKAKGQPR  360
EPQVCTLPPS RDELTKNQVS LSCAVKGFYP SDIAVEWESN GQPENNYKTT PPVLDSDGSF  420
FLVSKLTVDK SRWQQGNVFS CSVMHEALHN AYTQKSLSLS PGK                    463

SEQ ID NO: 36            moltype = AA   length = 214
FEATURE                  Location/Qualifiers
```

```
source                  1..214
                        mol_type = protein
                        organism = synthetic construct
                        note = Light chain 1 of CrossMAb IgG1 with AAA
                          mutations (VEGFang2-0012)
SEQUENCE: 36
DIQLTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 37           moltype = AA  length = 213
FEATURE                 Location/Qualifiers
source                  1..213
                        mol_type = protein
                        organism = synthetic construct
                        note = Light chain 2 of CrossMAb IgG1 with AAA
                          mutations (VEGF-Ang2-0012)
SEQUENCE: 37
SYVLTQPPSV SVAPGQTARI TCGGNNIGSK SVHWYQQKPG QAPVLVVYDD SDRPSGIPER    60
FSGSNSGNTA TLTISRVEAG DEADYYCQVW DSSSDHWVFG GGTKLTVLSS ASTKGPSVFP   120
LAPSSKSTSG GTAALGCLVK DYFPEPVTVS WNSGALTSGV HTFPAVLQSS GLYSLSSVVT   180
VPSSSLGTQT YICNVNHKPS NTKVDKKVEP KSC                                213

SEQ ID NO: 38           moltype = AA  length = 453
FEATURE                 Location/Qualifiers
source                  1..453
                        mol_type = protein
                        organism = synthetic construct
                        note = Heavy chain 1 of CrossMAb IgG1 with AAA
                          mutations and P329G LALA mutations (VEGFang2-0016)
SEQUENCE: 38
EVQLVESGGG LVQPGGSLRL SCAASGYDFT HYGMNWVRQA PGKGLEWVGW INTYTGEPTY    60
AADFKRRFTF SLDTSKSTAY LQMNSLRAED TAVYYCAKYP YYYGTSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMAS RTPEVTCVVV DVSHEDPEVK FNWYVDGVEV HNAKTKPREE   300
QYNSTYRVVS VLTVLAQDWL NGKEYKCKVS NKALGAPIEK TISKAKGQPR EPQVYTLPPC   360
RDELTKNQVS LWCLVKGFYP SDIAVEWESN GQPENNYKTT PPVLDSDGSF FLYSKLTVDK   420
SRWQQGNVFS CSVMHEALHN AYTQKSLSLS PGK                                453

SEQ ID NO: 39           moltype = AA  length = 463
FEATURE                 Location/Qualifiers
source                  1..463
                        mol_type = protein
                        organism = synthetic construct
                        note = Heavy chain 2 of CrossMAb IgG1 with AAA
                          mutations and P329G LALA mutations (VEGFang2-0016)
SEQUENCE: 39
QVQLVQSGAE VKKPGASVKV SCKASGYTFT GYYMHWVRQA PGQGLEWMGW INPNSGGTNY    60
AQKFQGRVTM TRDTSISTAY MELSRLRSDD TAVYYCARSP NPYYYDSSGY YYPGAFDIWG   120
QGTMVTVSSA SVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGECDKTH   240
TCPPCPAPEA AGGPSVFLFP PKPKDTLMAS RTPEVTCVVV DVSHEDPEVK FNWYVDGVEV   300
HNAKTKPREE QYNSTYRVVS VLTVLAQDWL NGKEYKCKVS NKALGAPIEK TISKAKGQPR   360
EPQVCTLPPS RDELTKNQVS LSCAVKGFYP SDIAVEWESN GQPENNYKTT PPVLDSDGSF   420
FLVSKLTVDK SRWQQGNVFS CSVMHEALHN AYTQKSLSLS PGK                     463

SEQ ID NO: 40           moltype = AA  length = 214
FEATURE                 Location/Qualifiers
source                  1..214
                        mol_type = protein
                        organism = synthetic construct
                        note = Light chain 1 of CrossMAb IgG1 with AAA
                          mutations and P329G LALA mutations (VEGFang2-0016)
SEQUENCE: 40
DIQLTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 41           moltype = AA  length = 213
FEATURE                 Location/Qualifiers
source                  1..213
                        mol_type = protein
                        organism = synthetic construct
                        note = Light chain 2 of CrossMAb IgG1 with AAA
                          mutations and P329G LALA mutations (VEGFang2-0016)
```

```
SEQUENCE: 41
SYVLTQPPSV SVAPGQTARI TCGGNNIGSK SVHWYQQKPG QAPVLVVYDD SDRPSGIPER   60
FSGSNSGNTA TLTISRVEAG DEADYYCQVW DSSSDHWVFG GGTKLTVLSS ASTKGPSVFP  120
LAPSSKSTSG GTAALGCLVK DYFPEPVTVS WNSGALTSGV HTFPAVLQSS GLYSLSSVVT  180
VPSSSLGTQT YICNVNHKPS NTKVDKKVEP KSC                               213

SEQ ID NO: 42             moltype = AA   length = 450
FEATURE                   Location/Qualifiers
source                    1..450
                          mol_type = protein
                          organism = synthetic construct
                          note = Heavy chain 1 of  CrossMAb IgG4 with AAA
                             mutations and with SPLE mutations
SEQUENCE: 42
EVQLVESGGG LVQPGGSLRL SCAASGYDFT HYGMNWVRQA PGKGLEWVGW INTYTGEPTY   60
AADFKRRFTF SLDTSKSTAY LQMNSLRAED TAVYYCAKYP YYYGTSHWYF DVWGQGTLVT  120
VSSASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPEFEGG  240
PSVFLFPPKP KDTLMASRTP EVTCVVVDVS QEDPEVQFNW YVDGVEVHNA KTKPREEQFN  300
STYRVVSVLT VLAQDWLNGK EYKCKVSNKG LPSSIEKTIS KAKGQPREPQ VCTLPPSQEE  360
MTKNQVSLSC AVKGFYPSDI AVEWESNGQP ENNYKTTPPV LDSDGSFFLV SRLTVDKSRW  420
QEGNVFSCSV MHEALHNAYT QKSLSLSLGK                                   450

SEQ ID NO: 43             moltype = AA   length = 460
FEATURE                   Location/Qualifiers
source                    1..460
                          mol_type = protein
                          organism = synthetic construct
                          note = Heavy chain 2 of  CrossMAb IgG4 with AAA
                             mutations and with SPLE mutations
SEQUENCE: 43
QVQLVQSGAE VKKPGASVKV SCKASGYTFT GYYMHWVRQA PGQGLEWMGW INPNSGGTNY   60
AQKFQGRVTM TRDTSISTAY MELSRLRSDD TAVYYCARSP NPYYYDSSGY YYPGAFDIWG  120
QGTMVTVSSA SVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECPPCP  240
PCPAPEFEGG PSVFLFPPKP KDTLMASRTP EVTCVVVDVS QEDPEVQFNW YVDGVEVHNA  300
KTKPREEQFN STYRVVSVLT VLAQDWLNGK EYKCKVSNKG LPSSIEKTIS KAKGQPREPQ  360
VYTLPPCQEE MTKNQVSLWC LVKGFYPSDI AVEWESNGQP ENNYKTTPPV LDSDGSFFLY  420
SRLTVDKSRW QEGNVFSCSV MHEALHNAYT QKSLSLSLGK                         460

SEQ ID NO: 44             moltype = AA   length = 214
FEATURE                   Location/Qualifiers
source                    1..214
                          mol_type = protein
                          organism = synthetic construct
                          note = Light chain 1 of  CrossMAb IgG4 with AAA
                             mutations and with SPLE mutations
SEQUENCE: 44
DIQLTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 45             moltype = AA   length = 213
FEATURE                   Location/Qualifiers
source                    1..213
                          mol_type = protein
                          organism = synthetic construct
                          note = Light chain 2 of  CrossMAb IgG4 with AAA
                             mutations and with SPLE mutations
SEQUENCE: 45
SYVLTQPPSV SVAPGQTARI TCGGNNIGSK SVHWYQQKPG QAPVLVVYDD SDRPSGIPER   60
FSGSNSGNTA TLTISRVEAG DEADYYCQVW DSSSDHWVFG GGTKLTVLSS ASTKGPSVFP  120
LAPCSRSTSE STAALGCLVK DYFPEPVTVS WNSGALTSGV HTFPAVLQSS GLYSLSSVVT  180
VPSSSLGTKT YTCNVDHKPS NTKVDKRVES KYG                                213

SEQ ID NO: 46             moltype = AA   length = 453
FEATURE                   Location/Qualifiers
source                    1..453
                          mol_type = protein
                          organism = synthetic construct
                          note = Heavy chain 1 of  OAscFab IgG1 with AAA
                             mutations
SEQUENCE: 46
EVQLVESGGG LVQPGGSLRL SCAASGYDFT HYGMNWVRQA PGKGLEWVGW INTYTGEPTY   60
AADFKRRFTF SLDTSKSTAY LQMNSLRAED TAVYYCAKYP YYYGTSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMAS RTPEVTCVVV DVSHEDPEVK FNWYVDGVEV HNAKTKPREE  300
```

```
QYNSTYRVVS VLTVLAQDWL NGKEYKCKVS NKALPAPIEK TISKAKGQPR EPQVCTLPPS    360
RDELTKNQVS LSCAVKGFYP SDIAVEWESN GQPENNYKTT PPVLDSDGSF FLVSKLTVDK    420
SRWQQGNVFS CSVMHEALHN AYTQKSLSLS PGK                                 453

SEQ ID NO: 47           moltype = AA  length = 705
FEATURE                 Location/Qualifiers
source                  1..705
                        mol_type = protein
                        organism = synthetic construct
                        note = Heavy chain 2 of  OAscFab IgG1 with AAA
                        mutations
SEQUENCE: 47
SYVLTQPPSV SVAPGQTARI TCGGNNIGSK SVHWYQQKPG QAPVLVVYDD SDRPSGIPER     60
FSGSNSGNTA TLTISRVEAG DEADYYCQVW DSSSDHWVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECSGGGGSG GGGSGGGGSG GGGSGGGGSG    240
GGGSGGQVQL VESGAEVKKP GASVKVSCKA SGYTFTGYYM HWVRQAPGQG LEWMGWINPN    300
SGGTNYAQKF QGRVTMTRDT SISTAYMELS RLRSDDTAVY YCARSPNPYY YDSSGYYYPG    360
AFDIWGQGTM VTVSSASTKG PSVFPLAPSS KSTSGGTAAL GCLVKDYFPE PVTVSWNSGA    420
LTSGVHTFPA VLQSSGLYSL SSVVTVPSSS LGTQTYICNV NHKPSNTKVD KKVEPKSCDK    480
THTCPPCPAP ELLGGPSVFL FPPKPKDTLM ASRTPEVTCV VVDVSHEDPE VKFNWYVDGV    540
EVHNAKTKPR EEQYNSTYRV VSVLTVLAQD WLNGKEYKCK VSNKALPAPI EKTISKAKGQ    600
PREPQVYTLP PCRDELTKNQ VSLWCLVKGF YPSDIAVEWE SNGQPENNYK TTPPVLDSDG    660
SFFLYSKLTV DKSRWQQGNV FSCSVMHEAL HNAYTQKSLS LSPGK                    705

SEQ ID NO: 48           moltype = AA  length = 214
FEATURE                 Location/Qualifiers
source                  1..214
                        mol_type = protein
                        organism = synthetic construct
                        note = Light chain 1 of  OAscFab IgG1 with AAA
                        mutations
SEQUENCE: 48
DIQLTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 49           moltype = AA  length = 450
FEATURE                 Location/Qualifiers
source                  1..450
                        mol_type = protein
                        organism = synthetic construct
                        note = Heavy chain 1 of  OAscFab IgG4 with AAA
                        mutations and with SPLE mutations
SEQUENCE: 49
EVQLVESGGG LVQPGGSLRL SCAASGYDFT HYGMNWVRQA PGKGLEWVGW INTYTGEPTY     60
AADFKRRFTF SLDTSKSTAY LQMNSLRAED TAVYYCAKYP YYYGTSHWYF DVWGQGTLVT    120
VSSASTKGPS VFPLAPCSRS TSESTAALGC LVKDYFPEPV TVSWNSGALT SGVHTFPAVL    180
QSSGLYSLSS VVTVPSSSLG TKTYTCNVDH KPSNTKVDKR VESKYGPPCP PCPAPEFEGG    240
PSVFLFPPKP KDTLMASRTP EVTCVVVDVS QEDPEVQFNW YVDGVEVHNA KTKPREEQFN    300
STYRVVSVLT VLAQDWLNGK EYKCKVSNKG LPSSIEKTIS KAKGQPREPQ VCTLPPSQEE    360
MTKNQVSLTC AVKGFYPSDI AVEWESNGQP ENNYKTTPPV LDSDGSFFLV SRLTVDKSRW    420
QEGNVFSCSV MHEALHNAYT QKSLSLSLGK                                     450

SEQ ID NO: 50           moltype = AA  length = 702
FEATURE                 Location/Qualifiers
source                  1..702
                        mol_type = protein
                        organism = synthetic construct
                        note = Heavy chain 2 of  OAscFab IgG4 with AAA
                        mutations and with SPLE mutations
SEQUENCE: 50
SYVLTQPPSV SVAPGQTARI TCGGNNIGSK SVHWYQQKPG QAPVLVVYDD SDRPSGIPER     60
FSGSNSGNTA TLTISRVEAG DEADYYCQVW DSSSDHWVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECSGGGGSG GGGSGGGGSG GGGSGGGGSG    240
GGGSGGQVQL VESGAEVKKP GASVKVSCKA SGYTFTGYYM HWVRQAPGQG LEWMGWINPN    300
SGGTNYAQKF QGRVTMTRDT SISTAYMELS RLRSDDTAVY YCARSPNPYY YDSSGYYYPG    360
AFDIWGQGTM VTVSSASTKG PSVFPLAPCS RSTSESTAAL GCLVKDYFPE PVTVSWNSGA    420
LTSGVHTFPA VLQSSGLYSL SSVVTVPSSS LGTKTYTCNV DHKPSNTKVD KRVESKYGPP    480
CPPCPAPEFE GGPSVFLFPP KPKDTLMASR TPEVTCVVVD VSQEDPEVQF NWYVDGVEVH    540
NAKTKPREEQ FNSTYRVVSV LTVLAQDWLN GKEYKCKVSN KGLPSSIEKT ISKAKGQPRE    600
PQVYTLPPCQ EEMTKNQVSL WCLVKGFYPS DIAVEWESNG QPENNYKTTP PVLDSDGSFF    660
LYSRLTVDKS RWQEGNVFSC SVMHEALHNA YTQKSLSLSL GK                       702

SEQ ID NO: 51           moltype = AA  length = 214
FEATURE                 Location/Qualifiers
```

| source | 1..214 |
| --- | --- |
| | mol_type = protein |
| | organism = synthetic construct |
| | note = Light chain 1 of OAscFab IgG4 with AAA |
| | mutations and with SPLE mutations |

SEQUENCE: 51

```
DIQLTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214
```

| SEQ ID NO: 52 | moltype = AA  length = 453 |
| --- | --- |
| FEATURE | Location/Qualifiers |
| source | 1..453 |
| | mol_type = protein |
| | organism = synthetic construct |
| | note = Heavy chain 1 of CrossMAb IgG1 wild |
| | type (without AAA mutations) (VEGFang2-0201) |

SEQUENCE: 52

```
EVQLVESGGG LVQPGGSLRL SCAASGYDFT HYGMNWVRQA PGKGLEWVGW INTYTGEPTY    60
AADFKRRFTF SLDTSKSTAY LQMNSLRAED TAVYYCAKYP YYYGTSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPC   360
RDELTKNQVS LWCLVKGFYP SDIAVEWESN GQPENNYKTT PPVLDSDGSF FLYSKLTVDK   420
SRWQQGNVFS CSVMHEALHN HYTQKSLSLS PGK                               453
```

| SEQ ID NO: 53 | moltype = AA  length = 463 |
| --- | --- |
| FEATURE | Location/Qualifiers |
| source | 1..463 |
| | mol_type = protein |
| | organism = synthetic construct |
| | note = Heavy chain 2 of CrossMAb IgG1 wild |
| | type (without AAA mutations) (VEGFang2-0201) |

SEQUENCE: 53

```
QVQLVQSGAE VKKPGASVKV SCKASGYTFT GYYMHWVRQA PGQGLEWMGW INPNSGGTNY    60
AQKFQGRVTM TRDTSISTAY MELSRLRSDD TAVYYCARSP NPYYYDSSGY YYPGAFDIWG   120
QGTMVTVSSA SVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGECDKTH   240
TCPPCPAPEL LGGPSVFLFP PKPKDTLMIS RTPEVTCVVV DVSHEDPEVK FNWYVDGVEV   300
HNAKTKPREE QYNSTYRVVS VLTVLHQDWL NGKEYKCKVS NKALPAPIEK TISKAKGQPR   360
EPQVCTLPPS RDELTKNQVS LSCAVKGFYP SDIAVEWESN GQPENNYKTT PPVLDSDGSF   420
FLVSKLTVDK SRWQQGNVFS CSVMHEALHN HYTQKSLSLS PGK                    463
```

| SEQ ID NO: 54 | moltype = AA  length = 214 |
| --- | --- |
| FEATURE | Location/Qualifiers |
| source | 1..214 |
| | mol_type = protein |
| | organism = synthetic construct |
| | note = Light chain 1 of CrossMAb IgG1 wild |
| | type ( without AAA mutations) (VEGFang2-0201) |

SEQUENCE: 54

```
DIQLTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214
```

| SEQ ID NO: 55 | moltype = AA  length = 213 |
| --- | --- |
| FEATURE | Location/Qualifiers |
| source | 1..213 |
| | mol_type = protein |
| | organism = synthetic construct |
| | note = Light chain 2 of CrossMAb IgG1 wild |
| | type (without AAA mutations) (VEGFang2-0201) |

SEQUENCE: 55

```
SYVLTQPPSV SVAPGQTARI TCGGNNIGSK SVHWYQQKPG QAPVLVVYDD SDRPSGIPER    60
FSGSNSGNTA TLTISRVEAG DEADYYCQVW DSSSDHWVFG GGTKLTVLSS ASTKGPSVFP   120
LAPSSKSTSG GTAALGCLVK DYFPEPVTVS WNSGALTSGV HTFPAVLQSS GLYSLSSVVT   180
VPSSSLGTQT YICNVNHKPS NTKVDKKVEP KSC                               213
```

| SEQ ID NO: 56 | moltype = AA  length = 453 |
| --- | --- |
| FEATURE | Location/Qualifiers |
| source | 1..453 |
| | mol_type = protein |
| | organism = synthetic construct |
| | note = Heavy chain 1 of CrossMAb IgG1 with |
| | P329G LALA mutations only (without AAA mutations) |
| | (VEGFang2-0015) |

```
SEQUENCE: 56
EVQLVESGGG LVQPGGSLRL SCAASGYDFT HYGMNWVRQA PGKGLEWVGW INTYTGEPTY     60
AADFKRRFTF SLDTSKSTAY LQMNSLRAED TAVYYCAKYP YYYGTSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALGAPIEK TISKAKGQPR EPQVYTLPPC    360
RDELTKNQVS LWCLVKGFYP SDIAVEWESN GQPENNYKTT PPVLDSDGSF FLYSKLTVDK    420
SRWQQGNVFS CSVMHEALHN HYTQKSLSLS PGK                                 453

SEQ ID NO: 57             moltype = AA   length = 463
FEATURE                   Location/Qualifiers
source                    1..463
                          mol_type = protein
                          organism = synthetic construct
                          note = Heavy chain 2 of CrossMAb IgG1 with
                          P329G LALA mutations only (without AAA mutations)
                          (VEGFang2-0015)
SEQUENCE: 57
QVQLVQSGAE VKKPGASVKV SCKASGYTFT GYYMHWVRQA PGQGLEWMGW INPNSGGTNY     60
AQKFQGRVTM TRDTSISTAY MELSRLRSDD TAVYYCARSP NPYYYDSSGY YYPGAFDIWG    120
QGTMVTVSSA SVAAPSVFIF PPSDEQLKSG TASVVCLLNN FYPREAKVQW KVDNALQSGN    180
SQESVTEQDS KDSTYSLSST LTLSKADYEK HKVYACEVTH QGLSSPVTKS FNRGECDKTH    240
TCPPCPAPEA AGGPSVFLFP PKPKDTLMIS RTPEVTCVVV DVSHEDPEVK FNWYVDGVEV    300
HNAKTKPREE QYNSTYRVVS VLTVLHQDWL NGKEYKCKVS NKALGAPIEK TISKAKGQPR    360
EPQVCTLPPS RDELTKNQVS LSCAVKGFYP SDIAVEWESN GQPENNYKTT PPVLDSDGSF    420
FLVSKLTVDK SRWQQGNVFS CSVMHEALHN HYTQKSLSLS PGK                      463

SEQ ID NO: 58             moltype = AA   length = 214
FEATURE                   Location/Qualifiers
source                    1..214
                          mol_type = protein
                          organism = synthetic construct
                          note = Light chain 1 of CrossMAb IgG1 with
                          P329G LALA mutations only (without AAA mutations)
                          (VEGFang2-0015)
SEQUENCE: 58
DIQLTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 59             moltype = AA   length = 213
FEATURE                   Location/Qualifiers
source                    1..213
                          mol_type = protein
                          organism = synthetic construct
                          note = Light chain 2 of CrossMAb IgG1 with
                          P329G LALA mutations only (without AAA mutations)
                          (VEGFang2-0015)
SEQUENCE: 59
SYVLTQPPSV SVAPGQTARI TCGGNNIGSK SVHWYQQKPG QAPVLVVYDD SDRPSGIPER     60
FSGSNSGNTA TLTISRVEAG DEADYYCQVW DSSSDHWVFG GGTKLTVLSS ASTKGPSVFP    120
LAPSSKSTSG GTAALGCLVK DYFPEPVTVS WNSGALTSGV HTFPAVLQSS GLYSLSSVVT    180
VPSSSLGTQT YICNVNHKPS NTKVDKKVEP KSC                                 213

SEQ ID NO: 60             moltype = AA   length = 227
FEATURE                   Location/Qualifiers
source                    1..227
                          mol_type = protein
                          organism = Homo sapiens
SEQUENCE: 60
DKTHTCPPCP APELLGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPGK                  227

SEQ ID NO: 61             moltype = AA   length = 326
FEATURE                   Location/Qualifiers
source                    1..326
                          mol_type = protein
                          organism = Homo sapiens
SEQUENCE: 61
ASTKGPSVFP LAPCSRSTSE STAALGCLVK DYFPEPVTVS WNSGALTSGV HTFPAVLQSS     60
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
VVSVLTVVHQ DWLNGKEYKC KVSNKGLPAP IEKTISKTKG QPREPQVYTL PPSREEMTKN    240
QVSLTCLVKG FYPSDISVEW ESNGQPENNY KTTPPMLDSD GSFFLYSKLT VDKSRWQQGN    300
VFSCSVMHEA LHNHYTQKSL SLSPGK                                         326
```

```
SEQ ID NO: 62             moltype = AA  length = 377
FEATURE                   Location/Qualifiers
source                    1..377
                          mol_type = protein
                          organism = Homo sapiens
SEQUENCE: 62
ASTKGPSVFP LAPCSRSTSG GTAALGCLVK DYFPEPVTVS WNSGALTSGV HTFPAVLQSS   60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                 377

SEQ ID NO: 63             moltype = AA  length = 229
FEATURE                   Location/Qualifiers
source                    1..229
                          mol_type = protein
                          organism = Homo sapiens
SEQUENCE: 63
ESKYGPPCPS CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK              229

SEQ ID NO: 64             moltype = AA  length = 227
FEATURE                   Location/Qualifiers
source                    1..227
                          mol_type = protein
                          organism = synthetic construct
                          note = human IgG1 Fc-region derived Fc-region polypeptide
                            with the mutations L234A, L235A
SEQUENCE: 64
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 65             moltype = AA  length = 227
FEATURE                   Location/Qualifiers
source                    1..227
                          mol_type = protein
                          organism = synthetic construct
                          note = human IgG1 Fc-region derived Fc-region polypeptide
                            with Y349C, T366S, L368A and Y407V mutations
SEQUENCE: 65
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 66             moltype = AA  length = 227
FEATURE                   Location/Qualifiers
source                    1..227
                          mol_type = protein
                          organism = synthetic construct
                          note = human IgG1 Fc-region derived Fc-region polypeptide
                            with S354C, T366W mutations
SEQUENCE: 66
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 67             moltype = AA  length = 227
FEATURE                   Location/Qualifiers
source                    1..227
                          mol_type = protein
                          organism = synthetic construct
                          note = human IgG1 Fc-region derived Fc-region polypeptide
                            with L234A, L235A mutations and Y349C, T366S, L368A, Y407V
                            mutations
SEQUENCE: 67
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227
```

```
SEQ ID NO: 68                moltype = AA  length = 227
FEATURE                      Location/Qualifiers
source                       1..227
                             mol_type = protein
                             organism = synthetic construct
                             note = human IgG1 Fc-region derived Fc-region polypeptide
                               with a L234A, L235A and S354C, T366W mutations
SEQUENCE: 68
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 69                moltype = AA  length = 227
FEATURE                      Location/Qualifiers
source                       1..227
                             mol_type = protein
                             organism = synthetic construct
                             note = human IgG1 Fc-region derived Fc-region polypeptide
                               with a P329G mutation
SEQUENCE: 69
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALGA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 70                moltype = AA  length = 227
FEATURE                      Location/Qualifiers
source                       1..227
                             mol_type = protein
                             organism = synthetic construct
                             note = human IgG1 Fc-region derived Fc-region polypeptide
                               with L234A, L235A mutations and P329G mutation
SEQUENCE: 70
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALGA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 71                moltype = AA  length = 227
FEATURE                      Location/Qualifiers
source                       1..227
                             mol_type = protein
                             organism = synthetic construct
                             note = human IgG1 Fc-region derived Fc-region polypeptide
                               with a P239G mutation and Y349C, T366S, L368A, Y407V
                               mutations
SEQUENCE: 71
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALGA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                 227

SEQ ID NO: 72                moltype = AA  length = 227
FEATURE                      Location/Qualifiers
source                       1..227
                             mol_type = protein
                             organism = synthetic construct
                             note = human IgG1 Fc-region derived Fc-region polypeptide
                               with a P329G mutation and S354C, T366W mutation
SEQUENCE: 72
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALGA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 73                moltype = AA  length = 227
FEATURE                      Location/Qualifiers
source                       1..227
                             mol_type = protein
                             organism = synthetic construct
                             note = human IgG1 Fc-region derived Fc-region polypeptide
                               with L234A, L235A, P329G and Y349C, T366S, L368A, Y407V
                               mutations
SEQUENCE: 73
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALGA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                 227
```

```
SEQ ID NO: 74            moltype = AA   length = 227
FEATURE                  Location/Qualifiers
source                   1..227
                         mol_type = protein
                         organism = synthetic construct
                         note = human IgG1 Fc-region derived Fc-region polypeptide
                           with L234A, L235A, P329G mutations and S354C, T366W
                           mutations
SEQUENCE: 74
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALGA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 75            moltype = AA   length = 229
FEATURE                  Location/Qualifiers
source                   1..229
                         mol_type = protein
                         organism = synthetic construct
                         note = human IgG4 Fc-region derived Fc-region polypeptide
                           with S228P and L235E mutations
SEQUENCE: 75
ESKYGPPCPP CPAPEFEGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK              229

SEQ ID NO: 76            moltype = AA   length = 229
FEATURE                  Location/Qualifiers
source                   1..229
                         mol_type = protein
                         organism = synthetic construct
                         note = human IgG4 Fc-region derived Fc-region polypeptide
                           with S228P, L235E mutations and P329G mutation
SEQUENCE: 76
ESKYGPPCPP CPAPEFEGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL GSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK              229

SEQ ID NO: 77            moltype = AA   length = 229
FEATURE                  Location/Qualifiers
source                   1..229
                         mol_type = protein
                         organism = synthetic construct
                         note = human IgG4 Fc-region derived Fc-region polypeptide
                           with S354C, T366W mutations
SEQUENCE: 77
ESKYGPPCPS CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPCQEEM TKNQVSLWCL VKGFYPSDIA VEWESNGQPE NNYKTTPPVL  180
DSDGSFFLYS RLTVDKSRWQ EGNVFSCSVM HEALHNHYTQ KSLSLSLGK              229

SEQ ID NO: 78            moltype = AA   length = 229
FEATURE                  Location/Qualifiers
source                   1..229
                         mol_type = protein
                         organism = synthetic construct
                         note = human IgG4 Fc-region derived Fc-region polypeptide
                           with Y349C, T366S, L368A, Y407V mutations
SEQUENCE: 78
ESKYGPPCPS CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV CTLPPSQEEM TKNQVSLSCA VKGFYPSDIA VEWESNGQPE NNYKTTPPVL  180
DSDGSFFLVS RLTVDKSRWQ EGNVFSCSVM HEALHNHYTQ KSLSLSLGK              229

SEQ ID NO: 79            moltype = AA   length = 229
FEATURE                  Location/Qualifiers
source                   1..229
                         mol_type = protein
                         organism = synthetic construct
                         note = human IgG4 Fc-region derived Fc-region polypeptide
                           with a S228P, L235E and S354C, T366W mutations
SEQUENCE: 79
ESKYGPPCPP CPAPEFEGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPCQEEM TKNQVSLWCL VKGFYPSDIA VEWESNGQPE NNYKTTPPVL  180
DSDGSFFLYS RLTVDKSRWQ EGNVFSCSVM HEALHNHYTQ KSLSLSLGK              229
```

```
SEQ ID NO: 80            moltype = AA  length = 229
FEATURE                  Location/Qualifiers
source                   1..229
                         mol_type = protein
                         organism = synthetic construct
                         note = human IgG4 Fc-region derived Fc-region polypeptide
                         with a S228P, L235E and Y349C, T366S, L368A, Y407V
                         mutations
SEQUENCE: 80
ESKYGPPCPP CPAPEFEGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV CTLPPSQEEM TKNQVSLSCA VKGFYPSDIA VEWESNGQPE NNYKTTPPVL  180
DSDGSFFLVS RLTVDKSRWQ EGNVFSCSVM HEALHNHYTQ KSLSLSLGK             229

SEQ ID NO: 81            moltype = AA  length = 229
FEATURE                  Location/Qualifiers
source                   1..229
                         mol_type = protein
                         organism = synthetic construct
                         note = human IgG4 Fc-region derived Fc-region polypeptide
                         with a P329G mutation
SEQUENCE: 81
ESKYGPPCPS CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL GSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 82            moltype = AA  length = 229
FEATURE                  Location/Qualifiers
source                   1..229
                         mol_type = protein
                         organism = synthetic construct
                         note = human IgG4 Fc-region derived Fc-region polypeptide
                         with a P239G and Y349C, T366S, L368A, Y407V mutations
SEQUENCE: 82
ESKYGPPCPS CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL GSSIEKTISK  120
AKGQPREPQV CTLPPSQEEM TKNQVSLSCA VKGFYPSDIA VEWESNGQPE NNYKTTPPVL  180
DSDGSFFLVS RLTVDKSRWQ EGNVFSCSVM HEALHNHYTQ KSLSLSLGK             229

SEQ ID NO: 83            moltype = AA  length = 229
FEATURE                  Location/Qualifiers
source                   1..229
                         mol_type = protein
                         organism = synthetic construct
                         note = human IgG4 Fc-region derived Fc-region polypeptide
                         with a P329G and S354C, T366W mutations
SEQUENCE: 83
ESKYGPPCPS CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL GSSIEKTISK  120
AKGQPREPQV YTLPPCQEEM TKNQVSLWCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 84            moltype = AA  length = 229
FEATURE                  Location/Qualifiers
source                   1..229
                         mol_type = protein
                         organism = synthetic construct
                         note = human IgG4 Fc-region derived Fc-region polypeptide
                         with a S228P, L235E, P329G and Y349C, T366S, L368A, Y407V
                         mutations
SEQUENCE: 84
ESKYGPPCPP CPAPEFEGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL GSSIEKTISK  120
AKGQPREPQV CTLPPSQEEM TKNQVSLSCA VKGFYPSDIA VEWESNGQPE NNYKTTPPVL  180
DSDGSFFLVS RLTVDKSRWQ EGNVFSCSVM HEALHNHYTQ KSLSLSLGK             229

SEQ ID NO: 85            moltype = AA  length = 229
FEATURE                  Location/Qualifiers
source                   1..229
                         mol_type = protein
                         organism = synthetic construct
                         note = human IgG4 Fc-region derived Fc-region polypeptide
                         with a S228P, L235E, P329G and S354C, T366W mutations
```

```
SEQUENCE: 85
ESKYGPPCPP CPAPEFEGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL GSSIEKTISK   120
AKGQPREPQV YTLPPCQEEM TKNQVSLWCL VKGFYPSDIA VEWESNGQPE NNYKTTPPVL   180
DSDGSFFLYS RLTVDKSRWQ EGNVFSCSVM HEALHNHYTQ KSLSLSLGK              229

SEQ ID NO: 86           moltype = AA   length = 105
FEATURE                 Location/Qualifiers
source                  1..105
                        mol_type = protein
                        organism = Homo sapiens
SEQUENCE: 86
QPKAAPSVTL FPPSSEELQA NKATLVCLIS DFYPGAVTVA WKADSSPVKA GVETTTPSKQ    60
SNNKYAASSY LSLTPEQWKS HRSYSCQVTH EGSTVEKTVA PTECS                   105

SEQ ID NO: 87           moltype = AA   length = 107
FEATURE                 Location/Qualifiers
source                  1..107
                        mol_type = protein
                        organism = Homo sapiens
SEQUENCE: 87
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 88           moltype = AA   length = 215
FEATURE                 Location/Qualifiers
source                  1..215
                        mol_type = protein
                        organism = synthetic construct
                        note = IGF-1R LC
SEQUENCE: 88
EIVLTQSPAT LSLSPGERAT LSCRASQSVS SYLAWYQQKP GQAPRLLIYD ASKRATGIPA    60
RFSGSGSGTD FTLTISSLEP EDFAVYYCQQ RSKWPPWTFG QGTKVESKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 89           moltype = AA   length = 447
FEATURE                 Location/Qualifiers
source                  1..447
                        mol_type = protein
                        organism = synthetic construct
                        note = IGF-1R wt
SEQUENCE: 89
QVELVESGGG VVQPGRSQRL SCAASGFTFS SYGMHWVRQA PGKGLEWVAI IWFDGSSTYY    60
ADSVRGRFTI SRDNSKNTLY LQMNSLRAED TAVYFCAREL GRRYFDLWGR GTLVSVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPG                                      447

SEQ ID NO: 90           moltype = AA   length = 447
FEATURE                 Location/Qualifiers
source                  1..447
                        mol_type = protein
                        organism = synthetic construct
                        note = IGF-1R AAA
SEQUENCE: 90
QVELVESGGG VVQPGRSQRL SCAASGFTFS SYGMHWVRQA PGKGLEWVAI IWFDGSSTYY    60
ADSVRGRFTI SRDNSKNTLY LQMNSLRAED TAVYFCAREL GRRYFDLWGR GTLVSVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMASRTPEV TCVVVDVSHE DPEVKFNWYV DGVEVHNAKT KPREEQYNST   300
YRVVSVLTVL AQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNAYTQK SLSLSPG                                      447

SEQ ID NO: 91           moltype = AA   length = 447
FEATURE                 Location/Qualifiers
source                  1..447
                        mol_type = protein
                        organism = synthetic construct
                        note = IGF-1R YTE
SEQUENCE: 91
QVELVESGGG VVQPGRSQRL SCAASGFTFS SYGMHWVRQA PGKGLEWVAI IWFDGSSTYY    60
ADSVRGRFTI SRDNSKNTLY LQMNSLRAED TAVYFCAREL GRRYFDLWGR GTLVSVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
```

```
VFLFPPKPKD TLYITREPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPG                                      447

SEQ ID NO: 92           moltype = AA  length = 448
FEATURE                 Location/Qualifiers
source                  1..448
                        mol_type = protein
                        organism = synthetic construct
                        note = IgG1 wtKiH
SEQUENCE: 92
QVELVESGGG VVQPGRSQRL SCAASGFTFS SYGMHWVRQA PGKGLEWVAI IWFDGSSTYY    60
ADSVRGRFTI SRDNSKNTLY LQMNSLRAED TAVYFCAREL GRRYFDLWGR GTLVSVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPCRDELT   360
KNQVSLWCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 93           moltype = AA  length = 448
FEATURE                 Location/Qualifiers
source                  1..448
                        mol_type = protein
                        organism = synthetic construct
                        note = VH-IGG1-FCSSHOLE
SEQUENCE: 93
QVELVESGGG VVQPGRSQRL SCAASGFTFS SYGMHWVRQA PGKGLEWVAI IWFDGSSTYY    60
ADSVRGRFTI SRDNSKNTLY LQMNSLRAED TAVYFCAREL GRRYFDLWGR GTLVSVSSGL   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVC TLPPSRDELT   360
KNQVSLSCAV KGFYPSDIAV EWESNGQPEN NYKTTPPVLD SDGSFFLVSK LTVDKSRWQQ   420
GNVFSCSVMH EALHNHYTQK SLSLSPGK                                     448

SEQ ID NO: 94           moltype = AA  length = 448
FEATURE                 Location/Qualifiers
source                  1..448
                        mol_type = protein
                        organism = synthetic construct
                        note = I253A, H310A, H435A
SEQUENCE: 94
QVELVESGGG VVQPGRSQRL SCAASGFTFS SYGMHWVRQA PGKGLEWVAI IWFDGSSTYY    60
ADSVRGRFTI SRDNSKNTLY LQMNSLRAED TAVYFCAREL GRRYFDLWGR GTLVSVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPCRDELT   360
KNQVSLWCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 95           moltype = AA  length = 448
FEATURE                 Location/Qualifiers
source                  1..448
                        mol_type = protein
                        organism = synthetic construct
                        note = VH-AK18-IGG1-FCSSHOLE-AAA1
SEQUENCE: 95
QVELVESGGG VVQPGRSQRL SCAASGFTFS SYGMHWVRQA PGKGLEWVAI IWFDGSSTYY    60
ADSVRGRFTI SRDNSKNTLY LQMNSLRAED TAVYFCAREL GRRYFDLWGR GTLVSVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMASRTPEV TCVVVDVSHE DPEVKFNWYV DGVEVHNAKT KPREEQYNST   300
YRVVSVLTVL AQDWLNGKEY KCKVSNKALP APIEKTISKA KGQPREPQVC TLPPSRDELT   360
KNQVSLSCAV KGFYPSDIAV EWESNGQPEN NYKTTPPVLD SDGSFFLVSK LTVDKSRWQQ   420
GNVFSCSVMH EALHNAYTQK SLSLSPGK                                     448

SEQ ID NO: 96           moltype = AA  length = 448
FEATURE                 Location/Qualifiers
source                  1..448
                        mol_type = protein
                        organism = synthetic construct
                        note = H310A, H433A, Y436A
SEQUENCE: 96
QVELVESGGG VVQPGRSQRL SCAASGFTFS SYGMHWVRQA PGKGLEWVAI IWFDGSSTYY    60
ADSVRGRFTI SRDNSKNTLY LQMNSLRAED TAVYFCAREL GRRYFDLWGR GTLVSVSSAS   120
TKGPSVFPLA PSSKSTSGGT AALGCLVKDY FPEPVTVSWN SGALTSGVHT FPAVLQSSGL   180
```

```
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVY TLPPCRDELT    360
KNQVSLWCLV KGFYPSDIAV EWESNGQPEN NYKTTPPVLD SDGSFFLYSK LTVDKSRWQQ    420
GNVFSCSVMH EALHNHYTQK SLSLSPGK                                       448

SEQ ID NO: 97              moltype = AA  length = 448
FEATURE                    Location/Qualifiers
source                     1..448
                           mol_type = protein
                           organism = synthetic construct
                           note = VH-IGG1-FCSSHOLE-AAA2
SEQUENCE: 97
QVELVESGGG VVQPGRSQRL SCAASGFTFS SYGMHWVRQA PGKGLEWVAI IWFDGSSTYY     60
ADSVRGRFTI SRDNSKNTLY LQMNSLRAED TAVYFCAREL GRRYFDLWGR GTLVSVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYNST    300
YRVVSVLTVL AQDWLNGKEY KCKVSNKALP APIEKTISKA KGQPREPQVC TLPPSRDELT    360
KNQVSLSCAV KGFYPSDIAV EWESNGQPEN NYKTTPPVLD SDGSFFLVSK LTVDKSRWQQ    420
GNVFSCSVMH EALANHATQK SLSLSPGK                                       448

SEQ ID NO: 98              moltype = AA  length = 448
FEATURE                    Location/Qualifiers
source                     1..448
                           mol_type = protein
                           organism = synthetic construct
                           note = M252Y, S254T, T256E
SEQUENCE: 98
QVELVESGGG VVQPGRSQRL SCAASGFTFS SYGMHWVRQA PGKGLEWVAI IWFDGSSTYY     60
ADSVRGRFTI SRDNSKNTLY LQMNSLRAED TAVYFCAREL GRRYFDLWGR GTLVSVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVY TLPPCRDELT    360
KNQVSLWCLV KGFYPSDIAV EWESNGQPEN NYKTTPPVLD SDGSFFLYSK LTVDKSRWQQ    420
GNVFSCSVMH EALHNHYTQK SLSLSPGK                                       448

SEQ ID NO: 99              moltype = AA  length = 448
FEATURE                    Location/Qualifiers
source                     1..448
                           mol_type = protein
                           organism = synthetic construct
                           note = VH-IGG1-FCSSHOLE-YTE
SEQUENCE: 99
QVELVESGGG VVQPGRSQRL SCAASGFTFS SYGMHWVRQA PGKGLEWVAI IWFDGSSTYY     60
ADSVRGRFTI SRDNSKNTLY LQMNSLRAED TAVYFCAREL GRRYFDLWGR GTLVSVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLYITREPEV TCVVVDVSHE DPEVKFNWYV DGVEVHNAKT KPREEQYNST    300
YRVVSVLTVL HQDWLNGKEY KCKVSNKALP APIEKTISKA KGQPREPQVC TLPPSRDELT    360
KNQVSLSCAV KGFYPSDIAV EWESNGQPEN NYKTTPPVLD SDGSFFLVSK LTVDKSRWQQ    420
GNVFSCSVMH EALHNHYTQK SLSLSPGK                                       448

SEQ ID NO: 100             moltype = AA  length = 448
FEATURE                    Location/Qualifiers
source                     1..448
                           mol_type = protein
                           organism = synthetic construct
                           note = DDD
SEQUENCE: 100
QVELVESGGG VVQPGRSQRL SCAASGFTFS SYGMHWVRQA PGKGLEWVAI IWFDGSSTYY     60
ADSVRGRFTI SRDNSKNTLY LQMNSLRAED TAVYFCAREL GRRYFDLWGR GTLVSVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVY TLPPCRDELT    360
KNQVSLWCLV KGFYPSDIAV EWESNGQPEN NYKTTPPVLD SDGSFFLYSK LTVDKSRWQQ    420
GNVFSCSVMH EALHNHYTQK SLSLSPGK                                       448

SEQ ID NO: 101             moltype = AA  length = 448
FEATURE                    Location/Qualifiers
source                     1..448
                           mol_type = protein
                           organism = synthetic construct
                           note = VH-IGG1-FCSSHOLE-DDD
SEQUENCE: 101
QVELVESGGG VVQPGRSQRL SCAASGFTFS SYGMHWVRQA PGKGLEWVAI IWFDGSSTYY     60
ADSVRGRFTI SRDNSKNTLY LQMNSLRAED TAVYFCAREL GRRYFDLWGR GTLVSVSSAS    120
```

```
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VPLFPPKPKD TDMISRTPEV TCVVVDVSHE DPEVKFNWYV DGVEVHNAKT KPREEQYNST    300
YRVVSVLTVL HQDWDNGKEY KCKVSNKALP APIEKTISKA KGQPREPQVC TLPPSRDELT    360
KNQVSLSCAV KGFYPSDIAV EWESNGQPEN NYKTTPPVLD SDGSFFLVSK LTVDKSRWQQ    420
GNVFSCSVMH EADHNYTQK  SLSLSPGK                                       448

SEQ ID NO: 102            moltype = AA  length = 453
FEATURE                   Location/Qualifiers
source                    1..453
                          mol_type = protein
                          organism = synthetic construct
                          note = Heavy chain 1 of  CrossMAb IgG1 wild
                            type (without AAA mutations) (VEGFang2-0201)
SEQUENCE: 102
EVQLVESGGG LVQPGGSLRL SCAASGYDFT HYGMNWVRQA PGKGLEWVGW INTYTGEPTY     60
AADFKRRFTF SLDTSKSTAY LQMNSLRAED TAVYYCAKYP YYYGTSHWYF DVWGQGTLVT    120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL    240
LGGPSVFLFP PKPKDTLMIS RTPEVTCVVV DVSHEDPEVK FNWYVDGVEV HNAKTKPREE    300
QYNSTYRVVS VLTVLAQDWL NGKEYKCKVS NKALPAPIEK TISKAKGQPR EPQVYTLPPC    360
RDELTKNQVS LWCLVKGFYP SDIAVEWESN GQPENNYKTT PPVLDSDGSF FLYSKLTVDK    420
SRWQQGNVFS CSVMHEALAN HATQKSLSLS PGK                                 453

SEQ ID NO: 103            moltype = AA  length = 463
FEATURE                   Location/Qualifiers
source                    1..463
                          mol_type = protein
                          organism = synthetic construct
                          note = Heavy chain 2 of  CrossMAb IgG1 wild
                            type (without AAA mutations) (VEGFang2-0201)
SEQUENCE: 103
QVQLVQSGAE VKKPGASVKV SCKASGYTFT GYYMHWVRQA PGQGLEWMGW INPNSGGTNY     60
AQKFQGRVTM TRDTSISTAY MELSRLRSDD TAVYYCARSP NPYYYDSSGY YYPGAFDIWG    120
QGTMVTVSSA SVAAPSVFIF PPSDEQLKSG TASVVCLLNN FYPREAKVQW KVDNALQSGN    180
SQESVTEQDS KDSTYSLSST LTLSKADYEK HKVYACEVTH QGLSSPVTKS FNRGECDKTH    240
TCPPCPAPEL LGGPSVFLFP PKPKDTLMIS RTPEVTCVVV DVSHEDPEVK FNWYVDGVEV    300
HNAKTKPREE QYNSTYRVVS VLTVLAQDWL NGKEYKCKVS NKALPAPIEK TISKAKGQPR    360
EPQVCTLPPS RDELTKNQVS LSCAVKGFYP SDIAVEWESN GQPENNYKTT PPVLDSDGSF    420
FLVSKLTVDK SRWQQGNVFS CSVMHEALAN HATQKSLSLS PGK                     463

SEQ ID NO: 104            moltype = AA  length = 453
FEATURE                   Location/Qualifiers
source                    1..453
                          mol_type = protein
                          organism = synthetic construct
                          note = Heavy chain 1 of  CrossMAb IgG1 wild
                            type (without AAA mutations) (VEGFang2-0201)
SEQUENCE: 104
EVQLVESGGG LVQPGGSLRL SCAASGYDFT HYGMNWVRQA PGKGLEWVGW INTYTGEPTY     60
AADFKRRFTF SLDTSKSTAY LQMNSLRAED TAVYYCAKYP YYYGTSHWYF DVWGQGTLVT    120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLAQDWL NGKEYKCKVS NKALGAPIEK TISKAKGQPR EPQVYTLPPC    360
RDELTKNQVS LWCLVKGFYP SDIAVEWESN GQPENNYKTT PPVLDSDGSF FLYSKLTVDK    420
SRWQQGNVFS CSVMHEALAN HATQKSLSLS PGK                                 453

SEQ ID NO: 105            moltype = AA  length = 463
FEATURE                   Location/Qualifiers
source                    1..463
                          mol_type = protein
                          organism = synthetic construct
                          note = Heavy chain 2 of  CrossMAb IgG1 wild
                            type (without AAA mutations) (VEGFang2-0201)
SEQUENCE: 105
QVQLVQSGAE VKKPGASVKV SCKASGYTFT GYYMHWVRQA PGQGLEWMGW INPNSGGTNY     60
AQKFQGRVTM TRDTSISTAY MELSRLRSDD TAVYYCARSP NPYYYDSSGY YYPGAFDIWG    120
QGTMVTVSSA SVAAPSVFIF PPSDEQLKSG TASVVCLLNN FYPREAKVQW KVDNALQSGN    180
SQESVTEQDS KDSTYSLSST LTLSKADYEK HKVYACEVTH QGLSSPVTKS FNRGECDKTH    240
TCPPCPAPEA AGGPSVFLFP PKPKDTLMIS RTPEVTCVVV DVSHEDPEVK FNWYVDGVEV    300
HNAKTKPREE QYNSTYRVVS VLTVLAQDWL NGKEYKCKVS NKALGAPIEK TISKAKGQPR    360
EPQVCTLPPS RDELTKNQVS LSCAVKGFYP SDIAVEWESN GQPENNYKTT PPVLDSDGSF    420
FLVSKLTVDK SRWQQGNVFS CSVMHEALAN HATQKSLSLS PGK                     463

SEQ ID NO: 106            moltype = AA  length = 450
FEATURE                   Location/Qualifiers
```

| source | 1..450 |
| --- | --- |
| | mol_type = protein |
| | organism = synthetic construct |
| | note = Heavy chain 1 of CrossMAb IgG4 with AAA mutations and with SPLE mutations |

SEQUENCE: 106

```
EVQLVESGGG LVQPGGSLRL SCAASGYDFT HYGMNWVRQA PGKGLEWVGW INTYTGEPTY   60
AADFKRRFTF SLDTSKSTAY LQMNSLRAED TAVYYCAKYP YYYGTSHWYF DVWGQGTLVT  120
VSSASTKGPS VFPLAPCSRS TSESTAALGC LVKDYFPEPV TVSWNSGALT SGVHTFPAVL  180
QSSGLYSLSS VVTVPSSLG TKTYTCNVDH KPSNTKVDKR VESKYGPPCP CPAPEFEGG   240
PSVFLFPPKP KDTLMASRTP EVTCVVVDVS QEDPEVQFNW YVDGVEVHNA KTKPREEQFN  300
STYRVVSVLT VLAQDWLNGK EYKCKVSNKG LPSSIEKTIS KAKGQPREPQ VCTLPPSQEE  360
MTKNQVSLSC AVKGFYPSDI AVEWESNGQP ENNYKTTPPV LDSDGSFFLV SRLTVDKSRW  420
QEGNVFSCSV MHEALANHAT QKSLSLSLGK                                  450
```

| SEQ ID NO: 107 | moltype = AA length = 460 |
| --- | --- |
| FEATURE | Location/Qualifiers |
| source | 1..460 |
| | mol_type = protein |
| | organism = synthetic construct |
| | note = Heavy chain 2 of CrossMAb IgG4 with AAA mutations and with SPLE mutations |

SEQUENCE: 107

```
QVQLVQSGAE VKKPGASVKV SCKASGYTFT GYYMHWVRQA PGQGLEWMGW INPNSGGTNY   60
AQKFQGRVTM TRDTSISTAY MELSRLRSDD TAVYYCARSP NPYYYDSSGY YYPGAFDIWG  120
QGTMVTVSSA SVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECPPCP  240
PCPAPEFEGG PSVFLFPPKP KDTLMISRTP EVTCVVVDVS QEDPEVQFNW YVDGVEVHNA  300
KTKPREEQFN STYRVVSVLT VLAQDWLNGK EYKCKVSNKG LPSSIEKTIS KAKGQPREPQ  360
VYTLPPCQEE MTKNQVSLWC LVKGFYPSDI AVEWESNGQP ENNYKTTPPV LDSDGSFFLY  420
SRLTVDKSRW QEGNVFSCSV MHEALANHAT QKSLSLSLGK                        460
```

| SEQ ID NO: 108 | moltype = AA length = 453 |
| --- | --- |
| FEATURE | Location/Qualifiers |
| source | 1..453 |
| | mol_type = protein |
| | organism = synthetic construct |
| | note = Heavy chain 1 of OAscFab IgG1 with AAA mutations |

SEQUENCE: 108

```
EVQLVESGGG LVQPGGSLRL SCAASGYDFT HYGMNWVRQA PGKGLEWVGW INTYTGEPTY   60
AADFKRRFTF SLDTSKSTAY LQMNSLRAED TAVYYCAKYP YYYGTSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLIAS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVCTLPPS  360
RDELTKNQVS LSCAVKGFYP SDIAVEWESN GQPENNYKTT PPVLDSDGSF FLVSKLTVDK  420
SRWQQGNVFS CSVMHEALAN HATQKSLSLS PGK                               453
```

| SEQ ID NO: 109 | moltype = AA length = 705 |
| --- | --- |
| FEATURE | Location/Qualifiers |
| source | 1..705 |
| | mol_type = protein |
| | organism = synthetic construct |
| | note = Heavy chain 2 of OAscFab IgG1 with AAA mutations |

SEQUENCE: 109

```
SYVLTQPPSV SVAPGQTARI TCGGNNIGSK SVHWYQQKPG QAPVLVVYDD SDRPSGIPER   60
FSGSNSGNTA TLTISRVEAG DEADYYCQVW DSSSDHWVFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECSGGGGSG GGGSGGGGSG GGGSGGGGSG  240
GGGSGGQVQL VESGAEVKKP GASVKVSCKA SGYTFTGYYM HWVRQAPGQG LEWMGWINPN  300
SGGTNYAQKF QGRVTMTRDT SISTAYMELS RLRSDDTAVY YCARSPNPYY YDSSGYYYPG  360
AFDIWGQGTM VTVSSASTKG PSVFPLAPSS KSTSGGTAAL GCLVKDYFPE PVTVSWNSGA  420
LTSGVHTFPA VLQSSGLYSL SSVVTVPSSS LGTQTYICNV NHKPSNTKVD KKVEPKSCDK  480
THTCPPCPAP ELLGGPSVFL FPPKPKDTLM ISRTPEVTCV VVDVSHEDPE VKFNWYVDGV  540
EVHNAKTKPR EEQYNSTYRV VSVLTVLAQD WLNGKEYKCK VSNKALPAPI EKTISKAKGQ  600
PREPQVYTLP PCRDELTKNQ VSLWCLVKGF YPSDIAVEWE SNGQPENNYK TTPPVLDSDG  660
SFFLYSKLTV DKSRWQQGNV FSCSVMHEAL ANHATQKSLS LSPGK                  705
```

| SEQ ID NO: 110 | moltype = AA length = 450 |
| --- | --- |
| FEATURE | Location/Qualifiers |
| source | 1..450 |
| | mol_type = protein |
| | organism = synthetic construct |
| | note = Heavy chain 1 of OAscFab IgG4 with AAA mutations and with SPLE mutations |

```
SEQUENCE: 110
EVQLVESGGG LVQPGGSLRL SCAASGYDFT HYGMNWVRQA PGKGLEWVGW INTYTGEPTY      60
AADFKRRFTF SLDTSKSTAY LQMNSLRAED TAVYYCAKYP YYYGTSHWYF DVWGQGTLVT     120
VSSASTKGPS VFPLAPCSRS TSESTAALGC LVKDYFPEPV TVSWNSGALT SGVHTFPAVL     180
QSSGLYSLSS VVTVPSSSLG TKTYTCNVDH KPSNTKVDKR VESKYGPPCP PCPAPEFEGG     240
PSVFLFPPKP KDTLMISRTP EVTCVVVDVS QEDPEVQFNW YVDGVEVHNA KTKPREEQFN     300
STYRVVSVLT VLAQDWLNGK EYKCKVSNKG LPSSIEKTIS KAKGQPREPQ VCTLPPSQEE     360
MTKNQVSLSC AVKGFYPSDI AVEWESNGQP ENNYKTTPPV LDSDGSFFLV SRLTVDKSRW     420
QEGNVFSCSV MHEALANHAT QKSLSLSLGK                                     450

SEQ ID NO: 111         moltype = AA   length = 702
FEATURE                Location/Qualifiers
source                 1..702
                       mol_type = protein
                       organism = synthetic construct
                       note = Heavy chain 2 of  OAscFab IgG4 with AAA
                        mutations and with SPLE mutations
SEQUENCE: 111
SYVLTQPPSV SVAPGQTARI TCGGNNIGSK SVHWYQQKPG QAPVLVVYDD SDRPSGIPER      60
FSGSNSGNTA TLTISRVEAG DEADYYCQVW DSSSDHWVFG GGTKLTVLGQ PKAAPSVTLF     120
PPSSEELQAN KATLVCLISD FYPGAVTVAW KADSSPVKAG VETTTPSKQS NNKYAASSYL     180
SLTPEQWKSH RSYSCQVTHE GSTVEKTVAP TECSGGGGSG GGGSGGGGSG GGGSGGGGSG     240
GGGSGGQVQL VESGAEVKKP GASVKVSCKA SGYTFTGYYM HWVRQAPGQG LEWMGWINPN     300
SGGTNYAQKF QGRVTMTRDT SISTAYMELS RLRSDDTAVY YCARSPNPYY YDSSGYYYPG     360
AFDIWGQGTM VTVSSASTKG PSVFPLAPCS RSTSESTAAL GCLVKDYFPE PVTVSWNSGA     420
LTSGVHTFPA VLQSSGLYSL SSVVTVPSSS LGTKTYTCNV DHKPSNTKVD KRVESKYGPP     480
CPPCPAPEFE GGPSVFLFPP KPKDTLMISR TPEVTCVVVD VSQEDPEVQF NWYVDGVEVH     540
NAKTKPREEQ FNSTYRVVSV LTVLAQDWLN GKEYKCKVSN KGLPSSIEKT ISKAKGQPRE     600
PQVYTLPPCQ EEMTKNQVSL WCLVKGFYPS DIAVEWESNG QPENNYKTTP PVLDSDGSFF     660
LYSRLTVDKS RWQEGNVFSC SVMHEALANH ATQKSLSLSL GK                       702

SEQ ID NO: 112         moltype = AA   length = 447
FEATURE                Location/Qualifiers
source                 1..447
                       mol_type = protein
                       organism = synthetic construct
                       note = IGF-1R wt
SEQUENCE: 112
QVELVESGGG VVQPGRSQRL SCAASGFTFS SYGMHWVRQA PGKGLEWVAI IWFDGSSTYY      60
ADSVRGRFTI SRDNSKNTLY LQMNSLRAED TAVYFCAREL GRRYFDLWGR GTLVSVSSAS     120
TKGPSVFPLA PSSKSTSGGT AALGCLVKDY FPEPVTVSWN SGALTSGVHT FPAVLQSSGL     180
YSLSSVVTVP SSSLGTQTYI CNVNHKPSNT KVDKKVEPKS CDKTHTCPPC PAPELLGGPS     240
VFLFPPKPKD TLMISRTPEV TCVVVDVSHE DPEVKFNWYV DGVEVHNAKT KPREEQYNST     300
YRVVSVLTVL AQDWLNGKEY KCKVSNKALP APIEKTISKA KGQPREPQVY TLPPSRDELT     360
KNQVSLTCLV KGFYPSDIAV EWESNGQPEN NYKTTPPVLD SDGSFFLYSK LTVDKSRWQQ     420
GNVFSCSVMH EALHNHYTQK SLSLSPG                                        447

SEQ ID NO: 113         moltype = AA   length = 232
FEATURE                Location/Qualifiers
source                 1..232
                       mol_type = protein
                       organism = Homo sapiens
SEQUENCE: 113
EPKSCDKTHT CPPCPAPELL GGPSVFLFPP KPKDTLMISR TPEVTCVVVD VSHEDPEVKF      60
NWYVDGVEVH NAKTKPREEQ YNSTYRVVSV LTVLHQDWLN GKEYKCKVSN KALPAPIEKT     120
ISKAKGQPRE PQVYTLPPSR DELTKNQVSL TCLVKGFYPS DIAVEWESNG QPENNYKTTP     180
PVLDSDGSFF LYSKLTVDKS RWQQGNVFSC SVMHEALHNH YTQKSLSLSP GK             232

SEQ ID NO: 114         moltype = AA   length = 228
FEATURE                Location/Qualifiers
source                 1..228
                       mol_type = protein
                       organism = Homo sapiens
SEQUENCE: 114
ERKCCVECPP CPAPPVAGPS VFLFPPKPKD TLMISRTPEV TCVVVDVSHE DPEVQFNWYV      60
DGVEVHNAKT KPREEQFNST FRVVSVLTVV HQDWLNGKEY KCKVSNKGLP APIEKTISKT     120
KGQPREPQVY TLPPSREEMT KNQVSLTCLV KGFYPSDISV EWESNGQPEN NYKTTPPMLD     180
SDGSFFLYSK LTVDKSRWQQ GNVFSCSVMH EALHNHYTQK SLSLSPGK                  228

SEQ ID NO: 115         moltype = AA   length = 277
FEATURE                Location/Qualifiers
source                 1..277
                       mol_type = protein
                       organism = Homo sapiens
SEQUENCE: 115
KTPLGDTTHT CPRCPEPKSC DTPPPCPRCP EPKSCDTPPP CPRCPEPKSC DTPPPCPRCP      60
APELLGGPSV FLFPPKPKDT LMISRTPEVT CVVVDVSHED PEVQFKWYVD GVEVHNAKTK     120
PREEQYNSTF RVVSVLTVLH QDWLNGKEYK CKVSNKALPA PIEKTISKTK GQPREPQVYT     180
```

```
LPPSREEMTK NQVSLTCLVK GFYPSDIAVE WESSGQPENN YNTTPPMLDS DGSFFLYSKL    240
TVDKSRWQQG NIFSCSVMHE ALHNRFTQKS LSLSPGK                             277

SEQ ID NO: 116           moltype = AA  length = 40
FEATURE                  Location/Qualifiers
source                   1..40
                         mol_type = protein
                         organism = synthetic construct
VARIANT                  1..40
                         note = This sequence may encompass 8-10 GGGS repeating units
SEQUENCE: 116
GGGSGGGSGG GSGGGSGGGS GGGSGGGSGG GSGGGSGGGS                          40

SEQ ID NO: 117           moltype = AA  length = 40
FEATURE                  Location/Qualifiers
source                   1..40
                         mol_type = protein
                         organism = synthetic construct
VARIANT                  1..40
                         note = This sequence may encompass 6-8 GGGGS repeating units
SEQUENCE: 117
GGGGSGGGGS GGGGSGGGGS GGGGSGGGGS GGGGSGGGGS                          40

SEQ ID NO: 118           moltype = AA  length = 32
FEATURE                  Location/Qualifiers
source                   1..32
                         mol_type = protein
                         organism = synthetic construct
SEQUENCE: 118
GGGGSGGGGS GGGGSGGGGS GGGGSGGGGS GG                                  32

SEQ ID NO: 119           moltype = AA  length = 35
FEATURE                  Location/Qualifiers
source                   1..35
                         mol_type = protein
                         organism = synthetic construct
VARIANT                  1..35
                         note = This sequence may encompass 6-7 GGGGS repeating units
SEQUENCE: 119
GGGGSGGGGS GGGGSGGGGS GGGGSGGGGS GGGGS                               35

SEQ ID NO: 120           moltype = AA  length = 35
FEATURE                  Location/Qualifiers
source                   1..35
                         mol_type = protein
                         organism = synthetic construct
SEQUENCE: 120
GGGGSGGGGS GGGGSGGGGS GGGGSGGGGS GGGGS                               35
```